(12) United States Patent
Ab et al.

(10) Patent No.: US 11,396,543 B2
(45) Date of Patent: Jul. 26, 2022

(54) BIPARATOPIC FR-α ANTIBODIES AND IMMUNOCONJUGATES

(71) Applicant: ImmnoGen, Inc., Waltham, MA (US)

(72) Inventors: Olga Ab, Millis, MA (US); Neeraj Kohli, Arlington, MA (US); Thomas Chittenden, Sudbury, MA (US); Julianto Setiady, Lexington, MA (US)

(73) Assignee: ImmunoGen, Inc., Waltham, MA (US)

( * ) Notice: Subject to any disclaimer, the term of this patent is extended or adjusted under 35 U.S.C. 154(b) by 207 days.

(21) Appl. No.: 16/860,822

(22) Filed: Apr. 28, 2020

(65) Prior Publication Data

US 2020/0362029 A1   Nov. 19, 2020

Related U.S. Application Data

(60) Provisional application No. 62/879,864, filed on Jul. 29, 2019, provisional application No. 62/840,297, filed on Apr. 29, 2019.

(51) Int. Cl.
| | | |
|---|---|---|
| C07K 16/28 | (2006.01) | |
| A61K 31/5365 | (2006.01) | |
| A61P 35/00 | (2006.01) | |
| A61K 47/68 | (2017.01) | |

(52) U.S. Cl.
CPC .......... *C07K 16/28* (2013.01); *A61K 31/5365* (2013.01); *A61K 47/6803* (2017.08); *A61P 35/00* (2018.01); *C07K 2317/31* (2013.01); *C07K 2317/569* (2013.01)

(58) Field of Classification Search
CPC ................ C07K 16/28; C07K 2317/31; C07K 2317/569; C07K 2317/526; C07K 2317/55; C07K 2317/622; C07K 2317/73; C07K 2317/90; C07K 2317/92; C07K 2317/94; A61K 31/5365; A61K 47/6803; A61K 47/6849; A61K 47/6879; A61K 2039/505; A61K 45/06; A61P 35/00
See application file for complete search history.

(56) References Cited

U.S. PATENT DOCUMENTS

| | | |
|---|---|---|
| 8,557,966 B2 | 10/2013 | Ab et al. |
| 8,709,432 B2 | 4/2014 | Carrigan et al. |
| 9,133,275 B2 | 9/2015 | Ab et al. |
| 9,200,073 B2 | 12/2015 | Carrigan et al. |
| 9,598,490 B2 | 3/2017 | Ab et al. |
| 9,637,547 B2 | 5/2017 | Ab et al. |
| 9,657,100 B2 | 5/2017 | Ab et al. |
| 9,670,278 B2 | 6/2017 | Ab et al. |
| 9,670,279 B2 | 6/2017 | Ab et al. |
| 9,670,280 B2 | 6/2017 | Ab et al. |
| 9,702,881 B2 | 7/2017 | Carrigan et al. |
| 10,017,578 B2 | 7/2018 | Ab et al. |
| 10,172,875 B2 | 1/2019 | Ponte et al. |
| 10,180,432 B2 | 1/2019 | Carrigan et al. |
| 10,301,385 B2 | 5/2019 | Ab et al. |
| 10,544,230 B2 | 1/2020 | Ab et al. |
| 10,603,388 B2 | 3/2020 | Payne et al. |
| 10,613,093 B2 | 4/2020 | Carrigan et al. |
| 11,033,564 B2 | 6/2021 | Ponte et al. |
| 11,135,305 B2 | 10/2021 | Carrigan et al. |
| 11,198,736 B2 | 12/2021 | Ab et al. |
| 11,274,121 B2 | 3/2022 | Milano et al. |
| 2010/0055034 A1 | 3/2010 | Martin et al. |
| 2012/0207771 A1 | 8/2012 | O'Shannessy et al. |
| 2013/0295119 A1* | 11/2013 | Ab .......................... A61P 35/02 424/174.1 |
| 2015/0132323 A1 | 5/2015 | Lutz et al. |
| 2016/0096887 A1 | 4/2016 | Ab et al. |
| 2017/0095571 A1* | 4/2017 | Ponte ..................... A61K 33/24 |
| 2017/0247449 A1 | 8/2017 | Ando et al. |
| 2018/0200383 A1 | 7/2018 | Carrigan et al. |
| 2019/0112359 A1 | 4/2019 | Liu et al. |
| 2019/0167704 A1 | 6/2019 | Ponte et al. |
| 2019/0345248 A1 | 11/2019 | Ab et al. |
| 2020/0046634 A1 | 2/2020 | Running et al. |
| 2020/0333347 A1 | 10/2020 | Carrigan et al. |

FOREIGN PATENT DOCUMENTS

| | | |
|---|---|---|
| WO | WO 2011106528 A1 | 9/2011 |
| WO | WO 2012135675 A2 | 10/2012 |
| WO | WO 2012138749 A1 | 10/2012 |
| WO | WO 2014036495 A2 | 3/2014 |
| WO | WO 2014186403 A2 | 11/2014 |

(Continued)

OTHER PUBLICATIONS

Shan, et al., J Immunol 1999 vol. 162, pp. 6589-6595 (Year: 1999).*
Tzartos, et al., Methods in Molecular Biology 1996, vol. 66 Epitope Mapping Protocols; Edited by GE Morns Humana Press, Inc. Totowa, NJ, pp. 55-66 (Year: 1996).*
Almagro & Fransson, Frontiers in Bioscience 2008; 13:1619-33 (Year: 2008).*
Edwards et al, J Mol Biol 2003 334:103-118 (Year: 2003).*
Ab, et al., "IMGN853, a Folate Receptor-a (FRα)-Targeting Antibody-Drug Conjugate, Exhibits Potent Targeted Antitumor Activity against FRα-Expressing Tumors," Mol Cancer Ther, 14(7), 1605-1613, AACR, United States (2015).

(Continued)

*Primary Examiner* — Julie Wu
*Assistant Examiner* — John L Van Druff
(74) *Attorney, Agent, or Firm* — Sterne, Kessler, Goldstein & Fox P.L.L.C.

(57) ABSTRACT

The present disclosure provides biparatopic antibodies comprising polypeptides that bind to folate receptor alpha (FRα) compositions comprising such biparatopic antibodies. In a specific aspect, the biparatopic antibodies bind to FRα and modulate FRα activity. The present disclosure also provides methods for treating disorders, such as cancer, by administering a biparatopic antibody that specifically binds to FRα and modulates FRα activity.

47 Claims, 22 Drawing Sheets

Specification includes a Sequence Listing.

(56) References Cited

FOREIGN PATENT DOCUMENTS

| WO | WO 2015031815 A2 | 3/2015 | | |
|---|---|---|---|---|
| WO | WO 2015054400 A2 | 4/2015 | | |
| WO | WO 2017049149 A1 | 3/2017 | | |
| WO | WO-2018160539 A1 * | 9/2018 | ......... | A61K 31/5365 |
| WO | WO 2019050935 A1 | 3/2019 | | |

OTHER PUBLICATIONS

Ab, Olga, et al., "IMGN151: A Next Generation Folate Receptor Alpha Targeting Antibody-Drug Conjugate Active Against Tumors with Low, Medium, and High Receptor Expression," Abstract 2890, AACR Jun. 22-24, 2020, 1 page.

Ab, Olga, et al., "2890/7-IMGN151—A next generation folate receptor alpha targeting antibody drug conjugate active against tumors with low, medium, and high receptor expression," Session PO.ET01.05-Antibody Drug Conjugates, AACR Virtual Annual Meeting II, Jun. 22, 2020, 2 pages.

Bissery, M., et al., "Experimental Antitumor Activity of Taxotere (RP 56976, NSC 628503), a Taxol Analogue," Cancer Res., 51(18): 4845-4852, American Association for Cancer Research, USA (1991).

Brinkmann, U., et al., "A recombinant immunotoxin containing a disulfide-stabilized Fv fragment," PNAS, 90(16): 7538-754, United States National Academy of Science, USA (1993).

Co-pending, U.S. Appl. No. 16/644,695, inventors Xu, R., et al., filed Mar. 5, 2020 (Not Published).

Co-pending, U.S. Appl. No. 16/707,940, inventors Ab, O., et al., filed Dec. 9, 2019 (Not Published).

Co-pending, U.S. Appl. No. 16/804,664, inventors Carrigan, C., et al., Feb. 28, 2020 (Not Published).

Co-pending, U.S. Appl. No. 16/892,962, inventors Ponte, J., et al., filed Jun. 4, 2020 (Not Published).

Co-pending, U.S. Appl. No. 16/934,143, inventors Ab, O., et al., filed Jul. 21, 2020 (Not Published).

Costoplus, J., et al., "Peptide-Cleavable Self-immolative Maytansinoid Antibody-Drug Conjugates Designed To Provide Improved Bystander Killing," ACS Med. Chem. Lett., 10(10): 1393-1399, American Chemical Society, United States (Sep. 2019).

Durocher, Y., et al., "High-level and high-throughput recombinant protein production by transient transfection of suspension-growing human 293-EBNA1 cells," Nucleic Acids Res., 30(2): E9, 9 pages, Oxford University Press, England (2002).

International Search Report and Written Opinion for International Patent Application No. PCT/US2020/030245, United States Patent and Trademark Office, Alexandria, Virginia, dated Aug. 17, 2020, 11 pages.

Lutz, R. J., "Targeting the folate receptor for the treatment of ovarian cancer," Transl Cancer Res, 4(1): 118-126, AME Publishing Company, Hong Kong (2015).

Ridgway, J.B. et al., "Knobs-into-holes' engineering of antibody CH3 domains for heavy chain heterodimerization," Protein Eng., 9(7): 617-621, Oxford University Press, United States (1996).

Final Office Action, dated May 1, 2013, in U.S. Appl. No. 13/033,723, filed Feb. 24, 2022.

Non-Final Office Action, dated Nov. 8, 2012, in U.S. Appl. No. 13/033,723, filed Feb. 24, 2022.

Non-Final Office Action, dated Dec. 31, 2014, in U.S. Appl. No. 13/800,835, filed Mar. 13, 2013.

Final Office Action, dated Sep. 23, 2016, in U.S. Appl. No. 14/819,209, filed Aug. 5, 2015.

Non-Final Office Action, dated Apr. 28, 2016, in U.S. Appl. No. 14/819,209, filed Aug. 5, 2015.

Non-Final Office Action, dated Nov. 3, 2016, in U.S. Appl. No. 14/946,423, filed Nov. 19, 2015.

Non-Final Office Action, dated Dec. 8, 2016, in U.S. Appl. No. 14/952,659, filed Nov. 25, 2015.

Non-Final Office Action, dated Jan. 21, 2016, in U.S. Appl. No. 14/970,433, filed Dec. 15, 2015.

Non-Final Office Action, dated Dec. 5, 2016, in U.S. Appl. No. 14/970,436, filed Dec. 15, 2015.

Co-pending, U.S. Appl. No. 17/463,156, inventors Carrigan, C.N., et al., filed Aug. 31, 2021.

Co-pending, U.S. Appl. No. 17/523,126, inventors Ab, O., et al., filed Nov. 10, 2021.

Co-pending, U.S. Appl. No. 17/720,766, inventors Running, K., et al., filed Apr. 15, 2022.

Co-pending, U.S. Appl. No. 17/150,379, inventors Lutz, R.J., et al., filed Jan. 15, 2021.

Co-pending, U.S. Appl. No. 17/651,459, inventors Pone, J., et al., filed Feb. 17, 2022.

Co-pending, U.S. Appl. No. 17/667,002, inventors Milano, D.F., et al., filed Feb. 8, 2022.

* cited by examiner

FIG. 2

| Format | Exemplary molecules | Characteristics | Scheme |
|---|---|---|---|
| Conventional Antibody | • M9346A ("huMov19", "M")<br>• FR57<br>• FRα-A<br>• FRα-B<br>• FRα-C | Bivalent monospecific | 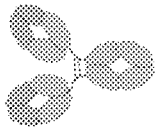 |
| Knob in Hole (KIH) | • FR57scFv2-knob-Mov19-hole ("KIH")<br>• FR57scFv3wt-knob-Mov19-hole | Bivalent biparatopic | 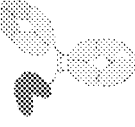 |
| Morrison | • Mov19-IgG1-FR13scFv1<br>• Mov19-IgG1-FR57scFv1<br>• FRα-A-IgG1-Mov19scFv1<br>• FR57-IgG1-Mov19scFv1<br>• FRα-AscFv2-Mov19-IgG1<br>• FRα-BscFv2-Mov19-IgG1<br>• FRα-CscFv2-Mov19-IgG1<br>• FR57scFv2-Mov19-IgG1 ("Tetravalent") | Tetravalent biparatopic | 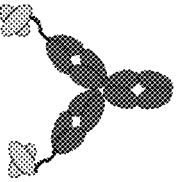 |

FIGs. 13A-13D
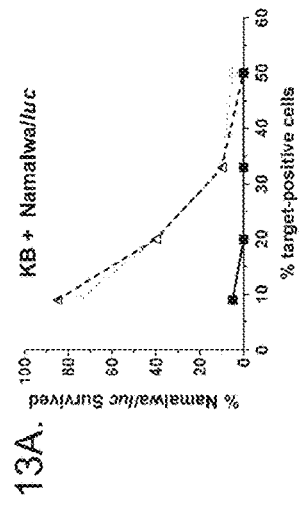
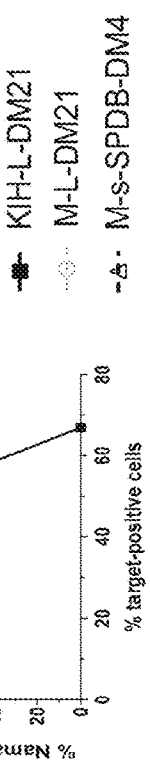

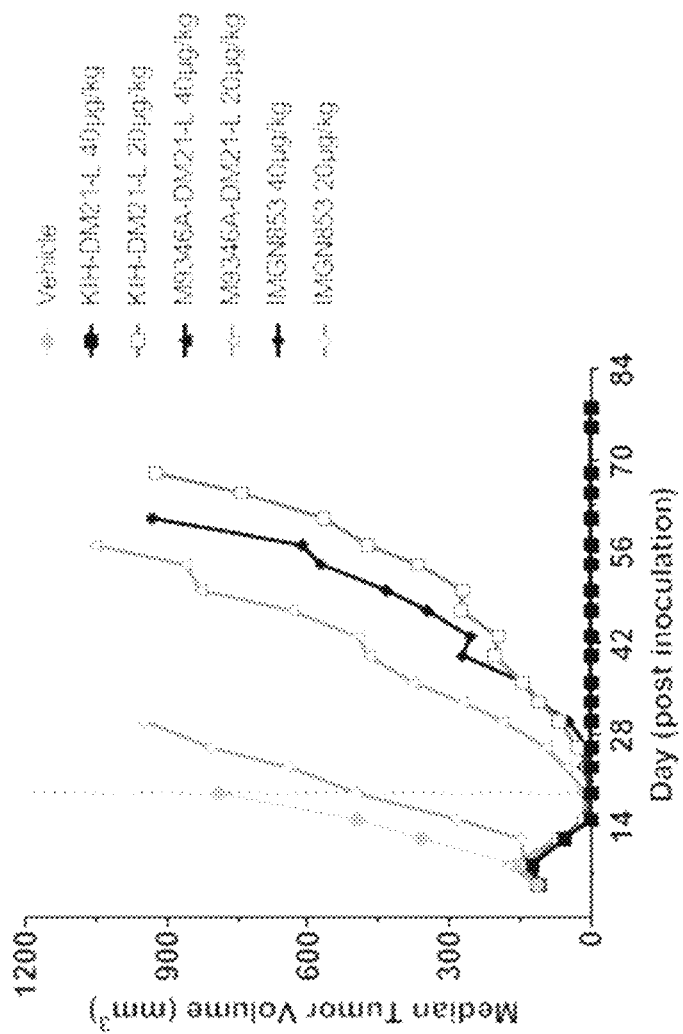

BIPARATOPIC FR-α ANTIBODIES AND IMMUNOCONJUGATES

REFERENCE TO RELATED APPLICATIONS

This application claims the priority benefit of U.S. Provisional Application No. 62/840,297, filed on Apr. 29, 2019, and 62/879,864, filed on Jul. 29, 2019, each of which is incorporated by reference herein in its entirety.

REFERENCE TO A SEQUENCE LISTING SUBMITTED ELECTRONICALLY VIA EFS-WEB

The content of the electronically submitted sequence listing (Name: 2921_1080002_Seqlisting_ST25; Size: 102,806 bytes and Date of Creation: Apr. 28, 2020) is incorporated herein by reference in its entirety.

FIELD OF THE DISCLOSURE

The field of this disclosure generally relates biparatopic antibodies and immunoconjugates that bind to human folate receptor 1 (FRα).

BACKGROUND OF THE DISCLOSURE

Cancer is one of the leading causes of death in the developed world, with over one million people diagnosed with cancer and 500,000 deaths per year in the United States alone. Overall it is estimated that more than 1 in 3 people will develop some form of cancer during their lifetime.

Antibody-drug conjugates (ADC) composed of highly cytotoxic agents conjugated to antibodies that bind to tumor-associated antigens represent a promising therapeutic strategy to enhance the potency of tumor-targeting antibodies. ADCs offer the potential to combine the favorable pharmacokinetics, biodistribution, and tumor-targeting properties of antibodies with the potent cell killing mechanism provided by the attached small molecule, or payload.

The folate receptor-α (FRα or FOLR1) is a glycosylphosphatidylinositol-linked cell-surface glycoprotein that has high affinity for folates. Its physiologic role in normal and cancerous tissues has not yet been fully elucidated. Most normal tissues do not express FRα, and transport of physiologic folates into most cells is thought to be mediated by several other proteins, most notably, reduced folate carrier. High levels of FRα have been found in serous and endometrioid epithelial ovarian cancer, endometrial adenocarcinoma, and non-small cell lung cancer of the adenocarcinoma subtype. Importantly, FRα expression is maintained in metastatic foci and recurrent carcinomas in ovarian cancer patients, and after chemotherapy in epithelial ovarian and endometrial cancers. These properties, together with the highly restricted expression of FRα on normal tissues, make FRα a highly promising target for targeted therapies such as ADCs.

Mirvetuximab soravtansine (IMGN853), a folate targeting ADC that comprises a FRα targeting antibody conjugated to a potent tubulin-acting maytansinoid, DM4, was recently evaluated in the clinic in platinum-resistant ovarian cancer patients exhibiting medium and high FRα levels. The FORWARD I Phase 3 trial randomized 366 patients 2:1 to receive either mirvetuximab soravtansine or the physician's choice of single-agent chemotherapy (pegylated liposomal doxorubicin, topotecan, or weekly paclitaxel). While the trial did not meet its primary endpoint of improvement in progression-free survival (PFS) (in the overall population hazard ratio (HR)=0.98, p=0.897), the pre-specified high FRα sub-population (218/366) showed an overall response rate of 24% with IMGN853 treatment versus 10% for standard of care chemotherapy. In addition, in the pre-specified high FRα sub-population, the PFS was longer in patients who received IMGN853 compared with chemotherapy (HR=0.69, p-value=0.049), and overall survival was longer in patients who received IMGN853 compared with chemotherapy (HR=0.62, p-value=0.033). While, these results are encouraging for patients expressing high levels of FRα, the results also demonstrated the limitations of IMGN853 in improving progression-free survival across a broader patient population.

Thus, there remains a need to identify additional folate targeting ADCs that can lead to even more efficacious treatment and higher ADC delivery.

SUMMARY OF THE DISCLOSURE

Provided herein is a biparatopic antibody or antigen binding fragment thereof that specifically binds a human folate receptor 1 (FRα), wherein the antibody or antigen-binding fragment thereof comprises (a) a first FRα-binding domain that comprises a first variable heavy chain (VH) and a first variable light chain (VL) and that bind to a first epitope of FRα; and (b) a second FRα-binding domain that comprises a second VH and a second VL and that binds to a second epitope of FRα.

In some embodiments, the first FRα binding domain specifically binds to the same FRα epitope as an antibody comprising a VH amino acid sequence selected from the group consisting of SEQ ID NOs:24, 25, and 26, and a VL amino acid sequence selected from the group consisting of SEQ ID NOs:19, 20, and 21. In some embodiments, the first FRα-binding domain specifically binds to the same FRα epitope as an antibody comprising a VH amino acid sequence selected from the group consisting of SEQ ID NOs:24, 57, and 26, and a VL amino acid sequence selected from the group consisting of SEQ ID NOs:19, 20, and 21. In some embodiments, the first FRα-binding domain competitively inhibits binding to the same FRα epitope as an antibody comprising a VH amino acid sequence selected from the group consisting of SEQ ID NOs:24, 25, and 26, and a VL amino acid sequence selected from the group consisting of SEQ ID NOs:19, 20, and 21. In some embodiments, the first FRα-binding domain competitively inhibits binding to the same FRα epitope as an antibody comprising a VH amino acid sequence selected from the group consisting of SEQ ID NOs:24, 57, and 26, and a VL amino acid sequence selected from the group consisting of SEQ ID NOs:19, 20, and 21. In some embodiments, the second FRα-binding domain specifically binds to the same FRα epitope as an antibody comprising a VH amino acid sequence of SEQ ID NO:22 or 23 and a VL amino acid sequence of SEQ ID NO:17 or 18. In some embodiments, the second FRα-binding domain competitively inhibits binding to the same FRα epitope as an antibody comprising a VH amino acid sequence of SEQ ID NO:22 or 23 and a VL amino acid sequence of SEQ ID NO:17 or 18.

In some embodiments, the first VH comprises VH CDR1-3 comprising the amino acid sequences of (a) SEQ ID NOs: 10-12 or (b) SEQ ID NOs: 15, 16, and 12, respectively and the first VL comprises VL CDR1-3 comprising the amino acid sequences of SEQ ID NOs: 4-6, respectively. In some embodiments, the first VH comprises the amino acid sequence selected from the group consisting of SEQ ID NOs:24, 25, and 26, and/or the first VL comprises the amino acid sequence selected from the group consisting of SEQ ID NOs:19, 20, and 21. In some embodiments, the first FRα-binding domain competitively inhibits binding to the same FRα epitope as an antibody comprising a VH amino acid sequence selected from the group consisting of SEQ ID NOs:24, 57, and 26, and a VL amino acid sequence selected from the group consisting of SEQ ID NOs:19, 20, and 21. In some embodiments, the second VH comprises VH CDR1-3 comprising the amino acid sequences of (a) SEQ ID NOs: 7-9 or (b) SEQ ID NOs: 13, 14, and 9, respectively and the second VL comprises VL CDR1-3 comprising the amino acid sequences of SEQ ID NOs: 1-3, respectively. In some embodiments, the second VH comprises the amino acid sequence of SEQ ID NO:22 or 23 and/or the second VL comprises the amino acid sequence of SEQ ID NO:17 or 18.

In some embodiments, the first VH and VL pair and/or the second VH and VL pair is murine, non-human, humanized, chimeric, resurfaced, or human. In some embodiments, the antibody or antigen-binding fragment thereof binds to human FRα but not FOLR2 or FOLR3. In some embodiments, the first FRα-binding domain is an single-chain variable fragment (scFv). In some embodiments, the scFv of the first FRα binding domain has a peptide orientation of VH-linker-VL. In some embodiments, the scFv of the first FRα binding domain has a peptide orientation of VL-linker-VH. In some embodiments, the second FRα-binding domain is an single-chain variable fragment (scFv). In some embodiments, the scFv of the second FRα binding domain has a peptide orientation of VH-linker-VL. In some embodiments, the scFv of the second FRα binding domain has a peptide orientation of VL-linker-VH. In some embodiments, the linker is a glycine-serine linker.

In some embodiments, the second FRα binding domain comprises an amino add sequence selected from SEQ ID NOs: 27-29. In some embodiments, the first FRα-binding domain comprises an amino acid sequence selected from SEQ NOs: 30-32. In some embodiments, the biparatopic antibody or antigen binding fragment thereof disclosed herein comprises the amino acid sequence of (i) SEQ ID NOs:33 and 34, (ii) SEQ ID NOs: 35 and 36, (iii) SEQ ID NOs: 37 and 38, or (iv) SEQ ID NOs: 39 and 40.

In some embodiments, the biparatopic antibody or antigen binding fragment thereof comprises the amino acid sequences of SEQ ID NOs: 41-43.

In some embodiments, the biparatopic antibody or antigen binding fragment thereof comprises the amino acid sequences of SEQ ID NOs: 44-46.

In some embodiments, the biparatopic antibody or antigen binding fragment thereof is a tetravalent biparatopic antibody or antigen binding fragment thereof. In some embodiments, the biparatopic antibody or antigen binding fragment thereof is a bivalent biparatopic antibody or antigen binding fragment thereof. In some embodiments, the biparatopic antibody or antigen-binding fragment thereof comprises FRα-binding domains selected from the group consisting of tandem scFvs, a diabody, a triabody, a tetrabody, and a knob-in-hole structure. In some embodiments, the biparatopic antibody or antigen binding fragment thereof has a knob-in-hole (KIH) structure.

In some embodiments, the biparatopic antibody or antigen binding fragment thereof comprises a FRα binding domain, wherein the FRα binding domain comprises SEQ ID NOs: 1-3 and 7-9 is on the knob side of the KIH structure. In some embodiments, the FRα binding domain comprises SEQ ID NOs: 1-3 and 7-9 is on the hole side of the KIH structure. In some embodiments, the FRα binding domain comprises SEQ ID NOs: 4-6 and 10-12 is on the knob side of the KIH structure. In some embodiments, the FRα binding domain comprises SEQ ID NOs: 4-6 and 10-12 is on the hole side of the KIH structure.

In some embodiments, the biparatopic antibody or antigen-binding fragment thereof comprises a full length antibody. In some embodiments, the biparatopic antibody or antigen-binding fragment thereof comprises a first FRα-binding domain, wherein the first FRα-binding domain is a full length antibody. In some embodiments, the biparatopic antibody or antigen-binding fragment thereof comprises a second FRα-binding domain, wherein the second FRα-binding domain is a full length antibody. In some embodiments, the biparatopic antibody or antigen-binding fragment thereof comprises an antigen-binding fragment. In some embodiments, the biparatopic antibody or antigen-binding fragment thereof comprises a first FRα-binding domain, wherein the first FRα-binding domain is an antigen-binding fragment. In some embodiments, the biparatopic antibody or antigen-binding fragment thereof comprises a second FRα-binding domain, wherein the second FRα-binding domain is an antigen-binding fragment. In some embodiments, the biparatopic antibody or antigen binding fragment thereof comprises the amino acid sequences of SEQ ID NOs: 41-43.

In some embodiments, provided herein is a combination of isolated nucleic acid molecules encoding the biparatopic antibody or antigen binding fragment thereof disclosed herein.

In some embodiments, provided herein is an isolated vector comprising one of the nucleic acid molecules disclosed herein.

In some embodiments, provided herein is a host cell comprising the combination of isolated nucleic acid molecules as disclosed herein, or the isolated vector as disclosed herein. In some embodiments, the host cell is selected from the group consisting of E. coli, Pseudomonas, Bacillus, Streptomyces, yeast, CHO, YB/20, NSO, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture.

In some embodiments, provided herein is a pharmaceutical composition comprising the biparatopic antibody or antigen as disclosed herein, the combination of nucleic acid molecule(s) as disclosed herein, a vector as disclosed herein, or a host cell as disclosed herein, and a pharmaceutically acceptable carrier or excipient. In some embodiments, the pharmaceutical composition as provided herein comprises a biparatopic antibody as disclosed herein, and a pharmaceutically carrier or excipient. In some embodiments, a pharmaceutical composition comprises an average of 1 to 10 drugs per antibody or antigen-binding fragment thereof. In some embodiments, a pharmaceutical composition comprises an average of 2 to 5 drugs per antibody or antigen-binding fragment thereof. In some embodiments, a pharmaceutical composition comprises an average of 3 to 4 drugs per antibody or antigen-binding fragment thereof.

In some embodiments, provided herein is a method of making the biparatopic antibody as disclosed herein comprising (a) culturing a cell expressing the antibody; and (b) isolating the antibody from the cultured cell. In some embodiments, the cultured cell is a eukaryotic cell.

In some embodiments, provided herein is an immunoconjugate represented by the following formula:

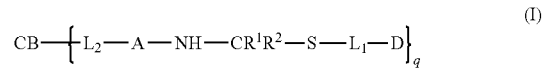

$$CB - \left[ L_2 - A - NH - CR^1R^2 - S - L_1 - D \right]_q \quad (I)$$

or a pharmaceutically acceptable salt thereof, wherein:

CB is any biparatopic antibody or an antigen-binding fragment thereof provided herein;

$L_2$ is represented by one of the following formula:

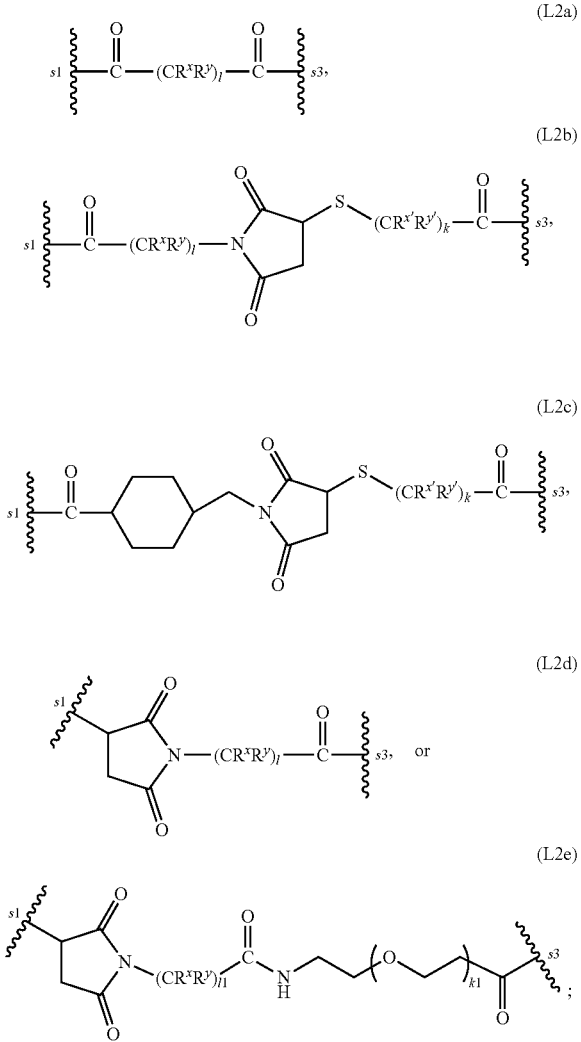

wherein:

$R^x$, $R^y$, $R^{x'}$ and $R^{y'}$, for each occurrence, are independently H, —OH, halogen, —O—($C_{1-4}$ alkyl), —SO$_3$H, —NR$_{40}$R$_{41}$R$_{42}^+$, or a $C_{1-4}$ alkyl optionally substituted with —OH, halogen, SO$_3$H or NR$_{40}$R$_{41}$R$_{42}^+$, wherein R$_{40}$, R$_{41}$ and R$_{42}$ are each independently H or a $C_{1-4}$ alkyl;

l and k are each independently an integer from 1 to 10;

l1 is an integer from 2 to 5;

k1 is an integer from 1 to 5; and s1 indicates the site connected to the cell-binding agent CB and s3 indicates the site connected to the A group;

A is an amino acid residue or a peptide comprising 2 to 20 amino acid residues;

$R^1$ and $R^2$ are each independently H or a $C_{1-3}$alkyl;

$L_1$ is represented by the following formula:

—CR$^3$R$^4$—(CH$_2$)$_{1-8}$—C(=O)— wherein R$^3$ and R$^4$ are each independently H or Me, and the —C(=O)— moiety in $L_1$ is connected to D;

D is represented by the following formula:

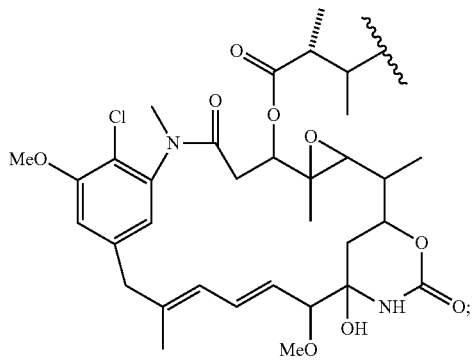 [SMILES: *C(C)[C@@H](C)C(=O)OC1CC(=O)N(C)c2cc(cc(OC)c2Cl)C/C(C)=C/C=C/C(OC)C2(O)CC(OC(=O)N2)C(C)C2OC12C]

q is an integer from 1 to 20. In some embodiments q is an integer from 1 to 10. In some embodiments q is an integer from 2 to 5. In some embodiments, q is an integer from 3 to 4.

In some embodiments, the $R^x$, $R^y$, $R^{x'}$ and $R^{y'}$ of the immunoconjugate are all H; and l and k are each independently an integer an integer from 2 to 6. In some embodiments, the A of the immunoconjugate is a peptide containing 2 to 5 amino acid residues.

In some embodiments, the A of the immunoconjugate is selected from the group consisting of Gly-Gly-Gly, Ala-Val, Val-Ala, D-Val-Ala, Val-Cit, D-Val-Cit, Val-Lys, Phe-Lys, Lys-Lys, Ala-Lys, Phe-Cit, Leu-Cit, Ile-Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Ala-Ala, D-Ala-Ala-Ala, Ala-D-Ala-Ala, Ala-Ala-D-Ala, Ala-Leu-Ala-Leu (SEQ ID NO:54), β-Ala-Leu-Ala-Leu (SEQ ID NO:55), Gly-Phe-Leu-Gly (SEQ ID NO:56), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, Gln-Val, Asn-Ala, Gln-Phe, Gln-Ala, D-Ala-Pro, and D-Ala-tBu-Gly, wherein the first amino acid in each peptide is connected to $L_2$ group and the last amino acid in each peptide is connected to —NH—CR$^1$R$^2$—S-L$_1$-D. In some embodiments, the $R^1$ and $R^2$ of the immunoconjugate are both H. In some embodiments, the $L_1$ of the immunoconjugate is —(CH$_2$)$_{4-6}$—C(=O)—.

In some embodiments, the D of the immunoconjugate is represented by the following formula:

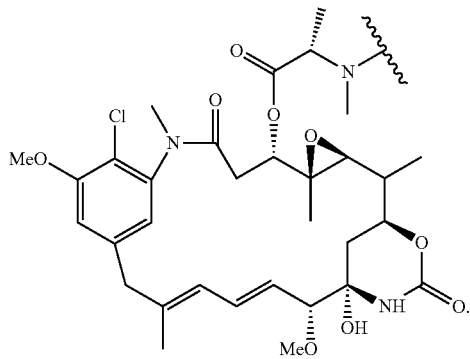

In some embodiments, the immunoconjugate is represented by the following formula:

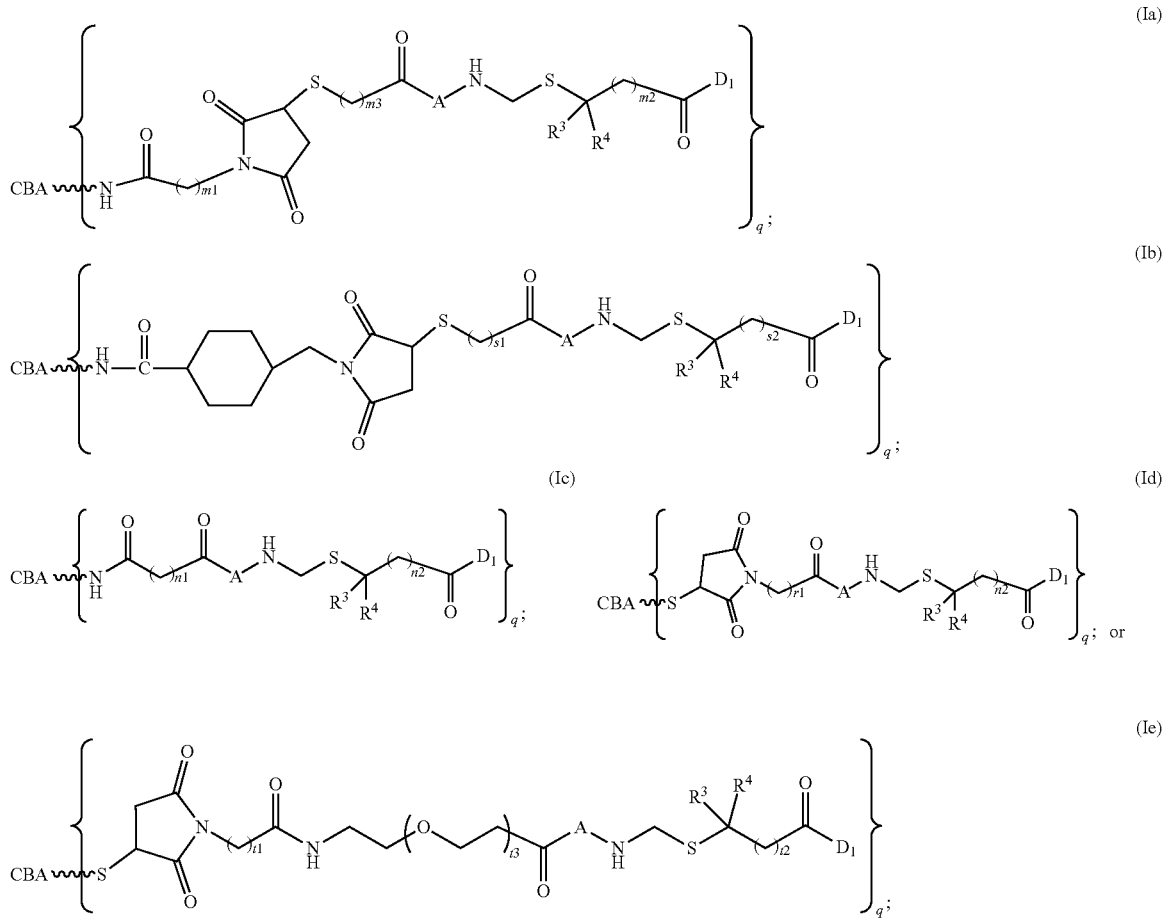

or a pharmaceutically acceptable salt thereof, wherein:

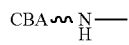

is any biparatopic antibody or an antigen-binding fragment thereof provided herein connected to the L2 group through a Lys amine group;

is any biparatopic antibody or an antigen-binding fragment thereof provided herein connected to the $L_2$ group through a Cys thiol group;

$R^3$ and $R^4$ are each independently H or Me;

m1, m3, n1, r1, s1 and t1 are each independently an integer from 1 to 6;

m2, n2, r2, s2 and t2 are each independently an integer from 1 to 7;

t3 is an integer from 1 to 12;

$D_1$ is represented by the following formula:

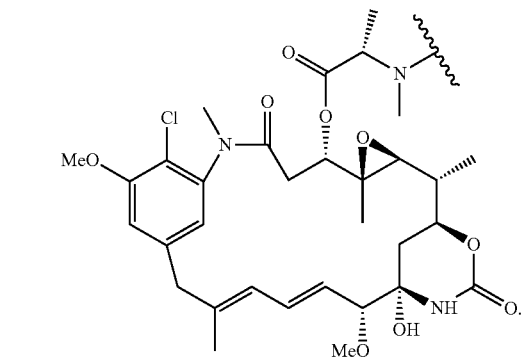

In some embodiments, the immunoconjugate is represented by the following formula:

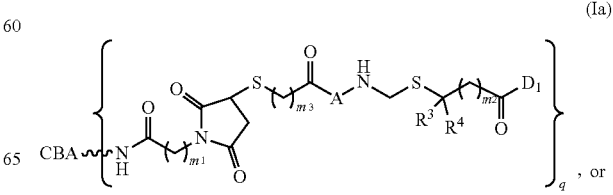

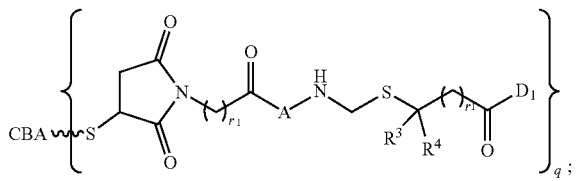
wherein:
m1 and m3 are each independently an integer from 2 to 4;
m2 is an integer from 2 to 5;
r1 is an integer from 2 to 6; and
r2 is an integer from 2 to 5.
In some embodiments, A of the immunoconjugate is Ala-Ala-Ala, Ala-D-Ala-Ala, Ala-Ala, D-Ala-Ala, Val-Ala, D-Val-Ala, D-Ala-Pro, or D-Ala-tBu-Gly.
In some embodiments, the immunoconjugate is represented by the following formula:
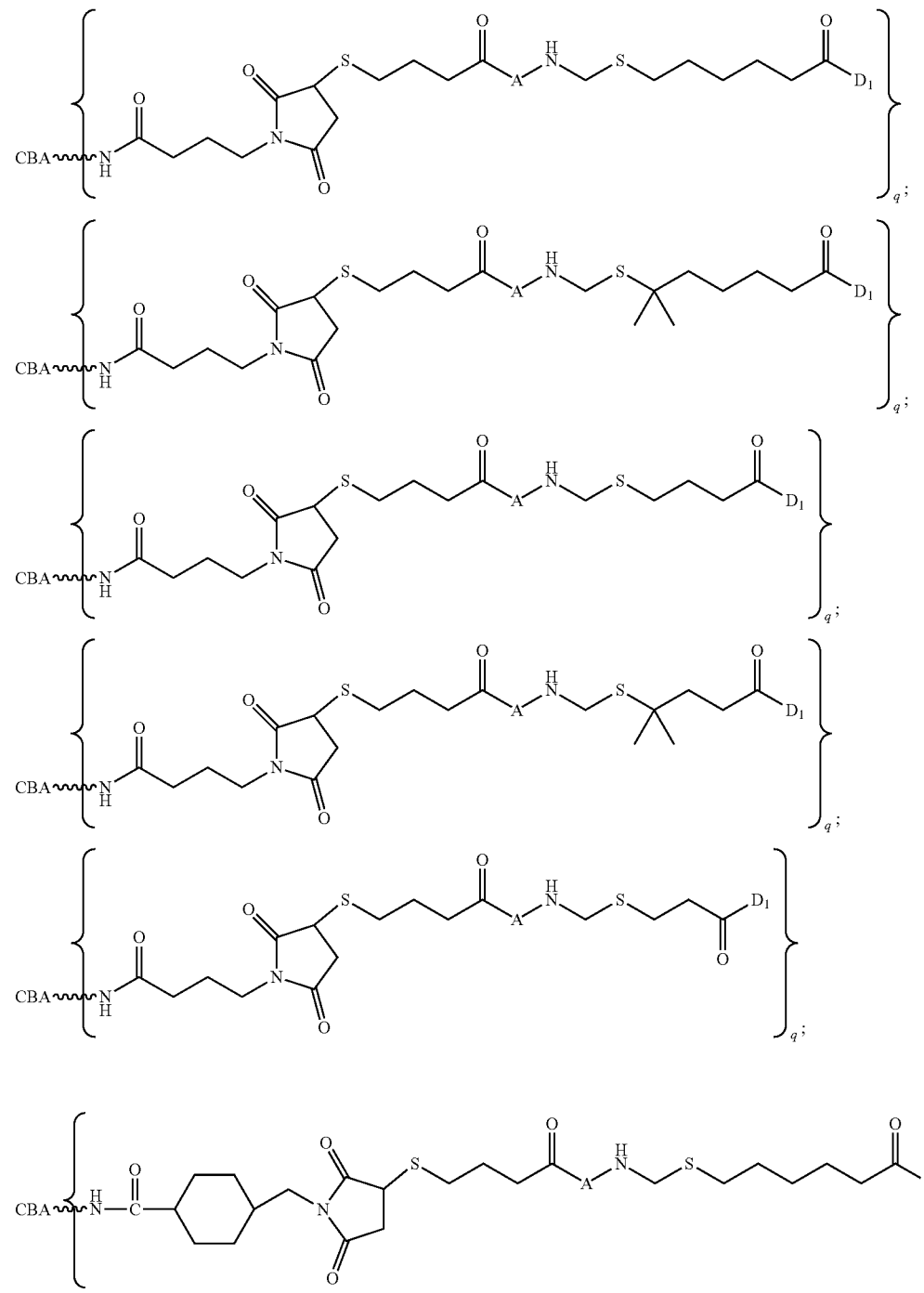

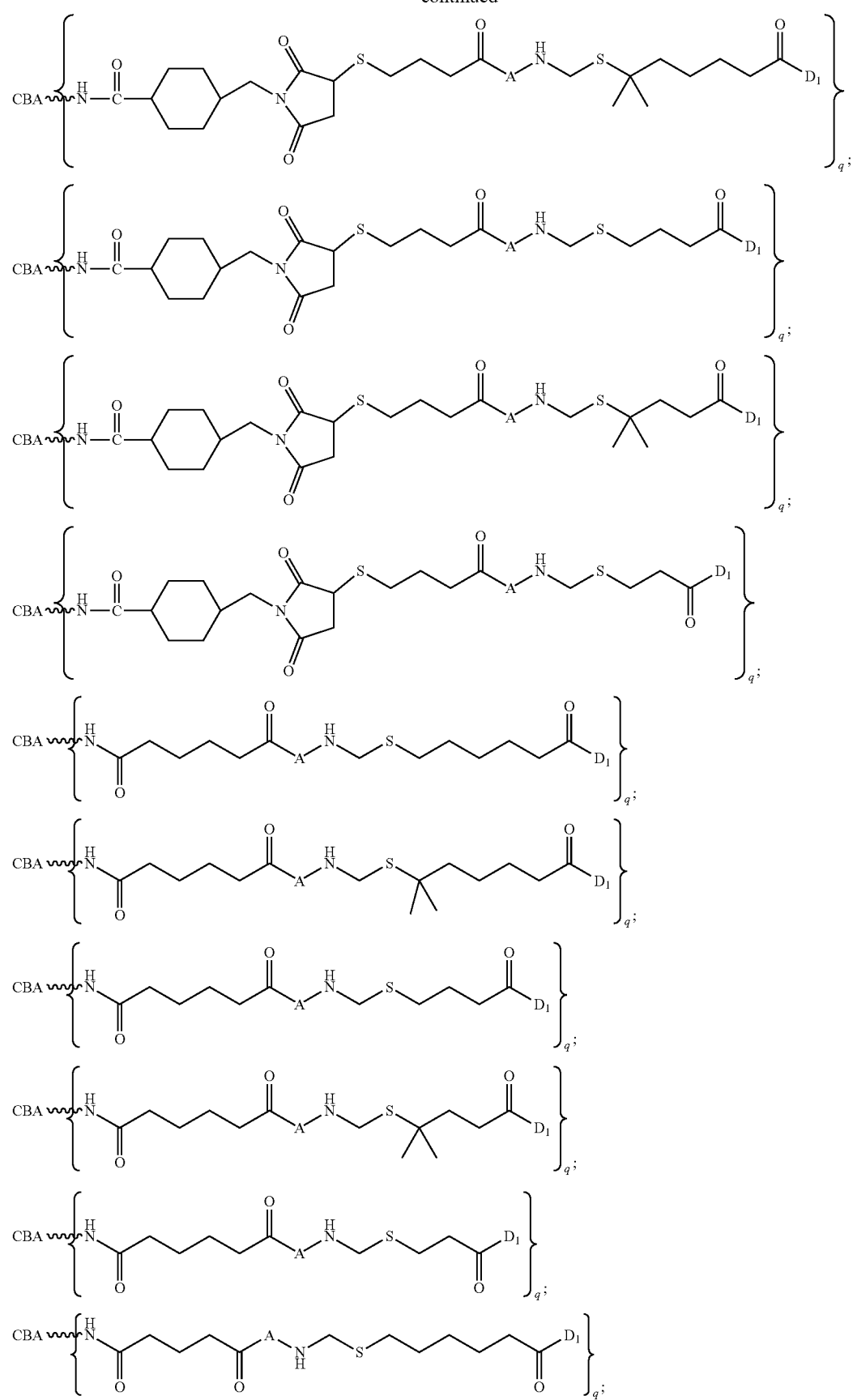

-continued
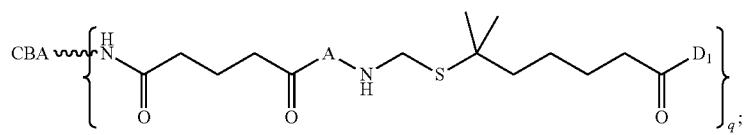
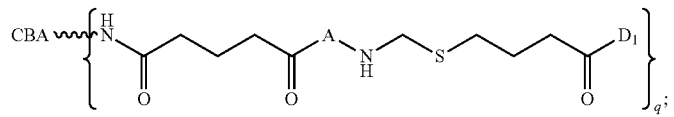
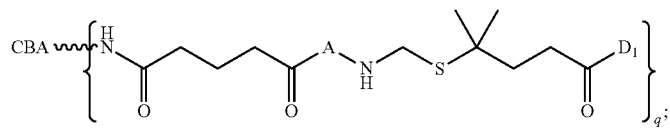
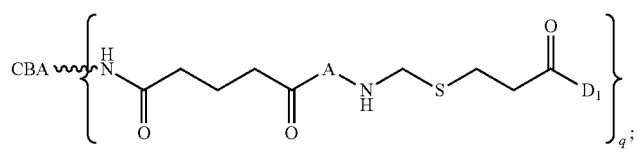
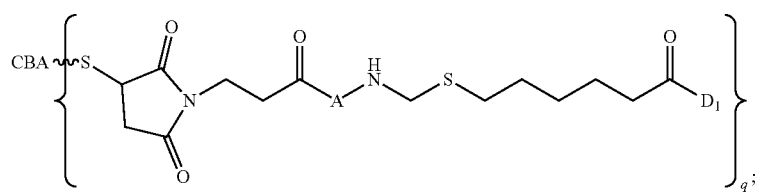
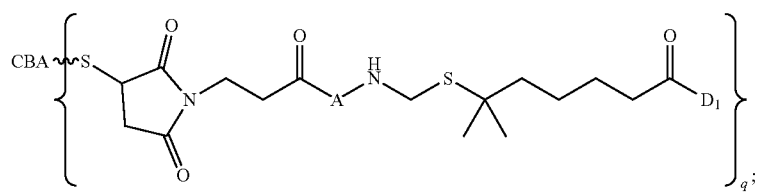
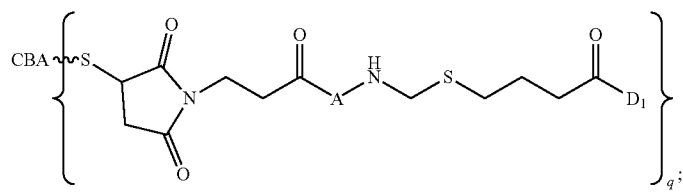
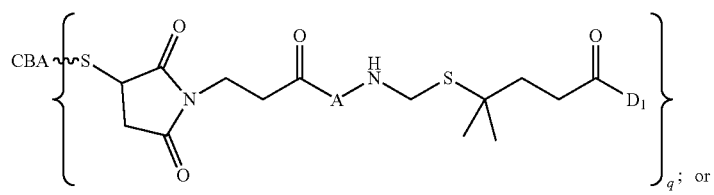
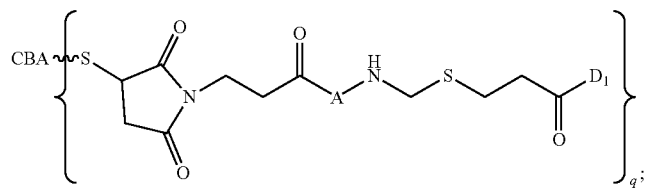
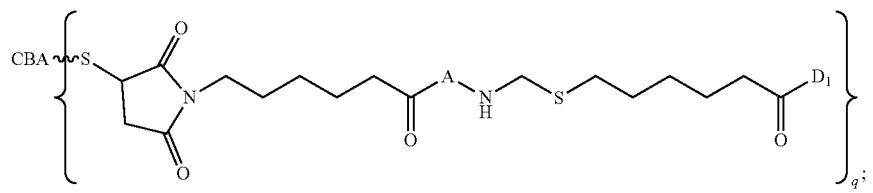

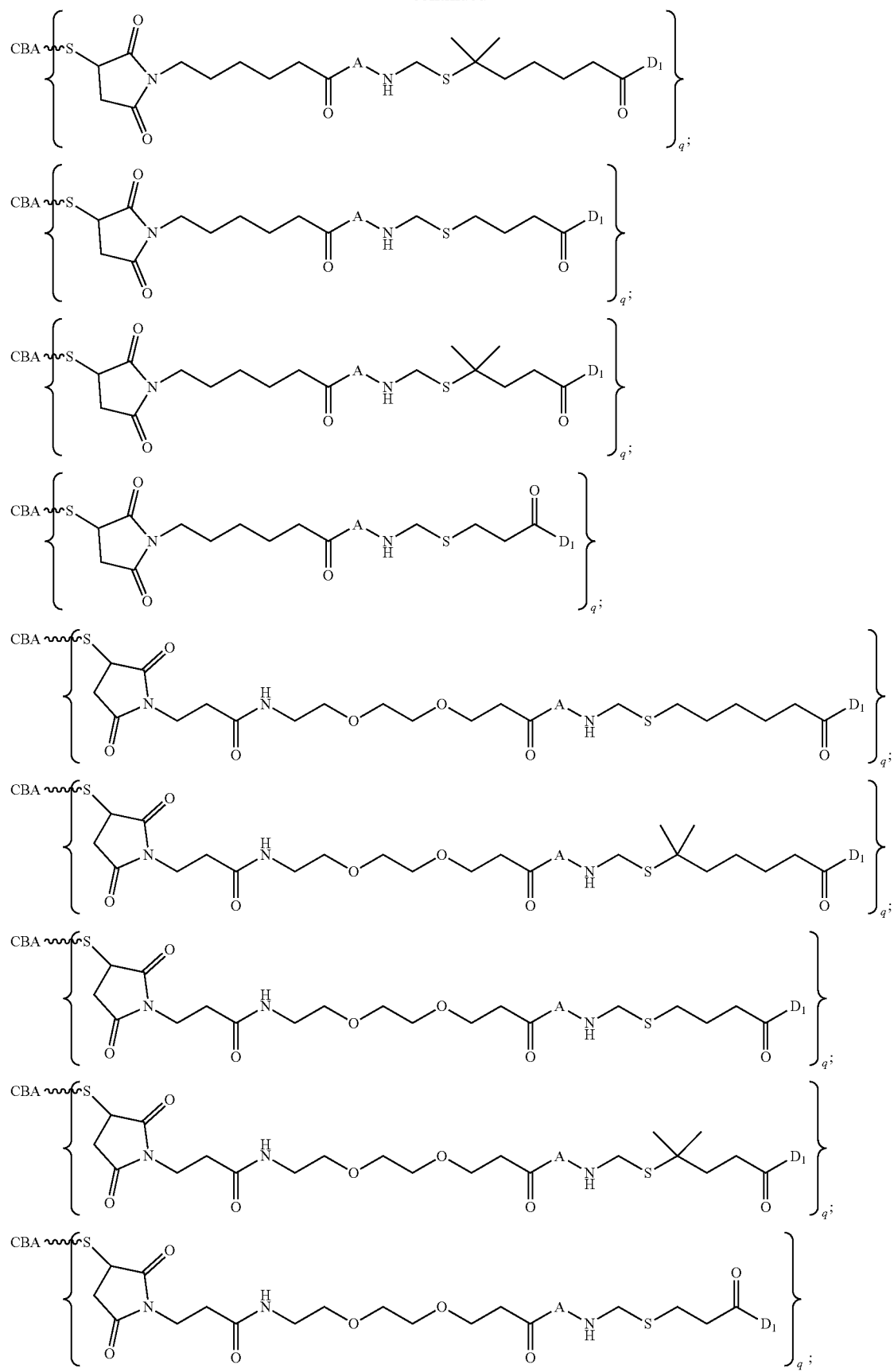

-continued
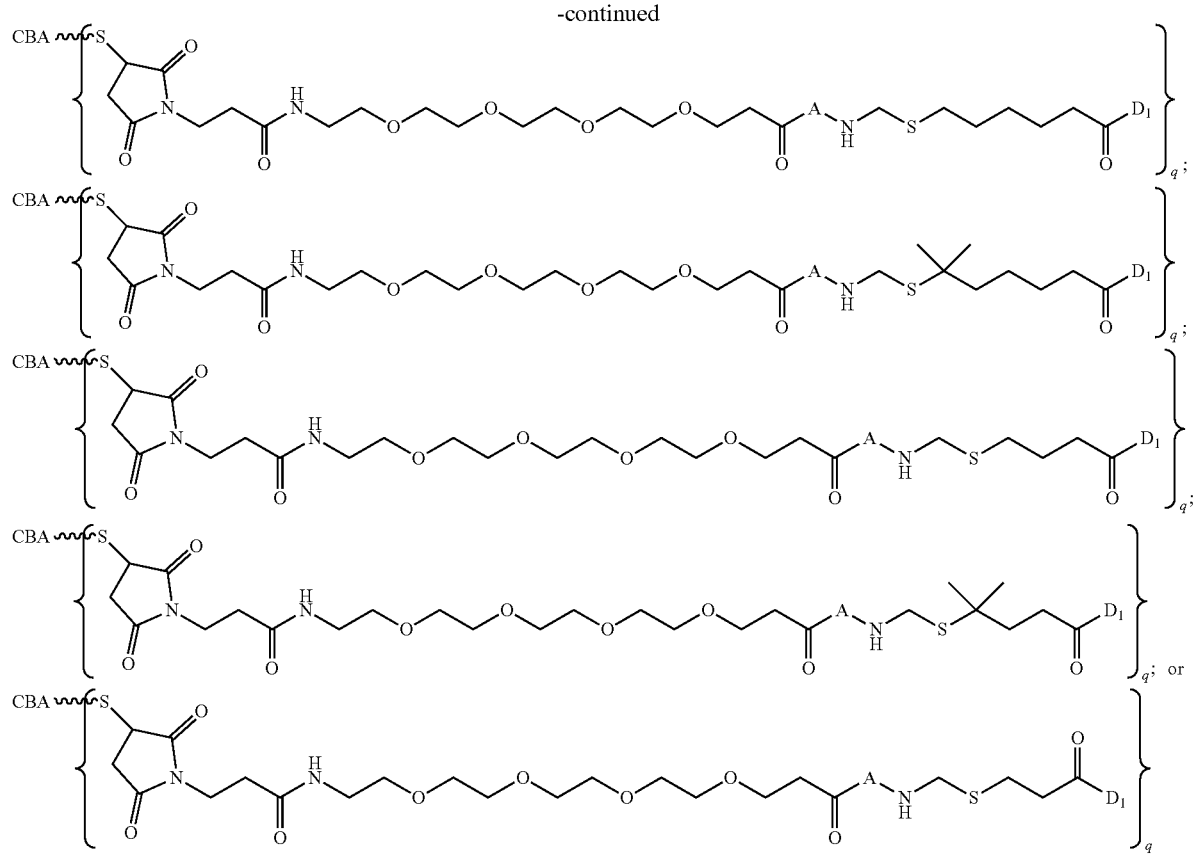
or a pharmaceutically acceptable salt thereof, wherein:
A is Ala-Ala-Ala, Ala-D-Ala-Ala, Ala-Ala, D-Ala-Ala, Val-Ala, D-Val-Ala, D-Ala-Pro, or D-Ala-tBu-Gly, and $D_1$ is represented by the following formula:
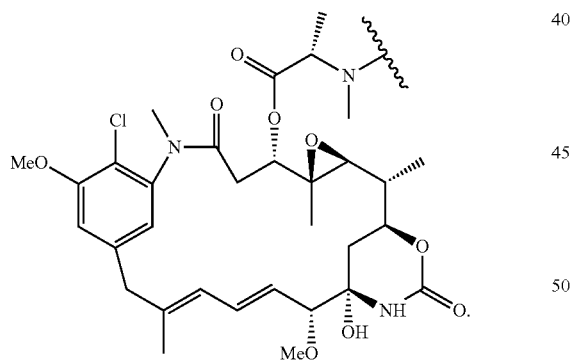
In some embodiments, the immunoconjugate is represented by the following formula:
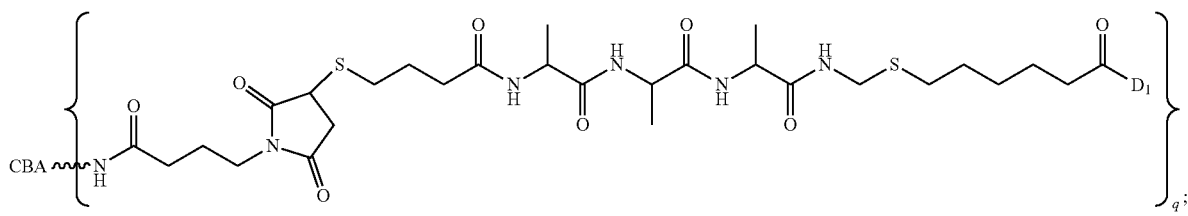

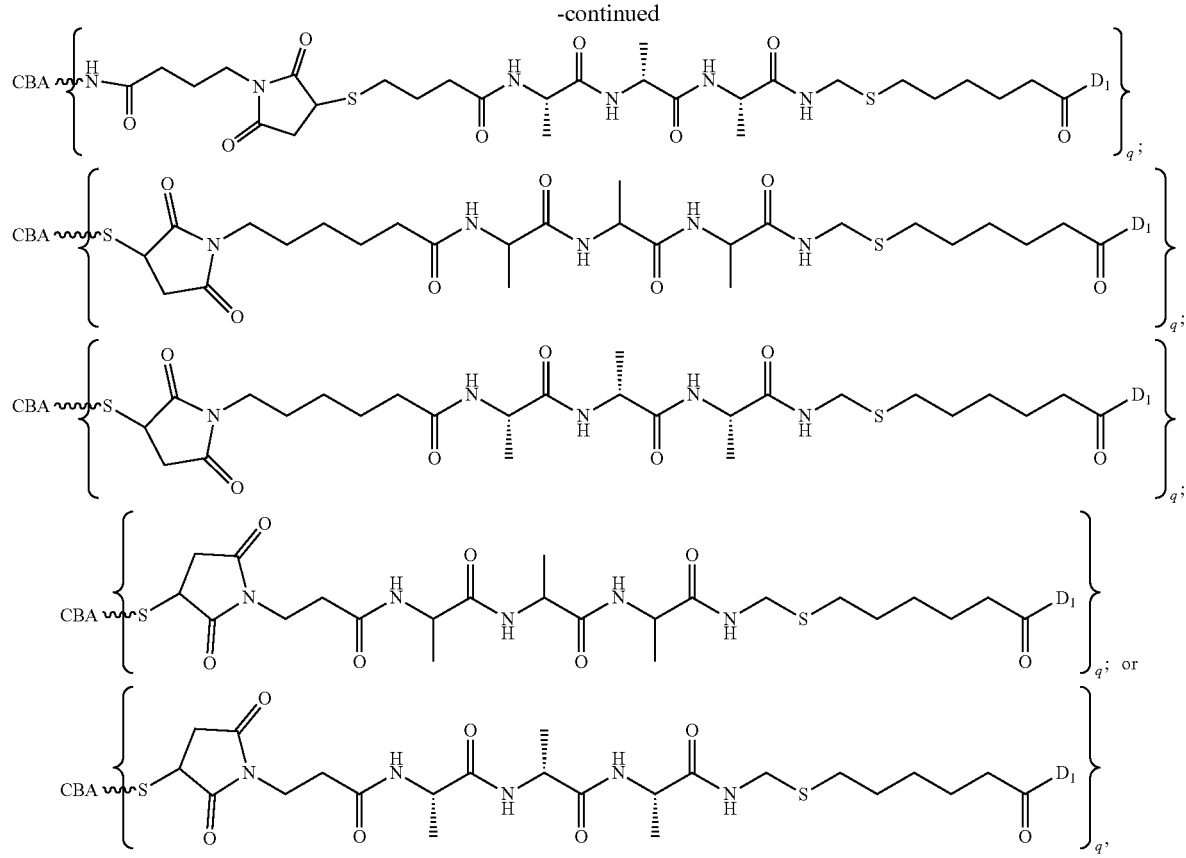
wherein $D_1$ is represented by the following formula:
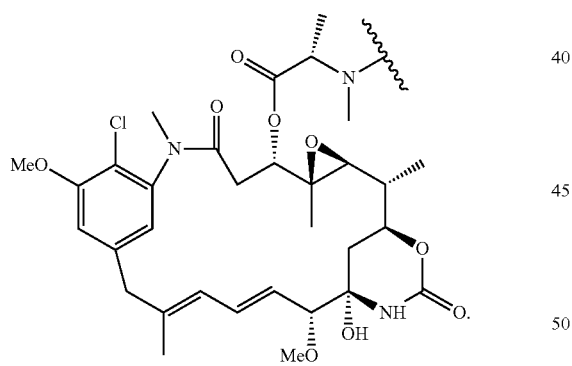
In some embodiments, the immunoconjugate is represented by the following formula:
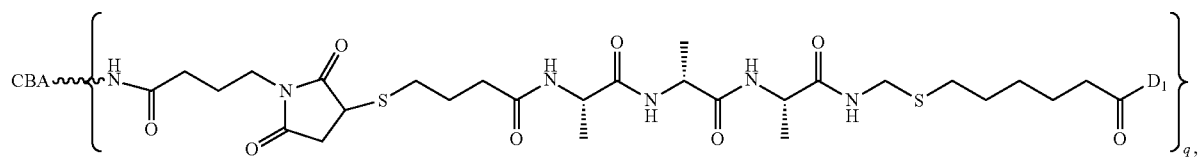

wherein:
CBA is any biparatopic antibody or an antigen-binding fragment thereof provided herein;
q is an integer from 1 to 10, e.g., 1 or 10;
$D_1$ is represented by the following formula:

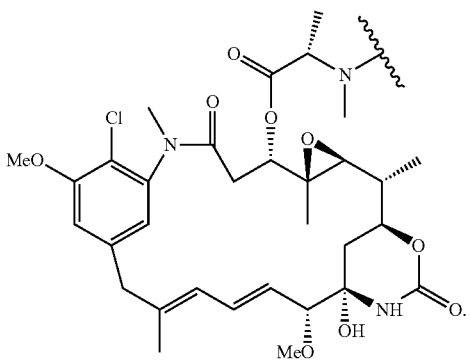 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In some embodiments q is an integer from 2 to 5. In some embodiments, q is an integer from 3 to 4.

In some embodiments, the immunoconjugate is represented by the following formula:

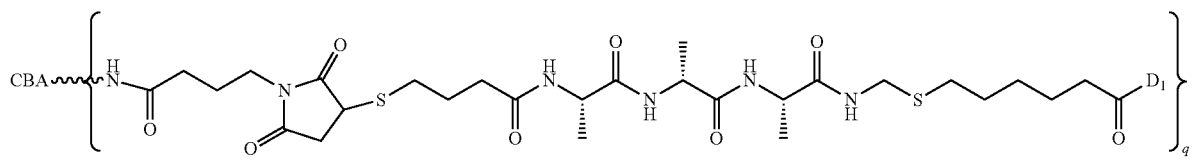

or a pharmaceutically acceptable salt thereof, wherein:
CBA is the biparatopic antibody or an antigen-binding fragment comprising the amino acid sequences of SEQ ID NOs: 41-43;
$D_1$ is represented by the following formula:

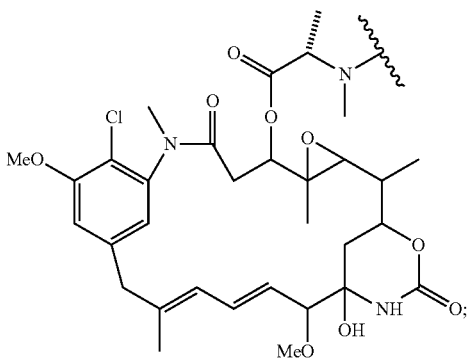

and
q is an integer from 1 to 10. In some embodiments q is an integer from 2 to 5. In some embodiments, q is an integer from 3 to 4.

In some embodiments, disclosed herein is an immunoconjugate having the formula (A)-(L)-(C), wherein:
(A) is any biparatopic antibody or antigen binding fragment provided herein;
(L) is a linker; and
(C) is a cytotoxic agent, wherein the linker (L) links (A) to (C).

In some embodiments, the linker of an immunoconjugate disclosed herein is selected from the group consisting of a cleavable linker, a non-cleavable linker, a hydrophilic linker, and a dicarboxylic acid based linker. In some embodiments, the linker is selected from the group consisting of N-(γ maleimidobutryloxy)sulfosuccinimide ester (sulfo-GMBS or sGMBS), γ maleimidobutyric acid N-succinimidyl ester (GMBS), N-succinimidyl 4-(2-pyridyldithio)-2-sulfobutanoate (sulfo-SPDB); N-succinimidyl 4-(2-pyridyldithio) pentanoate (SPP) or N-succinimidyl 4-(2-pyridyldithio)-2-sulfopentanoate (sulfo-SPP); N-succinimidyl 4-(2-pyridyldithio)butanoate (SPDB), N-succinimidyl 4-(maleimidomethyl)cyclohexanecarboxylate (SMCC); N-sulfosuccinimidyl 4-(maleimidomethyl)cyclohexanecarboxylate (sulfoSMCC); N-succinimidyl-4-(iodoacetyl)-aminobenzoate (SIAB); and N-succinimidyl-[(N-maleimidopropionamido)-tetraethyleneglycol] ester (NETS-PEG4-maleimide).

In some embodiments, the linker is sulfo-GMBS.
In some embodiments, the linker is GMBS.
In some embodiments, the linker is sulfo-SPDB.

In some embodiments, the cytotoxic agent of an immunoconjugate disclosed herein is selected from the group consisting of a maytansinoid, maytansinoid analog, benzodiazepine, taxoid, CC-1065, CC-1065 analog, duocarmycin, duocarmycin analog, calicheamicin, dolastatin, dolastatin analog, auristatin, tomaymycin derivative, and leptomycin derivative or a prodrug of the agent. In some embodiments, the cytotoxic agent is a maytansinoid.

In some embodiments, the immunoconjugate further comprises a second (C). In some embodiments, the immunoconjugate further comprises a third (C). In some embodiments, the immunoconjugate further comprises a fourth (C).

In some embodiments, provided herein is a composition comprising at least one immunoconjugate as disclosed herein, wherein the immunoconjugate comprises an average of 3-4 C per A.

In some embodiments, provided herein is a pharmaceutical composition comprising the immunoconjugate ad disclosed herein and a pharmaceutically acceptable carrier. In some embodiments, a pharmaceutical composition comprises an average of 1 to 10 drugs per antibody or antigen-binding fragment thereof. In some embodiments, a pharmaceutical composition comprises an average of 2 to 5 drugs per antibody or antigen-binding fragment thereof. In some embodiments, a pharmaceutical composition comprises an average of 3 to 4 drugs per antibody or antigen-binding fragment thereof.

In some embodiments, provided herein is a method of treating a cancer in a subject, comprising administering to the subject a therapeutically effective amount of the antibody or antigen binding fragment thereof as disclosed herein, an immunoconjugate as disclosed herein, or the pharmaceutical compositions as disclosed herein.

In some embodiments, provided herein is a method of treating a cancer. In some embodiments, the cancer is ovarian cancer, uterine cancer, peritoneal cancer, fallopian tube cancer, endometrial cancer, lung cancer, or brain cancer. In some embodiments, the cancer is ovarian cancer. In some embodiments, the ovarian cancer is platinum-resistant epithelial ovarian cancer. In some embodiments, the ovarian cancer is relapsed epithelial ovarian cancer. In some embodiments, the ovarian cancer is platinum-refractory epithelial ovarian cancer. In some embodiments, the cancer is uterine cancer. In some embodiments, the cancer is peritoneal cancer. In some embodiments, the cancer is fallopian tube cancer. In some embodiments, the cancer is endometrial cancer. In some embodiments, the cancer is lung cancer. In some embodiments, the cancer is brain cancer. In some embodiments, the cancer is IMGN853-resistant.

In some embodiments, the method further comprises administration of a steroid.

BRIEF DESCRIPTIONS OF THE DRAWINGS

FIG. 1 shows binding competition of huMov19-biotin with folate receptor antibodies FR57; FRα Antibody A ("FRα-A"); FRα Antibody B ("FRα-B"); FRα Antibody C ("FRα-C"); and non-biotinylated huMov19 ("huMov19") by FACS. (See Example 1.)

FIG. 2 shows exemplary molecules, characteristics, and schematics for conventional monospecific antibodies (such as huMov19 and FR57), bivalent biparatopic knob-in-hole (KIH) antibodies, and tetravalent biparatopic (Morrison) antibodies. (See Example 1.)

FIG. 3 shows a gel of several heavy chain and light chain plasmid transfection ratios that were used for producing asymmetric-Fc based molecules. L1: transfection with FR57scFv-knob only; L2: transfection of Mov19LC: Mov19HC-Hole: FR57scFv-knob at 4:4:1; L3: transfection of Mov19LC: Mov19HC-Hole: FR57scFv-knob at 6:2:1; L4: transfection of Mov19LC: Mov19HC-Hole: FR57scFv-knob at 6:6:1; L5: transfection of Mov19LC: Mov19HC-Hole: FR57scFv-knob at 9:3:1; L6: transfection of Mov19LC: Mov19HC-Hole: FR57scFv-knob at 2:3:1; L7 transfection of Mov19LC: Mov19HC-Hole: FR57scFv-knob at 1:1:1; L8: transfection of Mov19 LC: Mov19-hole at 3:1; L9: Isotype human IgG1 transfection. (See Example 1.)

FIGS. 4A-4H show binding activity of Morrison's antibodies or fragments thereof by competition FACS. (See Example 2). In particular, FIG. 4A shows the binding activity of Mov19-G1-FR57scFv1 (M9346A-FR57scFv); FIG. 4B shows the binding activity of FR57-G1-Mov19scFv1 (FR57-M9346AscFv); FIG. 4C shows the binding activity of Mov19-G1-FRα-Antibody-A-scFv1 (M9346A-FR-α-A:scFv); FIG. 4D shows the binding activity of FRα-Antibody-A-G1-Mov19scFv1 (FR-α-A: M9346AscFv); FIG. 4E shows the binding activity of FRα-Antibody-A-scFv2-G1-Mov19 (FR-α-A:scFv-M9346A); FIG. 4F shows the binding activity of FRα-Antibody-B-scFv2-G1-Mov19 (FR-α-B:scFV-M9346A); FIG. 4G shows the binding activity of FRα-Antibody-C-scFv2-G1-Mov19 (FR-α-C:scFv-M9346A); and FIG. 4H shows the binding activity of FR57scFv2-G1-Mov19 (FR57scFv-M9346A).

FIGS. 13A-13D show the in vitro bystander killing activity of the biparatopic KIH-L-DM21 immunoconjugate, the huMov19 immunoconjugate M-L-DM21, and huMov19 immunoconjugate M-s-SPDB-DM4 in target-negative cells Namalwa/luc mixed with KB cells (FIG. 13A), Igrov-1 cells (FIG. 13B), JEG-3 cells (FIG. 13C), and T47D cells (FIG. 13D). (See Example 5.)

Figures 18A, 18B:
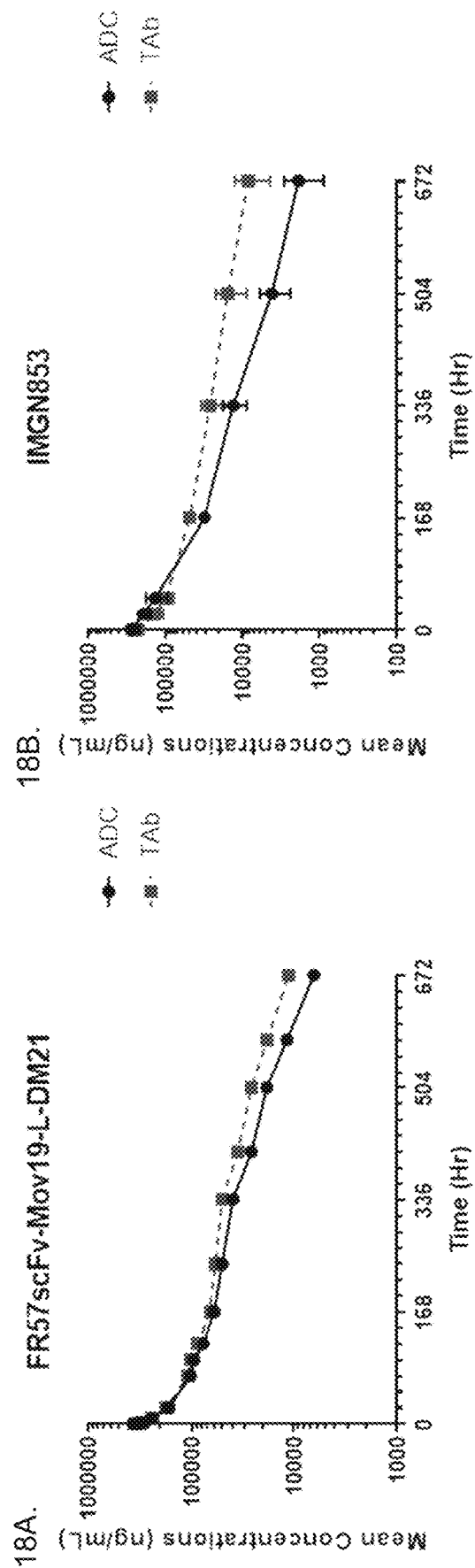

FIGS. 18A and 18B show the toxicity of the biparatopic KIH-sSPDB-DM21 immunoconjugate (FIG. 18A) and the huMov19 immunoconjugate M-s-SPDB-DM4 ("IMGN853") (FIG. 18B) compared to total antibody (TAb: total antibody; conjugated and unconjugated). (See Example 7.)

FIG. 19 shows the median tumor volume after administration of the biparatopic KIH-L-DM21 immunoconjugate to a IMGN853-resistant KB human cervical carcinoma xenograft model compared to vehicle, the huMov19 immunoconjugate M9346A-DM21-L, or the huMov19 immunoconjugate IMGN853. (See Example 6)

DETAILED DESCRIPTION OF THE DISCLOSURE

I. Definitions

To facilitate an understanding of the present disclosure, a number of terms and phrases are defined below.

The terms "human folate receptor 1," "FRα," "folate receptor alpha (FR-α)," or "FOLR1" as used herein, refers to any native human FRα polypeptide, unless otherwise indicated. The term "FRα" encompasses "full-length," unprocessed FRα polypeptide as well as any form of FRα polypeptide that results from processing within the cell. The term also encompasses naturally occurring variants of FRα, e.g., those encoded by splice variants and allelic variants. The FRα polypeptides described herein can be isolated from a variety of sources, such as from human tissue types or from another source, or prepared by recombinant or synthetic methods. Where specifically indicated, "FRα" can be used to refer to a nucleic acid that encodes a FRα polypeptide. Human FRα sequences are known and include, for example, the sequences publicly available at UniProtKB Accession No. P15328 (including isoforms). As used herein, the term "human FRα" refers to FRα comprising the sequence of SEQ ID NO:53.

(SEQ ID NO: 53)
MAQRMTTQLLLLLVWVAVVGEAQTRIAWARTELLNVCMNAKHHKEKPGPE

DKLHEQCRPWRKNACCSTNTSQEAHKDVSYLYRFNWNHCGEMAPACKRHF

IQDTCLYECSPNLGPWIQQVDQSWRKERVLNVPLCKEDCEQWWEDCRTSY

TCKSNWHKGWNWTSGFNKCAVGAACQPFHFYFPTPTVLCNEIWTHSYKVS

NYSRGSGRCIQMWFDPAQGNPNEEVARFYAAAMSGAGPWAAWPFLLSLAL

MLLWLLS.

The term "anti-FRα antibody" or "an antibody that binds to FRα" refers to an antibody that is capable of binding FRα with sufficient affinity such that the antibody is useful as a diagnostic and/or therapeutic agent in targeting FRα. As used herein, such antibodies include, for example, bispecific (e.g., biparatopic) antibodies. Unless otherwise specified, the extent of binding of an anti-FRα antibody to an unrelated, non-FRα protein is less than about 10% of the binding of the antibody to FRα as measured, e.g., by a radioimmunoassay (MA). Examples of FRα antibodies are known in the art and are disclosed in U.S. Published Application Nos. 2012/0009181 and 2012/0282175 and U.S. Pat. No. 9,200,073 B2, and PCT publication WO 2011/106528 A1, each of which is herein incorporated by reference in its entirety. The sequences of exemplary anti-FRα antibodies and antigen-binding fragments thereof are provided in Tables 1-8.

The term "IMGN853" (also known as "mirvetuximab soravtansine") refers to the immunoconjugate described herein containing the huMov19 (or M9346A) antibody, the sulfoSPDB linker, and the DM4 maytansinoid. The "huMov19" (or "M9346A") antibody is an anti-FRα antibody comprising the full length heavy chain of SEQ ID NO:47 (comprising the variable heavy chain sequence SEQ ID NO:24, which is underlined in the context of SEQ ID NO:47 below) and the full length light chain of SEQ ID NO:48 (comprising the variable light chain sequence SEQ ID NO:19, which is underlined in the context of SEQ ID NO:48 below).

(SEQ ID NO: 47)
<u>QVQLVQSGAEVVKPGASVKISCKASGYTFTGYFMNWVKQSPGQSLEWIGR</u>

<u>IHPYDGDTFYNQKFQGKATLTVDKSSNTAHMELLSLTSEDFAVYYCTRYD</u>

<u>GSRAMDYWGQGTTVTVSS</u>ASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG (SEQ ID NO: 48)
<u>DIVLTQSPLSLAVSLGQPAIISCKASQSVSFAGTSLMHWYHQKPGQQPRL</u>

<u>LIYRASNLEAGVPDRFSGSGSKTDFTLTISPVEAEDAATYYCQQSREYPY</u>

<u>TFGGGTKLEIK</u>RTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

The huMov19 (M9346A) antibody is encoded by the plasmids deposited with the American Type Culture Collection (ATCC), located at 10801 University Boulevard, Manassas, Va. 20110 on Apr. 7, 2010 under the terms of the Budapest Treaty and having ATCC deposit nos. PTA-10772 and PTA-10773 or 10774. DM4 refers to N2'-deacetyl-N2'-(4-mercapto-4-methyl-1-oxopentyl) maytansinoid. "SulfoS-PDB" refers to the N-succinimidyl 4-(2-pyridyldithio)-2-sulfobutanoate) linker.

The terms "elevated" FRα, "increased expression" of FRα, or "overexpression" of FRα in a particular tumor, tissue, or cell sample refers to FRα (a FRα polypeptide or a nucleic acid encoding such a polypeptide) that is present at a level higher than that which is present in a healthy or non-diseased (native, wild type) tissue or cells of the same type or origin. Such increased expression or overexpression can be caused, for example, by mutation, gene amplification, increased transcription, increased translation, or increased protein stability.

FRα expression can be measured by immunohistochemistry and given a "staining intensity score" or a "staining uniformity score" by comparison to calibrated controls exhibiting defined scores (e.g., an intensity score of 3 is given to the test sample if the intensity is comparable to the level 3 calibrated control or an intensity of 2 is given to the test sample if the intensity is comparable to the level 2 calibrated control). For example, a score of 1, 2, or 3, preferably a score of 2, or 3, by immunohistochemistry indicates an increased expression of FRα. A staining uniformity that is heterogeneous or homogeneous is also indicative of FRα expression. The staining intensity and staining uniformity scores can be used alone or in combination (e.g., 2 homo, 2 hetero, 3 homo, 3 hetero, etc.). Staining uniformity can also be expressed as percentage (%) of cells staining at a certain intensity (e.g., 25% of cells staining at intensity of 1, 2, or 3; 50% of cells staining at intensity of 1, 2, or 3; 70% of cells staining at intensity of 1, 2, or 3. In another example, an increase in FRα expression can be determined by detection of an increase of at least 2-fold, at least 3-fold, or at least 5-fold relative to control values (e.g., expression level in a tissue or cell from a subject without cancer or with a cancer that does not have elevated FRα values). FRα expression can be measured by immunohistochemistry and given a visual score where FRα positive may refer to greater than or equal to 50% of tumor cells with FRα membrane staining visible at less than or equal to 10× microscope objective.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. As used herein, such antibodies include, for example, bispecific (e.g., biparatopic) antibodies. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" or "antibody fragment thereof" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, and single chain antibodies. Antibody fragments can be naked or conjugated to other molecules such as toxins, radioisotopes, etc.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementarity determining region (CDR) are replaced by residues from the CDR of a non-human species (e.g. mouse, rat, rabbit, hamster) that have the desired specificity, affinity, and capability ("CDR grafted") (Jones et al., Nature 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody or fragment from a non-human species that has the desired specificity, affinity, and capability. The humanized antibody or antigen-binding fragment thereof can be further modified by the substitution of additional residues either in the Fv framework region and/or within the replaced non-human residues to refine and optimize antibody or antigen-binding fragment thereof specificity, affinity, and/or capability. In general, the humanized antibody or antigen-binding fragment thereof will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Natl. Acad. Sci., USA, 91(3):969-973 (1994), and Roguska et al., Protein Eng. 9(10):895-904 (1996). In some embodiments, a "humanized antibody" is a resurfaced antibody.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al., Sequences of Proteins of Immunological Interest, (5th ed., 1991, National Institutes of Health, Bethesda Md.), "Kabat"); and (2) an approach based on crystallographic studies of antigen-antibody complexes (Al-lazikani et al, J. Molec. Biol. 273:927-948 (1997)). In addition, combinations of these two approaches are sometimes used in the art to determine CDRs.

A "constant" region of an antibody is not involved directly in binding an antibody to an antigen, but exhibits various effector functions, such as participation of the antibody in antibody-dependent cellular toxicity The Kabat numbering system is generally used when referring to a residue in the variable domain (approximately residues 1-107 of the light chain and residues 1-113 of the heavy chain) (e.g., Kabat et al., Sequences of Immunological Interest. 5th Ed., 1991, National Institutes of Health, Bethesda, Md.) ("Kabat").

The amino acid position numbering as in Kabat, refers to the numbering system used for heavy chain variable domains or light chain variable domains of the compilation of antibodies in Kabat et al. (Sequences of Immunological Interest. 5th Ed., 1991, National Institutes of Health, Bethesda, Md.), ("Kabat"). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | | (Kabat Numbering) |
| H1 | H31-H35 | H26-H35 | H26-H32 |
| | | | (Chothia Numbering) |
| H2 | H50-H65 | H50-H58 | H52-H56 |
| H3 | H95-H102 | H95-H102 | H95-H102 |

The term "human" antibody or antigen-binding fragment thereof means an antibody or antigen-binding fragment thereof produced by a human or an antibody or antigen-binding fragment thereof having an amino acid sequence corresponding to an antibody or antigen-binding fragment thereof produced by a human made using any technique known in the art. This definition of a human antibody or antigen-binding fragment thereof includes intact or full-length antibodies and fragments thereof.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g. mouse, rat, rabbit, etc.) with the desired specificity, affinity, and capability while the constant regions are homologous to the sequences in antibodies or antigen-binding fragments thereof derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better," the antibody's affinity for the antigen is <0.6 nM, i.e. 0.59 nM, 0.58 nM, 0.57 nM etc. or any value less than 0.6 nM.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The phrase "substantially similar," or "substantially the same," as used herein, denotes a sufficiently high degree of similarity between two numeric values (generally one associated with an antibody of the disclosure and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this disclosure are based upon antibodies, in certain embodiments, the polypeptides can occur as single chains or associated chains.

The terms "polynucleotide" or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages can be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector" means a construct, which is capable of delivering, and optionally expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The terms "identical" or "percent identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, Proc. Natl. Acad. Sci., 87:2264-2268 (1990), as modified in Karlin et al., Proc. Natl. Acad. Sci., 90:5873-5877 (1993), and incorporated into the NBLAST and)(BLAST programs (Altschul et al., Nucleic Acids Res., 25:3389-3402 (1991)). In certain embodiments, Gapped BLAST can be used as described in Altschul et al., Nucleic Acids Res. 25:3389-3402 (1997). BLAST-2, WU-BLAST-2 (Altschul et al., Methods in Enzymology, 266: 460-480 (1996)), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (J. Mol. Biol. (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage "sequence identity" (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman (Advances in Applied Mathematics 2: 482 489 (1981)) to find the best segment of homology between two sequences. When using Bestfit or any other sequence alignment program to determine whether a particular sequence is, for instance, 95% identical to a reference sequence according to the present disclosure, the parameters are set such that the percentage of identity is calculated over the full length of the reference nucleotide sequence and that gaps in homology of up to 5% of the total number of nucleotides in the reference sequence are allowed.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies of the disclosure do not abrogate the binding of the polypeptide or antibody containing the amino acid sequence, to the antigen(s), i.e., the FRα to which the polypeptide or antibody binds. Methods of identifying nucleotide and amino acid conservative substitutions which do not eliminate antigen binding are well-known in the art (see, e.g., Brummell et al., Biochem. 32: 1180-1 187 (1993); Kobayashi et al. Protein Eng. 12(10):879-884 (1999); and Burks et al. Proc. Natl. Acad. Sci. USA 94: 412-417 (1997)).

"Bispecific antibodies" refer to antibodies that bind to two different epitopes. The epitopes can be on the same target antigen or can be on different target antigens.

"Biparatopic antibodies" are bispecific antibodies that bind to two different non-overlapping epitopes on the same target antigen (e.g., FRα).

In some embodiments, the FRα antibodies or antigen binding fragments thereof disclosed herein are multivalent molecules. The term "valent" as used within the current application denotes the presence of a specified number of binding sites in an antibody molecule. A natural antibody for example or a full length antibody according to the invention has two binding sites and is "bivalent." The term "tetravalent," denotes the presence of four binding sites in an antigen binding protein. The term "trivalent" denotes the presence of three binding sites in an antibody molecule. The term "bispecific, tetravalent," as used herein denotes an antigen binding protein according to the invention that has four antigen-binding sites of which at least one binds to a first antigen and at least one binds to a second antigen or another epitope of the antigen.

The term "immunoconjugate" or "conjugate" as used herein refers to a compound or a derivative thereof that is linked to a cell binding agent and is defined by a generic formula: C-L-A, wherein C=cytotoxin, L=linker, and A=antibody or antigen-binding fragment there of (e.g., an anti-FRα antibody or antibody fragment). Immunoconjugates can also be defined by the generic formula in reverse order: A-L-C.

A "linker" is any chemical moiety that is capable of linking a compound, usually a drug, such as maytansinoid, to a cell-binding agent such as an anti-FRα antibody or antigen-binding fragment thereof in a stable, covalent manner. Linkers can be susceptible to or be substantially resistant to cleavage (e.g., acid-induced cleavage, light-induced cleavage, peptidase-induced cleavage, esterase-induced cleavage, or disulfide bond cleavage) at conditions under which the compound or the antibody remains active. Suitable linkers are well known in the art and include, for example, disulfide groups and thioether groups.

As used herein, the term "cytotoxic agent" refers to a substance that inhibits or prevents one or more cellular functions and/or causes cell death. In some embodiments, the cytotoxic agent is a maytansinoid, e.g., DM21. Immunoconjugates comprising DM21 are disclosed in WO 2018/160539 A1, which is herein incorporated by reference in its entirety.

An immunoconjugate can comprise the site-specific DM21 linkage of "DM21C" represented by the following structural formula:

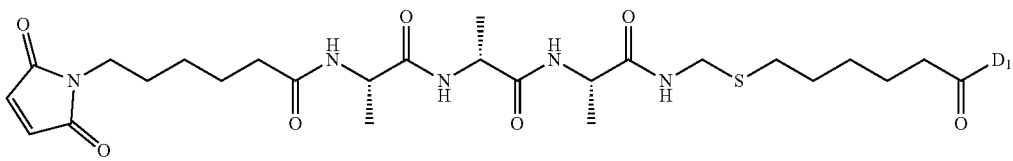

wherein $D_1$ is:

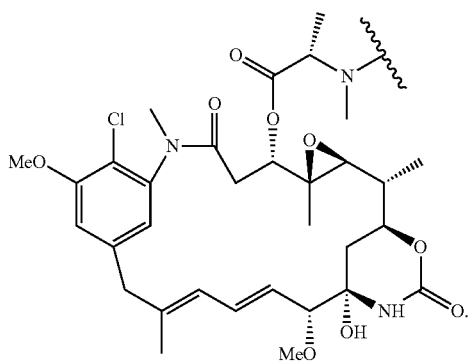 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

An immunoconjugate can also comprise the lysine-linked DM21 "L-DM21," "DM21-L," or "DM21L," which are represented by the following structural formula:

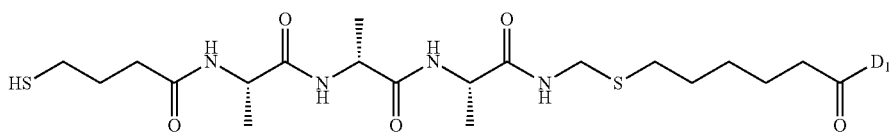

wherein $D_1$ is shown above, coupled to an antibody by a linker, e.g., a γ-maleimidobutyric acid N-succinimidyl ester (GMBS) or a N-(γ-maleimidobutryloxy)sulfosuccinimide ester (sulfo-GMBS or sGMBS) linker. The GMBS and sulfo-GMBS (or sGMBS) linkers are known in the art and can be presented by the following structural formula:

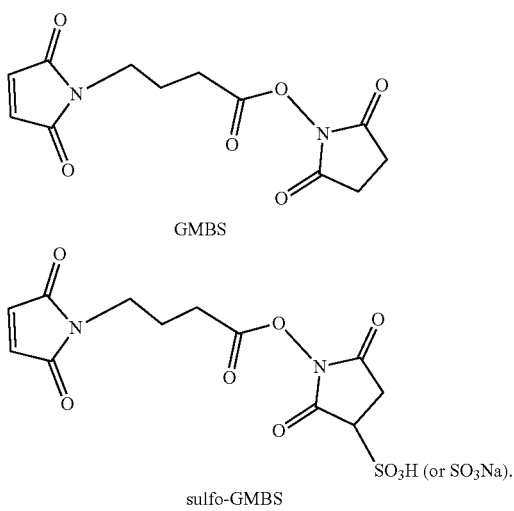

"Optional" or "optionally" means that the subsequently described circumstance may or may not occur, so that the application includes instances where the circumstance occurs and instances where it does not. For example, the phrase "optionally substituted" means that a nonhydrogen substituent may or may not be present on a given atom, and, thus, the application includes structures wherein a nonhydrogen substituent is present and structures wherein a nonhydrogen substituent is not present.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include fallopian tube cancer, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers. The cancer can be a cancer that expresses FRα ("FRα-expressing cancer").

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

An "advanced" cancer is one which has spread outside the site or organ of origin, either by local invasion or metastasis. The term "advanced" cancer includes both locally advanced and metastatic disease.

"Metastatic" cancer refers to cancer that has spread from one part of the body) to another part of the body.

A "refractory" cancer is one that progresses even though an anti-tumor treatment, such as a chemotherapy, is administered to the cancer patient.

A "recurrent" cancer is one that has regrown, either at the initial site or at a distant site, after a response to initial therapy.

A "relapsed" patient is one who has signs or symptoms of cancer after remission. Optionally, the patient has relapsed after adjuvant or neoadjuvant therapy.

The term "maintenance therapy" refers to therapy that is given to help keep cancer from coming back after it has disappeared following the initial therapy.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

An "effective amount" of an antibody, immunoconjugate, or other drug as disclosed herein is an amount sufficient to carry out a specifically stated purpose.

The term "therapeutically effective amount" refers to an amount of an antibody, immunoconjugate, or other drug effective to "treat" a disease or disorder in a subject or mammal. In the case of cancer, the therapeutically effective amount of the drug can reduce the number of cancer cells; reduce the tumor size or burden; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP), or any combination thereof. See the definition herein of "treating". To the extent the drug can prevent growth and/or kill existing cancer cells, it can be cytostatic and/or cytotoxic.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. In certain embodiments, a subject is successfully "treated" for cancer according to the methods of the present disclosure if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

The terms "administer," "administering," "administration," and the like, as used herein, refer to methods that may be used to enable delivery of the immunoconjugate to the desired site of biological action. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa. In one aspect, immunoconjugate is administered intravenously.

The term "instructing" means providing directions for applicable therapy, medication, treatment, treatment regimens, and the like, by any means, for example, in writing, such as in the form of package inserts or other written promotional material.

The terms "pre-treat" and "pre-treatment" refer to therapeutic measures that occur prior to the administration of a therapeutic antibody, antigen-binding fragment thereof, or immunoconjugate. For example, as described in more detail herein, a steroid (e.g., corticosteroid) can be administered as a prophylactic within about a week, about five days, about three days, about two days, or about one day or 24 hours prior to the administration of an immunoconjugate. The steroid can also be administered prior to the immunoconjugate on the same day as the immunoconjugate.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided. In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Any compositions or methods provided herein can be combined with one or more of any of the other compositions and methods provided herein.

II. Biparatopic Antibodies

Figure 1:
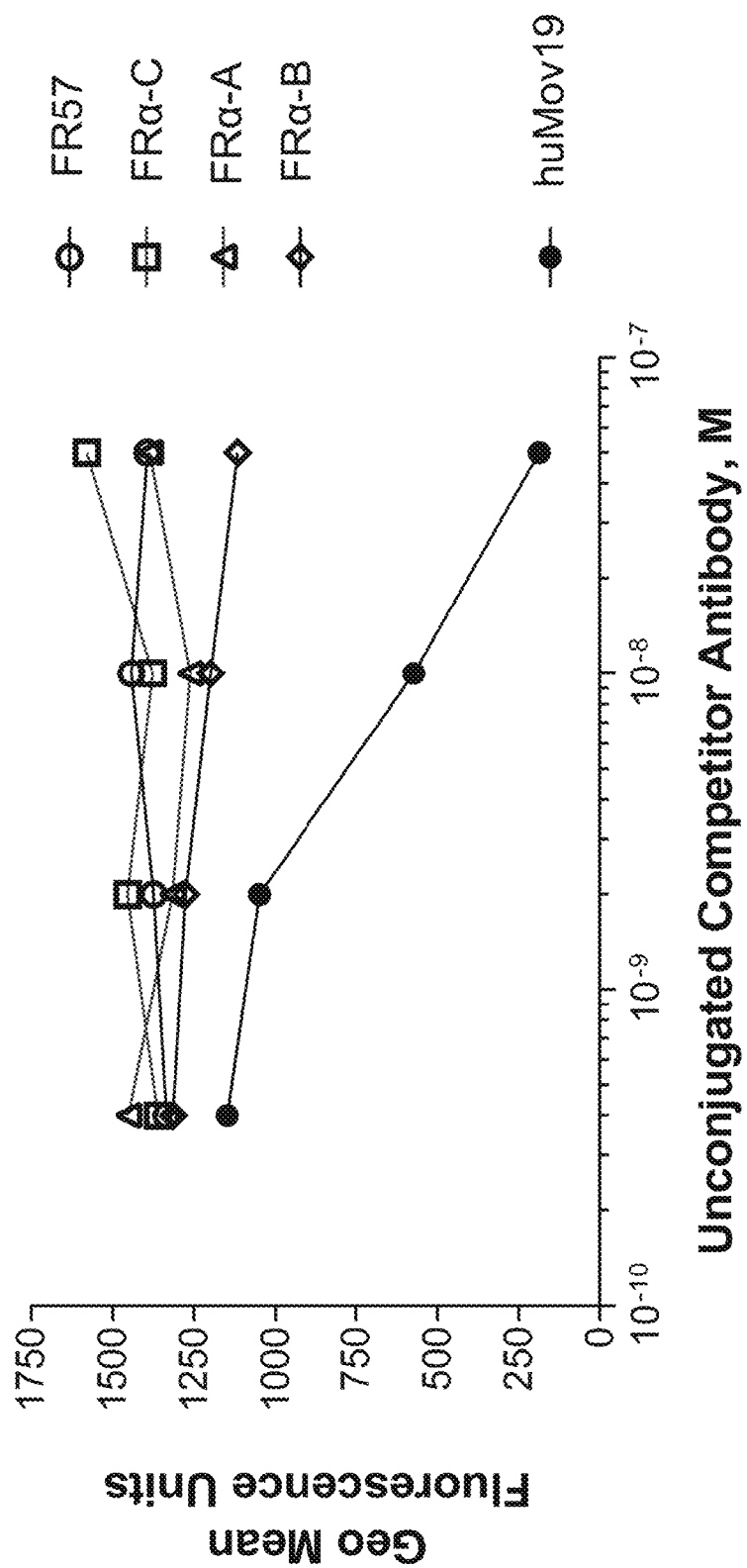

Provided herein are biparatopic anti-FRα antibodies and antigen-binding fragments thereof. These biparatopic antibodies and antigen-binding fragments thereof can comprise a first FRα-binding domain that binds to a first epitope of FRα and a second FRα-binding domain that binds to a second epitope of FRα. The first and the second epitopes of –FRα are non-overlapping epitopes. These biparatopic antibodies and antigen-binding fragments can contain additional FRα-binding domains. For example, a tetravalent biparatopic antibody or antigen-binding fragment can have two FRα-binding domains that bind to the first epitope and two FRα-binding domains that bind to the second epitope. Exemplary biparatopic antibodies and antigen-binding fragments thereof are shown in FIG. 1.

A. FRα-Binding Domains

Disclosed herein are FRα-binding domains that can be used to assemble biparatopic antibodies or antigen binding fragments thereof. A FRα-binding domain can comprise six complementarity determining regions (CDRs), i.e., a variable heavy chain (VH) CDR1, a VH CDR2, a VH CDR3, a variable light chain (VL) CDR1, a VL CDR2, and a VL CDR3. A FRα-binding domain can comprise a variable heavy chain (VH) and a variable light chain (VL). The VH and the VL can be separate polypeptides or can parts of the same polypeptide (e.g., in an scFv).

FRα antibodies and antigen binding fragments thereof are known in the art and have been disclosed, for example, in PCT Application Publication Nos. WO 2011/106528 A1; WO 2012/135675 A3; WO 2012/138749 A1; WO 2014/036495 A3; and WO 2015/031815 A2; each of which is herein incorporated by reference in its entirety. Additional FRα antibodies have been disclosed in U.S. Pat. Nos. 8,557,966 B2; 8,709,432 B2; 9,702,881 B2; and 9,637,547 B2; and U.S. Patent Application Publication No. US-2012-0282282 A1, each of which is herein incorporated by reference in its entirety. In addition, the FRα antibody huMov19 (M9346A) is encoded by the plasmids deposited with the American Type Culture Collection (ATCC), located at 10801 University Boulevard, Manassas, Va. 20110 on Apr. 7, 2010 under the terms of the Budapest Treaty and having ATCC deposit nos. PTA-10772 and PTA-10774. As provided herein, an FRα-binding domain can be the FRα-binding domain (e.g., the six CDRs or the VH and VL) of any of these antibodies or antigen-binding fragments thereof.

By way of example, an FRα-binding domain can comprise the CDR sequences, the VH sequence, and/or the VL sequence of the huMov19 antibody and/or the FR57 antibody. The CDR sequences of huMov19 and FR57 antibodies are provided in Tables 1 and 2 below.

In some embodiments, an FRα-binding domain disclosed herein comprises one or more polypeptides comprising one or more of the CDR sequences described herein. For example, an FRα-binding domain can comprise one or more of the light chain CDR sequences (i.e., LC CDR1, LC CDR2, and LC CDR3) and/or one or more of the heavy chain CDR sequences (i.e., HC CDR1, HC CDR2, and HC CDR3) shown below in Tables 1 and 2.

TABLE 1

Light chain CDR sequences (by Kabat Definition)

| Antibody | VL-CDR1 | VL-CDR2 | VL-CDR3 |
|---|---|---|---|
| FR57 | RASQNINNNLH (SEQ ID NO: 1) | YVSQSVS (SEQ ID NO: 2) | QQSNSWPHYT (SEQ ID NO: 3) |
| huMov19 | KASQSVSFAGTSLMH (SEQ ID NO: 4) | RASNLEA (SEQ ID NO: 5) | QQSREYPYT (SEQ ID NO: 6) |

TABLE 2

Heavy chain CDR sequences

| Antibody | VH-CDR1 | VH-CDR2 | VH-CDR3 |
|---|---|---|---|
| FR57 | SFGMH (SEQ ID NO: 7) AbM Defined: GFTFSSFGMH (SEQ ID NO: 13) | Kabat Defined: YISSGSSTISYADSVKG (SEQ ID NO: 8) AbM Defined: YISSGSSTIS (SEQ ID NO: 14) | Kabat or AbM Defined: EAYGSSMEY (SEQ ID NO: 9) |
| huMov19 | Kabat Defined: GYFMN (SEQ ID NO: 10) AbM Defined: GYTFTGYFMN (SEQ ID NO: 15) | Kabat Defined: RIHPYDGDTFYNQKFQG (SEQ ID NO: 11) AbM Defined: RIHPYDGDTF (SEQ ID NO: 16) | Kabat or AbM Defined: YDGSRAMDY (SEQ ID NO: 12) |

In some embodiments, an FRα-binding domain comprises (a) VL CDR1, VL CDR2, and VL CDR3 comprising the amino acid sequences of SEQ ID NOs: 1-3, respectively; and (b) VH CDR1, VH CDR2, and VH CDR3 comprising the amino acid sequences of SEQ ID NOs: 7-9, respectively. In some embodiments, an FRα-binding domain comprises (a) VL CDR1, VL CDR2, and VL CDR3 comprising the amino acid sequences of SEQ ID NOs: 1-3, respectively; and (b) VH CDR1, VH CDR2, and VH CDR3 comprising the amino acid sequences of SEQ ID NOs: 13, 14, and 9, respectively. In some embodiments, an FRα-binding domain comprises (a) VL CDR1, VL CDR2, and VL CDR3 comprising the amino acid sequences of SEQ ID NOs: 4-6, respectively and (b) VH CDR1, VH CDR2, and VH CDR3 comprising the amino acid sequences of SEQ ID NOs: 10-12, respectively. In some embodiments, an FRα-binding domain comprises (a) VL CDR1, VL CDR2, and VL CDR3 comprising the amino acid sequences of SEQ ID NOs: 4-6, respectively and (b) VH CDR1, VH CDR2, and VH CDR3 comprising the amino acid sequences of SEQ ID NOs: 15, 16, and 12, respectively.

By way of example, an FRα-binding domain can comprise the CDR sequences, the VH sequence, and/or the VL sequence of the huMov19 antibody and/or the FR57 antibody. The CDR sequences of huMov19 and FR57 are provided in Tables 1 and 2 below.

In some embodiments, an FRα-binding domain disclosed herein comprises one or more polypeptides comprising one or more of the CDR sequences described herein. For example, an FRα-binding domain can comprise one or more of the light chain CDR sequences (i.e., LC CDR1, LC CDR2, and LC CDR3) and/or one or more of the heavy chain CDR sequences (i.e., HC CDR1, HC CDR2, and HC CDR3) shown below in Tables 1 and 2.

In some embodiments, an FRα-binding domain comprises the light and/or heavy chain variable sequences of the huMov19 antibody and/or the FR57 antibody. The light chain variable sequences and heavy chain variable sequences of huMov19 and FR57 are provided in Tables 3 and 4 below.

TABLE 3

Light Chain Variable Sequence

| Antibody | Sequence |
|---|---|
| FR57 | EIVLTQSPATLSVTPGDRVSLSCRASQNINNNLHWYQQK PGQSPRLLIKYVSQSVSGIPDRFSGSGSGTDFTLSISSV EPEDFGMYFCQQSNSWPHYTFGQGTKLEIK (SEQ ID NO: 17) |
| FR57 F83E; Q101C | EIVLTQSPATLSVTPGDRVSLSCRASQNINNNLHWYQQK PGQSPRLLIKYVSQSVSGIPDRFSGSGSGTDFTLSISSV EPEDEGMYFCQQSNSWPHYTFGCGTKLEIK (SEQ ID NO: 18) |
| huMov19 | DIVLTQSPLSLAVSLGQPAIISCKASQSVSFAGTSLMHW YHQKPGQQPRLLIYRASNLEAGVPDRFSGSGSKTDFTLT ISPVEAEDAATYYCQQSREYPYTFGGGTKLEIK (SEQ ID NO: 19) |
| huMov19 G104C | DIVLTQSPLSLAVSLGQPAIISCKASQSVSFAGTSLMHW YHQKPGQQPRLLIYRASNLEAGVPDRFSGSGSKTDFTLT ISPVEAEDAATYYCQQSREYPYTFGCGTKLEIK (SEQ ID NO: 20) |
| huMov19 A87E; G104C | DIVLTQSPLSLAVSLGQPAIISCKASQSVSFAGTSLMHW YHQKPGQQPRLLIYRASNLEAGVPDRFSGSGSKTDFTLT ISPVEAEDEATYYCQQSREYPYTFGCGTKLEIK (SEQ ID NO: 21) |

TABLE 4

Heavy Chain Variable Sequence

| Antibody | Sequence |
|---|---|
| FR57 | EVQLVESGGGLVQPGGSRRLSCAASGFTFSSFGMHW VRQAPGKGLEWVAYISSGSSTISYADSVKGRFTISR DNSKKTLLLQMTSLRAEDTAMYYCAREAYGSSMEYW GQGTLVTVSS (SEQ ID NO: 22) |
| FR57 E6Q; G44C | EVQLVQSGGGLVQPGGSRRLSCAASGFTFSSFGMHW VRQAPGKCLEWVAYISSGSSTISYADSVKGRFTISR DNSKKTLLLQMTSLRAEDTAMYYCAREAYGSSMEYW GQGTLVTVSS (SEQ ID NO: 23) |
| huMov19 | QVQLVQSGAEVVKPGASVKISCKASGYTFTGYFMNW VKQSPGQSLEWIGRIHPYDGDTFYNQKFQGKATLTV DKSSNTAHMELLSLTSEDFAVYYCTRYDGSRAMDYW GQGTTVTVSS (SEQ ID NO: 24) |
| huMov19 S44C | QVQLVQSGAEVVKPGASVKISCKASGYTFTGYFMNW VKQSPGQCLEWIGRIHPYDGDTFYNQKFQGKATLTV DKSSNTAHMELLSLTSEDFAVYYCTRYDGSRAMDY (SEQ ID NO: 25) |
| huMov19 S44C | QVQLVQSGAEVVKPGASVKISCKASGYTFTGYFMNW VKQSPGQCLEWIGRIHPYDGDTFYNQKFQGKATLTV DKSSNTAHMELLSLTSEDFAVYYCTRYDGSRAMDYW GQGTTVTVSS (SEQ ID NO: 57) |
| huMov19 A16E; S44C | QVQLVQSGAEVVKPGESVKISCKASGYTFTGYFMNW VKQSPGQCLEWIGRIHPYDGDTFYNQKFQGKATLTV DKSSNTAHMELLSLTSEDFAVYYCTRYDGSRAMDYW GQGTTVTVSS (SEQ ID NO: 26) |

In some embodiments, an FRα-binding domain comprises a VL having at least about 70%, at least about 75%, at least about 80%, at least about 85%, at least about 90%, at least about 95%, at least about 96%, at least about 97%, at least about 98%, at least about 99%, or 100% sequence identity to SEQ ID NO:17, optionally wherein the VL comprises VL CDR1, VL CDR2, and VL CDR3 sequences of SEQ ID NOs: 1-3, respectively. In some embodiments, an FRα-binding domain comprises a VL having at least about 70%, at least about 75%, at least about 80%, at least about 85%, at least about 90%, at least about 95%, at least about 96%, at least about 97%, at least about 98%, at least about 99%, or 100% sequence identity to SEQ ID NO:19, optionally wherein the VL comprises VL CDR1, VL CDR2, and VL CDR3 sequences of SEQ ID NOs: 4-6, respectively.

In some embodiments, an FRα-binding domain comprises a VH having at least about 70%, at least about 75%, at least about 80%, at least about 85%, at least about 90%, at least about 95%, at least about 96%, at least about 97%, at least about 98%, at least about 99%, or 100% sequence identity to SEQ ID NO:22, optionally wherein the VH comprises VH CDR1, VH CDR2, and VH CDR3 sequences of SEQ ID NOs: 7-9, respectively or SEQ ID NOs: 13, 14, and 9, respectively. In some embodiments, an FRα-binding domain comprises a VH having at least about 70%, at least about 75%, at least about 80%, at least about 85%, at least about 90%, at least about 95%, at least about 96%, at least about 97%, at least about 98%, at least about 99%, or 100% sequence identity to SEQ ID NO:24, optionally wherein the VH comprises VH CDR1, VH CDR2, and VH CDR3 sequences of SEQ ID NOs: 10-12, respectively or SEQ ID NOs: 15, 16, and 12, respectively.

In some embodiments, an FRα-binding domain comprises a VL and a VH, wherein (i) the VL has at least about 70%, at least about 75%, at least about 80%, at least about 85%, at least about 90%, at least about 95%, at least about 96%, at least about 97%, at least about 98%, at least about 99%, or 100% sequence identity to SEQ ID NO:17, optionally wherein the VL comprises VL CDR1, VL CDR2, and VL CDR3 sequences of SEQ ID NOs: 1-3, respectively and (ii) the VH has at least about 70%, at least about 75%, at least about 80%, at least about 85%, at least about 90%, at least about 95%, at least about 96%, at least about 97%, at least about 98%, at least about 99%, or 100% sequence identity to SEQ ID NO:22, optionally wherein the VH comprises VH CDR1, VH CDR2, and VH CDR3 sequences of SEQ ID NOs: 7-9, respectively or SEQ ID NOs: 13, 14, and 9, respectively.

In some embodiments, an FRα-binding domain comprises a VL and a VH, wherein (i) the VL has at least about 70%, at least about 75%, at least about 80%, at least about 85%, at least about 90%, at least about 95%, at least about 96%, at least about 97%, at least about 98%, at least about 99%, or 100% sequence identity to SEQ ID NO:19, optionally wherein the VL comprises VL CDR1, VL CDR2, and VL CDR3 sequences of SEQ ID NOs: 4-6, respectively and (ii) the VH has at least about 70%, at least about 75%, at least about 80%, at least about 85%, at least about 90%, at least about 95%, at least about 96%, at least about 97%, at least about 98%, at least about 99%, or 100% sequence identity to SEQ ID NO:24, optionally wherein the VH comprises VH CDR1, VH CDR2, and VH CDR3 sequences of SEQ ID NOs: 10-12, respectively or SEQ ID NOs: 15, 16, and 12, respectively.

In some embodiments, an FRα-binding domain comprises a VL and a VH. The VL and the VH can be separate polypeptides. The VL and the VH can also be parts of the same polypeptide, e.g., a polypeptide comprising a VL, a linker, and a VH. A polypeptide comprising a VL, a linker, and a VH can be in the orientation VL-linker-VH or the orientation VH-linker-VL.

Accordingly, in some embodiments, an FRα-binding domain (e.g., scFv) comprises, from N- to C-terminus: a VL comprising the amino acid sequence of SEQ ID NO:17, a linker (e.g., a glycine-serine linker), and a VH comprising the amino acid sequence of SEQ ID NO:22. In some embodiments, an FRα-binding domain comprises, from N to C terminus: a VH comprising the amino acid sequence of SEQ ID NO:22, a linker (e.g., a glycine-serine linker), and a VL comprising the amino acid sequence of SEQ ID NO:17.

In some embodiments, an FRα-binding domain (e.g., scFv) comprises, from N- to C-terminus: a VL comprising the amino acid sequence of SEQ ID NO:19, a linker (e.g., a glycine-serine linker), and a VH comprising the amino acid sequence of SEQ ID NO:24. In some embodiments, an FRα-binding domain comprises, from N to C terminus: a VH comprising the amino acid sequence of SEQ ID NO:24, a linker (e.g., a glycine-serine linker), and a VL comprising the amino acid sequence of SEQ ID NO:19.

Linkers that can be used to connect a VH and a VL are known in the art. For example, a linker can be a glycine-serine linker. In some embodiments, the linker can be of any length and can comprise at least 1, 2, 3, 4, 5, 6, 7, 8, 9, 10, 11, 12, 13, 14, 15, 16, 17, 18, 19, 20, 25, 30, 31, 32, 33, 34, 35, 36, 37, 38, 39, 40, 50, or 60 or more amino acids. In other embodiments, a linker useful for the present disclosure has at least one amino acid and less than 100 amino acids, less than 90 amino acids, less than 80 amino acids, less than 70 amino acids, less than 60 amino acids, less than 50 amino acids, less than 40 amino acids, less than 30 amino acids, less than 20 amino acids, less than 19 amino acids, less than 18 amino acids, less than 17 amino acids, less than 16 amino acids, less than 15 amino acids, less than 14 amino acids, less than 13 amino acids, or less than 12 amino acids. In one embodiment, the linker sequence comprises glycine amino acid residues. In other instances, the linker sequence comprises a combination of glycine and serine amino acid residues.

In some embodiments, a FRα-binding domain comprises a linker fused in frame between the VH and the VL. In some embodiments, such glycine/serine linkers comprises any combination of the amino acid residues, including, but not limited to, the peptide GGGS (SEQ ID NO:49) or GGGGS (SEQ ID NO:50) or repeats of the same, including 1, 2, 3, 4, 5, 6, 7, 8, 9, 10 or more repeats of these given peptides. The glycine/serine linkers disclosed herein comprises an amino acid sequence of $(GS)_n$, $(GGS)_n$, $(GGGS)_n$, $(GGGGS)_n$, or $(GGGGS)_n$, wherein n is an integer of 1, 2, 3, 4, 5, 6, 7, 8, 9, or 10. In one embodiment, the linker sequence is GGGGSGGGGSGGGGS (SEQ ID NO:51) (also noted as $(Gly_4Ser)_3$). In another embodiment, the linker sequence is GGGGSGGGGSGGGGSGGGGS (SEQ ID NO:52) (also noted as $(Gly_4Ser)_4$).

In some embodiments, an FRα-binding domain is an scFv. Exemplary scFv FRα-binding domains are provided in Table 5 below.

TABLE 5 scFv Fusion Proteins

| Name | scFv Sequences |
|---|---|
| FR57scFv1 scFv in VH-$(G_4S)_4$-VL orientation | EVQLVESGGGLVQPGGSRRLSCAASGFTFSSFGMHWVRQAPGKGLEW VAYISSGSSTISYADSVKGRFTISRDNSKKTLLLQMTSLRAEDTAMY YCAREAYGSSMEYWGQGTLVTVSSGGGGSGGGGSGGGGSGGGGSEIV LTQSPATLSVTPGDRVSLSCRASQNINNNLHWYQQKPGQSPRLLIKY VSQSVSGIPDRFSGSGSGTDFTLSISSVEPEDFGMYFCQQSNSWPHY TFGQGTKLEIK(SEQ ID NO: 27) |
| FR57scFv2 scFv in VL (F83E; Q101C)-$(G_4S)_4$-VH (E6Q; G44C) orientation | EIVLTQSPATLSVTPGDRVSLSCRASQNINNNLHWYQQKPGQSPRLL IKYVSQSVSGIPDRFSGSGSGTDFTLSISSVEPED<u>E</u>GMYFCQQSNSW PHYTFG<u>C</u>GTKLEIKGGGGSGGGGSGGGGSGGGGSEV<u>Q</u>LVQSGGGLVQ PGGSRRLSCAASGFTFSSFGMEIWVRQAPGK<u>C</u>LEWVAYISSGSSTIS YADSVKGRFTISRDNSKKTLLLQMTSLRAEDTAMYYCAREAYGSSME YWGQGTLVTVSS(SEQ ID NO: 28) |
| FR57scFv3wt scFv in VL-$(G_4S)_4$-VH orientation | EIVLTQSPATLSVTPGDRVSLSCRASQNINNNLHWYQQKPGQSPRLL IKYVSQSVSGIPDRFSGSGSGTDFTLSISSVEPEDFGMYFCQQSNSW PHYTFGQGTKLEIKGGGGSGGGGSGGGGSGGGGSEVQLVESGGGLVQ PGGSRRLSCAASGFTFSSFGMHWVRQAPGKGLEWVAYISSGSSTISY ADSVKGRFTISRDNSKKTLLLQMTSLRAEDTAMYYCAREAYGSSMEY WGQGTLVTVSS(SEQ ID NO: 29) |
| Mov19scFv1 scFv in VH-$(G_4S)_4$-VL orientation | QVQLVQSGAEVVKPGASVKISCKASGYTFTGYFMNWVKQSPGQSLEW IGRIHPYDGDTFYNQKFQGKATLTVDKSSNTAHMELLSLTSEDFAVY YCTRYDGSRAMDYWGQGTTVTVSSGGGGSGGGGSGGGGSGGGGSDIV LTQSPLSLAVSLGQPAIISCKASQSVSFAGTSLMHWYHQKPGQQPRL LIYRASNLEAGVPDRFSGSGSKTDFTLTISPVEAEDAATYYCQQSRE YPYTFGGGTKLEIK(SEQ ID NO: 30) |
| Mov19scFv2 scFv in VL (G104C)-$(G_4S)_4$-VH (S44C) orientation | DIVLTQSPLSLAVSLGQPAIISCKASQSVSFAGTSLMHWYHQKPGQQ PRLLIYRASNLEAGVPDRFSGSGSKTDFTLTISPVEAEDAATYYCQQ SREYPYTFG<u>C</u>GTKLEIKGGGGSGGGGSGGGGSGGGGSQVQLVQSGAE VVKPGASVKISCKASGYTFTGYFMNWVKQSPGQ<u>C</u>LEWIGRIHPYDGD TFYNQKFQGKATLTVDKSSNTAHMELLSLTSEDFAVYYCTRYDGSRA MDYWGQGTTVTVSS(SEQ ID NO: 31) |

TABLE 5-continued scFv Fusion Proteins

| Name | scFv Sequences |
|---|---|
| Mov19scFv3 scFv in VL (A87E; G104C)-(G₄S)₄-VH (A16E; S44C) orientation | DIVLTQSPLSLAVSLGQPAIISCKASQSVSFAGTSLMHWYHQKPGQQ PRLLIYRASNLEAGVPDRFSGSGSKTDFTLTISPVEAEDEATYYCQQ SREYPYTFGCGTKLEIKGGGGSGGGGSGGGGSGGGGSQVQLVQSGAE VVKPGESVKISCKASGYTFTGYFMNWVKQSPGQCLEWIGRIHPYDGD TFYNQKFQGKATLTVDKSSNTAHMELLSLTSEDFAVYYCTRYDGSRA MDYWGQGTTVTVSS(SEQ ID NO: 32) |

In some embodiments, an FRα-binding domain comprises a scFv comprising an amino acid sequence at least about 70%, at least about 75%, at least about 80%, at least about 85%, at least about 90%, at least about 95%, at least about 96%, at least about 97%, at least about 98%, at least about 99%, or 100% sequence identity to SEQ ID NO:27, 28, or 29, optionally wherein the scFv comprises VL CDR1, VL CDR2, and VL CDR3 sequences of SEQ ID NOs:1-3, respectively and VH CDR1, VH CDR2, and VH CDR3 sequences of SEQ ID NOs: 7-9, respectively or SEQ ID NOs: 13, 14, and 9, respectively.

In some embodiments, an FRα-binding domain comprises a scFv comprising an amino acid sequence at least about 70%, at least about 75%, at least about 80%, at least about 85%, at least about 90%, at least about 95%, at least about 96%, at least about 97%, at least about 98%, at least about 99%, or 100% sequence identity to SEQ ID NO:30, 31, or 32, optionally wherein the scFv comprises VL CDR1, VL CDR2, and VL CDR3 sequences of SEQ ID NOs: 4-6, respectively and VH CDR1, VH CDR2, and VH CDR3 sequences of SEQ ID NOs: 10-12, respectively or SEQ ID NOs: 15, 16, and 12, respectively.

In certain embodiments, a FRα-binding domain binds to the same epitope of FRα as an antibody comprising the amino acid sequences of SEQ ID NO:17 and SEQ ID NO:22.

In certain embodiments, a FRα-binding domain binds to the same epitope of FRα as an antibody comprising the amino acid sequences of SEQ ID NO:19 and SEQ ID NO:24.

In certain embodiments, a FRα-binding domain is a murine, chimeric, or humanized FRα-binding domain. As used herein, a humanized FRα-binding domain can be a resurfaced FRα-binding domain.

In certain embodiments, a FRα-binding domain binds to human FRα but not FOLR2 or FOLR3.

B. Biparatopic Antibody Formats

The biparatopic anti-FRα antibodies or antigen binding fragments thereof can comprise a combination of the FRα-binding domains discussed above, wherein the FRα-binding domains bind to non-overlapping epitopes of FRα.

Many different types of bispecific constructs are known in the art and can be used in the biaparatopic anti-FRα antibodies or antigen binding fragments thereof provided herein.

Early attempts at bispecific antibody construction either utilized chemical cross-linking or hybrid hybridomas or quadromas to join the two halves of two different antibodies together. Although these techniques work to make bispecific antibodies, they are associated with production problems, such as the production of mixed populations containing different combinations of antigen-binding sites, difficulty in protein expression, the need to purify the bispecific antibody of interest, low yields, expense of production, etc.

More recent approaches have utilized genetically engineered constructs that are capable of producing homogeneous products of single bispecific antibodies, without the need for extensive purification to remove unwanted byproducts. Such constructs have included tandem scFv, diabodies, tandem diabodies, dual variable domain antibodies and heterodimerization using a motif such as Ch1/Ck domain or DNL® (Chames & Baty, 2009, Curr Opin Drug Discov Devel 12:276-83; Chames & Baty, mAbs 1:539-47). BITE® refers to tandem scFvs that are joined by a short peptide linker (Chames & Baty, mAbs 1:539-47). Other approaches to bispecific antibody production have included tetravalent IgG-scFv fusions (Dong et al., 2011, MAbs 3:273-88); dual-acting Fab (DAF) antibodies (Bostrom et al., 2009, Science 323:1610-14); Igg-like dual-variable domain antibodies (DVD-Ig) (Wu et al., 2007, Nat Biotechnol 25:1290-97); and use of dynamic exchange between IgG4 molecules (van der Neut Kolfschoten et al., 2007, Science 317:1554-57).

DOCK-AND-LOCK® (DNL®) complex (see, e.g., U.S. Pat. Nos. 7,521,056; 7,527,787; 7,534,866; 7,550,143; 7,666,400; 7,901,680; 7,906,118; 7,981,398; 8,003,111) represent another bispecific antibody format. Although the standard DNL® complex comprises a trimer with two DDD-linked molecules attached to one AD-linked molecule, variations in complex structure allow the formation of dimers, trimers, tetramers, pentamers, hexamers and other multimers.

In some embodiments, disclosed herein are biparatopic constructs with asymmetric-Fc molecules, including in "knob-in-hole" structures. See Kontermann, MAbs., 4(2): 182-97 (2012). Knobs-into-holes (KIHs) technology involves engineering $C_H3$ domains to create either a "knob" or a "hole" in each heavy chain to promote heterodimerization. KIH technology is described, for instance, in Ridgway et al., Protein Engineering 9(7):617-721 (1996); U.S. Pat. Nos. 5,731,168; 5,807,706; 5,821,333, each of which is herein incorporated by reference in its entirety. The "CrossMab" technique further involves the exchange of heavy and light chain domains within the Fab of one half of the bispecific antibody, making the two arms so different that light-heavy chain mispairing cannot occur (Schaefer et al., 2011, Proc Natl. Acad Sci USA 108:11187-92). The knobs-into-holes approach introduces amino acids with bulky side chains into the CH3 domain of one heavy chain that fit into appropriately designed cavities in the CH3 domain of the other heavy chain. The combination of approaches prevents mismatch of both heavy chain to heavy chain and heavy chain to light chain interactions, resulting in primarily a single product.

In some embodiments, a biparatopic anti-FRα antibody or antigen binding fragment thereof is bivalent (see e.g., the "knob in hole" example shown in FIG. 1). A bivalent biparatopic anti-FRα antibody or antigen binding fragment thereof can comprise, for example, two FRα-binding domains comprising scFvs, two FRα-binding domains comprising VHs and VLs on separate polypeptide chains, or one FRα-binding domain comprising an scFv and one FRα-binding domain that comprises a VH and a VL on separate polypeptide chains.

In some embodiments, a biparatopic anti-FRα antibody or antigen binding fragment thereof is trivalent.

In some embodiments, a biparatopic anti-FRα antibody or antigen-binding fragment thereof is tetravalent (see e.g., the "Morrison" example shown in FIG. 1). Tetravalent antibodies and are described, for instance, in M. J. Coloma, S. L. Morrison, *Nat. Biotechnol.*, 15(2):159-63 (1997), which is herein incorporated by reference in its entirety.

In some embodiments, a biparatopic anti-FRα antibody or antigen binding fragment thereof comprises an FRα-binding domain that is an scFv. In some embodiments, a biparatopic anti-FRα antibody or antigen-binding fragment thereof comprises an FRα-binding domain that comprises a VH and a VL on separate polypeptides. In some embodiments, a biparatopic anti-FRα antibody or antigen binding fragment thereof comprises an FRα-binding domain that is an scFv and an FRα-binding domain that comprises a VH and a VL on separate polypeptides.

In some embodiments, a bivalent biparatopic anti-FRα antibody or antigen binding fragment thereof comprises a single FRα-binding domain that is an scFv and a single FRα-binding domain that comprises a VH and a VL on separate polypeptides. In such embodiments, the scFv can be fused to a heavy chain constant region and the VH can be fused to a heavy chain constant region. In some embodiments, the constant regions have "knob and hole" sequences. The "knob" sequence can be in the heavy chain constant region fused to the scFv, and the "hole" sequence can be fused to the constant region fused to the VH. Alternatively the "hole" mutation can be in the heavy chain constant region fused to the scFv, and the "knob" sequence can be fused to the constant region fused to the VH. Sequences of exemplary biparatopic anti-FRα antibodies or antigen binding fragments thereof of such formats are found in Table 7.

In some embodiments, a tetravalent biparatopic anti-FRα antibody or antigen binding fragment thereof comprises two FRα-binding domains that are scFvs and two FRα-binding domains that comprises VHs and VLs on separate polypeptides. In such embodiments, the scFvs can be fused to the N- or C-terminal of the polypeptide comprising the VH. The scFvs can also be fused to the N- or C-terminal of the polypeptide comprising the VL.

A tetravalent biparatopic anti-FRα antibody or antigen binding fragment thereof can comprise two polypeptides wherein the first polypeptide comprises a heavy chain constant region, a VH, and an scFv and the second polypeptide comprises a light chain constant region and a VL. A tetravalent biparatopic anti-FRα antibody or antigen binding fragment thereof can also comprise two polypeptides wherein the first polypeptide comprises a heavy chain constant region and a VH and the second polypeptide comprises a light chain constant region, a VL, and an scFv. Sequences of exemplary biparatopic anti-FRα antibodies or antigen binding fragments thereof of such formats are found in Table 6.

In some embodiments, a biparatopic anti-FRα antibody or antigen binding fragment thereof is a bispecific heterodimeric diabody, e.g., a tetrameric bispecific heterodimeric diabody. As used herein, the term "bispecific heterodimeric diabody" refers to a complex of two or more polypeptide chains or proteins, and each can comprise at least one antibody VL and one antibody VH domain, and wherein the VL and VH domains in each polypeptide chain are from different antibodies.

In some embodiments, the biparatopic antibodies or antigen binding fragments thereof disclosed herein comprise one or more resurfaced FRα-binding domains. In some embodiments, all of the FRα-binding domains in a biparatopic antibody or antigen binding fragment thereof are resurfaced.

In some embodiments, the biparatopic antibodies or antigen-binding fragments thereof are human immunoglobulins in which residues from the complementary determining region (CDR) are replaced by residues from the CDR of a non-human species (e.g. mouse, rat, rabbit, hamster) that have the desired specificity, affinity, and capability ("CDR grafted") (Jones et al., *Nature* 321:522-525 (1986); Riechmann et al., *Nature* 332:323-327 (1988); Verhoeyen et al., *Science* 239:1534-1536 (1988)).

In a further embodiment, the biparatopic antibodies or antigen-binding fragments thereof are a CDR-grafted or resurfaced antibody comprising at least one heavy chain variable region and at least one light chain variable region, wherein said heavy chain variable region comprises three complementarity-determining regions having amino acid sequences represented by SEQ ID NOs:7-9, respectively, and wherein said light chain variable region comprises three complementarity-determining regions having amino acid sequences represented by SEQ ID NOs:1-3, respectively.

In a further embodiment, the biparatopic antibodies or antigen-binding fragments thereof are a CDR-grafted or resurfaced antibody comprising at least one heavy chain variable region and at least one light chain variable region, wherein said heavy chain variable region comprises three complementarity-determining regions having amino acid sequences represented by SEQ ID NOs:13, 14, and 9, respectively, and wherein said light chain variable region comprises three complementarity-determining regions having amino acid sequences represented by SEQ ID NOs:1-3, respectively.

In a further embodiment, the biparatopic antibodies or antigen-binding fragments thereof are a CDR-grafted or resurfaced antibody comprising at least one heavy chain variable region and at least one light chain variable region, wherein said heavy chain variable region comprises three complementarity-determining regions having amino acid sequences represented by SEQ ID NOs:10-12, respectively, and wherein said light chain variable region comprises three complementarity-determining regions having amino acid sequences represented by SEQ ID NOs:4-6, respectively.

In a further embodiment, the biparatopic antibodies or antigen-binding fragments thereof are a CDR-grafted or resurfaced antibody comprising at least one heavy chain variable region and at least one light chain variable region, wherein said heavy chain variable region comprises three complementarity-determining regions having amino acid sequences represented by SEQ ID NOs:15, 16, and 12, respectively, and wherein said light chain variable region comprises three complementarity-determining regions having amino acid sequences represented by SEQ ID NOs:4-6, respectively.

In a further embodiment, antibodies or antigen-binding fragments are provided having a humanized (e.g., resurfaced, CDR-grafted) heavy chain variable region that shares at least 90% sequence identity with an amino acid sequence corresponding to SEQ ID NOs:22-26, more preferably 95% sequence identity with SEQ ID NOs:22-26, most preferably 100% sequence identity with SEQ ID NOs:22-26. In particular embodiments, the antibody includes conservative mutations in the framework region outside of the CDRs.

Similarly, antibodies are provided having a humanized (e.g., resurfaced, CDR-grafted) light chain variable region that shares at least 90% sequence identity with an amino acid sequence corresponding to SEQ ID NOs:17-21, more preferably 95% sequence identity with SEQ ID NOs:17-21, most preferably 100% sequence identity with SEQ ID NOs:17-21. In particular embodiments, the antibody includes conservative mutations in the framework region outside of the CDRs.

In some embodiments, a biparatopic anti-FRα antibody or antigen binding fragment thereof comprises a heavy chain constant region, such as an IgG1, IgG2, IgG3, IgG4, IgA, IgE, IgM or IgD constant region. In some embodiments, the heavy chain constant region is an IgG1 heavy chain constant region or an IgG4 heavy chain constant region. Furthermore, in some embodiments, a biparatopic anti-FRα antibody or antigen binding fragment thereof can comprise a light chain constant region, either a kappa light chain constant region or a lambda light chain constant region. In some embodiments, the light chain constant region is a kappa light chain constant region.

In some embodiments, a biparatopic anti-FRα antibody or antigen binding fragment thereof comprises a first FRα-binding domain comprising VL and VH sequences selected from the group consisting of SEQ ID NOs:19 and 24; 20 and 25; and 21 and 26, respectively) and a second FRα-binding domain that does not compete with huMov19 for binding to FRα. In some embodiments, a biparatopic anti-FRα antibody or antigen binding fragment thereof comprises a first FRα-binding domain comprising VL and VH sequences of SEQ ID NOs:20 and 57, respectively) and a second FRα-binding domain that does not compete with huMov19 for binding to FRα.

In some embodiments, a biparatopic anti-FRα antibody or antigen binding fragment thereof comprises a first FRα-binding domain comprising the VL and VH sequences selected from the group consisting of SEQ ID NOs:17 and 22; and 18 and 23, respectively) and a second FRα-binding domain that does not compete with FR57 for binding to FRα.

In some embodiments, a biparatopic anti-FRα antibody or antigen binding fragment thereof comprises a FRα-binding domain that competitively inhibits binding to the same FRα epitope as an antibody comprising a VH amino acid sequence of SEQ ID NO:22 and a VL amino acid sequence of SEQ ID NO:17

In some embodiments, a biparatopic anti-FRα antibody or antigen binding fragment thereof comprises a FRα-binding domain that competitively inhibits binding to the same FRα epitope as an antibody comprising a VH amino acid sequence of SEQ ID NO:24 and a VL amino acid sequence of SEQ ID NO:19.

In some embodiments, a biparatopic anti-FRα antibody or antigen binding fragment thereof comprises (i) a first FRα-binding domain that competitively inhibits binding to the same FRα epitope as an antibody comprising a VH amino acid sequence of SEQ ID NO:22 and a VL amino acid sequence of SEQ ID NO:17 and (ii) a second FRα-binding domain that competitively inhibits binding to the same FRα epitope as an antibody comprising a VH amino acid sequence of SEQ ID NO:24 and a VL amino acid sequence of SEQ ID NO:19.

In some embodiments, a biparatopic anti-FRα antibody or antigen binding fragment thereof comprises a FRα-binding domain that binds to the same FRα epitope as an antibody comprising a VH amino acid sequence of SEQ ID NO:22 and a VL amino acid sequence of SEQ ID NO:17.

In some embodiments, a biparatopic anti-FRα antibody or antigen binding fragment thereof comprises a FRα-binding domain that binds to the same FRα epitope as an antibody comprising a VH amino acid sequence of SEQ ID NO:24 and a VL amino acid sequence of SEQ ID NO:19.

In some embodiments, a biparatopic anti-FRα antibody or antigen binding fragment thereof comprises (i) a first FRα-binding domain that binds to the same FRα epitope as an antibody comprising a VH amino acid sequence of SEQ ID NO:22 and a VL amino acid sequence of SEQ ID NO:17 and (ii) a second FRα-binding domain that binds to the same FRα epitope as an antibody comprising a VH amino acid sequence of SEQ ID NO:24 and a VL amino acid sequence of SEQ ID NO:19.

In some embodiments, the biparatopic antibodies or antigen binding fragments thereof of the disclosure comprise the variable light chain and/or variable heavy chain of FR57 (e.g., SEQ ID NOs: 17 and/or 22, respectively) and the variable light chain and/or variable heavy chain of huMOV19 (e.g., SEQ ID NOs: 19 and/or 24, respectively).

In some embodiments, the biparatopic antibodies or antigen binding fragments thereof of the disclosure comprise the variable light chain and/or variable heavy chain of FR57 (e.g., SEQ ID NOs: 17 and/or 22, respectively) and the variable light chain and/or variable heavy chain of huMOV19 (e.g., SEQ ID NOs: 19 and/or 25, respectively). In some embodiments, the biparatopic antibodies or antigen binding fragments thereof of the disclosure comprise the variable light chain and/or variable heavy chain of FR57 (e.g., SEQ ID NOs: 17 and/or 22, respectively) and the variable light chain and/or variable heavy chain of huMOV19 (e.g., SEQ ID NOs: 19 and/or 57, respectively).

In some embodiments, the biparatopic antibodies or antigen binding fragments thereof of the disclosure comprise the variable light chain and/or variable heavy chain of FR57 (e.g., SEQ ID NOs: 17 and/or 22, respectively) and the variable light chain and/or variable heavy chain of huMOV19 (e.g., SEQ ID NOs: 19 and/or 26, respectively).

In some embodiments, the biparatopic antibodies or antigen binding fragments thereof of the disclosure comprise the variable light chain and/or variable heavy chain of FR57 (e.g., SEQ ID NOs: 17 and/or 22, respectively) and the variable light chain and/or variable heavy chain of huMOV19 (e.g., SEQ ID NOs: 20 and/or 24, respectively).

In some embodiments, the biparatopic antibodies or antigen binding fragments thereof of the disclosure comprise the variable light chain and/or variable heavy chain of FR57 (e.g., SEQ ID NOs: 17 and/or 22, respectively) and the variable light chain and/or variable heavy chain of huMOV19 (e.g., SEQ ID NOs: 20 and/or 25, respectively). In some embodiments, the biparatopic antibodies or antigen binding fragments thereof of the disclosure comprise the variable light chain and/or variable heavy chain of FR57 (e.g., SEQ ID NOs: 17 and/or 22, respectively) and the variable light chain and/or variable heavy chain of huMOV19 (e.g., SEQ ID NOs: 20 and/or 57, respectively).

In some embodiments, the biparatopic antibodies or antigen binding fragments thereof of the disclosure comprise the variable light chain and/or variable heavy chain of FR57 (e.g., SEQ ID NOs: 17 and/or 22, respectively) and the variable light chain and/or variable heavy chain of huMOV19 (e.g., SEQ ID NOs: 20 and/or 26, respectively).

In some embodiments, the biparatopic antibodies or antigen binding fragments thereof of the disclosure comprise the variable light chain and/or variable heavy chain of FR57

(e.g., SEQ ID NOs: 17 and/or 22, respectively) and the variable light chain and/or variable heavy chain of huMOV19 (e.g., SEQ ID NOs: 21 and/or 24, respectively).

In some embodiments, the biparatopic antibodies or antigen binding fragments thereof of the disclosure comprise the variable light chain and/or variable heavy chain of FR57 (e.g., SEQ ID NOs: 17 and/or 22, respectively) and the variable light chain and/or variable heavy chain of huMOV19 (e.g., SEQ ID NOs: 21 and/or 25, respectively).

In some embodiments, the biparatopic antibodies or antigen binding fragments thereof of the disclosure comprise the variable light chain and/or variable heavy chain of FR57 (e.g., SEQ ID NOs: 17 and/or 22, respectively) and the variable light chain and/or variable heavy chain of huMOV19 (e.g., SEQ ID NOs: 21 and/or 57, respectively).

In some embodiments, the biparatopic antibodies or antigen binding fragments thereof of the disclosure comprise the variable light chain and/or variable heavy chain of FR57 (e.g., SEQ ID NOs: 17 and/or 22, respectively) and the variable light chain and/or variable heavy chain of huMOV19 (e.g., SEQ ID NOs: 21 and/or 26, respectively).

In some embodiments, the biparatopic antibodies or antigen binding fragments thereof of the disclosure comprise the variable light chain and/or variable heavy chain of FR57 (e.g., SEQ ID NOs: 17 and/or 23, respectively) and the variable light chain and/or variable heavy chain of huMOV19 (e.g., SEQ ID NOs: 19 and/or 24, respectively).

In some embodiments, the biparatopic antibodies or antigen binding fragments thereof of the disclosure comprise the variable light chain and/or variable heavy chain of FR57 (e.g., SEQ ID NOs: 17 and/or 23, respectively) and the variable light chain and/or variable heavy chain of huMOV19 (e.g., SEQ ID NOs: 19 and/or 25, respectively).

In some embodiments, the biparatopic antibodies or antigen binding fragments thereof of the disclosure comprise the variable light chain and/or variable heavy chain of FR57 (e.g., SEQ ID NOs: 17 and/or 23, respectively) and the variable light chain and/or variable heavy chain of huMOV19 (e.g., SEQ ID NOs: 19 and/or 57, respectively).

In some embodiments, the biparatopic antibodies or antigen binding fragments thereof of the disclosure comprise the variable light chain and/or variable heavy chain of FR57 (e.g., SEQ ID NOs: 17 and/or 23, respectively) and the variable light chain and/or variable heavy chain of huMOV19 (e.g., SEQ ID NOs: 19 and/or 26, respectively).

In some embodiments, the biparatopic antibodies or antigen binding fragments thereof of the disclosure comprise the variable light chain and/or variable heavy chain of FR57 (e.g., SEQ ID NOs: 17 and/or 23, respectively) and the variable light chain and/or variable heavy chain of huMOV19 (e.g., SEQ ID NOs: 20 and/or 24, respectively).

In some embodiments, the biparatopic antibodies or antigen binding fragments thereof of the disclosure comprise the variable light chain and/or variable heavy chain of FR57 (e.g., SEQ ID NOs: 17 and/or 23, respectively) and the variable light chain and/or variable heavy chain of huMOV19 (e.g., SEQ ID NOs: 20 and/or 25, respectively).

In some embodiments, the biparatopic antibodies or antigen binding fragments thereof of the disclosure comprise the variable light chain and/or variable heavy chain of FR57 (e.g., SEQ ID NOs: 17 and/or 23, respectively) and the variable light chain and/or variable heavy chain of huMOV19 (e.g., SEQ ID NOs: 20 and/or 57, respectively).

In some embodiments, the biparatopic antibodies or antigen binding fragments thereof of the disclosure comprise the variable light chain and/or variable heavy chain of FR57 (e.g., SEQ ID NOs: 17 and/or 23, respectively) and the variable light chain and/or variable heavy chain of huMOV19 (e.g., SEQ ID NOs: 20 and/or 26, respectively).

In some embodiments, the biparatopic antibodies or antigen binding fragments thereof of the disclosure comprise the variable light chain and/or variable heavy chain of FR57 (e.g., SEQ ID NOs: 17 and/or 23, respectively) and the variable light chain and/or variable heavy chain of huMOV19 (e.g., SEQ ID NOs: 21 and/or 24, respectively).

In some embodiments, the biparatopic antibodies or antigen binding fragments thereof of the disclosure comprise the variable light chain and/or variable heavy chain of FR57 (e.g., SEQ ID NOs: 17 and/or 23, respectively) and the variable light chain and/or variable heavy chain of huMOV19 (e.g., SEQ ID NOs: 21 and/or 25, respectively).

In some embodiments, the biparatopic antibodies or antigen binding fragments thereof of the disclosure comprise the variable light chain and/or variable heavy chain of FR57 (e.g., SEQ ID NOs: 17 and/or 23, respectively) and the variable light chain and/or variable heavy chain of huMOV19 (e.g., SEQ ID NOs: 21 and/or 57, respectively).

In some embodiments, the biparatopic antibodies or antigen binding fragments thereof of the disclosure comprise the variable light chain and/or variable heavy chain of FR57 (e.g., SEQ ID NOs: 17 and/or 23, respectively) and the variable light chain and/or variable heavy chain of huMOV19 (e.g., SEQ ID NOs: 21 and/or 26, respectively).

In some embodiments, the biparatopic antibodies or antigen binding fragments thereof of the disclosure comprise the variable light chain and/or variable heavy chain of FR57 (e.g., SEQ ID NOs: 18 and/or 22, respectively) and the variable light chain and/or variable heavy chain of huMOV19 (e.g., SEQ ID NOs: 19 and/or 24, respectively).

In some embodiments, the biparatopic antibodies or antigen binding fragments thereof of the disclosure comprise the variable light chain and/or variable heavy chain of FR57 (e.g., SEQ ID NOs: 18 and/or 22, respectively) and the variable light chain and/or variable heavy chain of huMOV19 (e.g., SEQ ID NOs: 19 and/or 25, respectively).

In some embodiments, the biparatopic antibodies or antigen binding fragments thereof of the disclosure comprise the variable light chain and/or variable heavy chain of FR57 (e.g., SEQ ID NOs: 17 and/or 23, respectively) and the variable light chain and/or variable heavy chain of huMOV19 (e.g., SEQ ID NOs: 21 and/or 57, respectively).

In some embodiments, the biparatopic antibodies or antigen binding fragments thereof of the disclosure comprise the variable light chain and/or variable heavy chain of FR57 (e.g., SEQ ID NOs: 18 and/or 22, respectively) and the variable light chain and/or variable heavy chain of huMOV19 (e.g., SEQ ID NOs: 19 and/or 26, respectively).

In some embodiments, the biparatopic antibodies or antigen binding fragments thereof of the disclosure comprise the variable light chain and/or variable heavy chain of FR57 (e.g., SEQ ID NOs: 18 and/or 22, respectively) and the variable light chain and/or variable heavy chain of huMOV19 (e.g., SEQ ID NOs: 20 and/or 24, respectively).

In some embodiments, the biparatopic antibodies or antigen binding fragments thereof of the disclosure comprise the variable light chain and/or variable heavy chain of FR57 (e.g., SEQ ID NOs: 18 and/or 22, respectively) and the variable light chain and/or variable heavy chain of huMOV19 (e.g., SEQ ID NOs: 20 and/or 25, respectively).

In some embodiments, the biparatopic antibodies or antigen binding fragments thereof of the disclosure comprise the variable light chain and/or variable heavy chain of FR57 (e.g., SEQ ID NOs: 18 and/or 22, respectively) and the variable light chain and/or variable heavy chain of huMOV19 (e.g., SEQ ID NOs: 20 and/or 57, respectively).

In some embodiments, the biparatopic antibodies or antigen binding fragments thereof of the disclosure comprise the variable light chain and/or variable heavy chain of FR57 (e.g., SEQ ID NOs: 18 and/or 22, respectively) and the variable light chain and/or variable heavy chain of huMOV19 (e.g., SEQ ID NOs: 20 and/or 26, respectively).

In some embodiments, the biparatopic antibodies or antigen binding fragments thereof of the disclosure comprise the variable light chain and/or variable heavy chain of FR57 (e.g., SEQ ID NOs: 18 and/or 22, respectively) and the variable light chain and/or variable heavy chain of huMOV19 (e.g., SEQ ID NOs: 21 and/or 24, respectively).

In some embodiments, the biparatopic antibodies or antigen binding fragments thereof of the disclosure comprise the variable light chain and/or variable heavy chain of FR57 (e.g., SEQ ID NOs: 18 and/or 22, respectively) and the variable light chain and/or variable heavy chain of huMOV19 (e.g., SEQ ID NOs: 21 and/or 25, respectively). In some embodiments, the biparatopic antibodies or antigen binding fragments thereof of the disclosure comprise the variable light chain and/or variable heavy chain of FR57 (e.g., SEQ ID NOs: 18 and/or 22, respectively) and the variable light chain and/or variable heavy chain of huMOV19 (e.g., SEQ ID NOs: 21 and/or 57, respectively).

In some embodiments, the biparatopic antibodies or antigen binding fragments thereof of the disclosure comprise the variable light chain and/or variable heavy chain of FR57 (e.g., SEQ ID NOs: 18 and/or 22, respectively) and the variable light chain and/or variable heavy chain of huMOV19 (e.g., SEQ ID NOs: 21 and/or 26, respectively).

In some embodiments, the biparatopic antibodies or antigen binding fragments thereof of the disclosure comprise the variable light chain and/or variable heavy chain of FR57 (e.g., SEQ ID NOs: 18 and/or 23, respectively) and the variable light chain and/or variable heavy chain of huMOV19 (e.g., SEQ ID NOs: 19 and/or 24, respectively).

In some embodiments, the biparatopic antibodies or antigen binding fragments thereof of the disclosure comprise the variable light chain and/or variable heavy chain of FR57 (e.g., SEQ ID NOs: 18 and/or 23, respectively) and the variable light chain and/or variable heavy chain of huMOV19 (e.g., SEQ ID NOs: 19 and/or 25, respectively). In some embodiments, the biparatopic antibodies or antigen binding fragments thereof of the disclosure comprise the variable light chain and/or variable heavy chain of FR57 (e.g., SEQ ID NOs: 18 and/or 22, respectively) and the variable light chain and/or variable heavy chain of huMOV19 (e.g., SEQ ID NOs: 21 and/or 57, respectively).

In some embodiments, the biparatopic antibodies or antigen binding fragments thereof of the disclosure comprise the variable light chain and/or variable heavy chain of FR57 (e.g., SEQ ID NOs: 18 and/or 23, respectively) and the variable light chain and/or variable heavy chain of huMOV19 (e.g., SEQ ID NOs: 19 and/or 26, respectively).

In some embodiments, the biparatopic antibodies or antigen binding fragments thereof of the disclosure comprise the variable light chain and/or variable heavy chain of FR57 (e.g., SEQ ID NOs: 18 and/or 23, respectively) and the variable light chain and/or variable heavy chain of huMOV19 (e.g., SEQ ID NOs: 20 and/or 24, respectively).

In some embodiments, the biparatopic antibodies or antigen binding fragments thereof of the disclosure comprise the variable light chain and/or variable heavy chain of FR57 (e.g., SEQ ID NOs: 18 and/or 23, respectively) and the variable light chain and/or variable heavy chain of huMOV19 (e.g., SEQ ID NOs: 20 and/or 25, respectively).

In some embodiments, the biparatopic antibodies or antigen binding fragments thereof of the disclosure comprise the variable light chain and/or variable heavy chain of FR57 (e.g., SEQ ID NOs: 18 and/or 23, respectively) and the variable light chain and/or variable heavy chain of huMOV19 (e.g., SEQ ID NOs: 20 and/or 57, respectively).

In some embodiments, the biparatopic antibodies or antigen binding fragments thereof of the disclosure comprise the variable light chain and/or variable heavy chain of FR57 (e.g., SEQ ID NOs: 18 and/or 23, respectively) and the variable light chain and/or variable heavy chain of huMOV19 (e.g., SEQ ID NOs: 20 and/or 26, respectively).

In some embodiments, the biparatopic antibodies or antigen binding fragments thereof of the disclosure comprise the variable light chain and/or variable heavy chain of FR57 (e.g., SEQ ID NOs: 18 and/or 23, respectively) and the variable light chain and/or variable heavy chain of huMOV19 (e.g., SEQ ID NOs: 21 and/or 24, respectively).

In some embodiments, the biparatopic antibodies or antigen binding fragments thereof of the disclosure comprise the variable light chain and/or variable heavy chain of FR57 (e.g., SEQ ID NOs: 18 and/or 23, respectively) and the variable light chain and/or variable heavy chain of huMOV19 (e.g., SEQ ID NOs: 21 and/or 25, respectively).

In some embodiments, the biparatopic antibodies or antigen binding fragments thereof of the disclosure comprise the variable light chain and/or variable heavy chain of FR57 (e.g., SEQ ID NOs: 18 and/or 23, respectively) and the variable light chain and/or variable heavy chain of huMOV19 (e.g., SEQ ID NOs: 21 and/or 57, respectively).

In some embodiments, the biparatopic antibodies or antigen binding fragments thereof of the disclosure comprise the variable light chain and/or variable heavy chain of FR57 (e.g., SEQ ID NOs: 18 and/or 23, respectively) and the variable light chain and/or variable heavy chain of huMOV19 (e.g., SEQ ID NOs: 21 and/or 26, respectively).

In some embodiments, a biparatopic anti-FRα antibody or antigen binding fragment thereof comprises (i) an scFv that binds to the same epitope as FR57 and (ii) an scFv that binds to the same epitope as huMov19. In some embodiments, the biparatopic anti-FRα antibodies or antigen binding fragments thereof comprise SEQ ID NO:27 and SEQ ID NO:30. In some embodiments, the biparatopic anti-FRα antibodies or antigen binding fragments thereof comprise SEQ ID NO:27 and SEQ ID NO:31. In some embodiments, the biparatopic anti-FRα antibodies or antigen binding fragments thereof comprise SEQ ID NO:27 and SEQ ID NO:32.

In some embodiments, the anti-FRα biparatopic antibodies or antigen binding fragments thereof comprise SEQ ID NO:28 and SEQ ID NO:30. In some embodiments, the biparatopic anti-FRα antibodies or antigen binding fragments thereof comprise SEQ ID NO:28 and SEQ ID NO:31. In some embodiments, the anti-FRα biparatopic antibodies or antigen binding fragments thereof comprise SEQ ID NO:28 and SEQ ID NO:32.

In some embodiments, the biparatopic anti-FRα antibodies or antigen binding fragments thereof comprise SEQ ID NO:29 and SEQ ID NO:30. In some embodiments, the biparatopic anti-FRα antibodies or antigen binding fragments thereof comprise SEQ ID NO:29 and SEQ ID NO:31. In some embodiments, the biparatopic anti-FRα antibodies or antigen binding fragments thereof comprise SEQ ID NO:29 and SEQ ID NO:32.

It is to be understood that the VH and VL sequences for SEQ ID NOs: 27-32 could be arranged in a different order. For example, the N-terminus to C-terminus orientation as recited in SEQ ID NO:27 is VH-(G4S)₄-VL. However, disclosed herein are scFv polypeptide sequences in which orientations in which the VH and VL sequences are exchanged around the glycine-serine linker (e.g., VL-(G4S)₄-VH).

In some embodiments, the biparatopic anti-FRα antibodies or antigen binding fragments thereof comprise SEQ ID NO:27, SEQ ID NO:19, and SEQ ID NO:24. In some embodiments, the biparatopic anti-FRα antibodies or antigen binding fragments thereof comprise SEQ ID NO:27, SEQ ID NO:19, and SEQ ID NO:25. In some embodiments, the biparatopic anti-FRα antibodies or antigen binding fragments thereof comprise SEQ ID NO:27, SEQ ID NO:19, and SEQ ID NO:57. In some embodiments, the biparatopic anti-FRα antibodies or antigen binding fragments thereof comprise SEQ ID NO:27, SEQ ID NO:19, and SEQ ID NO:26.

In some embodiments, the biparatopic anti-FRα antibodies or antigen binding fragments thereof comprise SEQ ID NO:27, SEQ ID NO:20, and SEQ ID NO:24. In some embodiments, the biparatopic anti-FRα antibodies or antigen binding fragments thereof comprise SEQ ID NO:27, SEQ ID NO:20, and SEQ ID NO:25. In some embodiments, the biparatopic anti-FRα antibodies or antigen binding fragments thereof comprise SEQ ID NO:27, SEQ ID NO:20, and SEQ ID NO:57. In some embodiments, the biparatopic anti-FRα antibodies or antigen binding fragments thereof comprise SEQ ID NO:27, SEQ ID NO:20, and SEQ ID NO:26.

In some embodiments, a biparatopic anti-FRα antibody or antigen binding fragment thereof comprises (i) an scFv that binds to the same epitope as FR57 and (ii) an FRα-binding domain comprising a VH and VL on separate polypeptides that binds to the same epitope as huMov19. In some embodiments, the biparatopic anti-FRα antibodies or antigen binding fragments thereof comprise SEQ ID NO:27, SEQ ID NO:21, and SEQ ID NO:24. In some embodiments, the biparatopic anti-FRα antibodies or antigen binding fragments thereof comprise SEQ ID NO:27, SEQ ID NO:21, and SEQ ID NO:25. In some embodiments, the biparatopic anti-FRα antibodies or antigen binding fragments thereof comprise SEQ ID NO:27, SEQ ID NO:21, and SEQ ID NO:57. In some embodiments, the biparatopic anti-FRα antibodies or antigen binding fragments thereof comprise SEQ ID NO:27, SEQ ID NO:21, and SEQ ID NO:26.

In some embodiments, the biparatopic anti-FRα antibodies or antigen binding fragments thereof comprise SEQ ID NO:28, SEQ ID NO:19, and SEQ ID NO:24. In some embodiments, the biparatopic anti-FRα antibodies or antigen binding fragments thereof comprise SEQ ID NO:28, SEQ ID NO:19, and SEQ ID NO:25. In some embodiments, the biparatopic anti-FRα antibodies or antigen binding fragments thereof comprise SEQ ID NO:28, SEQ ID NO:19, and SEQ ID NO:57. In some embodiments, the biparatopic anti-FRα antibodies or antigen binding fragments thereof comprise SEQ ID NO:28, SEQ ID NO:19, and SEQ ID NO:26.

In some embodiments, the biparatopic anti-FRα antibodies or antigen binding fragments thereof comprise SEQ ID NO:28, SEQ ID NO:20, and SEQ ID NO:24. In some embodiments, the biparatopic anti-FRα antibodies or antigen binding fragments thereof comprise SEQ ID NO:28, SEQ ID NO:20, and SEQ ID NO:25. In some embodiments, the biparatopic anti-FRα antibodies or antigen binding fragments thereof comprise SEQ ID NO:28, SEQ ID NO:20, and SEQ ID NO:57. In some embodiments, the biparatopic anti-FRα antibodies or antigen binding fragments thereof comprise SEQ ID NO:28, SEQ ID NO:20, and SEQ ID NO:26.

In some embodiments, the biparatopic anti-FRα antibodies or antigen binding fragments thereof comprise SEQ ID NO:28, SEQ ID NO:21, and SEQ ID NO:24. In some embodiments, the biparatopic anti-FRα antibodies or antigen binding fragments thereof comprise SEQ ID NO:28, SEQ ID NO:21, and SEQ ID NO:25. In some embodiments, the biparatopic anti-FRα antibodies or antigen binding fragments thereof comprise SEQ ID NO:28, SEQ ID NO:21, and SEQ ID NO:57. In some embodiments, the biparatopic anti-FRα antibodies or antigen binding fragments thereof comprise SEQ ID NO:28, SEQ ID NO:21, and SEQ ID NO:26.

In some embodiments, the biparatopic anti-FRα antibodies or antigen binding fragments thereof comprise SEQ ID NO:29, SEQ ID NO:19, and SEQ ID NO:24. In some embodiments, the biparatopic anti-FRα antibodies or antigen binding fragments thereof comprise SEQ ID NO:29, SEQ ID NO:19, and SEQ ID NO:25. In some embodiments, the biparatopic anti-FRα antibodies or antigen binding fragments thereof comprise SEQ ID NO:29, SEQ ID NO:19, and SEQ ID NO:57. In some embodiments, the biparatopic anti-FRα antibodies or antigen binding fragments thereof comprise SEQ ID NO:29, SEQ ID NO:19, and SEQ ID NO:26.

In some embodiments, the biparatopic anti-FRα antibodies or antigen binding fragments thereof comprise SEQ ID NO:29, SEQ ID NO:20, and SEQ ID NO:24. In some embodiments, the biparatopic anti-FRα antibodies or antigen binding fragments thereof comprise SEQ ID NO:29, SEQ ID NO:20, and SEQ ID NO:25. In some embodiments, the biparatopic anti-FRα antibodies or antigen binding fragments thereof comprise SEQ ID NO:29, SEQ ID NO:20, and SEQ ID NO:57. In some embodiments, the biparatopic anti-FRα antibodies or antigen binding fragments thereof comprise SEQ ID NO:29, SEQ ID NO:20, and SEQ ID NO:26.

In some embodiments, the biparatopic anti-FRα antibodies or antigen binding fragments thereof comprise SEQ ID NO:29, SEQ ID NO:21, and SEQ ID NO:24. In some embodiments, the biparatopic anti-FRα antibodies or antigen binding fragments thereof comprise SEQ ID NO:29, SEQ ID NO:21, and SEQ ID NO:25. In some embodiments, the biparatopic anti-FRα antibodies or antigen binding fragments thereof comprise SEQ ID NO:29, SEQ ID NO:21, and SEQ ID NO:57. In some embodiments, the biparatopic anti-FRα antibodies or antigen binding fragments thereof comprise SEQ ID NO:29, SEQ ID NO:21, and SEQ ID NO:26.

In some embodiments, a biparatopic anti-FRα antibody or antigen binding fragment thereof comprises (i) an scFv that binds to the same epitope as huMov19 and (ii) an FRα-binding domain comprising a VH and VL on separate polypeptides that binds to the same epitope as FR57. In some embodiments, the biparatopic anti-FRα antibodies or antigen binding fragments thereof comprise SEQ ID NO:30, SEQ ID NO:17, and SEQ ID NO:22. In some embodiments, the biparatopic anti-FRα antibodies or antigen binding fragments thereof comprise SEQ ID NO:30, SEQ ID NO:17, and SEQ ID NO:23.

In some embodiments, the biparatopic anti-FRα antibodies or antigen binding fragments thereof comprise SEQ ID NO:30, SEQ ID NO:18, and SEQ ID NO:22. In some embodiments, the biparatopic anti-FRα antibodies or antigen binding fragments thereof comprise SEQ ID NO:30, SEQ ID NO:18, and SEQ ID NO:23.

In some embodiments, a biparatopic anti-FRα antibody or antigen binding fragment thereof comprises (i) an scFv that binds to the same epitope as huMov19 and (ii) an FRα-binding domain comprising a VH and VL on separate polypeptides that binds to the same epitope as FR57. In some embodiments, the biparatopic anti-FRα antibodies or antigen binding fragments thereof comprise SEQ ID NO:31, SEQ ID NO:18, and SEQ ID NO:22. In some embodiments, the biparatopic anti-FRα antibodies or antigen binding fragments thereof comprise SEQ ID NO:31, SEQ ID NO:18, and SEQ ID NO:23.

In some embodiments, the biparatopic anti-FRα antibodies or antigen binding fragments thereof comprise SEQ ID NO:31, SEQ ID NO:17, and SEQ ID NO:22. In some embodiments, the biparatopic anti-FRα antibodies or antigen binding fragments thereof comprise SEQ ID NO:31, SEQ ID NO:17, and SEQ ID NO:23.

In some embodiments, the biparatopic anti-FRα antibodies or antigen binding fragments thereof comprise SEQ ID NO:32, SEQ ID NO:17, and SEQ ID NO:22. In some embodiments, the biparatopic anti-FRα antibodies or antigen binding fragments thereof comprise SEQ ID NO:32, SEQ ID NO:17, and SEQ ID NO:23.

In some embodiments, the biparatopic anti-FRα antibodies or antigen binding fragments thereof comprise SEQ ID NO:32, SEQ ID NO:18, and SEQ ID NO:22. In some embodiments, the biparatopic anti-FRα antibodies or antigen binding fragments thereof comprise SEQ ID NO:32, SEQ ID NO:18, and SEQ ID NO:23.

In some embodiments, the biparatopic antibodies or antigen binding fragments thereof comprise polypeptide sequences disclosed in Table 6 below.

TABLE 6

| Morrison format (C-terminus scFv) Fusion Proteins | | |
|---|---|---|
| | Name | scFv Sequences |
| Molecule-1: mov19-IgG1-FR57scFv1 | mov19-IgG1-FR57scFv-HC | QVQLVQSGAEVVKPGASVKISCKASGYTFTGYFMNW VKQSPGQSLEWIGRIHPYDGDTFYNQKFQGKATLTV DKSSNTAHMELLSLTSEDFAVYYCTRYDGSRAMDYW GQGTTVTVSSASTKGPSVFPLAPSSKSTSGGTAALG CLVKDYFPEPVTVSWNSGALTSGVHTFPAVLQSSGL YSLSSVVTVPSSSLGTQTYICNVNHKPSNTKVDKKV EPKSCDKTHTCPPCPAPELLGGPSVFLFPPKPKDTL MISRTPEVTCVVVDVSHEDPEVKFNWYVDGVEVHNA KTKPREEQYNSTYRVVSVLTVLHQDWLNGKEYKCKV SNKALPAPIEKTISKAKGQPREPQVYTLPPSRDELT KNQVSLTCLVKGFYPSDIAVEWESNGQPENNYKTTP PVLDSDGSFFLYSKLTVDKSRWQQGNVFScSVMHEA LHNHYTQKSLSLSPGSGGGGSGGGGSGGGGSEVQLV ESGGGLVQPGGSRRLSCAASGFTFSSFGMHWVRQAP GKGLEWVAYISSGSSTISYADSVKGRFTISRDNSKK TLLLQMTSLRAEDTAMYYCAREAYGSSMEYWGQGTL VTVSSGGGGSGGGGSGGGGSGGGGSEIVLTQSPATL SVTPGDRVSLSCRASQNINNNLHWYQQKPGQSPRLL IKYVSQSVSGIPDRFSGSGSGTDFTLSISSVEPEDE GMYECQQSNSWPHYTFGQGTKLEIKRT(SEQ ID NO: 33) |
| | huMov19LC | DIVLTQSPLSLAVSLGQPAIISCKASQSVSFAGTSL MHWYHQKPGQQPRLLIYRASNLEAGVPDRFSGSGSK TDFTLTISPVEAEDAATYYCQQSREYPYTFGGGTKL EIKRTVAAPSVFIEPPSDEQLKSGTASVVCLLNNFY PREAKVQWKVDNALQSGNSQESVTEQDSKDSTYSLS STLTLSKADYEKHKVYACEVTHQGLSSPVTKSFNRG EC(SEQ ID NO: 34) |
| Molecule 2: FR57-IgG1-mov19scFv1 | FR57-IgG1-mov19scFv1-HC | EVQLVESGGGLVQPGGSRRLSCAASGFTFSSFGMHW VRQAPGKGLEWVAYISSGSSTISYADSVKGRFTISR DNSKKTLLLQMTSLRAEDTAMYYCAREAYGSSMEYW GQGTLVTVSSASTKGPSVFPLAPSSKSTSGGTAALG CLVKDYFPEPVTVSWNSGALTSGVHTFPAVLQSSGL YSLSSVVTVPSSSLGTQTYICNVNHKPSNTKVDKKV EPKSCDKTHTCPPCPAPELLGGPSVELEPPKPKDTL MISRTPEVTCVVVDVSHEDPEVKFNWYVDGVEVHNA KTKPREEQYNSTYRVVSVLTVLHQDWLNGKEYKCKV SNKALPAPIEKTISKAKGQPREPQVYTLPPSRDELT KNQVSLTCLVKGFYPSDIAVEWESNGQPENNYKTTP PVLDSDGSFFLYSKLTVDKSRWQQGNVFScSVMHEA LHNHYTQKSLSLSPGSGGGGSGGGGSGGGGSQVQLV QSGAEVVKPGASVKISCKASGYTFTGYFMNWVKQSP GQSLEWIGRIHPYDGDTEYNQKFQGKATLTVDKSSN TAHMELLSLTSEDFAVYYCTRYDGSRAMDYWGQGTT VTVSSGGGGSGGGGSGGGGSGGGGSDIVLTQSPLSL AVSLGQPAIISCKASQSVSFAGTSLMHWYHQKPGQQ PRLLIYRASNLEAGVPDRFSGSGSKTDFTLTISPVE AEDAATYYCQQSREYPYTFGGGTKLEIKRT(SEQ ID NO: 35) |
| | FR57LC | EIVLTQSPATLSVTPGDRVSLSCRASQNINNNLHWY QQKPGQSPRLLIKYVSQSVSGIPDRFSGSGSGTDFT |

TABLE 6-continued

Morrison format (C-terminus scFv) Fusion Proteins

| Name | scFv Sequences |
|---|---|
| | LSISSVEPEDFGMYFCQQSNSWPHYTFGQGTKLEIK<br>RTVAAPSVFIEPPSDEQLKSGTASVVCLLNNFYPRE<br>AKVQWKVDNALQSGNSQESVTEQDSKDSTYSLSSTL<br>TLSKADYEKHKVYACEVTHQGLSSPVTKSFNRGEC<br>(SEQ ID NO: 36) |
| Molecule 3: FR57scFv2-<br>FR57scFv2- mov19-IgG1-<br>mov19-IgG1 HC | EIVLTQSPATLSVTPGDRVSLSCRASQNINNNLHWY<br>QQKPGQSPRLLIKYVSQSVSGIPDRFSGSGSGTDFT<br>LSISSVEPEDEGMYFCQQSNSWPHYTFGCGTKLEIK<br>GGGGSGGGGSGGGGSGGGGSEVQLVQSGGGLVQPGG<br>SRRLSCAASGFTFSSFGMHWVRQAPGKCLEWVAYIS<br>SGSSTISYADSVKGRFTISRDNSKKTLLLQMTSLRA<br>EDTAMYYCAREAYGSSMEYWGQGTLVTVSSGGGGSG<br>GGGSGGGGSQVQLVQSGAEVVKPGASVKISCKASGY<br>TFTGYFMNWVKQSPGQSLEWIGRIHPYDGDTFYNQK<br>FQGKATLTVDKSSNTAHMELLSLTSEDFAVYYCTRY<br>DGSRAMDYWGQGTTVTVSSASTKGPSVFPLAPSSKS<br>TSGGTAALGCLVKDYFPEPVTVSWNSGALTSGVHTF<br>PAVLQSSGLYSLSSVVTVPSSSLGTQTYICNVNHKP<br>SNTKVDKKVEPKSCDKTHTCPPCPAPELLGGPSVFL<br>FPPKPKDTLMISRTPEVTCVVVDVSHEDPEVKFNWY<br>VDGVEVHNAKTKPREEQYNSTYRVVSVLTVLHQDWL<br>NGKEYKCKVSNKALPAPIEKTISKAKGQPREPQVYT<br>LPPSRDELTKNQVSLTCLVKGFYPSDIAVEWESNGQ<br>PENNYKTTPPVLDSDGSFFLYSKLTVDKSRWQQGNV<br>FSCSVMHEALHNHYTQKSLSLSPG(SEQ ID NO:<br>37) |
| huMov19LCv1-6 | DIVLTQSPLSLAVSLGQPAIISCKASQSVSFAGTSL<br>MHWYHQKPGQQPRLLIYRASNLEAGVPDRFSGSGSK<br>TDFTLTISPVEAEDAATYYCQQSREYPYTFGGGTKL<br>EIKRTVAAPSVFIFPPSDEQLKSGTASVVCLLNNFY<br>PREAKVQWKVDNALQSGNSQESVTEQDSKDSTYSLS<br>STLTLSKADYEKHKVYACEVTHQGLSSPVTKSFNRG<br>EC(SEQ ID NO: 38) |
| Molecule 4: FR57scFv3wt-<br>FR57scFv3wt-mov19-IgG1-HC<br>mov19-IgG1 | EIVLTQSPATLSVTPGDRVSLSCRASQNINNNLHWY<br>QQKPGQSPRLLIKYVSQSVSGIPDRFSGSGSGTDFT<br>LSISSVEPEDFGMYFCQQSNSWPHYTFGQGTKLEIK<br>GGGGSGGGGSGGGGSGGGGSEVQLVESGGGLVQPGG<br>SRRLSCAASGFTFSSFGMHWVRQAPGKGLEWVAYIS<br>SGSSTISYADSVKGRFTISRDNSKKTLLLQMTSLRA<br>EDTAMYYCAREAYGSSMEYWGQGTLVTVSSGGGGSG<br>GGGSGGGGSQVQLVQSGAEVVKPGASVKISCKASGY<br>TFTGYFMNWVKQSPGQSLEWIGRIHPYDGDTFYNQK<br>FQGKATLTVDKSSNTAHMELLSLTSEDFAVYYCTRY<br>DGSRAMDYWGQGTTVTVSSASTKGPSVFPLAPSSKS<br>TSGGTAALGCLVKDYFPEPVTVSWNSGALTSGVHTF<br>PAVLQSSGLYSLSSVVTVPSSSLGTQTYICNVNHKP<br>SNTKVDKKVEPKSCDKTHTCPPCPAPELLGGPSVFL<br>FPPKPKDTLMISRTPEVTCVVVDVSHEDPEVKFNWY<br>VDGVEVHNAKTKPREEQYNSTYRVVSVLTVLHQDWL<br>NGKEYKCKVSNKALPAPIEKTISKAKGQPREPQVYT<br>LPPSRDELTKNQVSLTCLVKGFYPSDIAVEWESNGQ<br>PENNYKTTPPVLDSDGSFFLYSKLTVDKSRWQQGNV<br>FSCSVMHEALHNHYTQKSLSLSPG(SEQ ID NO:<br>39) |
| huMov19LCv1-6 | DIVLTQSPLSLAVSLGQPAIISCKASQSVSFAGTSL<br>MHWYHQKPGQQPRLLIYRASNLEAGVPDRFSGSGSK<br>TDFTLTISPVEAEDAATYYCQQSREYPYTFGGGTKL<br>EIKRTVAAPSVFIFPPSDEQLKSGTASVVCLLNNFY<br>PREAKVQWKVDNALQSGNSQESVTEQDSKDSTYSLS<br>STLTLSKADYEKHKVYACEVTHQGLSSPVTKSFNRG<br>EC(SEQ ID NO: 40) |

In some embodiments, a biparatopic anti-FRα antibody or antigen-binding fragment thereof comprises the polypeptide sequences of SEQ ID NO:33 and SEQ ID NO:34. In some embodiments, a biparatopic anti-FRα antibody or antigen-binding fragment thereof comprises the polypeptide sequences selected from SEQ ID NO:35 and SEQ ID NO:36. In some embodiments, a biparatopic anti-FRα antibody or antigen-binding fragment thereof comprises the polypeptide sequences selected from SEQ ID NO:37 and SEQ ID NO:38. In some embodiments, a biparatopic anti-FRα antibody or antigen-binding fragment thereof comprises the polypeptide sequences selected from SEQ ID NO:39 and SEQ ID NO:40.

In some embodiments, the biparatopic antibodies or antigen binding fragments thereof comprise polypeptide sequences disclosed in Table 7 below.

TABLE 7

Asymmetric-Fc molecules (Knob-in-hole)

| Name | Sequences |
| --- | --- |
| Molecule 5: FR57scFv2-Fc-knob (C220S, T366W) FR57scFv2-knob-Mov19-hole | EIVLTQSPATLSVTPGDRVSLSCRASQNINNNLHWYQ QKPGQSPRLLIKYVSQSVSGIPDRFSGSGSGTDFTLS ISSVEPEDEGMYFCQQSNSWPHYTFGCGTKLEIKGGG GSGGGGSGGGGSGGGGSEVQLVQSGGGLVQPGGSRRL SCAASGFTFSSFGMHWVRQAPGKCLEWVAYISSGSST ISYADSVKGRFTISRDNSKKTLLLQMTSLRAEDTAMY YCAREAYGSSMEYWGQGTLVTVSSGSEPKSSDKTHTC PPCPAPELLGGPSVFLFPPKPKDTLMISRTPEVTCVV VDVSHEDPEVKFNWYVDGVEVHNAKTKPREEQYNSTY RVVSVLTVLHQDWLNGKEYKCKVSNKALPAPIEKTIS KAKGQPREPQVYTLPPSREEMTKNQVSLWCLVKGFYP SDIAVEWESNGQPENNYKTTPPVLDSDGSFFLYSKLT VDKSRWQQGNVFSCSVMHEALHNHYTQKSLSLSPG (SEQ ID NO: 41) |
| Mov19-Fc-hole (T366S, L368A, Y407V) | QVQLVQSGAEVVKPGASVKISCKASGYTFTGYFMNWV KQSPGQSLEWIGRIHPYDGDTFYNQKFQGKATLTVDK SSNTAHMELLSLTSEDFAVYYCTRYDGSRAMDYWGQG TTVTVSSASTKGPSVFPLAPSSKSTSGGTAALGCLVK DYFPEPVTVSWNSGALTSGVHTFPAVLQSSGLYSLSS VVTVPSSSLGTQTYICNVNHKPSNTKVDKKVEPKSCD KTHTCPPCPAPELLGGPSVFLFPPKPKDTLMISRTPE VTCVVVDVSHEDPEVKFNWYVDGVEVHNAKTKPREEQ YNSTYRVVSVLTVLHQDWLNGKEYKCKVSNKALPAPI EKTISKAKGQPREPQVYTLPPSREEMTKNQVSLSCAV KGFYPSDIAVEWESNGQPENNYKTTPPVLDSDGSFFL VSKLTVDKSRWQQGNVFSCSVMHEALHNHYTQKSLSL SPG(SEQ ID NO: 42) |
| Mov19-LC | DIVLTQSPLSLAVSLGQPAIISCKASQSVSFAGTSLM HWYHQKPGQQPRLLIYRASNLEAGVPDRFSGSGSKTD FTLTISPVEAEDAATYYCQQSREYPYTFGGGTKLEIK RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC(SEQ ID NO: 43) |
| Molecule 6: FR57scFv3wt-Fc-knob (C220S, T366W) FR57scFv3wt-knob-Mov19-hole | EIVLTQSPATLSVTPGDRVSLSCRASQNINNNLHWYQ QKPGQSPRLLIKYVSQSVSGIPDRFSGSGSGTDFTLS ISSVEPEDFGMYFCQQSNSWPHYTFGQGTKLEIKGGG GSGGGGSGGGGSGGGGSEVQLVESGGGLVQPGGSRRL SCAASGFTFSSFGMHWVRQAPGKGLEWVAYISSGSST ISYADSVKGRFTISRDNSKKTLLLQMTSLRAEDTAMY YCAREAYGSSMEYWGQGTLVTVSSGSEPKSSDKTHTC PPCPAPELLGGPSVFLFPPKPKDTLMISRTPEVTCVV VDVSHEDPEVKFNWYVDGVEVHNAKTKPREEQYNSTY RVVSVLTVLHQDWLNGKEYKCKVSNKALPAPIEKTIS KAKGQPREPQVYTLPPSREEMTKNQVSLWCLVKGFYP SDIAVEWESNGQPENNYKTTPPVLDSDGSFFLYSKLT VDKSRWQQGNVFSCSVMHEALHNHYTQKSLSLSPG (SEQ ID NO: 44) |
| Mov19-Fc-hole (T366S, L368A, Y407V) | QVQLVQSGAEVVKPGASVKISCKASGYTFTGYFMNWV KQSPGQSLEWIGRIHPYDGDTFYNQKFQGKATLTVDK SSNTAHMELLSLTSEDFAVYYCTRYDGSRAMDYWGQG TTVTVSSASTKGPSVFPLAPSSKSTSGGTAALGCLVK DYFPEPVTVSWNSGALTSGVHTFPAVLQSSGLYSLSS VVTVPSSSLGTQTYICNVNHKPSNTKVDKKVEPKSCD KTHTCPPCPAPELLGGPSVFLFPPKPKDTLMISRTPE VTCVVVDVSHEDPEVKFNWYVDGVEVHNAKTKPREEQ YNSTYRVVSVLTVLHQDWLNGKEYKCKVSNKALPAPI EKTISKAKGQPREPQVYTLPPSREEMTKNQVSLSCAV KGFYPSDIAVEWESNGQPENNYKTTPPVLDSDGSFFL VSKLTVDKSRWQQGNVFScSVMHEALHNHYTQKSLSL SPG(SEQ ID NO: 45) |

TABLE 7-continued

Asymmetric-Fc molecules (Knob-in-hole)

| Name | Sequences |
|---|---|
| Mov19-LC | DIVLTQSPLSLAVSLGQPAIISCKASQSVSFAGTSLM<br>HWYHQKPGQQPRLLIYRASNLEAGVPDRFSGSGSKTD<br>FTLTISPVEAEDAATYYCQQSREYPYTFGGGTKLEIK<br>RTVAAPSVFIFPPSDEQLKSGTASVVCLLNNFYPREA<br>KVQWKVDNALQSGNSQESVTEQDSKDSTYSLSSTLTL<br>SKADYEKHKVYACEVTHQGLSSPVTKSFNRGEC (SEQ<br>ID NO: 46) |

In one embodiment, a biparatopic anti-FRα antibody or antigen-binding fragment thereof comprises the polypeptides of SEQ ID NOs: 41-43. In one embodiment, a biparatopic anti-FRα antibody or antigen-binding fragment thereof comprises the polypeptides of SEQ ID NOs: 44-46.

The biparatopic antibodies or antigen binding fragments thereof of the present disclosure can further comprise a linker. In some embodiments, the linker can link a first antibody or antigen binding fragment thereof to the second antibody or antigen binding fragment thereof from N-terminus to C-terminus. In other embodiments, the linker can link the second polypeptide to the first polypeptide from N-terminus to C-terminus.

In one embodiment, the biparatopic antibodies or antigen binding fragments thereof comprises a linker sequence located between the first peptide, antibody or antigen binding fragment thereof and the second peptide, antibody or antigen binding fragment thereof. The linker can be of any length and can comprise at least 1, 2, 3, 4, 5, 6, 7, 8, 9, 10, 11, 12, 13, 14, 15, 16, 17, 18, 19, 20, 25, 30, 31, 32, 33, 34, 35, 36, 37, 38, 39, 40, 50, or 60 or more amino acids. In other embodiments, a linker useful for the present disclosure has at least one amino acid and less than 100 amino acids, less than 90 amino acids, less than 80 amino acids, less than 70 amino acids, less than 60 amino acids, less than 50 amino acids, less than 40 amino acids, less than 30 amino acids, less than 20 amino acids, less than 19 amino acids, less than 18 amino acids, less than 17 amino acids, less than 16 amino acids, less than 15 amino acids, less than 14 amino acids, less than 13 amino acids, or less than 12 amino acids. In one embodiment, the linker sequence comprises glycine amino acid residues. In other instances, the linker sequence comprises a combination of glycine and serine amino acid residues.

In some embodiments, such glycine/serine linkers can comprises any combination of the amino acid residues, including, but not limited to, the peptide GGGS (SEQ ID NO:49) or GGGGS (SEQ ID NO:50) or repeats of the same, including 1, 2, 3, 4, 5, 6, 7, 8, 9, 10 or more repeats of these given peptides. The glycine/serine linkers disclosed herein comprises an amino acid sequence of $(GS)_n$, $(GGS)_n$, $(GGGS)_n$, $(GGGGS)_n$, or $(GGGGS)_n$, wherein n is an integer of 1, 2, 3, 4, 5, 6, 7, 8, 9, or 10. In one embodiment, the linker sequence is GGGGSGGGGSGGGGS (SEQ ID NO:51) (also noted as $(Gly_4Ser)_3$). In another embodiment, the linker sequence is GGGGSGGGGSGGGGSGGGGS (SEQ ID NO:52) (also noted as $(Gly_4Ser)_4$).

In some embodiments, the biparatopic anti-FRα antibody comprises an altered (e.g., mutated or engineered) Fc region. For example, in some aspects, the Fc region has been altered to reduce or enhance the effector functions of the antibody, alter serum half-life or other functional properties of the antibody. Reduction or elimination of effector function is desirable in certain cases, for example in the case of antibodies whose mechanism of action involves blocking or antagonism, but not killing of the cells bearing a target antigen. Increased effector function is generally desirable when directed to undesirable cells, such as tumor and foreign cells, where the FcγRs are expressed at low levels, for example, tumor-specific B cells with low levels of FcγRIIB (e.g., non-Hodgkin's lymphoma, CLL, and Burkitt's lymphoma). Immunoconjugates of the invention possessing such conferred or altered effector function activity are useful for the treatment and/or prevention of a disease, disorder or infection in which an enhanced efficacy of effector function activity is desired. In some aspects, the Fc region is an isotype selected from IgM, IgA, IgG, IgE, or other isotype.

Although the Fc Region of the biparatopic anti-FRα antibody or antigen-binding fragment may possess the ability to bind to one or more Fc receptors (e.g., FcγR(s)), in certain embodiments the antibody or antibody fragment comprises a variant Fc region having an altered binding to FcγRIA (CD64), FcγRIIA (CD32A), FcγRIIB (CD32B), FcγRIIIA (CD16a) or FcγRIIIB (CD16b) (relative to the binding exhibited by a wild-type Fc Region), e.g., will have enhanced binding to an activating receptor and/or will have substantially reduced or no ability to bind to inhibitory receptor(s). Thus, the Fc region of the biparatopic anti-FRα antibody or antigen-binding fragment may include some or all of the CH2 domain and/or some or all of the CH3 domain of a complete Fc region, or may comprise a variant CH2 and/or a variant CH3 sequence (that may include, for example, one or more insertions and/or one or more deletions with respect to the CH2 or CH3 domains of a complete Fc Region). Such Fc regions may comprise non-Fc polypeptide portions, or may comprise portions of non-naturally complete Fc regions, or may comprise non-naturally occurring orientations of CH2 and/or CH3 domains (such as, for example, two CH2 domains or two CH3 domains, or in the N-terminal to C-terminal direction, a CH3 domain linked to a CH2 domain, etc.).

Fc Region modifications identified as altering effector function are known in the art, including modifications that increase binding to activating receptors (e.g., FcγRIIA (CD16A) and reduce binding to inhibitory receptors (e.g., FcγRIM (CD32B) (see, e.g., Stavenhagen, et al., Cancer Res. 57(18):8882-8890 (2007)). Table 8 lists exemplary single, double, triple, quadruple and quintuple substitutions (numbering is that of the EU index as in Kabat, and substitutions are relative to the amino acid sequence of SEQ ID NO:59) of exemplary modification that increase binding to activating receptors and/or reduce binding to inhibitory receptors.

TABLE 8

Variations of Preferred Activating Fc Regions

Single-Site Variations

| | | | |
|---|---|---|---|
| F243L | R292G | D270E | R292P |
| Y300L | P396L | | |

Double-Site Variations

| | | | |
|---|---|---|---|
| F243L and R292P | F243L and Y300L | F243L and P396L | R292P and Y300L |
| D270E and P396L | R292P and V305I | P396L and Q419H | P247L and N421K |
| R292P and P396L | Y300L and P396L | R255L and P396L | R292P and P305I |
| K392T and P396L | | | |

Triple-Site Variations

| | |
|---|---|
| F243L, P247L and N421K | P247L, D270E and N421K |
| F243L, R292P and Y300L | R255L, D270E and P396L |
| F243L, R292P and V305I | D270E, G316D and R416G |
| F243L, R292P and P396L | D270E, K392T and P396L |
| F243L, Y300L and P396L | D270E, P396L and Q419H |
| V284M, R292L and K370N | R292P, Y300L and P396L |

Quadruple-Site Variations

| | |
|---|---|
| L234F, F243L, R292P and Y300L | F243L, P247L, D270E and N421K |
| L234F, F243L, R292P and Y300L | F243L, R255L, D270E and P396L |
| L235I, F243L, R292P and Y300L | F243L, D270E, G316D and R416G |
| L235Q, F243L, R292P and Y300L | F243L, D270E, K392T and P396L |
| P247L, D270E, Y300L and N421K | F243L, R292P, Y300L, and P396L |
| R255L, D270E, R292G and P396L | F243L, R292P, V305I and P396L |
| R255L, D270E, Y300L and P396L | F243L, D270E, P396L and Q419H |
| D270E, G316D, P396L and R416G | |

Quintuple-Site Variations

| | |
|---|---|
| L235V, F243L, R292P, Y300L and P396L | F243L, R292P, V305I, Y300L and P396L |
| L235P, F243L, R292P, Y300L and P396L | |

Exemplary variants of human IgG1 Fc Regions with reduced binding to CD32B and/or increased binding to CD16A contain F243L, R292P, Y300L, V305I, or P396L substitutions, wherein the numbering is that of the EU index as in Kabat. These amino acid substitutions may be present in a human IgG1 Fc Region in any combination. In one embodiment, the variant human IgG1 Fc Region contains a F243L, R292P and Y300L substitution. In another embodiment, the variant human IgG1 Fc Region contains a F243L, R292P, Y300L, V305I and P396L substitution.

In some embodiments, the biparatopic anti-FRα antibody or antigen-binding fragment comprises an immunoglobulin heavy chain constant region containing a modification that decreases effector function (see, e.g., Idusogie et al., *J. Immunol.* 166:2571-2575 (2001); Sazinsky et al., *PNAS USA* 105:20167-20172 (2008); Davis et al., *J. Rheumatol.* 34:2204-2210 (2007); Bolt et al., *Eur. J. Immunol.* 23:403-411 (1993); Alegre et al., *Transplantation* 57:1537-1543 (1994); Xu et al., *Cell Immunol.* 200:16-26 (2000); Cole et al., *Transplantation* 68:563-571 (1999); Hutchins et al., *PNAS USA* 92:11980-11984 (1995); Reddy et al., *J. Immunol.* 164:1925-1933 (2000); WO97/11971, and WO07/106585; U.S. Appl. Publ. 2007/0148167A1; McEarchern et al., *Blood* 109:1185-1192 (2007); Strohl, *Curr. Op. Biotechnol.* 20:685-691 (2009); and Kumagai et al., *J. Clin. Pharmacol.* 47:1489-1497 (2007), the contents of each of which is herein incorporated by reference in its entirety).

In some embodiments, it is preferred for the Fc region of the biparatopic anti-FRα antibody or antigen-binding fragment to exhibit decreased (or substantially no) binding to an effector receptor selected from the group consisting of: FcγRIA (CD64), FcγRIIA (CD32A)(allotypes R131 and H131), FcγRIIB (CD32B), FcγRIIIA (CD16a) (allotype V158 and F158) and FcγRIIIB (CD16b)(allotype FcγIIIb-NA1 and FcγIIIb-NA2); relative to the binding exhibited by the wild-type IgG Fc Region (SEQ ID NO:59). In some embodiments, the biparatopic anti-FRα antibody or antigen-binding fragment Fc region variant effector receptor binding affinity has been reduced to $\frac{1}{10}$ or less, $\frac{1}{50}$ or less, or $\frac{1}{100}$ or less as, compared to the binding affinity of the corresponding antibody or antibody binding fragment comprising the wild-type Fc region of the corresponding immunoglobulin.

In a specific embodiment, the biparatopic anti-FRα antibody or antigen-binding fragment comprises an IgG Fc region that exhibits reduced effector function (e.g., reduced ADCC) and comprise a modification at one or more amino acid positions selected from the group consisting of: 233, 234, 235, 236, 237, 238, 239, 265, 266, 267, 269, 270, 271, 295, 296, 297, 298, 300, 324, 325, 327, 328, 329, 331, and 332, wherein the amino acid position numbering is according to the EU index as set forth in Kabat. In one embodiment, the CH2-CH3 domain of the biparatopic anti-FRα antibody or antigen-binding fragment includes any 1, 2, 3, or 4 of the substitutions: L234A, L235A, D265A, N297Q, N297A, and N297G, wherein the numbering is that of the EU index as in Kabat. In another embodiment, the CH2-CH3 domains contain an N297Q substitution, an N297A substitution, or L234A and L235A substitutions, as these mutations abolish FcR binding. Alternatively, the biparatopic anti-FRα antibody or antigen-binding fragment comprises a CH2-CH3 domain of a naturally occurring Fc region that inherently exhibits decreased (or substantially no) binding to FcγRIIIA (CD16a) and/or reduced effector function (relative to the binding and effector function exhibited by the wild-type IgG1 Fc region (SEQ ID NO:59). In a specific embodiment, the Fc constant region of the biparatopic anti-FRα antibody comprises an IgG2 Fc region (SEQ ID NO:60) or an IgG4 Fc region (SEQ ID NO:61).

Since the N297A, N297G, N297Q, L234A, L235A and D265A substitutions abolish effector function, in circumstances in which effector function is desired, these substitutions would preferably not be employed.

A preferred IgG1 sequence for the CH2 and CH3 Domains of the Fc region-containing biparatopic anti-FRα antibody or antigen-binding fragment that has reduced or abolished effector function comprises the substitutions L234A/L235A (shown underlined) (SEQ ID NO:62):

```
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSRDELTK NQVSLTCLVK GFYPSDIAVE WESNGQPENN

YKTTPPVLDS DGSFFLYSKL TVDKSRWQQG NVFSCSVMHE

ALHNHYTQKS LSLSPG
```

A preferred IgG1 sequence for the CH2 and CH3 Domains of the Fc region-containing biparatopic anti-FRα antibody or antigen-binding fragment that has reduced or abolished effector function comprises the substitution N297A (shown underlined) (SEQ ID NO:63):

```
APELLGGPSV FLFPPKPKDT LMISRTPEVT CVVVDVSHED

PEVKFNWYVD GVEVHNAKTK PREEQYASTY RVVSVLTVLH

QDWLNGKEYK CKVSNKALPA PIEKTISKAK GQPREPQVYT

LPPSRDELTK NQVSLTCLVK GFYPSDIAVE WESNGQPENN

YKTTPPVLDS DGSFFLYSKL TVDKSRWQQG NVFSCSVMHE

ALHNHYTQKS LSLSPG
```

A preferred IgG1 sequence for the CH2 and CH3 Domains of the Fc region-containing biparatopic anti-FRα antibody or antigen-binding fragment that has reduced or abolished effector function comprises the substitution N297Q (shown underlined) (SEQ ID NO:64):

```
APELLGGPSV FLFPPKPKDT LMISRTPEVT CVVVDVSHED

PEVKFNWYVD GVEVHNAKTK PREEQYQSTY RVVSVLTVLH

QDWLNGKEYK CKVSNKALPA PIEKTISKAK GQPREPQVYT

LPPSRDELTK NQVSLTCLVK GFYPSDIAVE WESNGQPENN

YKTTPPVLDS DGSFFLYSKL TVDKSRWQQG NVFSCSVMHE

ALHNHYTQKS LSLSPG
```

In some embodiments, the biparatopic anti-FRα antibody or antigen-binding fragment comprises an Fc (immunoglobulin) sequence selected from SEQ ID NO: 62, SEQ ID NO: 63, or SEQ ID NO:64. In some embodiments, the biparatopic anti-FRα antibody or antigen-binding fragment comprises an Fc (immunoglobulin) sequence with reduced or abolished effector function (e.g., comprising the substitutions shown above in SEQ ID NO:62, SEQ ID NO:63, and/or SEQ ID NO:64) and comprises one or more knob-in-hole mutations as disclosed herein. In some embodiments, the Fc sequence comprises a knob mutation as disclosed herein. In some embodiments, the Fc sequence comprises a hole mutation as disclosed herein.

In some embodiments, the biparatopic anti-FRα antibody or antigen-binding fragment comprises one or more modifications corresponding to: IgG1-C220S, C226S, C229S, P238S; IgG1-C226S, C229S; IgG1-C226S, C229S, E233P, L234V, L235A; IgG1-L234A, L235A; IgG1-L234F, L235E, P331S; IgG1-L234F, L235E, P331S; IgG1-H268Q, A330S, P331S; IgG1-G236R, L328R; IgG1-L235G, G236R, IgG1-N297A; IgG1-N325A, L328R; IgG1-N325L, L328R; IgG1-K326W, E333S; IgG2-V234A, G237A; IgG2-E333S; IgG2 H268Q, V309L, A330S, A331S; IgG4-S228P, L236E; IgG4-F234A, L235A; IgG4-F234A, G237A, E318A; IgG4-L235A, G237A, E318A; IgG4-L236E; IgG2-EU sequence 118-260; and IgG4-EU sequence 261-447; wherein the position numbering is according to the EU index as in Kabat.

In some embodiments, the biparatopic anti-FRα antibody or antigen-binding fragment comprises a heavy chain immunoglobulin constant domain that has reduced CDC activity. In particular aspects, biparatopic anti-FRα antibody or antigen-binding fragment comprises an IgG1 heavy chain constant region containing a mutation that decreases CDC activity (see, e.g., WO 1997/11971 and WO 2007/106585; U.S. Appl. Publ. 2007/0148167A1; McEarchern et al., *Blood* 109:1185-1192 (2007); Hayden-Ledbetter et al., *Clin. Cancer* 15:2739-2746 (2009); Lazar et al., *PNAS USA* 103:4005-4010 (2006); Bruckheimer et al., *Neoplasia* 11:509-517 (2009); Strohl, *Curr. Op. Biotechnol.* 20:685-691 (2009); and Sazinsky et al., *PNAS USA* 105:20167-20172 (2008); each of which is herein incorporated by reference in its entirety). Examples of heavy chain constant domain sequence modifications that decrease CDC include one or more modifications corresponding to: IgG1-C226S, C229S, E233P, L234V, L235A; IgG1-C226S, P230S; IgG1-L234F, L235E, P331S; IgG1-S239D, A330L, I332E; IgG2 EU sequence 118-260; IgG4-EU sequence 261-447; and IgG2-H268Q, V309L, A330S, A331S, according to the EU index In some embodiments, the provided biparatopic anti-FRα antibody or antigen-binding fragment comprises a heavy chain immunoglobulin constant domain that contains one or more half-life extending amino acid modifications (e.g., substitutions). Numerous mutations capable of increasing the half-life of an Fc region-containing molecule are known in the art and are encompassed as components of the biparatopic anti-FRα antibody or antigen-binding fragments provided herein. See, e.g., U.S. Pat. Nos. 6,277,375; 7,083,784; 7,217,797, and 8,088,376; U.S. Publ. Nos. 2002/0147311; and 2007/0148164; and PCT Publication Nos. WO 1998/23289; WO 2009/058492; and WO 2010/033279, the contents of each of which is herein incorporated by reference in its entirety.

The serum half-life of proteins comprising Fc regions may be increased by increasing the binding affinity of the Fc Region for FcRn. The term "half-life" as used herein means a pharmacokinetic property of a molecule that is a measure of the mean survival time of the molecules following their administration. Half-life can be expressed as the time required to eliminate fifty percent (50%) of a known quantity of the molecule from a subject's (e.g., a human patient or other mammal) body or a specific compartment thereof, for example, as measured in serum, i.e., circulating half-life, or in other tissues. In general, an increase in half-life results in an increase in mean residence time (MRT) in circulation for the administered molecule.

In some embodiments, the biparatopic anti-FRα antibody or antigen-binding fragment comprises a half-life extending amino acid substitution at one or more positions selected from the group consisting of: 238, 250, 252, 254, 256, 257, 256, 265, 272, 286, 288, 303, 305, 307, 308, 309, 311, 312, 317, 340, 356, 360, 362, 376, 378, 380, 382, 413, 424, 428, 433, 434, 435, and 436, wherein the amino acid position numbering is according to the EU index. In some embodiments, the biparatopic anti-FRα antibody or antigen-binding fragment contains one or more amino acid substitutions of amino acid residues at positions 251-257, 285-290, 308-314, 385-389, and 428-436, wherein the amino acid position numbering is according to the EU index. In some embodiments, the biparatopic anti-FRα antibody or antigen-binding fragment contains one or more of a substitution of the amino acid at Kabat position 252 with Tyr, Phe, Trp, or Thr; a substitution of the amino acid at Kabat position 254 with Thr; a substitution of the amino acid at Kabat position 256 with Ser, Arg, Gln, Glu, Asp, or Thr; a substitution of the amino acid at Kabat position 257 with Leu; a substitution of the amino acid at Kabat position 309 with Pro; a substitution of the amino acid at Kabat position 311 with Ser; a substitution of the amino acid at Kabat position 428 with Thr, Leu, Phe, or Ser; a substitution of the amino acid at Kabat position 433 with Arg, Ser, Iso, Pro, or Gln; or a substitution of the amino acid at Kabat position 434 with Trp, Met, Ser, His, Phe, or Tyr. More specifically, the biparatopic anti-FRα antibody or antigen-binding fragment domain can contain amino acid substitutions relative to a wild-type human IgG constant domain including a substitution of the amino acid at Kabat position 252 with Tyr, a substitution of the amino acid at Kabat position 254 with Thr, and a substitution of the amino acid at Kabat position 256 with Glu.

In some embodiments, the biparatopic anti-FRα antibody or antigen-binding fragment comprises a least one substitution selected from: T250Q, M252Y, S254T, T256E, K288D, T307Q, V308P, A378V, M428L, N434A, N434S, N434H, N434Y, H435K, and Y436I, wherein the numbering is that of the EU index as in Kabat. In further embodiments, the biparatopic anti-FRα antibody or antigen-binding fragment comprises substitutions selected from: (a) M252Y, S254T and T256E; (b) M252Y and S254T; (c) M252Y and T256E; (d) T250Q and M428L; (e) T307Q and N434A; (f) A378V and N434A; (g) N434A and Y436I; (h) V308P and N434A; and (i) K288D and H435K.

In a preferred embodiment, the biparatopic anti-FRα antibody or antigen-binding fragment contains a variant IgG Fc Region comprising any 1, 2, or 3 of the substitutions: M252Y, S254T and T256E. The disclosure further provides biparatopic anti-FRα antibody or antigen-binding fragments possessing variant Fc regions comprising: (a) one or more mutations which alter effector function and/or FcγR; and (b) one or more mutations which extend serum half-life.

TABLE 9

Immunoglobulin Sequences

| | |
|---|---|
| Exemplary IgG1 Fc Region | APELLGGPSVFLFPPKPKDTLMISRTPEVTCVVVDVSHE DPEVKFNWYVDGVEVHNAKTKPREEQYNSTYRVVSVLTV LHQDWLNGKEYKCKVSNKALPAPIEKTISKAKGQPREPQ VYTLPPSRDELTKNQVSLTCLVKGFYPSDIAVEWESNGQ PENNYKTTPPVLDSDGSFFLYSKLTVDKSRWQQGNVFSC SVMHEALHNHYTQKSLSLSPG (SEQ ID NO: 59) |
| Exemplary IgG2 Fc Region | APPVAGPSVFLFPPKPKDTLMISRTPEVTCVVVDVSHED PEVQFNWYVDGVEVHNAKTKPREEQFNSTFRVVSVLTVV HQDWLNGKEYKCKVSNKGLPAPIEKTISKTKGQPREPQV YTLPPSREEMTKNQVSLTCLVKGFYPSDIAVEWESNGQP ENNYKTTPPMLDSDGSFFLYSKLTVDKSRWQQGNVFSCS VMHEALHNHYTQKSLSLSPG (SEQ ID NO: 60) |

TABLE 9-continued

Immunoglobulin Sequences

| | |
|---|---|
| Exemplary IgG4 Fc Region | APEFLGGPSVFLFPPKPKDTLMISRTPEVTCVVVDVSQE DPEVQFNWYVDGVEVHNAKTKPREEQFNSTYRVVSVLTV LHQDWLNGKEYKCKVSNKGLPSSIEKTISKAKGQPREPQ VYTLPPSQEEMTKNQVSLTCLVKGFYPSDIAVEWESNGQ PENNYKTTPPVLDSDGSFFLYSRLTVDKSRWQEGNVFSC SVMHEALHNHYTQKSLSLSLG (SEQ ID NO: 61) |
| Exemplary L234A/ L235A IgG1 Fc Region | APEAAGGPSVFLFPPKPKDTLMISRTPEVTCVVVDVSHE DPEVKFNWYVDGVEVHNAKTKPREEQYNSTYRVVSVLTV LHQDWLNGKEYKCKVSNKALPAPIEKTISKAKGQPREPQ VYTLPPSRDELTKNQVSLTCLVKGFYPSDIAVEWESNGQ PENNYKTTPPVLDSDGSFFLYSKLTVDKSRWQQGNVFSC SVMHEALHNHYTQKSLSLSPG (SEQ ID NO: 62) |
| Exemplary N297A IgG1 Fc Region | APELLGGPSVFLFPPKPKDTLMISRTPEVTCVVVDVSHE DPEVKFNWYVDGVEVHNAKTKPREEQYASTYRVVSVLTV LHQDWLNGKEYKCKVSNKALPAPIEKTISKAKGQPREPQ VYTLPPSRDELTKNQVSLTCLVKGFYPSDIAVEWESNGQ PENNYKTTPPVLDSDGSFFLYSKLTVDKSRWQQGNVFSC SVMHEALHNHYTQKSLSLSPG (SEQ ID NO: 63) |
| Exemplary N297Q IgG1 Fc Region | APELLGGPSVFLFPPKPKDTLMISRTPEVTCVVVDVSHE DPEVKFNWYVDGVEVHNAKTKPREEQYQSTYRVVSVLTV LHQDWLNGKEYKCKVSNKALPAPIEKTISKAKGQPREPQ VYTLPPSRDELTKNQVSLTCLVKGFYPSDIAVEWESNGQ PENNYKTTPPVLDSDGSFFLYSKLTVDKSRWQQGNVFSC SVMHEALHNHYTQKSLSLSPG (SEQ ID NO: 64) |

III. Biparatopic Antibody Production

Biparatopic antibodies or antigen binding fragments thereof that immunospecifically bind to FRα can be produced by any method known in the art for the synthesis of antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

Biparatopic antibodies or antigen binding fragments thereof as provided herein can be prepared by chemically linking two different monoclonal antibodies or by fusing two hybridoma cell lines to produce a hybrid-hybridoma.

In a specific embodiment, a biparatopic antibody or antigen binding fragment thereof described is prepared, expressed, created or isolated by any means that involves creation, e.g., via synthesis, genetic engineering of DNA sequences. In certain embodiments, such a biparatopic antibody or antigen binding fragment thereof comprises sequences (e.g., DNA sequences or amino acid sequences) that do not naturally exist within the antibody germline repertoire of an animal or mammal (e.g., human) in vivo.

Methods of making bispecific, bivalent antibodies or antigen binding fragments thereof, are described, for instance in U.S. Pat. Nos. 5,731,168, 5,807,706, 5,821,333, and U.S. Appl. Publ. Nos. 2003/020734 and 2002/0155537; each of which is herein incorporated by reference in its entirety. Bispecific tetravalent antibodies, and methods of making them are described, for instance, in Int. Appl. Publ. Nos. WO02/096948 and WO00/44788, the disclosures of both of which are herein incorporated by reference in its entirety. See generally, Int. Appl. Publ. Nos. WO93/17715, WO92/08802, WO91/00360, and WO92/05793; Tutt et al., J. Immunol. 147:60-69 (1991); U.S. Pat. Nos. 4,474,893; 4,714,681; 4,925,648; 5,573,920; and 5,601,819; and Kostelny et al., J. Immunol. 148:1547-1553 (1992); each of which is herein incorporated by reference in its entirety.

One method for generating bispecific antibodies has been termed the "knobs-into-holes" strategy (see, e.g., Intl. Publ. WO2006/028936). The mispairing of Ig heavy chains is reduced in this technology by mutating selected amino acids forming the interface of the CH3 domains in IgG. At positions within the CH3 domain at which the two heavy chains interact directly, an amino acid with a small side chain (hole) is introduced into the sequence of one heavy chain and an amino acid with a large side chain (knob) into the counterpart interacting residue location on the other heavy chain. In some embodiments, compositions of the invention have immunoglobulin chains in which the CH3 domains have been modified by mutating selected amino acids that interact at the interface between two polypeptides so as to preferentially form a bispecific antibody. The bispecific antibodies can be composed of immunoglobulin chains of the same subclass (e.g., IgG1 or IgG3) or different subclasses (e.g., IgG1 and IgG3, or IgG3 and IgG4).

In one embodiment, a biparatopic antibody or antigen binding fragment thereof comprises a T366W mutation in the "knobs chain" and T366S, L368A, Y407V mutations in the "hole chain," and optionally an additional interchain disulfide bridge between the CH3 domains by, e.g., introducing a Y349C mutation into the "knobs chain" and a E356C mutation or a S354C mutation into the "hole chain;" R409D, K370E mutations in the "knobs chain" and D399K, E357K mutations in the "hole chain;" a T366W mutation in the "knobs chain" and T366S, L368A, Y407V mutations in the "hole chain;" R409D, K370E mutations in the "knobs chain" and D399K, E357K mutations in the "hole chain;" Y349C, T366W mutations in one of the chains and E356C, T366S, L368A, Y407V mutations in the counterpart chain; and Y349C, T366W mutations in one chain and S354C, T366S, L368A, Y407V mutations in the counterpart chain (numbering according to the EU numbering system).

A bispecific antibody as described herein can also be generated according to the DuoBody technology platform (Genmab A/S) as described, e.g., in International Publication Nos. WO 2011/131746, WO 2011/147986, WO 2008/119353, and WO 2013/060867, and in Labrijn A F et al., (2013) PNAS 110(13): 5145-5150. The DuoBody technology can be used to combine one half of a first FRα-binding domain containing two heavy and two light chains with one half of a second FRα-binding domain containing two heavy and two light chains. The resultant heterodimer contains one heavy chain and one light chain from the first FRα-binding domain paired with one heavy chain and one light chain from the second FRα-binding domain.

Biparatopic antibodies or antigen binding fragments thereof, in some instances, contain IgG4 and IgG1, IgG4 and IgG2, IgG4 and IgG2, IgG4 and IgG3, or IgG1 and IgG3 chain heterodimers. Such heterodimeric heavy chain antibodies, can routinely be engineered by, for example, modifying selected amino acids forming the interface of the CH3 domains in human IgG4 and the IgG1 or IgG3 so as to favor heterodimeric heavy chain formation.

In particular embodiments, a biparatopic antibody or antigen binding fragment thereof can comprise chimeric FRα-binding domains or humanized FRα-binding domains. In certain embodiments, a biparatopic antibody or antigen binding fragment thereof can be a F(ab')2 fragment. A F(ab')2 fragment contains the two antigen-binding arms of a tetrameric antibody molecule linked by disulfide bonds in the hinge region.

Biparatopic antibodies or antigen binding fragments thereof described herein can be generated by any technique known to those of skill in the art. For example, F(ab')2 fragments described herein can be produced by proteolytic cleavage of immunoglobulin molecules, using enzymes such as pepsin.

In a certain aspect, provided herein is a method of making biparatopic antibody or antigen binding fragment thereof comprising culturing a cell or cells described herein. In a certain aspect, provided herein is a method of making a biparatopic antibody or antigen binding fragment thereof comprising expressing (e.g., recombinantly expressing) the antibody or antigen-binding fragment using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody or antigen-binding fragment obtained from the cell or host cell.

FRα-binding domains can be prepared, e.g., from monoclonal antibodies, using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981). The term "monoclonal antibody" as used herein is not limited to antibodies produced through hybridoma technology. For example, monoclonal antibodies can be produced recombinantly from host cells exogenously expressing an antibody described herein. Monoclonal antibodies described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

Further, the FRα-binding domains described herein can also be generated using various phage display methods known in the art. In phage display methods, proteins are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antibody or fragment that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108.

As described in the above references, after phage selection, the antibody coding regions from the phage can be isolated and used to generate FRα-binding domains, including human FRα-binding domains, and expressed in any desired host, including mammalian cells, insect cells, plant cells, yeast, and bacteria, e.g., as described below. Techniques to recombinantly produce FRα-binding domains such as Fab, Fab' and F(ab')2 fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043.

In one aspect, to generate FRα-binding domains or antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express antibodies, e.g., IgG, using techniques known to those of skill in the art.

IV. Polynucleotides Encoding Biparatopic Antibodies

In certain embodiments, the disclosure encompasses polynucleotides comprising a nucleic acid that encodes a biparatopic anti-FRα antibody or antigen binding fragment thereof, or a domain of such an antibody or fragment, e.g., a VH, a VL, a VH with a VL (e.g., in an scFv), a heavy chain, a light chain, a heavy chain with an scFv, a light chain with an scFv, a constant region, or a constant region with an scFv.

Accordingly, provided herein are polynucleotides encoding SEQ ID NOs:17-40. Also provided herein are compositions comprising combinations of polynucleotides encoding any biparatopic anti-FRα antibody or antigen-binding fragment thereof (e.g., a composition comprising a polynucleotide encoding SEQ ID NO:17 and a polynucleotide encoding SEQ ID NO:22, a composition comprising a polynucleotide encoding SEQ ID NO:18 and a polynucleotide encoding SEQ ID NO:23, a composition comprising a polynucleotide encoding SEQ ID NO:19 and a polynucleotide encoding SEQ ID NO:24, a composition comprising a polynucleotide encoding SEQ ID NO:20 and a polynucleotide encoding SEQ ID NO:25, a composition comprising a polynucleotide encoding SEQ ID NO:21 and a polynucleotide encoding SEQ ID NO:26, a composition comprising a polynucleotide encoding SEQ ID NO:33 and a polynucleotide encoding SEQ ID NO:34, a composition comprising a polynucleotide encoding SEQ ID NO:35 and a polynucleotide encoding SEQ ID NO:36, a composition comprising a polynucleotide encoding SEQ ID NO:37 and a polynucleotide encoding SEQ ID NO:38, a composition comprising a polynucleotide encoding SEQ ID NO:39 and a polynucleotide encoding SEQ ID NO:40, a composition comprising a polynucleotide encoding SEQ ID NO:41, a polynucleotide encoding SEQ ID NO:42, and a polynucleotide encoding SEQ ID NO:43, or a composition comprising a polynucleotide encoding SEQ ID NO:44, a polynucleotide encoding SEQ ID NO:45, and a polynucleotide encoding SEQ ID NO:46.) Also provided herein are compositions comprising combinations of polynucleotides encoding any biparatopic anti-FRα antibody or antigen-binding fragment thereof (e.g., a composition comprising a polynucleotide encoding SEQ ID NO:20 and a polynucleotide encoding SEQ ID NO:57.)

In certain embodiments, the biparatopic anti-FRα antibody or antigen binding fragment thereof is encoded by the plasmids deposited with the American Type Culture Collection (ATCC), located at 10801 University Boulevard, Manassas, Va. 20110 under the terms of the Budapest Treaty and having ATCC deposit nos. PTA-10774 (deposited in Apr. 7, 2010), PTA-125915 ("Mov19-Fc-hole"; deposited to the ATCC on Apr. 29, 2019 and received by the ATCC on Apr. 30, 2019), and PTA-125916 ("FR57scFv2-Fc-knob"; deposited to the ATCC on Apr. 29, 2019 and received by the ATCC on Apr. 30, 2019).

The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand. In some embodiments, the polynucleotide is a cDNA or a DNA lacking one more endogenous introns.

In some embodiments, a polynucleotide is a non-naturally occurring polynucleotide. In some embodiments, a polynucleotide is recombinantly produced.

In certain embodiments, the polynucleotides are isolated. In certain embodiments, the polynucleotides are substantially pure. In some embodiments, a polynucleotide is purified from natural components.

In some embodiments, a polynucleotide provided herein is codon optimized for expression in a particular host (change codons in the human mRNA to those preferred by a bacterial host such as *E. coli*).

V. Cells and Vectors

Vectors and cells comprising the polynucleotides described herein are also provided.

In certain aspects, provided herein are cells (e.g., host cells) expressing (e.g., recombinantly) antibodies, antigen binding fragments thereof described herein which specifically bind to FRα and comprising related polynucleotides and expression vectors. Provided herein are vectors (e.g., expression vectors) comprising polynucleotides comprising nucleotide sequences encoding anti-FRα antibodies or a fragment thereof for recombinant expression in host cells, preferably in mammalian cells. Also provided herein are host cells comprising such vectors for recombinantly expressing anti-FRα antibodies or antigen-binding fragment thereof described herein. In a particular aspect, provided herein are methods for producing an antibody or antigen binding fragments thereof described herein, comprising expressing such antibody or antigen binding fragments thereof in a host cell.

Recombinant expression of an antibody or antigen binding fragment thereof described herein involves construction of an expression vector containing a polynucleotide that encodes the antibody or a fragment thereof (e.g., a heavy or light chain), a fusion protein comprising a heavy or light chain (e.g., a heavy or light chain fused to one or more variable domains (e.g., an scFv)), a variable domain, a polypeptide comprising a VH and a VL (e.g., scFv), a constant domain, and/or a fusion protein comprising a constant domain (e.g., a constant domain fused to one or more variable domains (e.g., an ScFv)). Once a polynucleotide encoding an antibody or a fragment thereof described herein has been obtained, the vector for the production of the antibody or a fragment thereof can be produced by recombinant DNA technology using techniques well known in the art. Thus, methods for preparing a protein by expressing a polynucleotide a nucleotide sequence encoding an antibody or fragment thereof are described herein. Methods which are well known to those skilled in the art can be used to construct expression vectors containing coding sequences for an antibody or a fragment thereof and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody or a fragment thereof, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464), and variable domains of the antibody can be cloned into such a vector for expression of the entire heavy, the entire light chain, or both the entire heavy and light chains. A nucleotide sequence encoding an additional variable domain or an FRα-binding domain (e.g., scFv) can also be cloned into such a vector for expression of fusion proteins comprising a heavy or light chain fused to an FRα-binding domain or fragment (e.g., VH or VL) thereof.

An expression vector can be transferred to a cell (e.g., host cell) by conventional techniques and the resulting cells can then be cultured by conventional techniques to produce an antibody or fragment (e.g., a heavy or light chain, a fusion protein comprising a heavy or light chain (e.g., a heavy or light chain fused to one or more variable domains (e.g., an scFv), a variable domain, a polypeptide comprising a VH and a VL (e.g., scFv), a constant domain, and/or a fusion protein comprising a constant domain (e.g., a constant domain fused to one or more variable domains (e.g., an ScFv) described herein. Thus, provided herein are host cells containing a polynucleotide encoding an antibody or a fragment thereof described herein operably linked to a promoter for expression of such sequences in the host cell.

In certain embodiments, for the expression of multiple-chained antibodies, vectors encoding all of chains, individually, can be co-expressed in the host cell for expression of the entire immunoglobulin molecule.

In certain embodiments, a host cell contains a vector comprising polynucleotides encoding all of the chains of an antibody or antigen binding fragment thereof described herein. In specific embodiments, a host cell contains multiple different vectors encoding all of the chains of an antibody or antigen binding fragment thereof described herein.

A vector or combination of vectors can comprise polynucleotides encoding two polypeptides that interact to form an antibody or antigen binding fragment thereof described herein: e.g., a first polynucleotide encoding a fusion protein comprising a heavy chain and an scFv with a second polynucleotide encoding a light chain; a first polynucleotide encoding a fusion protein comprising a light chain and an scFv with a second polynucleotide encoding a heavy chain; a first polynucleotide encoding a fusion protein comprising a heavy chain and a VH with a second polynucleotide encoding a fusion protein comprising a light chain and a VL, etc. Where the two polypeptides are encoded by polynucleotides in two separate vectors, the vectors can be transfected into a host cell at a ratio of 3 polynucleotides encoding a fusion protein comprising a heavy chain: 1 polynucleotide encoding a fusion protein comprising a light chain.

A vector or combination of vectors can comprise polynucleotides encoding three polypeptides that interact to form an antibody or antigen binding fragment thereof described herein: e.g., a first polynucleotide encoding a heavy chain, a second polynucleotide encoding a light chain, and a third polynucleotide encoding a fusion protein comprising a heavy chain constant domain, a VH, and a VL (optionally wherein the VH and VL are an scFv). Where the three polypeptides are encoded by polynucleotides in three separate vectors, the vectors can be transfected into a host cell at a ratio of 6 polynucleotides encoding a heavy chain: 3 polynucleotides encoding a light chain: 1 polynucleotide encoding a fusion protein.

A vector or combination of vectors can comprise polynucleotides encoding four polypeptides that interact to form an antibody or antigen binding fragment thereof described herein: e.g., a first polynucleotide encoding a first heavy chain, a second polynucleotide encoding a second heavy chain, a third polynucleotide encoding a first light chain, and fourth polynucleotide encoding a second light chain.

In some embodiments a host cell comprises the vector or combination of vectors described above. In other embodiments, two host cells, three host cells, or four host cells comprise the vector or combination of vectors described above.

A variety of host-expression vector systems can be utilized to express antibody molecules or fragments thereof (e.g., a heavy or light chain, a fusion protein comprising a heavy or light chain (e.g., a heavy or light chain fused to one or more variable domains (e.g., an scFv), a variable domain, a polypeptide comprising a VH and a VL (e.g., scFv), a constant domain, and/or a fusion protein comprising a constant domain (e.g., a constant domain fused to one or more variable domains (e.g., an ScFv) described herein. Such host-expression systems represent vehicles by which the coding sequences of interest can be produced and subsequently purified, but also represent cells which can, when transformed or transfected with the appropriate nucleotide coding sequences, express an antibody or fragment thereof described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccha-* romyces *Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NSO, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein or an antigen-binding fragment thereof are CHO cells, for example CHO cells from the CHO GS System™ (Lonza). In a specific embodiment, the expression of nucleotide sequences encoding antibodies described herein which immunospecifically bind FRα (e.g., human FRα) is regulated by a constitutive promoter, inducible promoter or tissue specific promoter.

Once an antibody molecule or a fragment thereof (e.g., a heavy or light chain, a variable domain, and/or a polypeptide comprising a VH and a VL (e.g., scFv)) described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

VI. Immunoconjugates Containing Biparatopic Antibodies

In one aspect, the present disclosure relates to immunoconjugates comprising a biparatopic FRα-binding agent (e.g., an antibody or an antigen-binding fragment thereof) described herein and a cytotoxic agent. The cytotoxic agent may be coupled or conjugated either directly to the FRα-binding agent or indirectly, through a linker using techniques known in the art to produce an "immunoconjugate," "conjugate," or "ADC."

A. Exemplary Immunoconjugates

In a first embodiment, an immunoconjugate provided herein comprises a biparatopic FRα antibody or antigen binding fragment thereof described herein covalently linked to a maytansinoid compound described herein through the ε-amino group of one or more lysine residues located on the biparatopic FRα antibody or antigen binding fragment thereof. In one embodiment, the immunoconjugate is represented by formula (I):

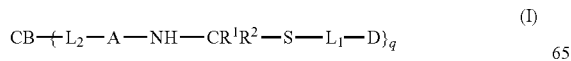

or a pharmaceutically acceptable salt thereof, wherein:

CB is a biparatopic anti-FRα antibody or antigen binding fragment thereof;

$L_2$ is represented by one of the following formula:

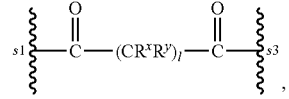
(L2a)

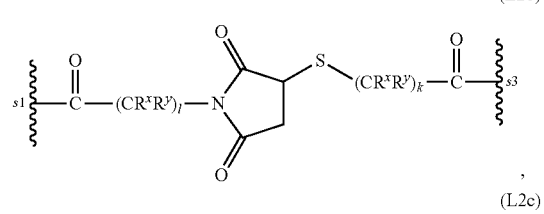
(L2b)

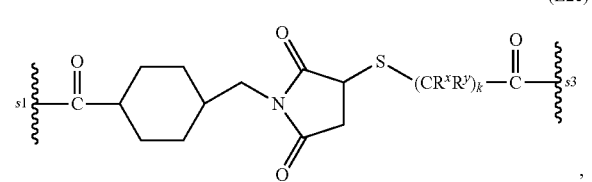
(L2c)

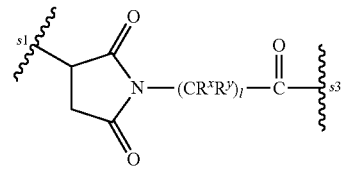
(L2d)

, or

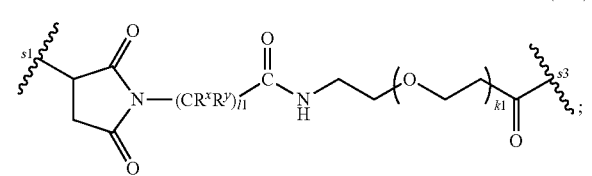
(L2e)

wherein:

$R^x, R^y, R^{x'}$ and $R^{y'}$, for each occurrence, are independently H, —OH, halogen, —O—($C_{1-4}$ alkyl), —SO$_3$H, —NR$_{40}$R$_{41}$R$_{42}^+$, or a $C_{1-4}$ alkyl optionally substituted with —OH, halogen, SO$_3$H or NR$_{40}$R$_{41}$R$_{42}^+$, wherein R$_{40}$, R$_{41}$ and R$_{42}$ are each independently H or a $C_{1-4}$ alkyl;

l and k are each independently an integer from 1 to 10;

l1 is an integer from 2 to 5;

k1 is an integer from 1 to 5; and s1 indicates the site connected to the cell-binding agent CB and s3 indicates the site connected to the A group;

A is an amino acid residue or a peptide comprising 2 to 20 amino acid residues;

$R^1$ and $R^2$ are each independently H or a $C_{1-3}$alkyl;

$L_1$ is represented by the following formula:

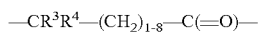

wherein $R^3$ and $R^4$ are each independently H or Me, and the —C(=O)— moiety in $L_1$ is connected to D;

D is represented by the following formula:

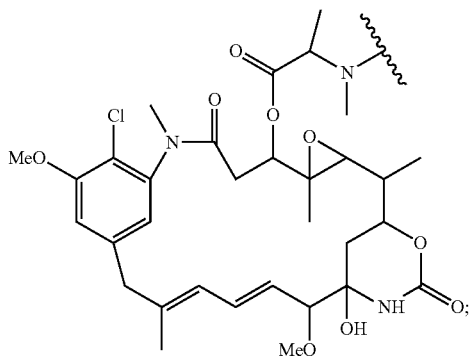 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

and q is an integer from 1 to 20. In some embodiments q is an integer from 1 to 10. In some embodiments q is an integer from 2 to 5. In some embodiments, q is an integer from 3 to 4.

In a $1^{st}$ specific embodiment of the first embodiment, an immunoconjugate provided herein is represented by formula (I) described above, wherein $R^x$, $R^y$, $R^{x'}$ and $B^{y'}$ are all H; and l and k are each independently an integer an integer from 2 to 6; and the remaining variables are as described above for formula (I).

In a $2^{nd}$ specific embodiment of the first embodiment, an immunoconjugate provided herein is represented by formula (I) described above, wherein A is a peptide containing 2 to 5 amino acid residues; and the remaining variables are as described above for formula (I) in the first embodiment or the $1^{st}$ specific embodiment. In some embodiments, A is a peptide cleavable by a protease. In some embodiments, a peptide cleavable by a protease expressed in tumor tissue. In some embodiments, A is a peptide having an amino acid that is covalently linked with —NH—CR$^1$R$^2$—S-L$_1$-D selected from the group consisting of Ala, Arg, Asn, Asp, Cit, Cys, selino-Cys, Gln, Glu, Gly, Ile, Leu, Lys, Met, Phe, Pro, Ser, Thr, Trp, Tyr and Val, each independently as L or D isomer. In some embodiments, the amino acid connected to —NH—CR$^1$R$^2$—S-L$_1$-D is an L amino acid.

In a $3^{rd}$ specific embodiment of the first embodiment, an immunoconjugate provided herein is represented by formula (I) described above, wherein A is selected from the group consisting of Gly-Gly-Gly, Ala-Val, Val-Ala, D-Val-Ala, Val-Cit, D-Val-Cit, Val-Lys, Phe-Lys, Lys-Lys, Ala-Lys, Phe-Cit, Leu-Cit, Ile-Cit, Phe-Ala, Phe-N9-tosyl-Arg, Phe-N9-nitro-Arg, Phe-Phe-Lys, D-Phe-Phe-Lys, Gly-Phe-Lys, Leu-Ala-Leu, Ile-Ala-Leu, Val-Ala-Val, Ala-Ala-Ala, D-Ala-Ala-Ala, Ala-D-Ala-Ala, Ala-Ala-D-Ala, Ala-Leu-Ala-Leu (SEQ ID NO: 54), β-Ala-Leu-Ala-Leu (SEQ ID NO:55), Gly-Phe-Leu-Gly (SEQ ID NO:56), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, Gln-Val, Asn-Ala, Gln-Phe, Gln-Ala, D-Ala-Pro, and D-Ala-tBu-Gly, wherein the first amino acid in each peptide is connected to L2 group and the last amino acid in each peptide is connected to —NH—CR$_1$R$_2$—S-L$_1$-D; and the remaining variables are as described for formula (I) in the first embodiment or the 1st specific embodiment.

In a $4^{th}$ specific embodiment of the first embodiment, an immunoconjugate provided herein is represented by formula (I) described above, wherein R$^1$ and R$^2$ are both H; and the remaining variables are as described for formula (I) in the first embodiment or the $1^{st}$, $2^{nd}$, or $3^{rd}$ specific embodiment.

In a $5^{th}$ specific embodiment of the first embodiment, an immunoconjugate provided herein is represented by formula (I) described above, wherein L$_1$ is —(CH$_2$)$_{4-6}$—C(=O)—; and the remaining variables are as described for formula (I) in the first embodiment or the $1^{st}$, $2^{nd}$, $3^{rd}$ or $4^{th}$ specific embodiment.

In a $6^{th}$ specific embodiment of the first embodiment, an immunoconjugate provided herein is represented by formula (I) described above, wherein D is represented by the following formula:

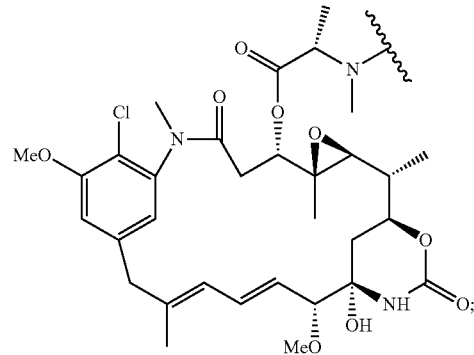 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

and the remaining variables are as described for formula (I) in the first embodiment or the $1^{st}$, $2^{nd}$, $3^{rd}$, $4^{th}$ or $5^{th}$ specific embodiment.

In a $7^{th}$ specific embodiment, an immunoconjugate provided herein is represented by the following formula:

(Ia)

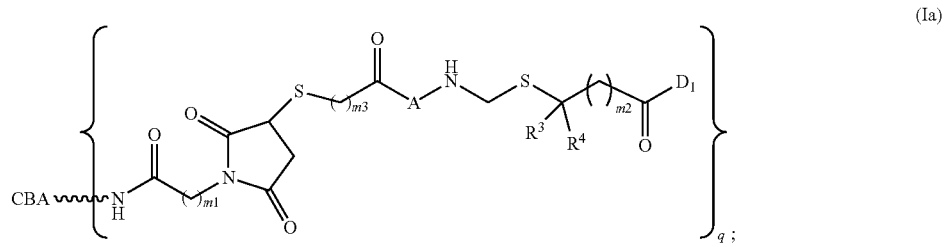

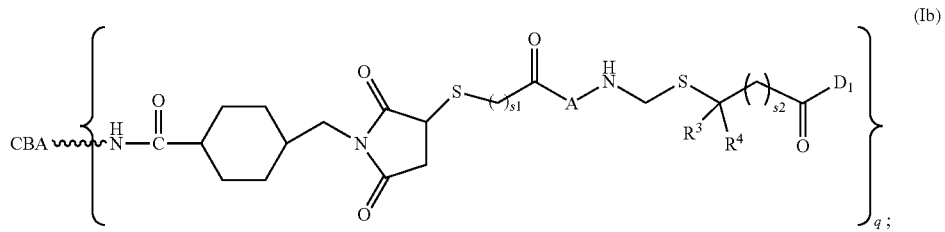

(Ib)

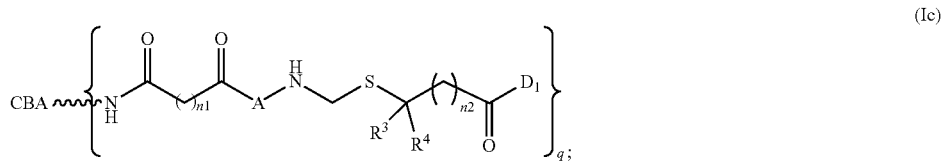

(Ic)

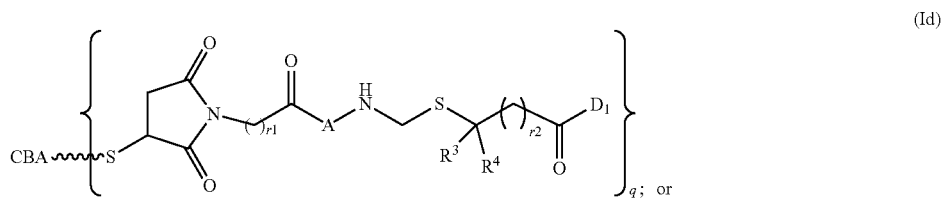

(Id)

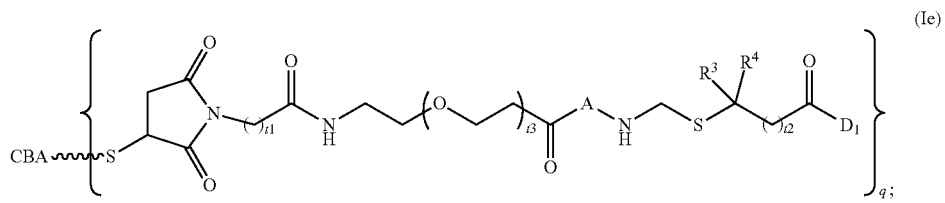

(Ie)

or a pharmaceutically acceptable salt thereof, wherein:

is the biparatopic anti-FRα antibody or antigen-binding fragment thereof connected to the $L_2$ group through a Lys amine group;

is the biparatopic anti-FRα antibody or antigen-binding fragment thereof connected to the $L_2$ group through a Cys thiol group;

$R^3$ and $R^4$ are each independently H or Me;

m1, m3, n1, r1, s1 and t1 are each independently an integer from 1 to 6;

m2, n2, r2, s2 and t2 are each independently an integer from 1 to 7;

t3 is an integer from 1 to 12;

$D_1$ is represented by the following formula:

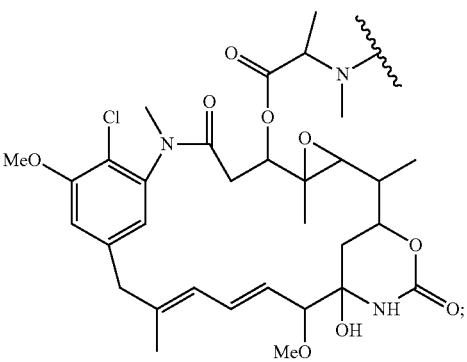

and q is an integer from 1 to 20. In some embodiments q is an integer from 1 to 10. In some embodiments q is an integer from 2 to 5. In some embodiments, q is an integer from 3 to 4. In a more specific embodiment, $D_1$ is represented by the following formula:

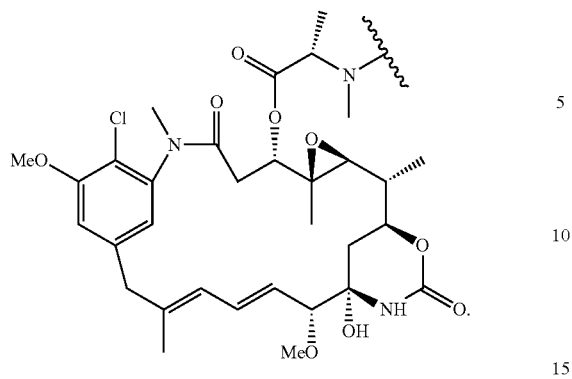

In a 8th specific embodiment, an immunoconjugate provided herein is represented by the following formula:

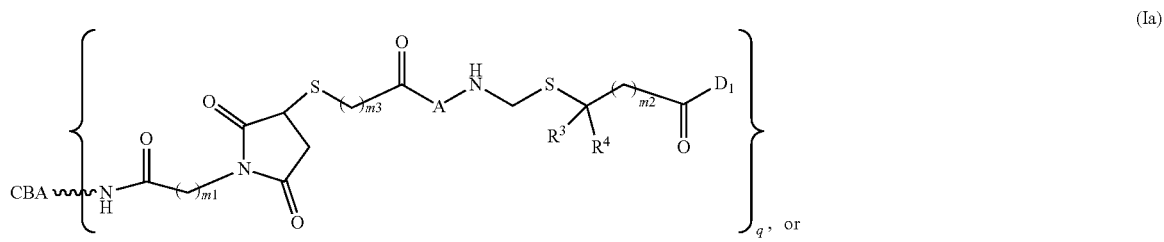
(Ia)

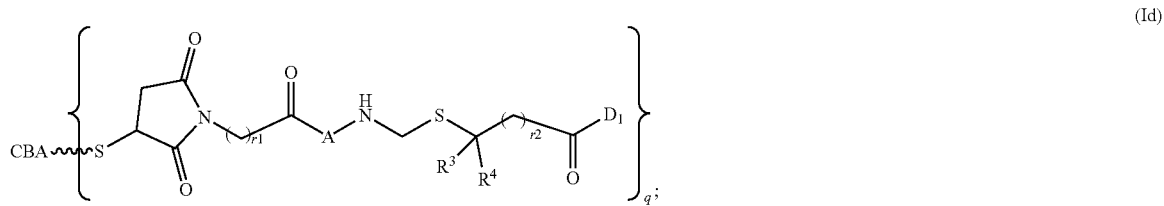
(Id)

wherein:
m1 and m3 are each independently an integer from 2 to 4;
m2 is an integer from 2 to 5;
r1 is an integer from 2 to 6;
r2 is an integer from 2 to 5; and
the remaining variables are as described in the 7th specific embodiment.

In a 9th specific embodiment, for the immunoconjugates described in the 7th or 8th specific embodiment, A is Ala-Ala-Ala, Ala-D-Ala-Ala, Ala-Ala, D-Ala-Ala, Val-Ala, D-Val-Ala, D-Ala-Pro, or D-Ala-tBu-Gly. In a more specific embodiment, for the immunoconjugates described in the 7th or 8th specific embodiment, A is L-Ala-D-Ala-L-Ala.

In a 10th specific embodiment, an immunoconjugate provided herein is represented by the following formula:

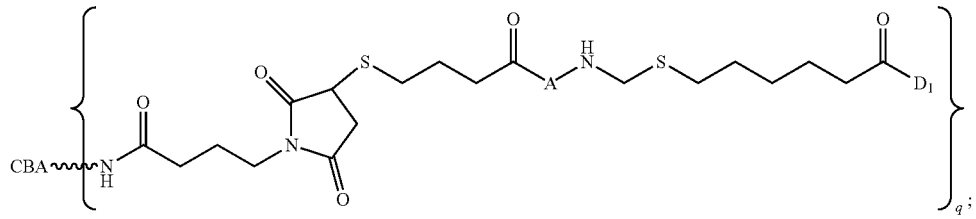

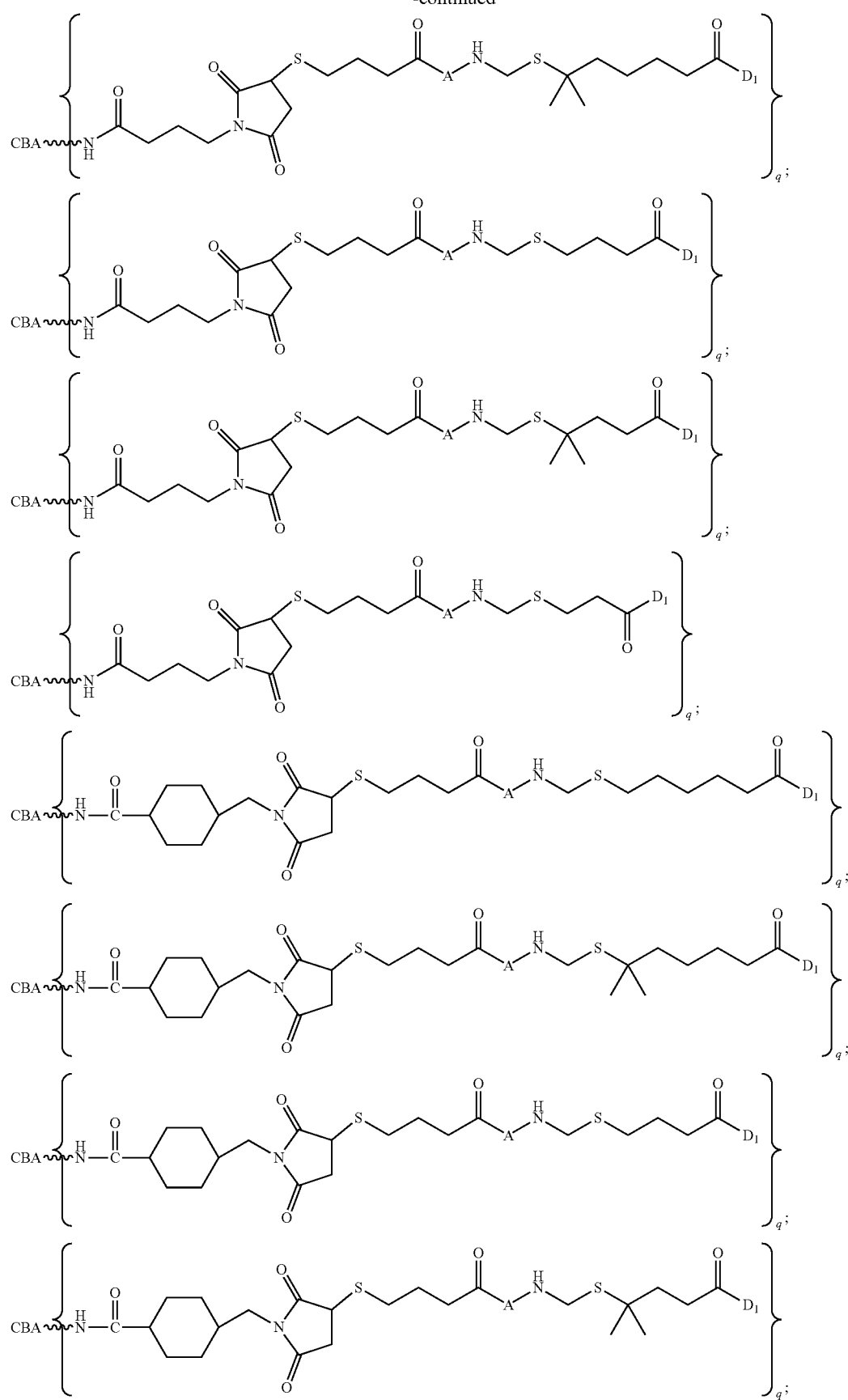

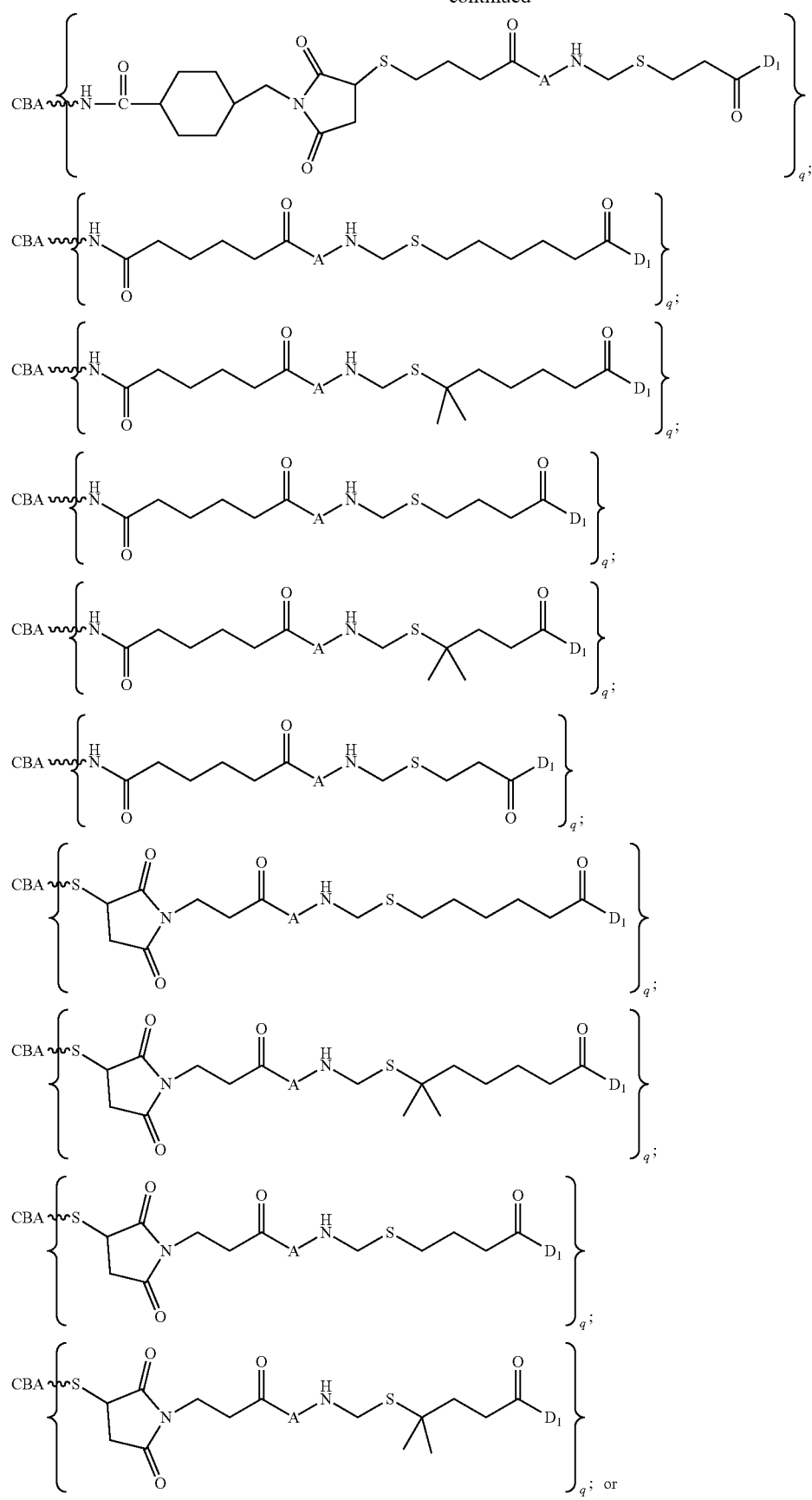

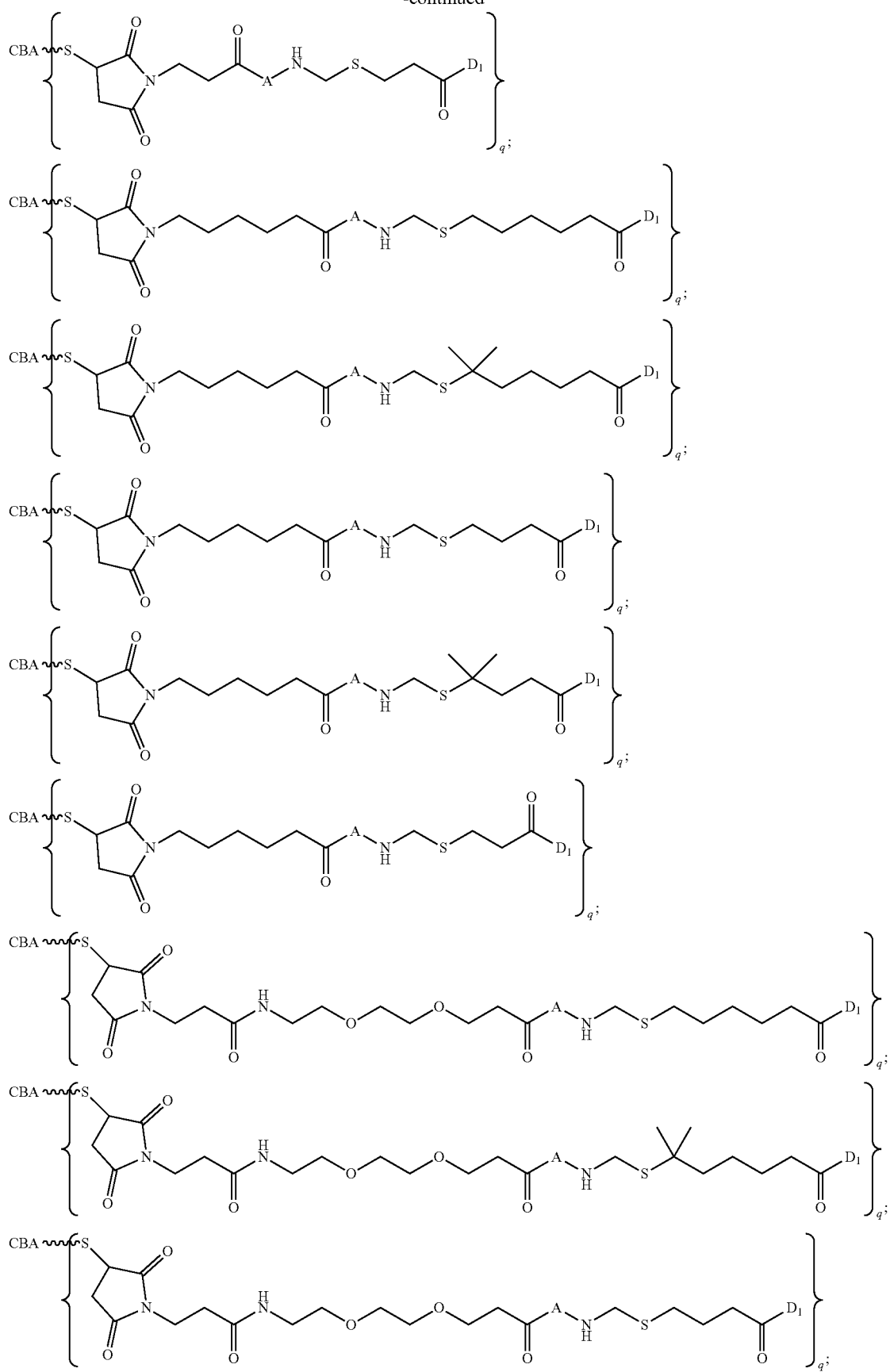

-continued
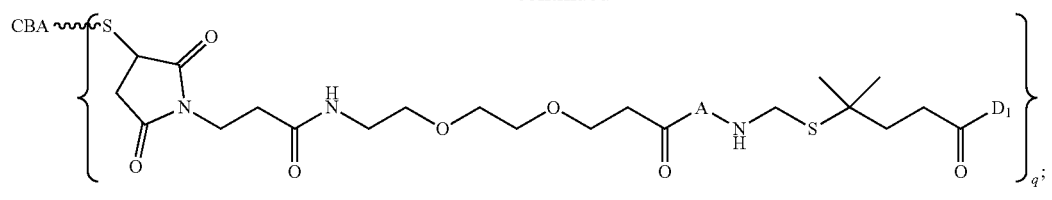
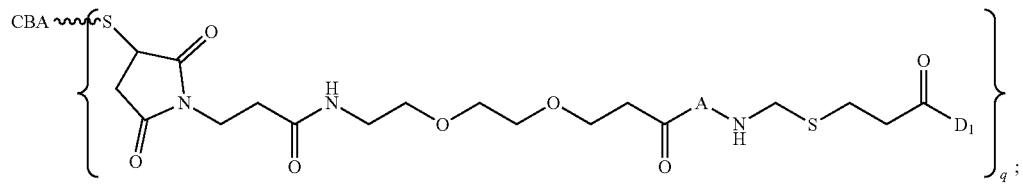
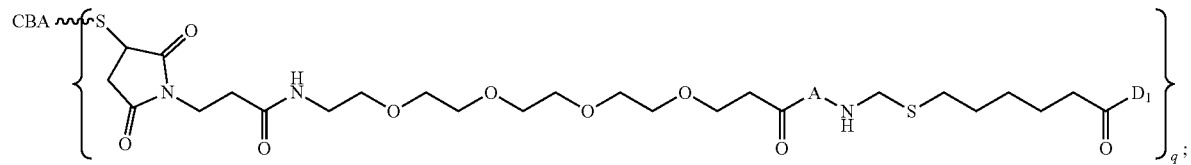
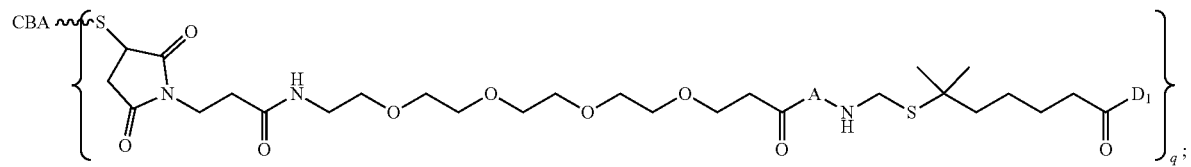
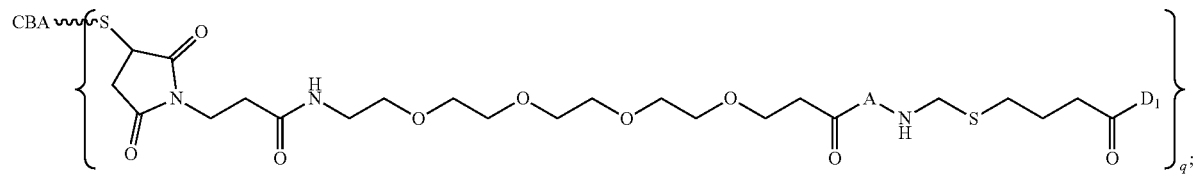
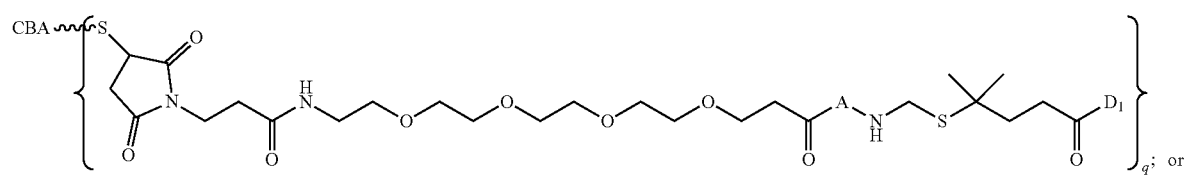; or
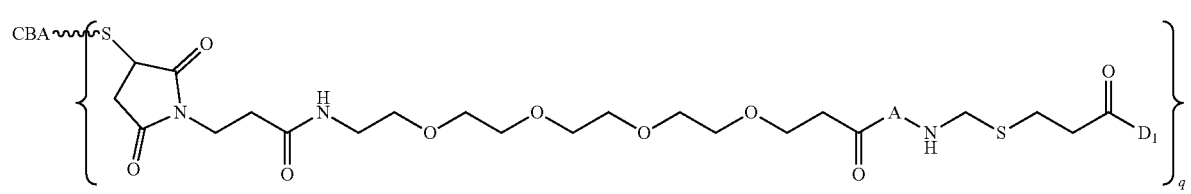

or a pharmaceutically acceptable salt thereof, wherein:
A is Ala-Ala-Ala, Ala-D-Ala-Ala, Ala-Ala, D-Ala-Ala, Val-Ala, D-Val-Ala, D-Ala-Pro, or D-Ala-tBu-Gly, and $D_1$ is represented by the following formula:

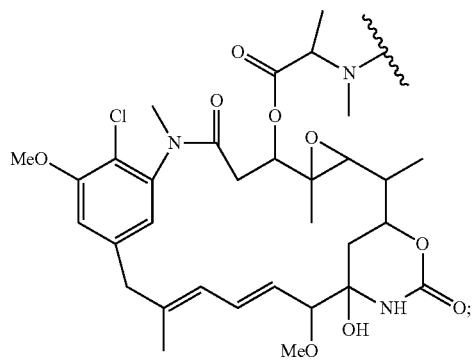

and the remaining variables are as described in the 7$^{th}$, 8$^{th}$ or 9$^{th}$ specific embodiment. In a more specific embodiment, A is L-Ala-D-Ala-L-Ala. In a more specific embodiment, $D_1$ is represented by the following formula:

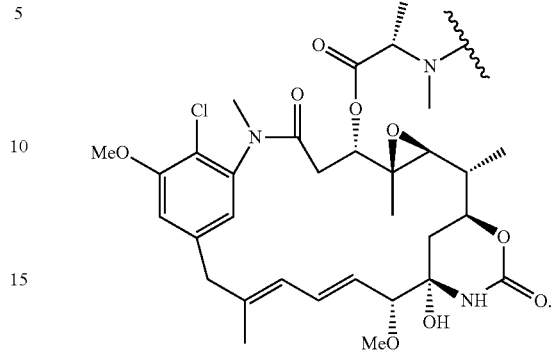

In a 11$^{th}$ specific embodiment, an immunoconjugate provided herein is represented by the following formula:

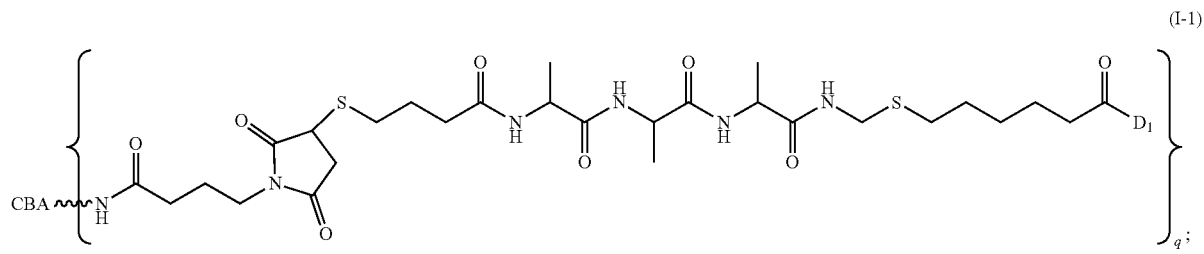
(I-1)

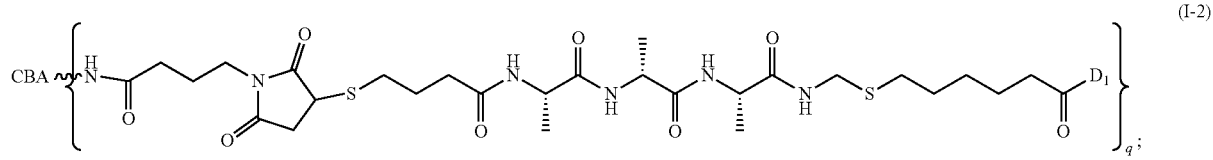
(I-2)

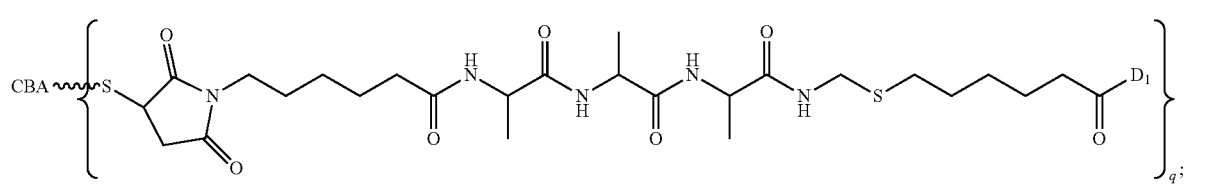
(I-3)

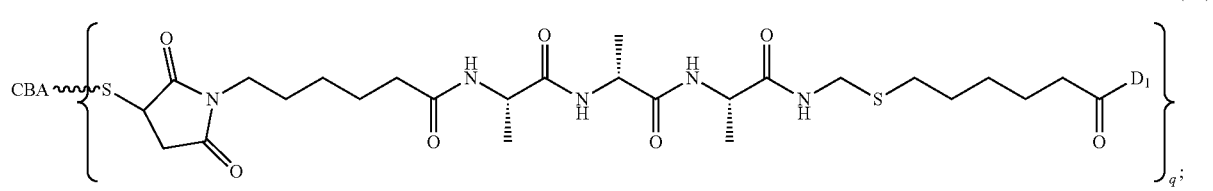
(I-4)

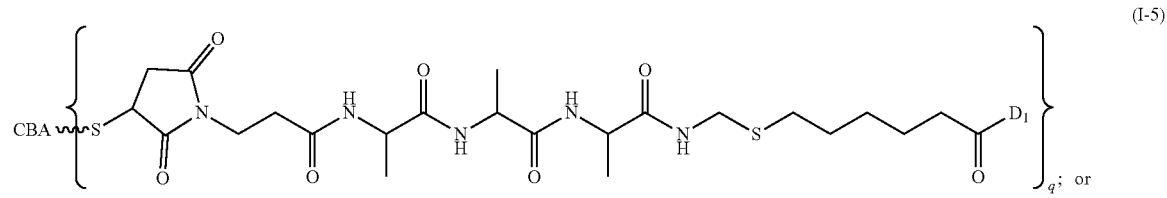
(I-5)

-continued

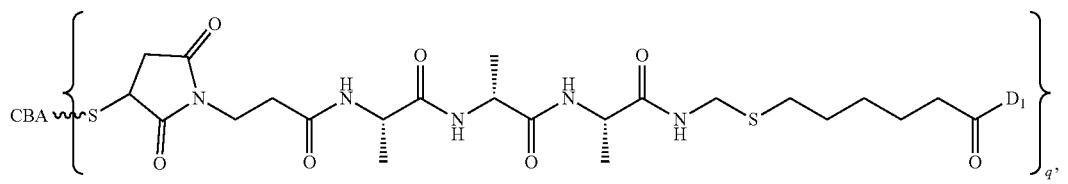
(I-6)

wherein $D_1$ is represented by the following formula:

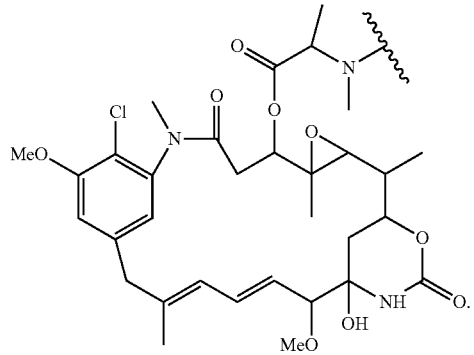

In a more specific embodiment, $D_1$ is represented by the following formula:

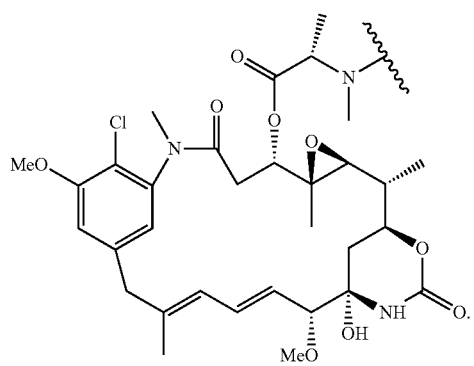

In a 12$^{th}$ specific embodiment, an immunoconjugate provided herein is represented by the following formula:

wherein:
CBA is a biparatopic anti-FRα antibody or antigen-binding fragment thereof, wherein said antibody or antigen-binding fragment thereof comprises (i) light chain complementary determining regions L-CDR1, L-CDR2, and L-CDR3 having the sequences of SEQ ID NOs: 1-3 and heavy chain complementary determining regions H-CDR1, H-CDR2, and H-CDR3 having the sequences of SEQ ID NOs:7-9 and (ii) light chain complementary determining regions L-CDR1, L-CDR2, and L-CDR3 having the sequences of SEQ ID NOs:4-6 and heavy chain complementary determining regions H-CDR1, H-CDR2, and H-CDR3 having the sequences of SEQ ID NOs:10-12, respectively;
q is 1 or 2;
$D_1$ is represented by the following formula:

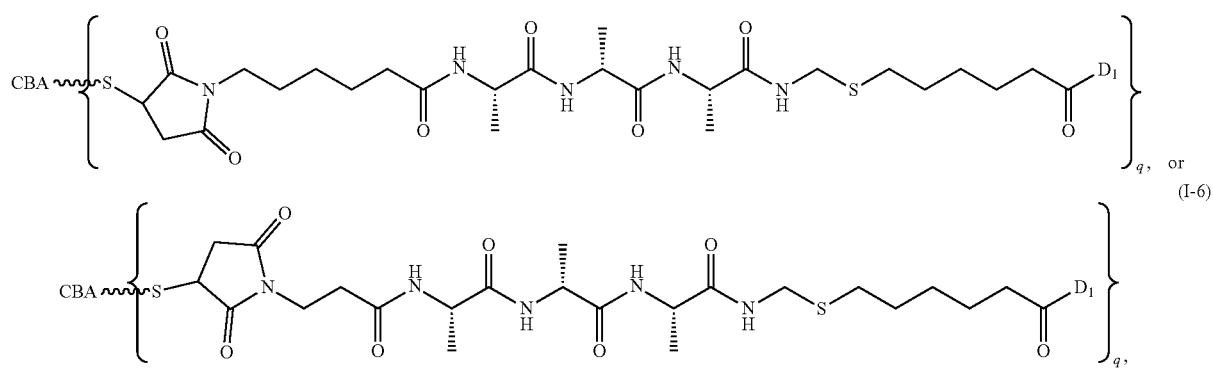

In certain embodiments, for the immunoconjugate of formula (I-4) or (I-6), the a biparatopic anti-FRα antibody or antigen-binding fragment thereof comprises a VL comprising the amino acid sequence of SEQ ID NO:18, a VH comprising the amino acid sequence of SEQ ID NO:23, a VL comprising the amino acid sequence of SEQ ID NO:19, and a VH comprising the amino acid sequence of SEQ ID NO:24.

In a 13th specific embodiment, an immunoconjugate provided herein is represented by the following formula:

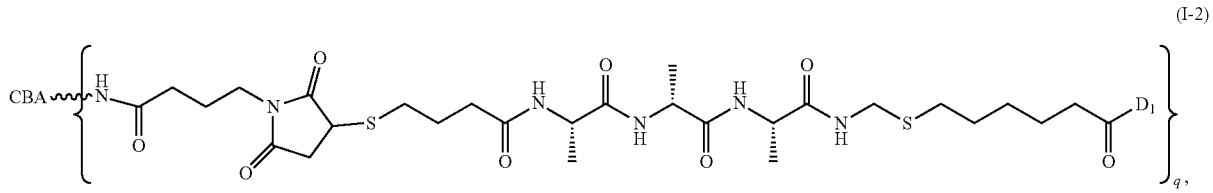

(I-2)

wherein:
CBA is a biparatopic anti-FRα antibody or antigen-binding fragment thereof, wherein said antibody or antigen-binding fragment thereof comprises (i) light chain complementary determining regions L-CDR1, L-CDR2, and L-CDR3 having the sequences of SEQ ID NOs: 1-3 and heavy chain complementary determining regions H-CDR1, H-CDR2, and H-CDR3 having the sequences of SEQ ID NOs:7-9 and (ii) light chain complementary determining regions L-CDR1, L-CDR2, and L-CDR3 having the sequences of SEQ ID NOs:4-6 and heavy chain complementary determining regions H-CDR1, H-CDR2, and H-CDR3 having the sequences of SEQ ID NOs:10-12, respectively;
q is an integer from 1 to 10, e.g., 1 or 10; and
$D_1$ is represented by the following formula:

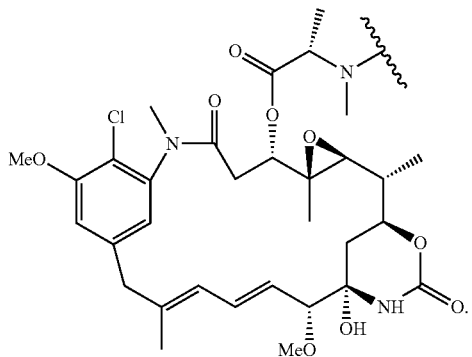 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In certain embodiments, for the immunoconjugate of formula (I-2), the a biparatopic anti-FRα antibody or antigen-binding fragment thereof comprises a VL comprising the amino acid sequence of SEQ ID NO:18, a VH comprising the amino acid sequence of SEQ ID NO:23, a VL comprising the amino acid sequence of SEQ ID NO:19, and a VH comprising the amino acid sequence of SEQ ID NO:24. In certain embodiments, for the immunoconjugate of formula (I-2), the a biparatopic anti-FRα antibody or antigen-binding fragment thereof comprises polypeptides having the amino acid sequences of SEQ ID NOs: 41, 42, and 43.

In a 14th embodiment, an immunoconjugate provided herein comprises an biparatopic anti-FRα antibody coupled to a maytansinoid compound DM21C (also referred to as Mal-LDL-DM or MalC5-LDL-DM or compound 17a) represented by the following structural formula:

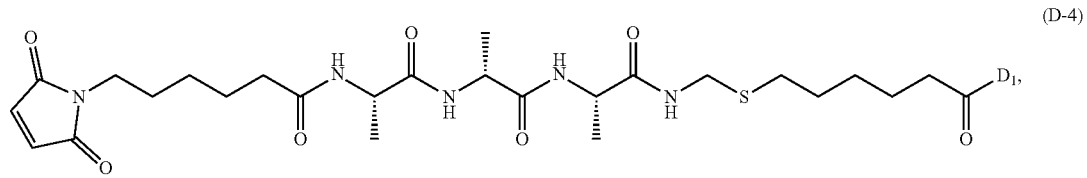

(D-4)

wherein the biparatopic anti-FRα antibody or antigen binding fragment thereof comprises (i) a light chain variable region and a heavy chain variable region having the sequences of SEQ ID NO:18 and SEQ ID NO:23, respectively, and (ii) a light chain variable region and a heavy chain variable region having the sequences of SEQ ID NO:19 and SEQ ID NO:24, respectively; and $D_1$ is represented by the following formula:

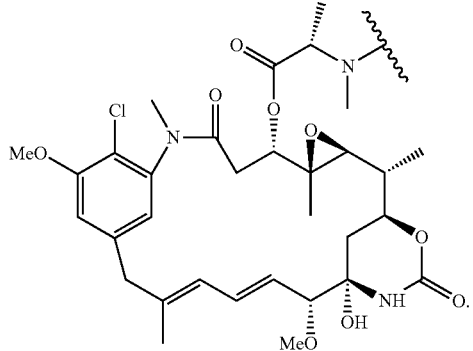 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In one embodiment, the immunoconjugate is represented by the following structural formula:

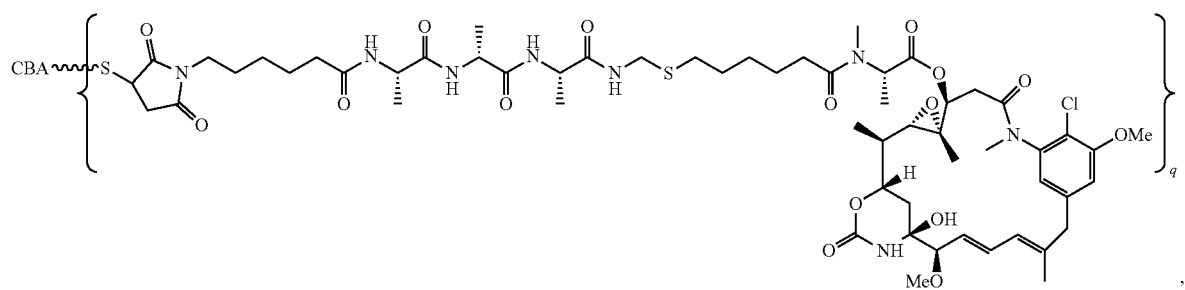

wherein:
CBA is a biparatopic anti-FRα antibody or antigen binding fragment thereof comprises (i) a light chain variable region and a heavy chain variable region having the sequences of SEQ ID NO:18 and SEQ ID NO:23, respectively, and (ii) a light chain variable region and a heavy chain variable region having the sequences of SEQ ID NO:19 and SEQ ID NO:24, respectively; and
q is 1 or 2.

In certain embodiments, for compositions (e.g., pharmaceutical compositions) comprising immunoconjugates of the 14$^{th}$ specific embodiment, DAR is in the range of 1.5 to 2.2, 1.7 to 2.2 or 1.9 to 2.1. In some embodiment, the DAR is 1.7, 1.8, 1.9, 2.0 or 2.1.

In a 15$^{th}$ specific embodiment, an immunoconjugate provided herein comprises a biparatopic anti-FRα antibody or antigen-binding fragment thereof coupled to a maytansinoid compound DM21 (also referred to as DM21L, LDL-DM, or compound 14c) represented by the following structural formula:

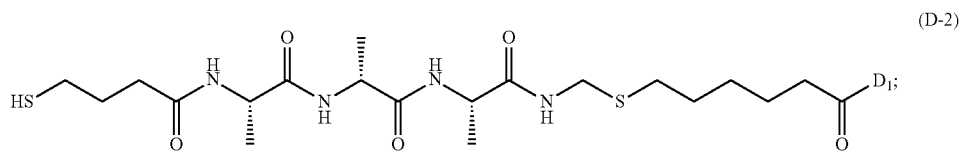

(D-2)

via γ-maleimidobutyric acid N-succinimidyl ester (GMBS) or a N—(γ-maleimidobutryloxy)sulfosuccinimide ester (sulfo-GMBS or sGMBS) linker. The biparatopic anti-FRα antibody or antigen binding fragment thereof comprises (i) a light chain variable region and a heavy chain variable region having the sequences of SEQ ID NO:18 and SEQ ID NO:23, respectively, and (ii) a light chain variable region and a heavy chain variable region having the sequences of SEQ ID NO:19 and SEQ ID NO:24, respectively.

The GMBS and sulfo-GMBS (or sGMBS) linkers are known in the art and can be presented by the following structural formula:

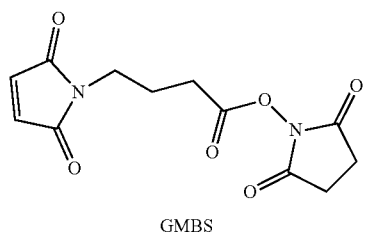

GMBS

-continued

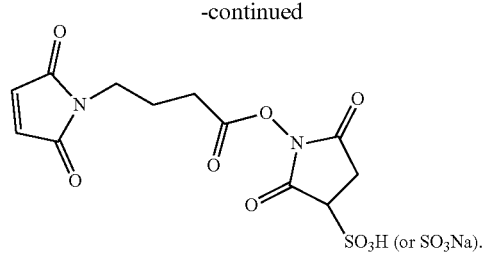

sulfo-GMBS

In one embodiment, the immunoconjugate is represented by the following structural formula:

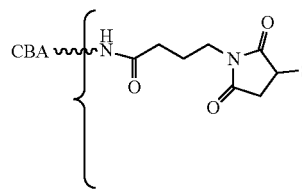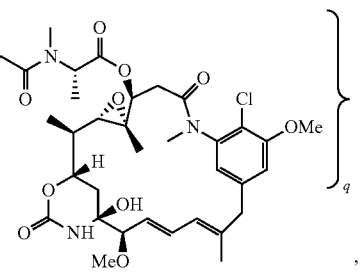

wherein:
CBA is a biparatopic anti-FRα antibody or antigen binding fragment thereof comprises (i) a light chain variable region and a heavy chain variable region having the sequences of SEQ ID NO:18 and SEQ ID NO:23, respectively, and (ii) a light chain variable region and a heavy chain variable region having the sequences of SEQ ID NO:19 and SEQ ID NO:24, respectively; and
q is an integer from 1 to 10, e.g., 1 or 10. In some embodiments q is an integer from 2 to 5. In some embodiments, q is an integer from 3 to 4.

In certain embodiments, for immunoconjugates of the 15$^{th}$ specific embodiment, the a biparatopic anti-FRα antibody or antigen-binding fragment thereof comprises polypeptides having the amino acid sequences of SEQ ID NOs: 41, 42, and 43.

In certain embodiments, for compositions (e.g., pharmaceutical compositions) comprising immunoconjugates of the 15$^{th}$ specific embodiment, DAR is in the range of 3.0 to 4.0, 3.2 to 3.8, 3.1 to 3.7, or 3.4 to 3.7. In some embodiments, the DAR is 3.2, 3.3, 3.4, 3.5, 3.5, 3.7, or 3.8. In some embodiments, the DAR is 3.5.

In certain embodiments, for compositions comprising lysine conjugates, DAR is in the range of 1.5 to 3.1. In some embodiments, the DAR is about 2.0.

In certain embodiments, for compositions (e.g., pharmaceutical compositions) comprising immunoconjugates of the first embodiment, or the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$, 12$^{th}$, 13$^{th}$, 14$^{th}$ or 15$^{th}$ specific embodiment, the average number of the cytotoxic agent per antibody molecule (i.e., average value of q), also known as Drug-Antibody Ratio (DAR) in the composition is in the range of 1.0 to 8.0. In some embodiments, DAR is in the range of 1.0 to 5.0, 1.0 to 4.0, 1.5 to 4.0, 2.0 to 4.0, 2.5 to 4.0, 1.0 to 3.4, 1.0 to 3.0, 3.0 to 4.0, 3.1 to 3.5, 3.1 to 3.7, 3.4 to 3.6, 1.5 to 2.5, 2.0 to 2.5, 1.7 to 2.3, or 1.8 to 2.2. In some embodiments, the DAR is less than 4.0, less than 3.8, less than 3.6, less than 3.5, less than 3.0 or less than 2.5. In some embodiments, the DAR is in the range of 3.1 to 3.7. In some embodiments, the DAR is in the range of 3.1 to 3.4. In some embodiments, the DAR is in the range of 3.3 to 3.7. In some embodiments, the DAR is in the range of 3.5 to 3.9. In some embodiments, the DAR is 3.1, 3.2, 3.3, 3.4, 3.5, 3.6, 3.7 or 3.8. In some embodiments, the DAR is 3.5. In some embodiments, the DAR is in the range of 1.8 to 2.0. In some embodiments, the DAR is in the range of 1.7 to 1.9. In some embodiments, the DAR is in the range of 1.9 to 2.1. In some embodiments, the DAR is 1.9, 2.0 or 2.1. In some embodiments, for the immunoconjugates of the present invention comprising a biparatopic anti-FRα antibody or an antigen-binding fragment thereof linked to the maytansinoid compound through one or more cysteine thiol group, the DAR is in the range of 1.5 to 2.5, 1.8 to 2.2, 1.1 to 1.9 or 1.9 to 2.1. In some embodiments, the DAR is 1.8, 1.9, 2.0 or 2.1

B. Linkers

Any suitable linkers known in the art can be used in preparing the immunoconjugates of the present disclosure. In certain embodiments, the linkers are bifunctional linkers. As used herein, the term "bifunctional linker" refers to modifying agents that possess two reactive groups; one of which is capable of reacting with a cell binding agent while the other one reacts with the maytansinoid compound to link the two moieties together. Such bifunctional crosslinkers are well known in the art (see, for example, Isalm and Dent in *Bioconjugation* chapter 5, p 218-363, Groves Dictionaries Inc. New York, 1999). For example, bifunctional crosslinking agents that enable linkage via a thioether bond include N-succinimidyl-4-(N-maleimidomethyl)-cyclohexane-1-carboxylate (SMCC) to introduce maleimido groups, or with N-succinimidyl-4-(iodoacetyl)-aminobenzoate (SIAB) to introduce iodoacetyl groups. Other bifunctional crosslinking agents that introduce maleimido groups or haloacetyl groups on to a cell binding agent are well known in the art (see US Patent Publication Nos. 2008/0050310, 20050169933, available from Pierce Biotechnology Inc. P.O. Box 117, Rockland, Ill. 61105, USA) and include, but not limited to, bis-maleimidopolyethyleneglycol (BMPEO), BM(PEO)$_2$, BM(PEO)$_3$, N—(β-maleimidopropyloxy)succinimide ester (BMPS), γ-maleimidobutyric acid N-succinimidyl ester (GMBS), ε-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate), which is a "long chain" analog of SMCC (LC-SMCC), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), κ-maleimidoundecanoic acid N-succinimidyl ester (KMUA), N-succinimidyl 4-(p-maleimidophenyl)-butyrate (SMPB), succinimidyl-6-(β-maleimidopropionamido)hexanoate (SMPH), succinimidyl-(4-vinyl sulfonyl) benzoate (SVSB), dithiobis-maleimidoethane (DTME), 1,4-bis-maleimidobutane (BMB), 1,4-bismaleimidyl-2,3-dihydroxybutane (BMDB), bis-maleimidohexane (BMH), bis-maleimidoethane (BMOE), sulfosuccinimidyl 4-(N-maleimido-methyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MB S), N—(γ-maleimidobutryloxy)sulfosuccinimide ester (sulfo-GMBS or sGMBS), N—(ε-maleimidocaproyloxy)sulfosuccimido ester (sulfo-EMCS), N-κ-maleimidoundecanoyloxy)sulfosuccinimide ester (sulfo-KMUS), and sulfosuccinimidyl 4-(p-maleimidophenyl) butyrate (sulfo-SMPB).

Heterobifunctional crosslinking agents are bifunctional crosslinking agents having two different reactive groups. Heterobifunctional crosslinking agents containing both an amine-reactive N-hydroxysuccinimide group (NHS group) and a carbonyl-reactive hydrazine group can also be used to link the cytotoxic compounds described herein with a cell-binding agent (e.g., antibody). Examples of such commercially available heterobifunctional crosslinking agents include succinimidyl 6-hydrazinonicotinamide acetone hydrazone (SANH), succinimidyl 4-hydrazidoterephthalate hydrochloride (SHTH) and succinimidyl hydrazinium nicotinate hydrochloride (SHNH). Conjugates bearing an acid-labile linkage can also be prepared using a hydrazine-bearing benzodiazepine derivative of the present disclosure. Examples of bifunctional crosslinking agents that can be used include succinimidyl-p-formyl benzoate (SFB) and succinimidyl-p-formylphenoxyacetate (SFPA).

Bifunctional crosslinking agents that enable the linkage of cell binding agent with cytotoxic compounds via disulfide bonds are known in the art and include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB or sSPDB) to introduce dithiopyridyl groups. Other bifunctional crosslinking agents that can be used to introduce disulfide groups are known in the art and are disclosed in U.S. Pat. Nos. 6,913,748, 6,716,821 and US Patent Publications 2009/0274713 and 2010/0129314, each of which is herein incorporated by reference in its entirety. Alternatively, crosslinking agents such as 2-iminothiolane, homocysteine thiolactone or S-acetylsuccinic anhydride that introduce thiol groups can also be used.

C. Cytotoxic Agents

In some embodiments, provided herein are cytotoxic agents that can be used for making the immunoconjugates of the present disclosure. The cytotoxic agent used in the immunoconjugates provided herein can be any compound that results in the death of a cell, or induces cell death, or in some manner decreases cell viability, and includes, for example, maytansinoids and maytansinoid analogs, benzodiazepines, taxoids, CC-1065 and CC-1065 analogs, duocarmycins and duocarmycin analogs, enediynes, such as calicheamicins, dolastatin and dolastatin analogs including auristatins, tomaymycin derivatives, leptomycin derivatives, methotrexate, cisplatin, carboplatin, daunorubicin, doxorubicin, vincristine, vinblastine, melphalan, mitomycin C, chlorambucil and morpholino doxorubicin. In certain embodiments, the cytotoxic agents are maytansinoids and maytansinoids analogs.

Examples of suitable maytansinoids include esters of maytansinol and maytansinol analogs. Included are any drugs that inhibit microtubule formation and that are highly toxic to mammalian cells, as are maytansinol and maytansinol analogs Exemplary cytotoxic agents were described previously in WO 2018/160539 A1 and WO 2011/106528, each of which is herein incorporated by reference in its entirety.

The immunoconjugates provided herein can comprise a maytansinoid compound represented by the following formula:

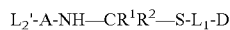
(II)

or a pharmaceutically acceptable salt thereof, wherein:

$L_2'$ is represented by the following structural formulas:

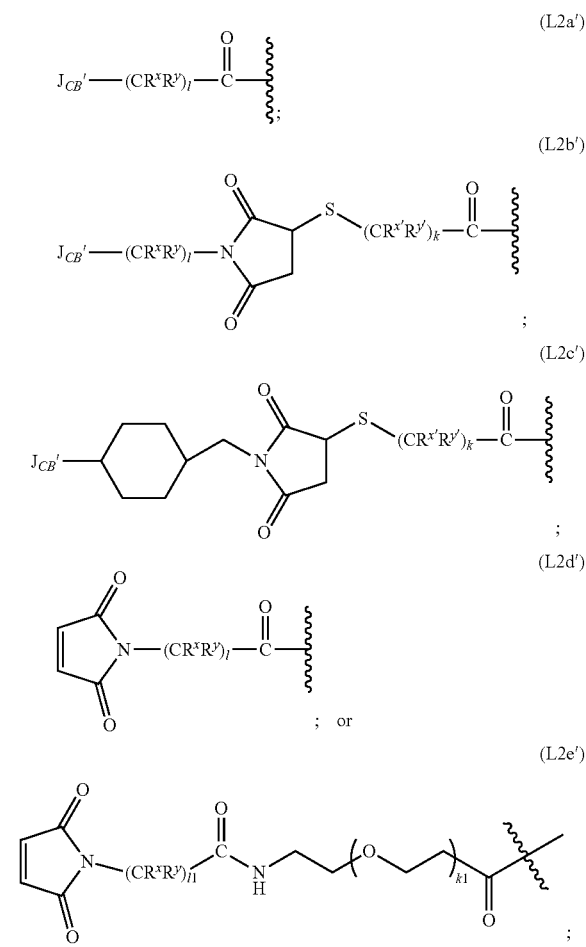

wherein:

$R^x$, $R^y$, $R^{x'}$ and $R^{y'}$, for each occurrence, are independently H, —OH, halogen, —O—($C_{1-4}$ alkyl), —$SO_3H$, —$NR_{40}R_{41}R_{42}^+$, or a $C_{1-4}$ alkyl optionally substituted with —OH, halogen, —$SO_3H$ or $NR_{40}R_{41}R_{42}^+$, wherein $R_{40}$, $R_{41}$ and $R_{42}$ are each independently H or a $C_{1-4}$ alkyl;

l and k are each independently an integer from 1 to 10;

$J_{CB}'$ is —C(=O)OH or —COE, wherein —COE is a reactive ester;

A is an amino acid or a peptide comprising 2 to 20 amino acids;

$R^1$ and $R^2$ are each independently H or a $C_{1-3}$alkyl;

$L_1$ is represented by the following formula:

wherein $R^3$ and $R^4$ are each independently H or Me, and the —C(=O)— moiety in $L_1$ is connected to D;

D is represented by the following formula:

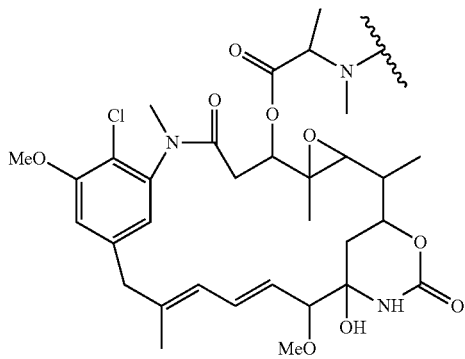 [SMILES: *N(C)C(C)C(=O)OC1CC(=O)N(C)c2cc(cc(OC)c2Cl)C/C(C)=C/C=C/C(OC)C2(O)CC(OC(=O)N2)C(C)C2OC12C]

and q is an integer from 1 to 20. In some embodiments q is an integer from 1 to 10. In some embodiments q is an integer from 2 to 5. In some embodiments, q is an integer from 3 to 4.

In some embodiments, the maytansinoid of the present invention is represented by the following formula:

$$A'\text{-NH}-CR^1R^2-S-L_1-D \quad (III)$$

or a pharmaceutically acceptable salt thereof, wherein:
A' is an amino acid or a peptide comprising 2 to 20 amino acids (i.e., A-NH$_2$);
R$^1$ and R$^2$ are each independently H or a C$_{1-3}$alkyl;
L$_1$ is —CR$^3$R$^4$—(CH$_2$)$_{1-8}$—C(=O)—; R$^3$ and R$^4$ are each independently H or Me;
D is represented by the following formula:

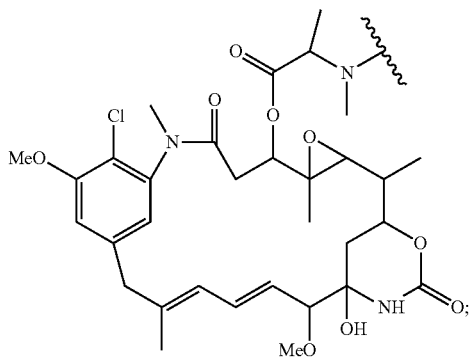 [SMILES: *N(C)[C@@H](C)C(=O)OC1CC(=O)N(C)c2cc(cc(OC)c2Cl)C/C(C)=C/C=C/C(OC)C2(O)CC(OC(=O)N2)C(C)C2OC12C]

and q is an integer from 1 to 20. In some embodiments q is an integer from 1 to 10. In some embodiments q is an integer from 2 to 5. In some embodiments, q is an integer from 3 to 4.

In some embodiments, the maytansinoid of the present invention is represented by the following formula:

(IV)

or a pharmaceutically acceptable salt thereof, wherein:
R$^{x'}$ and R$^{y'}$, for each occurrence, are independently H, —OH, halogen, —O—(C$_{1-4}$ alkyl), —SO$_3$H, —NR$_{40}$R$_{41}$R$_{42}$$^+$, or a C$_{1-4}$ alkyl optionally substituted with —OH, halogen, SO$_3$H or NR$_{40}$R$_{41}$R$_{42}$$^+$, wherein R$_{40}$, R$_{41}$ and R$_{42}$ are each independently H or a C$_{1-4}$ alkyl;
k is an integer from 1 to 10
A is an amino acid residue or a peptide comprising 2 to 20 amino acid residues;
R$^1$ and R$^2$ are each independently H or a C$_{1-3}$alkyl;
L$_1$ is —CR$^3$R$^4$—(CH$_2$)$_{1-8}$—C(=O)—; R$^3$ and R$^4$ are each independently H or Me;
D is represented by the following formula:

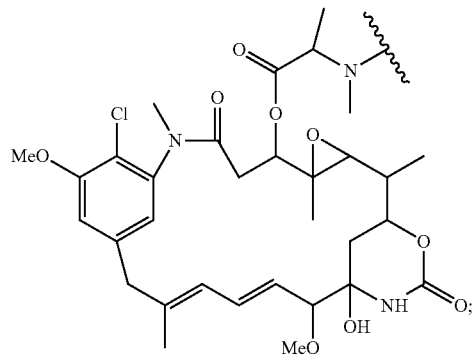

and q is an integer from 1 to 20. In some embodiments q is an integer from 1 to 10. In some embodiments q is an integer from 2 to 5. In some embodiments, q is an integer from 3 to 4.

In some embodiments, for maytansinoid compounds of formulas (II), (III) or (IV), the variables are as described in the first embodiment, or in the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$ or 11$^{th}$ specific embodiment in the first embodiment.

In a specific embodiment, the maytansinoid compound is represented by the following formula:

(D-1)

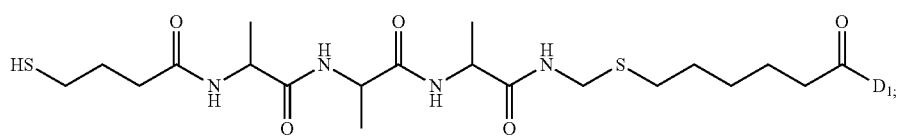

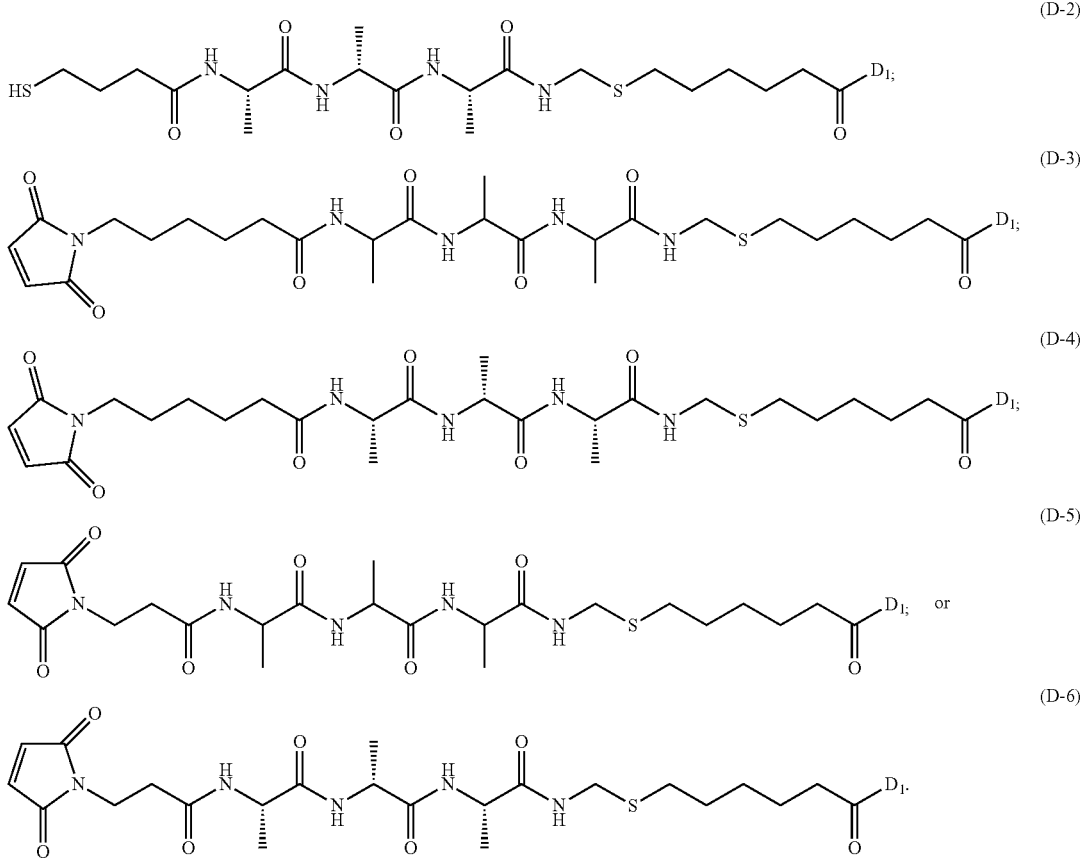

Additional examples of suitable maytansinol esters include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 7,276,497 and 7,473,796. In addition, several descriptions for producing such antibody-maytansinoid conjugates are provided in U.S. Pat. Nos. 6,333,410, 6,441,163, 6,716,821, and 7,368,565, each of which is herein incorporated by reference in its entirety.

In some embodiments, the immunoconjugate comprises $N^{2'}$-deacetyl-$N^{2'}$-(3-mercapto-1-oxopropyl)-maytansine (DM1), $N^{2'}$-deacetyl (4-mercapto-1-oxopentyl)-maytansine (termed DM3), $N^{2'}$-deacetyl-$N^{T}$-(4-mercapto-4-methyl-1-oxopentyl) maytansine (DM4), both of which were previously described in PCT Application Publication No. WO 2011/106528 A1 and U.S. Pat. No. 8,557,966 B2, each of which is herein incorporated by reference in its entirety.

D. Drug Conjugation

The immunoconjugates comprising a biparatopic FRα-binding antibody or antigen-binding fragment thereof covalently linked to a cytotoxic agent (e.g., maytansinoid) described herein can be prepared according to any suitable methods known in the art.

In certain embodiments, the immunoconjugates of the first embodiment can be prepared by a first method comprising the steps of reacting the biparatopic FRα-binding antibody or antigen-binding fragment thereof with the maytansinoid compound of formula (II) described in the second embodiment.

In certain embodiments, the immunoconjugates of the first embodiment can be prepared by a second method comprising the steps of:
(a) reacting the maytansinoid compound of formula (III) or (IV) with a linker compound described herein to form a cytotoxic agent-maytansinoid compound having an amine-reactive group or a thiol-reactive group bound thereto (e.g., compound of formula (II)) that can be covalently linked to the biparatopic FRα-binding antibody or antigen-binding fragment thereof; and
(b) reacting the biparatopic FRα-binding antibody or antigen-binding fragment thereof with the maytansinoid-linker compound to form the immunoconjugate.

In certain embodiments, the immunoconjugates of the first embodiment can be prepared by a third method comprising the steps of:
(a) reacting the biparatopic FRα-binding antibody or antigen-binding fragment thereof with a linker compound described herein to form a modified biparatopic FRα-binding antibody or antigen-binding fragment thereof having an amine-reactive group or a thiol-reactive group bound thereto that can be covalently linked to the maytansinoid compound of formula (III) or (IV); and
(b) reacting the modified biparatopic FRα-binding antibody or antigen-binding fragment thereof with the maytansinoid compound of formula (III) or (IV) to form the immunoconjugate.

In certain embodiments, for the second, third or fourth methods described above, the linker compound is represented by any one of the formula (a1L)-(a10L):

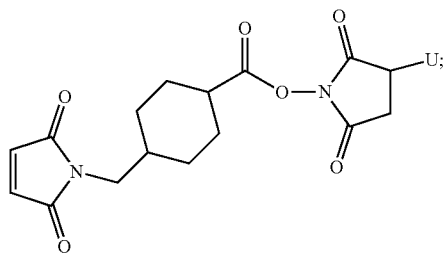 (a1L)
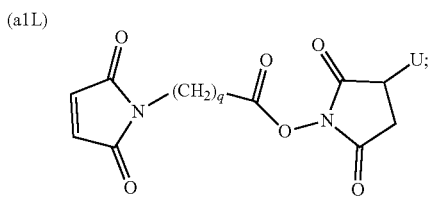 (a2L)
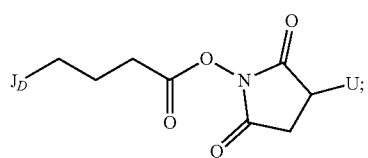 (a3L)
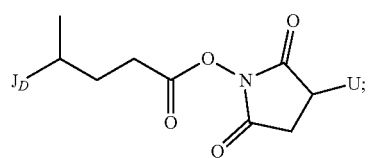 (a4L)
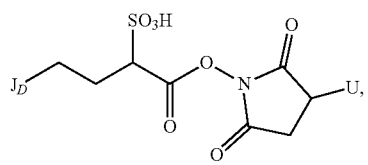 (a5L)
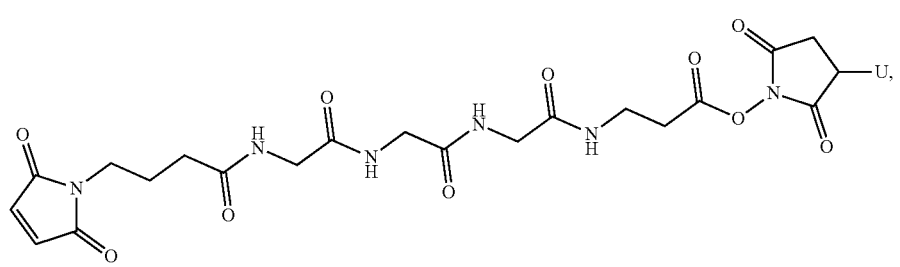 (a6L)
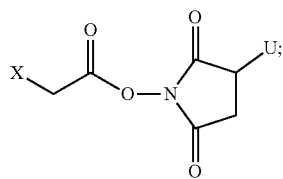 (a7L)
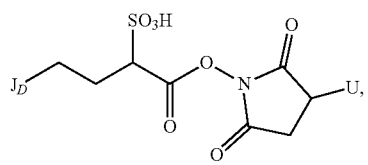 (a8L)
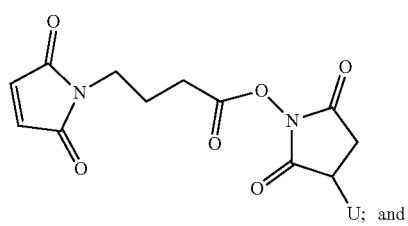 (a9L) U; and
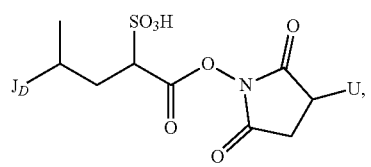 (a10L)

wherein X is halogen; $J_D$-SH, or —$SSR^d$; $R^d$ is phenyl, nitrophenyl, dinitrophenyl, carboxynitrophenyl, pyridyl or nitropyridyl; $R^g$ is an alkyl; and U is —H or $SO_3H$ or a pharmaceutically acceptable salt thereof.

In one embodiment, the linker compound is GMBS or sulfo-GMBS (or sGMBS) represented by represented by formula (a9L), wherein U is —H or $SO_3H$ or a pharmaceutically acceptable salt thereof.

In a specific embodiment, the immunoconjugate of the present invention is represented by the following formula:

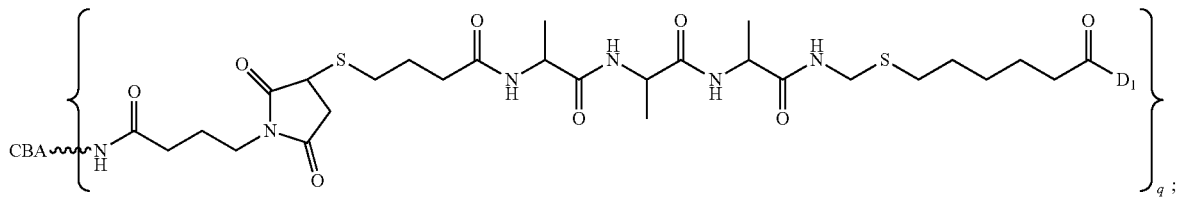

(I-1)

and the immunoconjugate can be prepared by the second, third or fourth method described above, wherein the linker compound is GMBS or sulfo-GMBS represented by represented by formula (a9L), wherein U is —H or $SO_3H$ or a pharmaceutically acceptable salt thereof; and the maytansinoid compound is represented by formula (D-1) described above. In a more specific embodiment, the immunoconjugate of formula (I-1) is prepared by reacting the maytansinoid compound of formula (D-1) with the linker compound GMBS or sulfo-GMBS to form a maytansinoid-linker compound, followed by reacting the biparatopic FRα-binding antibody or antigen-binding fragment thereof with the maytansinoid-linker compound. In an even more specific embodiment, the maytansinoid linker compound is not purified before reacting with the biparatopic FRα-binding antibody or antigen-binding fragment thereof.

In another specific embodiment, the immunoconjugate is represented by the following formula:

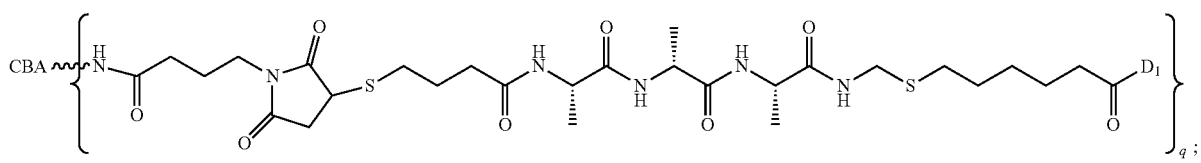

(I-2)

and the immunoconjugate can be prepared by the second, third or fourth method described above, wherein the linker compound is GMBS or sulfo-GMBS represented by represented by formula (a9L), wherein U is —H or $SO_3H$ or a pharmaceutically acceptable salt thereof; and the maytansinoid compound is represented by formula (D-2) described above. In a more specific embodiment, the immunoconjugate of formula (I-2) is prepared by reacting the maytansinoid compound of formula (D-2) with the linker compound GMBS or sulfo-GMBS to form a maytansinoid-linker compound, followed by reacting the biparatopic FRα-binding antibody or antigen-binding fragment thereof with the maytansinoid-linker compound. In an even more specific embodiment, the maytansinoid linker compound is not purified before reacting with the biparatopic FRα-binding antibody or antigen-binding fragment thereof.

In another specific embodiment, the immunoconjugate is represented by the following formula:

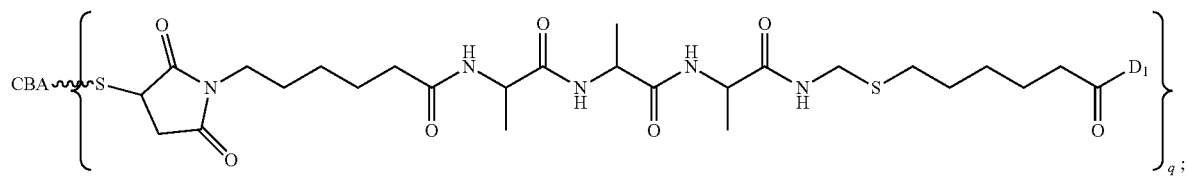

(I-3)

and the immunoconjugate is prepared according to the first method described above by reacting the biparatopic FRα-binding antibody or antigen-binding fragment thereof with the maytansinoid compound of formula (D-3) described above.

In another specific embodiment, the immunoconjugate is represented by the following formula:

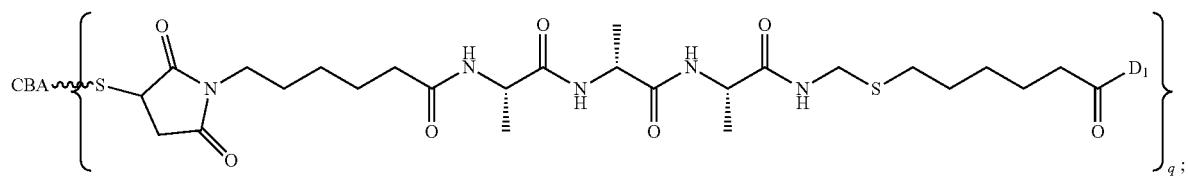

(I-4)

and the immunoconjugate is prepared according to the first method described above by reacting the biparatopic FRα-binding antibody or antigen-binding fragment thereof with the maytansinoid compound of formula (D-4) described above.

In another specific embodiment, the immunoconjugate is represented by the following formula:

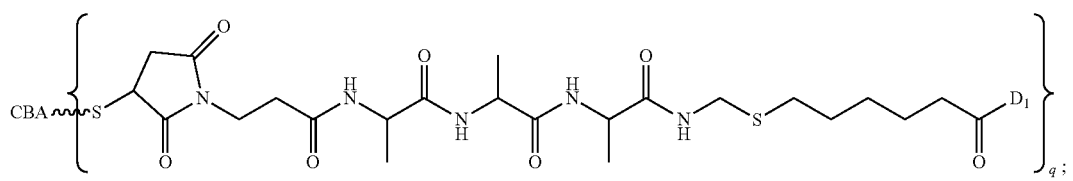

(I-5)

and the immunoconjugate is prepared according to the first method described above by reacting the anti-FRα antibody or an antigen-binding fragment thereof with the maytansinoid compound of formula (D-5) described above.

In another specific embodiment, the immunoconjugate is represented by the following formula:

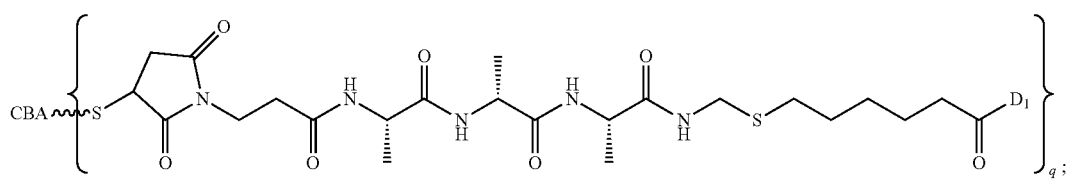

(I-6)

and the immunoconjugate is prepared according to the first method described above by reacting the biparatopic FRα-binding antibody or antigen-binding fragment thereof with the maytansinoid compound of formula (D-6) described above.

In some embodiments, the immunoconjugates represented by formulas I-3 through I-6 disclosed above are prepared according to the methods described in U.S. Provisional Application 62/821,707 filed on Mar. 21, 2019 and related U.S. application Ser. No. 16/825,127.

In some embodiments, the immunoconjugates prepared by any methods described above is subject to a purification step. In this regard, the immunoconjugate can be purified from the other components of the mixture using tangential flow filtration (TFF), non-adsorptive chromatography, adsorptive chromatography, adsorptive filtration, selective precipitation, or any other suitable purification process, as well as combinations thereof.

In some embodiments, the immunoconjugate is purified using a single purification step (e.g., TFF). Preferably, the conjugate is purified and exchanged into the appropriate formulation using a single purification step (e.g., TFF). In other embodiments of the invention, the immunoconjugate is purified using two sequential purification steps. For example, the immunoconjugate can be first purified by selective precipitation, adsorptive filtration, absorptive chromatography or non-absorptive chromatography, followed by purification with TFF. One of ordinary skill in the art will appreciate that purification of the immunoconjugate enables the isolation of a stable conjugate comprising the cell-binding agent chemically coupled to the cytotoxic agent.

Any suitable TFF systems may be utilized for purification, including a Pellicon type system (Millipore, Billerica, Mass.), a Sartocon Cassette system (Sartorius A G, Edgewood, N.Y.), and a Centrasette type system (Pall Corp., East Hills, N.Y.)

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (JT Baker, Phillipsburg N.J.) Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., Mab Select, GE Healthcare, Piscataway, N.J.), where the cell-binding agent is an antibody, and lectin affinity resins, e.g., Lentil Lectin Sepharose resin (GE Healthcare, Piscataway, N.J.), where the cell-binding agent bears appropriate lectin binding sites. Alternatively an antibody specific to the cell-binding agent may be used. Such an antibody can be immobilized to, for instance, Sepharose 4 Fast Flow resin (GE Healthcare, Piscataway, N.J.). Examples of suitable reversed phase resins include C4, C8, and C18 resins (Grace Vydac, Hesperia, Calif.).

Any suitable non-adsorptive chromatography resin may be utilized for purification. Examples of suitable non-adsorptive chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

VII. Composition and Kits

Provided herein are compositions comprising an immunoconjugate, antibody, or antigen-binding fragment thereof described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed.

A pharmaceutical composition may be formulated for a particular route of administration to a subject. For example, a pharmaceutical composition can be formulated for parenteral, e.g., intravenous, administration. The compositions to be used for in vivo administration can be sterile. This is readily accomplished by filtration through, e.g., sterile filtration membranes.

The pharmaceutical compositions described herein are in one embodiment for use as a medicament. Pharmaceutical compositions described herein can be useful in treating a condition such as cancer. Examples of cancer that can be treated as described herein include, but are not limited to, carcinoma, lymphoma, blastoma, sarcoma, and leukemia. More particular examples of such cancers include fallopian tube cancer, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers. The cancer can be an FRα-expressing cancer.

A pharmaceutical composition provided herein can comprise immunoconjugates and the pharmaceutical composition (immunoconjugates in the pharmaceutical composition) can have an average of 1 to 20 drugs per biparatopic antibody or antigen-binding fragment thereof. In some embodiments, a pharmaceutical composition comprises an average of 1 to 10 drugs per biparatopic antibody or antigen-binding fragment thereof. In some embodiments, a pharmaceutical composition comprises an average of 2 to 5 drugs per biparatopic antibody or antigen-binding fragment thereof. In some embodiments, a pharmaceutical composition comprises an average of 3 to 4 drugs per biparatopic antibody or antigen-binding fragment thereof.

VIII. Methods and Uses

The biparatopic anti-FRα antibodies, antigen binding fragments thereof, and immunoconjugates of the disclosure are useful in a variety of applications including, but not limited to, therapeutic treatment methods, such as the treatment of cancer. In certain embodiments, the agents are useful for inhibiting tumor growth and/or reducing tumor volume. The methods of use may be in vitro or in vivo methods.

The present disclosure provides for methods of treating cancer comprising administering a therapeutically effective amount of a biparatopic anti-FRα antibody, antigen binding fragment thereof, or immunoconjugate to a subject (e.g., a subject in need of treatment). In certain embodiments, the cancer is a cancer including, but are not limited to, fallopian tube cancer, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer (e.g., triple negative breast cancer (TNBC)), colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

More particular examples of such cancers include ovarian cancer, epithelial ovarian cancer, ovarian primary peritoneal cancer, or fallopian tube cancer. In certain embodiments, the cancer is ovarian cancer. In certain embodiments, the ovarian cancer is epithelial ovarian cancer (EOC). In certain embodiments, the ovarian cancer (e.g., an EOC) is platinum resistant, relapsed, or refractory. In certain embodiments, the cancer is peritoneal cancer. In certain embodiments, the peritoneal cancer is primary peritoneal cancer. In certain embodiments, the cancer is endometrial cancer. In certain embodiments, the endometrial cancer is serous endometrial cancer. In certain embodiments, cancer is lung cancer. In certain embodiments, the lung cancer is non-small cell lung cancer (NSCLC). In certain embodiments, the lung cancer is lung cancer is adenocarcinoma or bronchioloalveolar carcinoma. In certain embodiments, the cancer is uterine cancer.

In certain embodiments, the cancer is platinum refractory. In certain embodiments, the cancer is primary platinum refractory. In certain embodiments, the cancer is platinum sensitive.

In certain embodiments, the cancer is IMGN853-resistant.

In certain embodiments, the cancer is a metastatic or advanced cancer.

In certain embodiments, the cancer expresses the folate receptor to which the FRα-binding agent or antibody binds. In certain embodiments, the cancer overexpresses the human FRα.

In some embodiments, the biparatopic anti-FRα antibody, antigen binding fragment thereof, immunoconjugate, or pharmaceutical composition comprising the same is administered to a patient with an increased expression level of FRα, for example, as described in U.S. Published Application No. 2012/0282175 or International Published Application No. WO 2012/135675, both of which are incorporated by reference herein in their entireties. Exemplary antibodies, assays, and kits for the detection of FRα are provided in WO 2014/036495 and WO 2015/031815, both of which are incorporated by reference herein in their entireties. Thus, in some embodiments, the FRα protein expression is measured by immunohistochemistry (IHC) and given a staining intensity score and/or a staining uniformity score by comparison to controls (e.g., calibrated controls) exhibiting defined scores (e.g. an intensity score of 3 is given to the test sample if the intensity is comparable to the level 3 calibrated control or an intensity of 2 (moderate) is given to the test sample if the intensity is comparable to the level 2 calibrated control). A staining uniformity that is "heterogeneous" (i.e., at least 25% and less than 75% cells stained) or "homogeneous" (i.e., at least 75% cells stained) instead of "focal" (i.e., greater than 0% and less than 25% cells stained) is also indicative of increased FRα expression. The staining intensity and staining uniformity scores can be used alone or in combination (e.g., 2 homo, 2 hetero, 3 homo, 3 hetero, etc.). In another example, an increase in FRα expression can be determined by detection of an increase of at least 2-fold, at least 3-fold, or at least 5-fold) relative to control values (e.g., expression level in a tissue or cell from a subject without cancer or with a cancer that does not have elevated FRα values). In some embodiments, the staining uniformity score is based on the percent of stained cells.

In some embodiments, the cancer is a cancer that expresses FRα at a level of 1 hetero or higher by IHC. In some embodiments, the cancer is a cancer that expresses FRα at a level of 2 hetero or higher by IHC. In some embodiments, the cancer is a cancer that expresses FRα at a level of 3 hetero or higher by IHC. In some embodiments, the cancer is a lung cancer that expresses FRα at a level of 2 hetero or higher by IHC. In some embodiments, the cancer is a lung cancer that expresses FRα at a level of 3 hetero or higher by IHC. In some embodiments, the cancer is an ovarian cancer that expresses FRα at a level of 2 hetero or higher by IHC. In some embodiments, the cancer is an ovarian cancer that expresses FRα at a level of 3 hetero or higher by IHC. In some embodiments, the cancer is an endometrial cancer that expresses FRα at a level of 2 hetero or higher by IHC. In some embodiments, the cancer is an endometrioid cancer that expresses FRα at a level of 1 hetero or higher by IHC.

In some embodiments, at least one cell in sample obtained from a patient has an FRα score of at least 1. In some embodiments, at least one cell in sample obtained from a patient has an FRα score of at least 2 (moderate). In some embodiments, at least one cell in sample obtained from a patient has an FRα score of at least 3.

In some embodiments, at least 25% of the cells in a sample obtained from a patient have a FRα IHC score of at least 1. In some embodiments, at least 33% of the cells in a sample obtained from a patient have a FRα IHC score of at least 1. In some embodiments, at least 50% of the cells in a sample obtained from a patient have a FRα IHC score of at least 1. In some embodiments, at least 66% of the cells in a sample obtained from a patient have a FRα IHC score of at least 1. In some embodiments, at least 75% of the cells in a sample obtained from a patient have a FRα IHC score of at least 1.

In some embodiments, at least 25% of the cells in a sample obtained from a patient have a FRα IHC score of at least 2 (moderate). In some embodiments, at least 33% of the cells in a sample obtained from a patient have a FRα IHC score of at least 2 (moderate). In some embodiments, 25-75% of the cells in a sample obtained from a patient have a FRα IHC score of at least 2 (moderate). In some embodiments, at least 50% of the cells in a sample obtained from a patient have a FRα IHC score of at least 2 (moderate). In some embodiments, at least 66% of the cells in a sample obtained from a patient have a FRα IHC score of at least 2 (moderate). In some embodiments, at least 75% of the cells in a sample obtained from a patient have a FRα IHC score of at least 2 (moderate).

In some embodiments, at least 25% of the cells in a sample obtained from a patient have a FRα IHC score of at least 3. In some embodiments, at least 33% of the cells in a sample obtained from a patient have a FRα IHC score of at least 3. In some embodiments, at least 50% of the cells in a sample obtained from a patient have a FRα IHC score of at least 3. In some embodiments, at least 66% of the cells in a sample obtained from a patient have a FRα IHC score of at least 3. In some embodiments, at least 75% of the cells in a sample obtained from a patient have a FRα IHC score of at least 3.

In some embodiments, FRα expression can be measured by immunohistochemistry and given a visual score where FRα positive may refer to greater than or equal to 50% of tumor cells with FRα membrane staining visible at less than or equal to 10× microscope objective. In some embodiments, FRα expression can be measured by immunohistochemistry and given a visual score where FRα positive may refer to greater than or equal to 66% of tumor cells with FRα membrane staining visible at less than or equal to 10× microscope objective. In some embodiments, FRα expression can be measured by immunohistochemistry and given a visual score where FRα positive may refer to greater than or equal to 75% of tumor cells with FRα membrane staining visible at less than or equal to 10× microscope objective.

In certain embodiments, the subject is a human.

The present disclosure further provides methods for inhibiting tumor growth using the biparatopic anti-FRα antibodies, antigen binding fragments thereof, and immunoconjugates described herein. In certain embodiments, the method of inhibiting the tumor growth comprises contacting a tumor with the biparatopic anti-FRα antibodies, antigen binding fragments thereof, and immunoconjugates provided herein in vitro. For example, an immortalized cell line or a cancer cell line that expresses FRα is cultured in medium to which biparatopic anti-FRα antibodies, antigen binding fragments thereof, and immunoconjugates are added to inhibit tumor growth. In some embodiments, tumor cells are isolated from a patient sample such as, for example, a tissue biopsy, pleural effusion, or blood sample and cultured in medium to which biparatopic anti-FRα antibodies, antigen binding fragments thereof, and immunoconjugates are added to inhibit tumor growth.

In some embodiments, the method of inhibiting tumor growth comprises contacting the tumor or tumor cells with the biparatopic anti-FRα antibodies, antigen binding fragments thereof, and immunoconjugates in vivo. In certain embodiments, contacting a tumor or tumor cell with a biparatopic anti-FRα antibodies, antigen binding fragments thereof, and immunoconjugates is undertaken in an animal model. For example, biparatopic anti-FRα antibodies, antigen binding fragments thereof, and immunoconjugates can be administered to xenografts expressing one or more tumors that have been grown in immunocompromised mice (e.g. NOD/SCID mice) to inhibit tumor growth. In some embodiments, cancer stem cells are isolated from a patient sample such as, for example, a tissue biopsy, pleural effusion, or blood sample and injected into immunocompromised mice that are then administered biparatopic anti-FRα antibodies, antigen binding fragments thereof, and immunoconjugates to inhibit tumor cell growth.

In certain embodiments, the method of inhibiting tumor growth comprises administering to a subject a therapeutically effective amount of biparatopic anti-FRα antibodies, antigen binding fragments thereof, and immunoconjugates. In certain embodiments, the subject is a human. In certain embodiments, the subject has a tumor or has had a tumor removed.

Administration can be parenteral, including intravenous, administration.

The amount of biparatopic immunoconjugate, antibody or antigen-binding fragment thereof, or composition which will be effective in the treatment of a condition will depend on the nature of the disease. The precise dose to be employed in a composition will also depend on the route of administration, and the seriousness of the disease.

In some embodiments, provided herein are biparatopic anti-FRα antibodies, antigen binding fragments thereof, immunoconjugates, or pharmaceutical compositions comprising the same for use as a medicament. In some aspects, provided herein are biparatopic anti-FRα antibodies, antigen binding fragments thereof, immunoconjugates, or pharmaceutical compositions for use in a method for the treatment of cancer. In some aspects, provided herein are biparatopic anti-FRα antibodies, antigen binding fragments thereof, immunoconjugates, or pharmaceutical compositions for use in a method for the treatment of cancer in a subject, comprising administering to the subject an effective amount of the biparatopic anti-FRα antibodies, antigen binding fragments thereof, immunoconjugates, or pharmaceutical compositions provided herein.

In one aspect, biparatopic anti-FRα antibodies, antigen binding fragments thereof, and immunoconjugates of the disclosure are useful for detecting the presence of FRα, e.g., in a biological sample. The term "detecting" as used herein encompasses quantitative or qualitative detection. In certain embodiments, a biological sample comprises a cell or tissue. In certain embodiments, such tissues include normal and/or cancerous tissues that express FRα at higher levels relative to other tissues. In certain embodiments, FRα overexpression detects the presence of ovarian cancer, lung cancer, brain cancer, breast cancer, uterine cancer, renal cancer or pancreatic cancer.

In certain embodiments, the method of detecting the presence of FRα in a biological sample comprises contacting the biological sample with a biparatopic anti-FRα antibody, antigen binding fragment thereof, or immunoconjugate under conditions permissive for binding of biparatopic anti-FRα antibody, antigen binding fragment thereof, or immunoconjugate, and detecting whether a complex is formed between the biparatopic anti-FRα antibody, antigen binding fragment thereof, or immunoconjugate and FRα.

In certain embodiments, a biparatopic anti-FRα antibody, antigen binding fragment thereof, or immunoconjugate is labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application.

Example 1. Generation of Biparatopic Antibodies

Expression of Bispecific Antibodies

As described previously, a panel of murine anti-FRα antibodies were generated by standard hybridoma technology and humanized using a resurfacing method (see, e.g., WO 2011/106528 A1). Antibodies were classified into two bins depending upon whether they compete with Mov19 for binding (Bin 1) or not (Bin 2: FRα Antibody A, FRα Antibody B, FRα Antibody C, and FR57) using a FACS competition assay. Briefly, M9346A-biotinylated antibody at $1.5 \times 10^{-9}$ M was mixed with FRα Antibody A, FRα Antibody B, FRα Antibody C, and FR57 at a range of concentrations, generally from $5 \times 10^{-8}$ M to $5 \times 10^{-11}$ M. As a control of complete binding competition, non-biotinylated M9346A antibody was used. The mixture was added to 96-well plates containing 20,000 FRα-positive KB cells per well, and the plates were incubated on ice for one hour. The cells were than washed with cold phosphate buffered saline/1% bovine serum albumin, and bound huM9346A-biotin was detected with a streptavidin-PE reagent. The samples were analyzed using a FACSCalibur flow cytometer. As shown in FIG. 1, only control antibody M9346A competed with huM9346A-biotin for binding; none of the four analyzed FR-antibodies interfered with huM9346A-biotin for binding.

Using the variable regions (VH and VL) of Bin1 and Bin 2 antibodies, several biparatopic molecules were constructed using two different formats: Morrison's format and Asymmetric-Fc. Briefly, for Morrison's format based molecules, sequences corresponding to the VH and VL region of either Bin1 or Bin2 antibodies were connected by a (G4S)4 linker to create a single chain fragment (scFv) which was then fused to the C or N-terminus of the heavy chain of either Bin 2 or Bin1 IgG1 using a (G4S)3 linker. The asymmetric-Fc based biparatopic molecules were created with FR57scFv and Mov19 Fab using the Knobs-in-holes technology (Protein Eng. 1996 July; 9(7):617-21. 'Knobs-into-holes' engineering of antibody CH3 domains for heavy chain heterodimerization. Ridgway J B, Presta L C, Carter, P). Briefly, FR1-57scFv was fused to an engineered Fc region containing the C220S (mutate unpaired cysteine to serine) and knob mutation (T366W); and the Mov19 Fab region to an engineered Fc containing the hole mutation (T366S, L368A and Y407V). Unless otherwise noted, all numberings are based on the EU system. FIG. 2 shows the various antibody formats evaluated in subsequent experiments.

Figure 3:
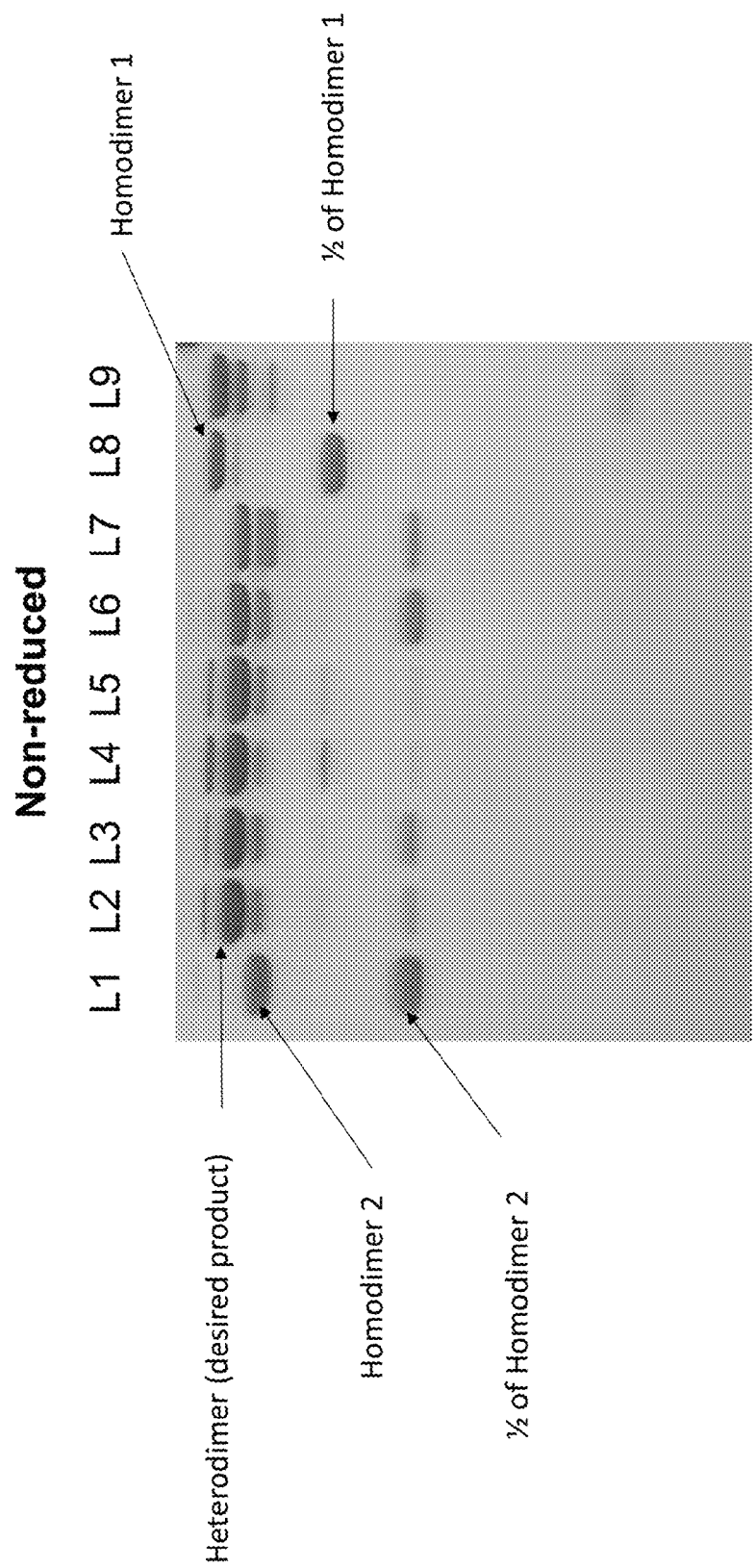
Figures 4A, 4B:
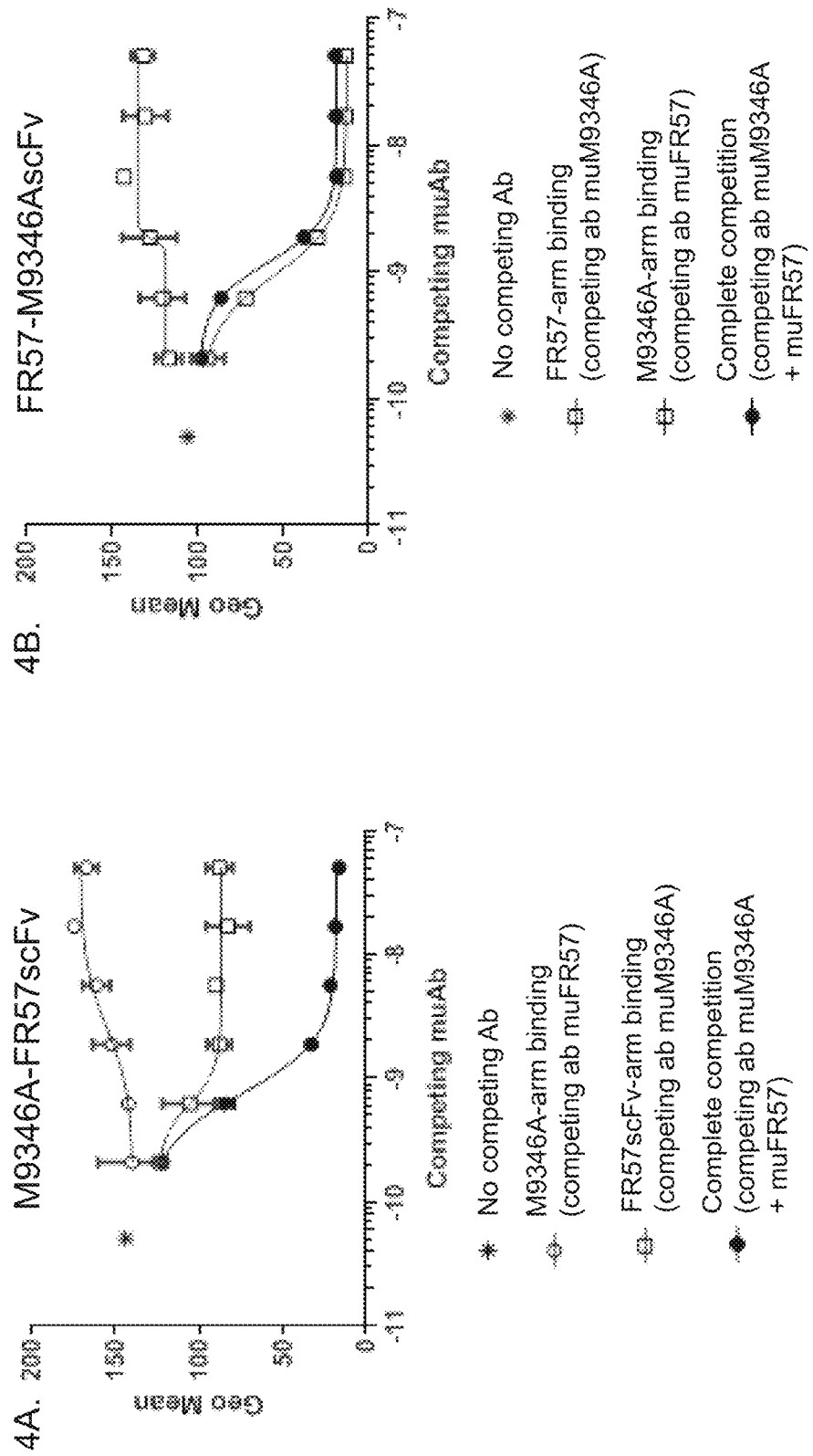
Figures 4C, 4D:
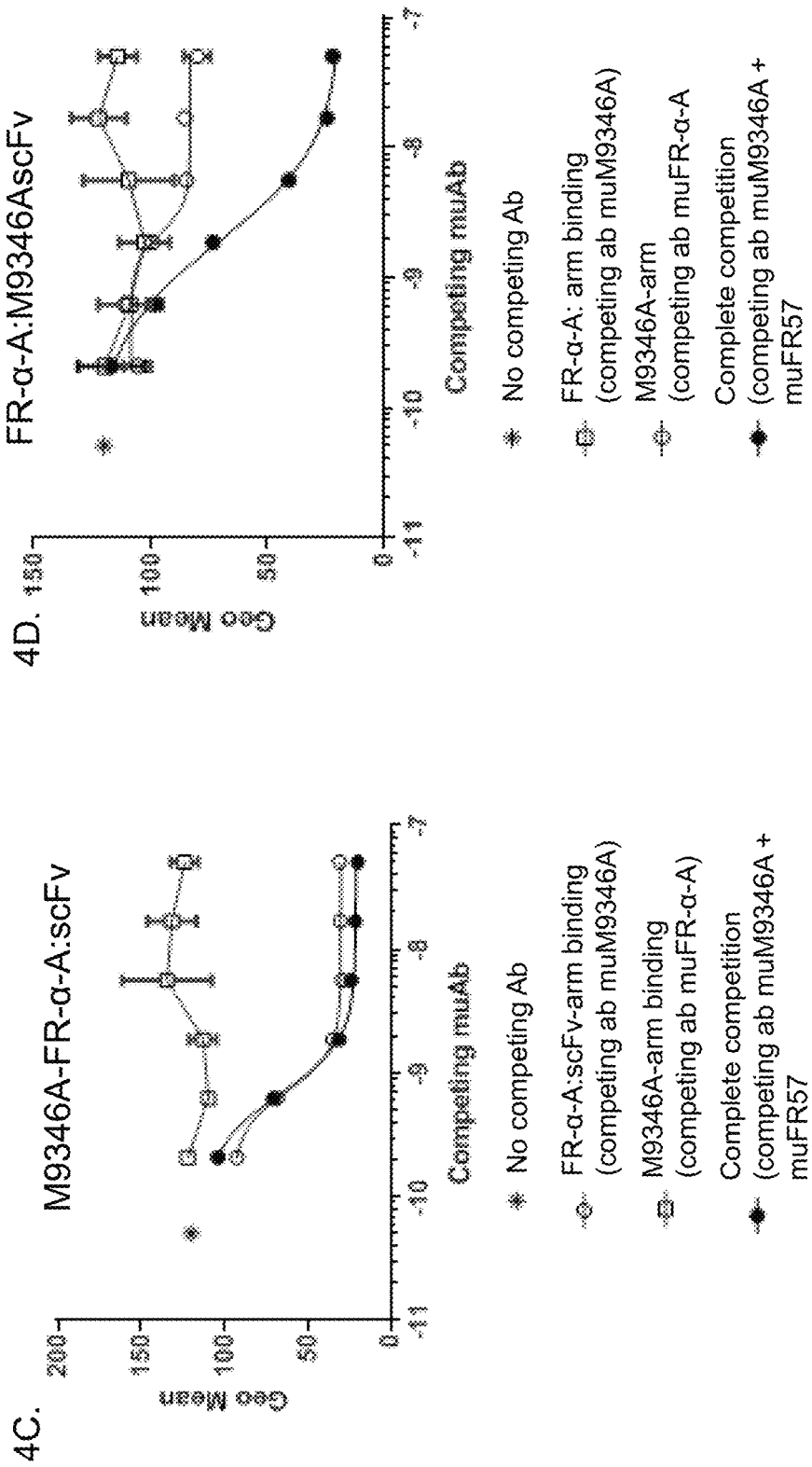
Figures 4E, 4F:
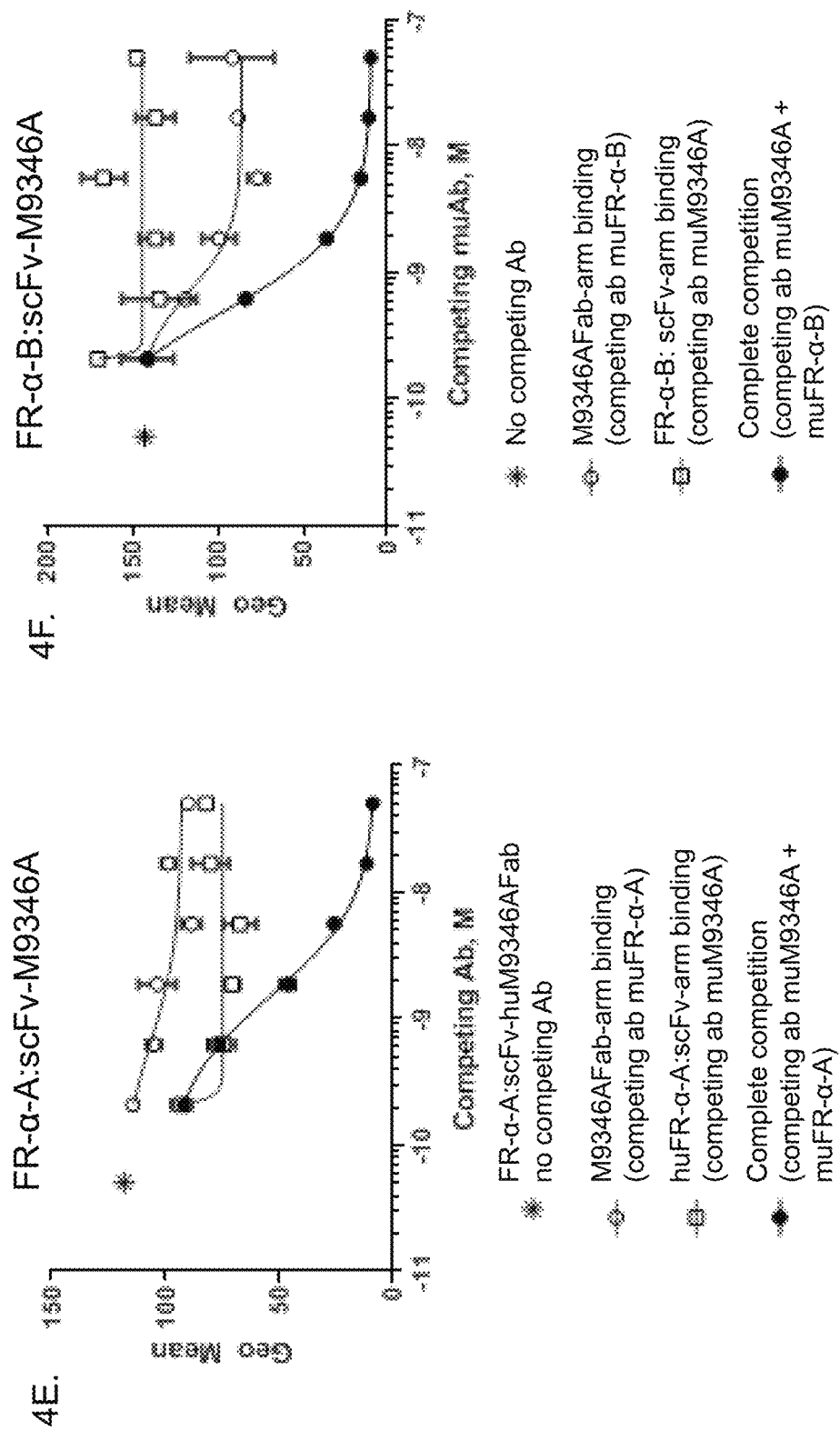
Figures 4G, 4H:
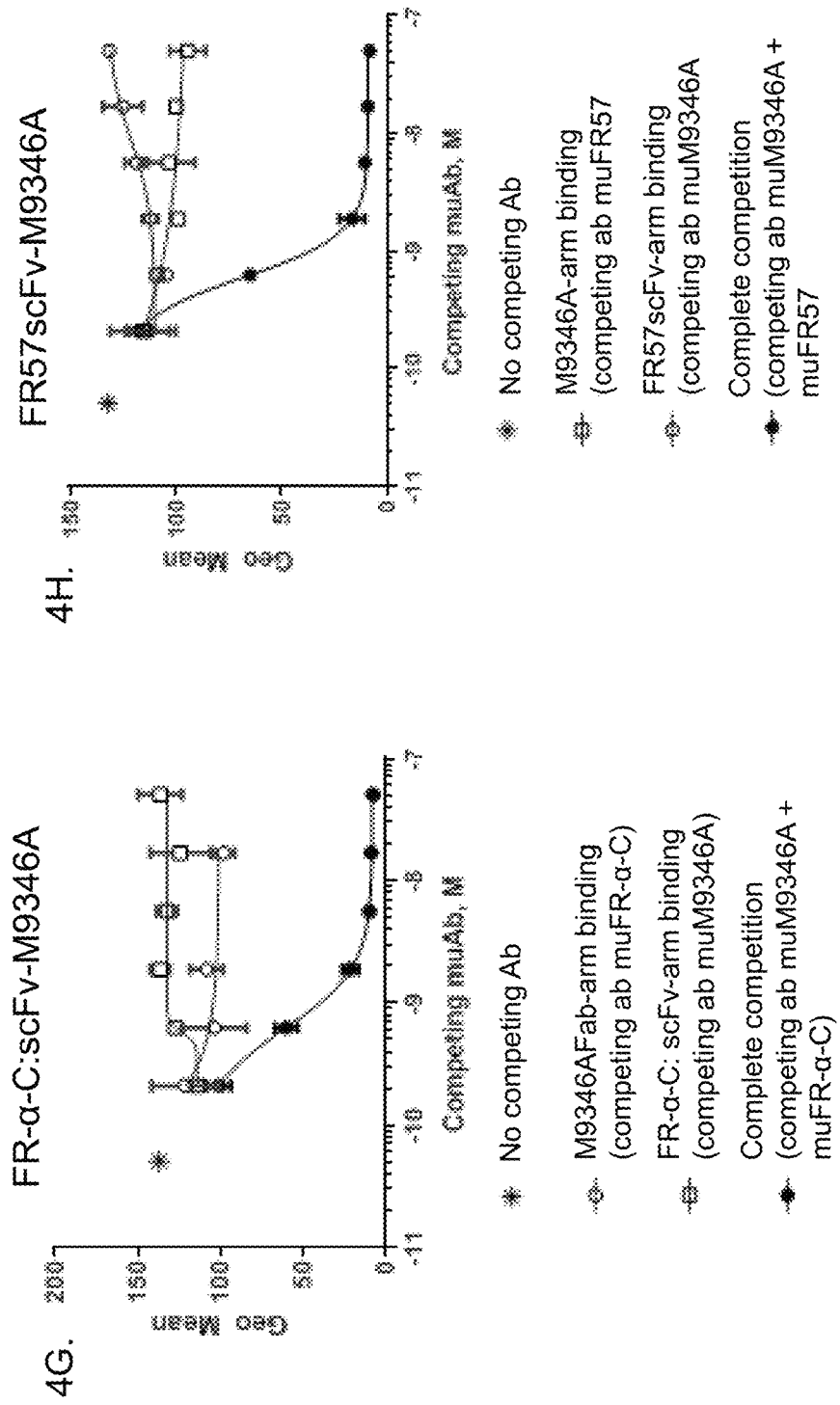

The sequences of certain constructed molecules are provided in Tables 6-7. The genes corresponding to these bispecific antibodies were codon-optimized, synthesized and cloned into plasmids using standard molecular biology techniques. The ratio of the light and heavy chain plasmids for transfections was kept at 1:3 for Morrison's based molecules; and 9:3:1 (Mov19LC: Mov19 HC-hole: FR57scFv-knob) for asymmetric-Fc based molecules. As shown in FIG. 3, several heavy chain and light chain plasmid transfection ratios were explored for producing asymmetric-Fc based molecules, with the ratio of 9:3:1 showing a minimal amount of homodimers.

All the bispecific antibody molecules were produced transiently in 293T. Briefly, for 293T transfections, the expression constructs were transiently produced in suspension adapted HEK-293T cells using PEI as transfection reagent in shake flasks. The PEI transient transfections were performed as previously described (Durocher et al., Nucleic Acids Res. 30(2):E9 (2002)), except the HEK-293T cells were grown in Freestyle 293 and the culture volume was left undiluted after the addition of the PEI-DNA complexes. The transfections were incubated for a week and harvested.

Antibody Purification

The filtered supernatant was purified using a scheme that essentially consists of two chromatography steps: protein A affinity and ceramic hydroxyapatite (CHT). Briefly, the filtered supernatant was loaded on a protein A column which had been pre-equilibrated with 1×PBS (pH 7.3±0.1). The column was washed with 1×PBS (pH 7.3±0.1) to reduce non-specific host cell proteins. The bound antibody was eluted using 25 mM acetic acid containing 50 mM sodium chloride (pH 3.2) and neutralized immediately with 1M Tris-base to a pH of 7.0±0.2. The neutralized pool was diluted 1:10 in CHT binding buffer (15 mM sodium phosphate, pH 7.0±0.1) and loaded onto a Type II CHT column (40 µm particle size) pre-equilibrated with CHT binding buffer. The bound protein was eluted using a linear gradient (15 mM to 160 mM sodium phosphate in 10 column volumes), and fractions of interest (high percent monomers by size exclusion chromatography, SEC) were pooled, dialyzed against 1×PBS (pH 7.3±0.1), and filter sterilized. The final antibody concentration was determined by measuring absorbance at 280 nm and an extinction coefficient of 1.44 mL mg$^{-1}$ cm$^{-1}$.

All the purification experiments were conducted on an AKTA purification system which was equipped with in-line UV, conductivity and pH probes. The SEC analysis was performed using an Agilent HPLC 1100 system by injecting 40 µg of a sample on a TSKgel G3000SWXL column (7.8×300 mm) which also had an in-line guard column (6.0×40 mm) to extend column life. The mobile phase contained 50 mm sodium phosphate buffer and 400 mm sodium perchlorate, the flow rate was 1.0 mL/min, and the elution isocratic.

Example 2. Effect of Biparatopic Antibody Format on Antibody Production, Stability, and Functional Activity Binding Characteristics of Parental (Bin 1 and Bin 2) Antibodies Table 10 summarizes the kinetic parameters of binding of Bin1 and Bin 2 antibodies with recombinant FRα antigen. KD values were obtained via biolayer interferometry performed on Octet96 system (Fortebio) essentially according to manufacturer's recommended procedure. Briefly, anti-human- or anti-murine –Fc sensors were presoaked in 1× Kinetic Buffer (Fortebio) for 10 min and incubated with 5 µg/mL of either Bin 1 or Bin 2 IgG for 5 min. The sensors were then sequentially moved to 1× Kinetic Buffer for 5 min to determine baseline, serial dilutions of antigen for association (10 min), and 1× Kinetic Buffer for dissociation (10 min). The raw data was collected, processed and fitted to a simple 1:1 binding model using Fortebio analysis software to determine the kinetic parameters Kon and Koff.

TABLE 10

| Name | KD (M) | Kon (1/Ms) | Koff (1/s) |
| --- | --- | --- | --- |
| Mov19 (Bin 1) | $6 \times 10^{-10}$ | $5 \times 10^5$ | $3 \times 10^{-4}$ |
| FR57 (Bin 2) | $1 \times 10^{-9}$ | $3 \times 10^5$ | $4 \times 10^{-4}$ |
| FRα Antibody A (Bin 2) | $4 \times 10^{-9}$ | $1 \times 10^5$ | $4 \times 10^{-4}$ |
| FRα Antibody B (Bin 2) | $1 \times 10^{-8}$ | $3 \times 10^5$ | $4 \times 10^{-3}$ |
| FRα Antibody C (Bin 2) | $3 \times 10^{-9}$ | $3 \times 10^5$ | $7 \times 10^{-4}$ |

Stability of Biparatopic Antibodies

Biparatopic antibodies were created by combining Mov19 antibody with an antibody recognizing another nonoverlapping epitope. In particular, IgGs based on Morrison's format were generated by fusing scFv from one of the Bin IgGs to the C or N terminus of an IgG from another bin. Table 11 lists all the combinations which were explored. The scFvs fused to the C-terminus were in VH-VL orientation; and those fused to the N-terminus were in VL-VH orientation. Mov19 was explored as a scFv only on the C-terminus in both VH-VL and VL-VH orientations with or without Brinkmann's VH44-VL100 disulfide stabilizing mutations (PNAS 1993 August; 90 (16): 7538-754. A recombinant immunotoxin containing a disulfide-stabilized Fv fragment. U Brinkmann, Y Reiter, S H Jung, B Lee, and I Pastan).

TABLE 11

| Name | Titer (mg/L): 293T | % Monomer post protein A | Change in % monomer over 1 week | scFv location |
|---|---|---|---|---|
| Morrison's format | | | | |
| Mov19-G1-FRα-Antibody-A-scFv1* | 2.35 | 93 | >5% | C-terminus |
| Mov19-G1-FRα-Antibody-B-scFv1 | 2.24 | <70 | | C-terminus |
| Mov19-G1-FRα-Antibody-C-scFv1 | 0.4 | <70 | | C-terminus |
| Mov19-G1-FR57scFv1* | 4.43 | 91 | <0.1% | C-terminus |
| FRα-Antibody-A-G1-Mov19scFv1* | 6.37 | 75 | | C-terminus |
| FRα-Antibody-B-G1-Mov19scFv1 | 9.35 | <70 | | C-terminus |
| FRα-Antibody-C-G1-Mov19scFv1 | 10.1 | <70 | | C-terminus |
| FRα-Antibody-C-G1-Mov19scFv2 | 1.38 | <70 | | C-terminus |
| FRα-Antibody-C-G1-Mov19scFv3 | 2.78 | <70 | | C-terminus |
| FR57-G1-Mov19scFy1* | 5 | 73 | >5% | C-terminus |
| FRα-Antibody-A-scFv2-G1-Mov19* | 11.2 | 72 | >5% | N-terminus |
| FRα-Antibody-B-scFv2-G1-Mov19* | 12.0 | 89 | >5% | N-terminus |
| FRα-Antibody-C-scFv2-G1-Mov19* | 6.2 | 83 | >5% | N-terminus |
| FR57scFv2-G1-Mov19* | 13.3 | 90 | <0.1% | N-terminus |
| Asymmetric-Fc | | | | |
| FR57scFv2-knob/Mov19-hole | 26 | 87 | | N.A |
| FR57scFv3wt-knob/Mov19-hole | 15 | 70 | | N.A |

As shown in Table 9, a significant number of biparatopic molecules based on Morrison's format had low percent monomers post-protein A affinity purification. Since scalability or manufacturability could be a challenge for constructs with low percent monomer or titer, eight constructs (indicated by asterisks in Table 9) that exhibited higher titers and % monomers greater than 70 were selected for further evaluation. These eight constructs were further polished using ceramic hydroxyapatite chromatography to greater than 95% purity and subjected to further characterization. To account for the effects of overall molecule conformation or potential structural changes of the scFv arms on the binding of the biparatopic arms, the binding efficiency of each arm of the eight Morrison's constructs was assayed by a competition FACS assay. Briefly, FRα-positive T47D cells were incubated with 0.8 nM of a Morrison's antibody mixed with a corresponding murine parental antibody at a range of concentrations, generally from 50 nM to 0.2 nM. After incubation on ice for 2 hours, cells were washed from unbound antibodies, and bound Morrison's antibody was detected with secondary anti-human FITC-labeled antibody. Reduced binding of the Morrison's antibody in the presence of increasing concentration of the parental antibody indicated an effect on binding of the second set of arms. As shown in FIGS. 4A-4H and Table 12, five out of eight Morrison's antibodies had either completely inactive or partially affected arms. Among the three Morrison's antibodies having both sets of functional arms, two antibodies (FRα-Antibody-A-scFv2-Mov19-IgG1 and FRα-Antibody-C-scFv2-Mov19-IgG1) exhibited stability issues. Based on these data, FR57scFv2-Mov19-IgG1 ("Tetravalent") was selected for further evaluation.

TABLE 12

| Tetravalent Ab | Arm binding (according to competition FACS) | |
|---|---|---|
| | Fab | scFv |
| Mov19:FRα-Antibody-A-scFv | Active | Inactive |
| FRα-Antibody-A:Mov19scFv | Active | Partially affected |
| Mov19:FR57scFv | Active | Partially affected |
| FR57:Mov19scFv | Active | Inactive |
| FRα-Antibody-A-scFv:Mov19 | Active | Active |
| FRα-Antibody-B-scFv:Mov19 | Partially affected | Active |
| FRα-Antibody-C-scFv:Mov19 | Active | Active |
| FR57scFv:Mov19 | Active | Active |

Figure 5:
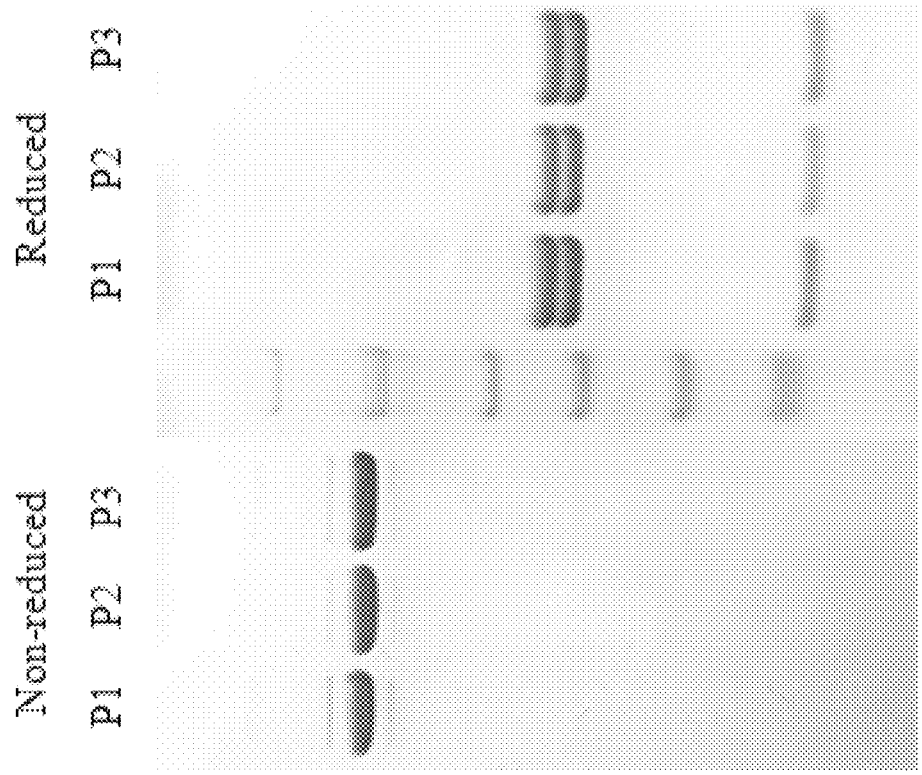
FIG. 5 shows an SDS PAGE gel of three purified preparations (P1, P2, and P3) of the FR57scFv2-knob-Mov19-hole antibody under non-reducing and reducing conditions. The FR57scFv2-knob-Mov19-hole antibody is a biparatopic antibody in the knob-in-hole (KIH) format with an FR57 scFv on the knob side of the antibody and huMov19 antibody sequences on the hole side of the antibody. (See Example 2.)

In a separate experiment, two biparatopic molecules based on the asymmetric-Fc format (FR57scFv2-knob-Mov19-hole and FR57scFv3 wt-knob-Mov19-hole) were also expressed. FR57scFv2-knob-Mov19-hole ("KIH") exhibited higher % monomer and titer and was selected for further evaluation. As shown in FIG. 5, this molecule runs as a single band (corresponding to ~125 kDa) in gel electrophoresis under non-reducing conditions and breaks down into 3 bands (one corresponding to light chain (~25 kDa) and two corresponding to heavy chains (FR57scFv-Fc-knob and Mov19-HC-hole) of similar size (~50 kDa each)) under reducing conditions. These results suggest that FR57scFv2-knob-Mov19-hole is assembled correctly in cell-culture and does not fall apart during purification.

Figure 6:
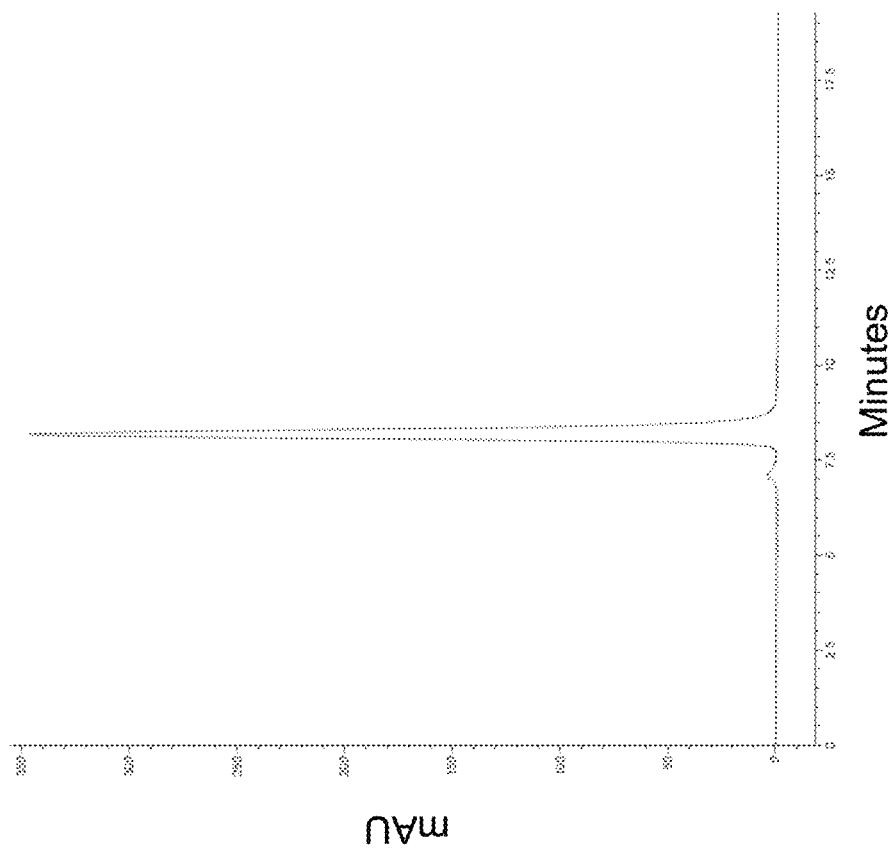
FIG. 6 shows an overlay of size exclusion chromatography results obtained from Day 0 and Day 14 samples of the FR57scFv2-knob-Mov19-hole antibody. mAU: milli-Absorbance Units. (See Example 2.)

Next, the stability of the FR57scFv2-knob-Mov19-hole molecule was assessed by heating the molecule at 40° C. (conc: 10 mg/mL in 1×PBS) for 2 weeks and performing an SEC analysis essentially using the procedures described in Example 1. FIG. 6 shows the SEC overlay of a Day 0 and Day 14 sample. In particular, no aggregation or cleavage was observed, suggesting good stability of the molecule.

Antibody Binding and Processing

The effect of antibody format on antibody binding and processing was assessed in vitro with using 3 [H]-antibodies. Briefly, FRα-positive KB cells were exposed to a saturating concentration of the parental, KIH biparatopic, or Morrison's antibody for 30 min at 37° C., washed in PBS to remove any unbound antibody, resuspended in fresh culture medium, and incubated at 37° C. in a humidified 6% CO2 atmosphere for 22 h. The amount of protein-free radioactivity (processed antibody) and protein-associated radioactivity (unprocessed antibody) was assessed following acetone extraction and liquid scintillation counting, and the data were used to calculate the antibody binding sites per cell (ABC), % processed antibody, and amount of processed antibody. A preliminary experiment showed that processing of the parental antibodies M9346A and huFR57 was similar. Accordingly, only one parental antibody (M9346A) was used in further experiments.

Figures 7A, 7B, 7C, 7D, 7E, 7F:
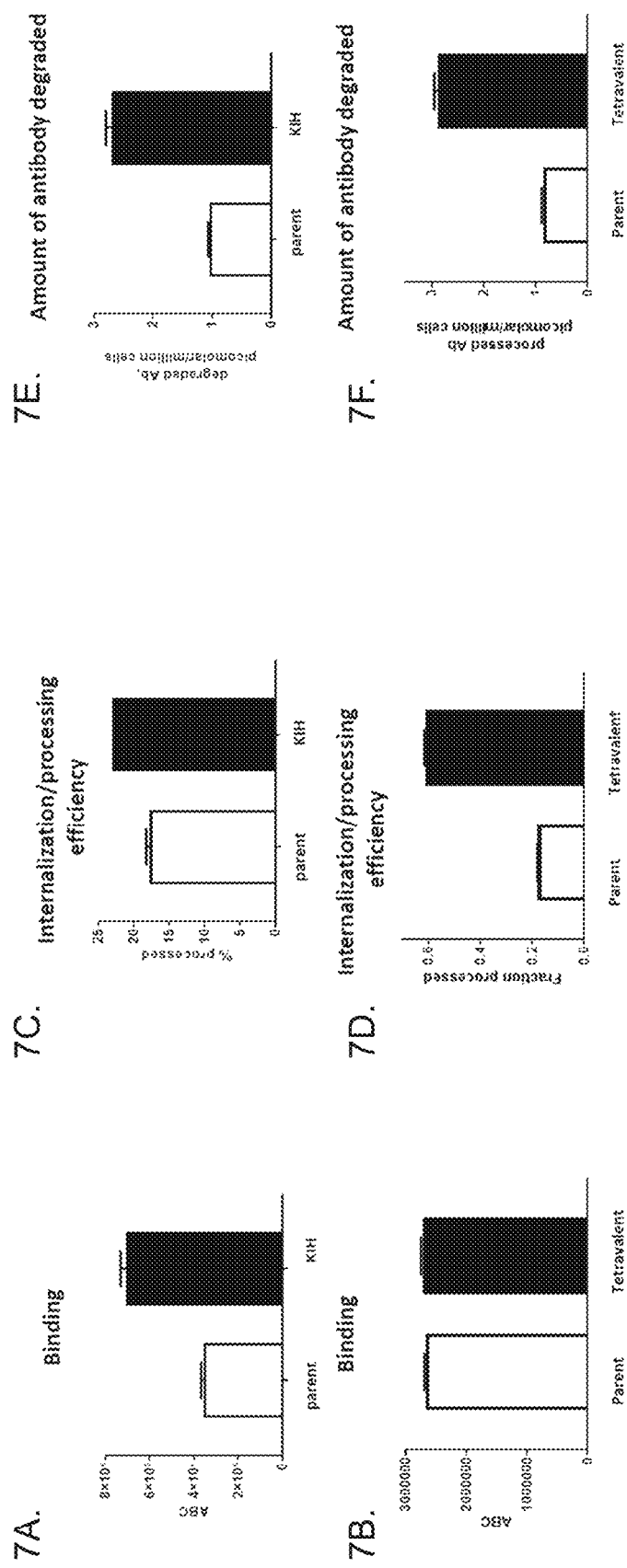
FIGS. 7A-7F show the binding (FIGS. 7A and 7B), internalization and processing (FIGS. 7C and 7D), and degradation (FIGS. 7E and 7F) of a Knob-in-hole (KIH) biparatopic antibody (FIGS. 7A, 7C, and 7E) or a tetravalent biparatopic antibody (FIGS. 7B, 7D, and 7F) compared to the huMov19 ("parent") antibody. (See Example 2.)

Both biparatopic formats (KIH and tetravalent) showed increased amount of antibody processed compared to the parental antibody (FIGS. 7C and 7D). Intriguingly, mechanisms of improved delivery/processing of the two biparatopic formats were different. The KIH biparatopic antibody had higher ABC and similar internalization efficiency as the monospecific parental antibody (FIGS. 7A-7D), while the Morrison's tetravalent antibody showed improved internalization efficiency with ABC values comparable to the parental antibody (FIGS. 7C and 7D). The amount of antibody degraded for the two biparatopic formats was similar (FIGS. 7E and 7F).

Example 3. Preparation of Biparatopic FRα-Targeting Immunoconjugates

Preparation of FR57scfv-huMov19-Sulfo-SPDB-DM4 Conjugates

The molar concentration of FR57scfv-huMov19, sulfo-SPDB, and DM4 were calculated according to Beer's law using the UV/Vis absorbance values at 280, 343, and 412 nm and the extinction coefficients respectively. The linker concentration was determined by reacting the linker with 25 mM DTT in 50 mM potassium phosphate buffer, 50 mM sodium chloride with 2 mM EDTA at pH 7.5 and measuring thiopyridine release at 343 nm. The drug concentration was determined by reacting DM4 with 10 mM DTNB [5,5-dithiobis-(2-nitrobenzoic acid)] in 50 mM potassium phosphate buffer, 50 mM sodium chloride with 2 mM EDTA at pH 7.5 and measuring absorbance at 412 nm.

Prior to antibody conjugation, sulfo-SPDB-DM4 in-situ mixture was prepared by reacting 1.5 mM sulfo-SPDB with 1.95 mM DM4 in 30% aqueous [15 mM potassium phosphate pH 7.6) and 70% organic [(N—N-dimethylacetamide, DMA, SAFC)] at 25° C. for 90 min. During the conjugation reaction, a solution of 2.5 mg/mL of antibody was reacted with 8 to 8.5-fold molar excess of sulfo-SPDB-DM4 over antibody in 15 mM potassium phosphate pH 7.6 with 10% DMA (v/v), for 15-20 hours at 25° C. The reaction was purified into 10 mM acetate, 9% sucrose, 0.01% Tween 20, pH 5.0 formulation buffer using Sephadex 25 desalting columns on AKTA and filtered through a syringe filter with a 0.22 µm PVDF membrane.

The molar ratio of DM4 conjugated to antibody (DAR) and the percentage of unconjugated maytansinoid species were determined as described below. The purified conjugate was found to have 3.4 mol DM4/mol antibody by UV-Vis, 99.8% monomer by SEC, and below 2% free drug by HPLC Hisep column analysis.

DAR was determined by measuring the UV/Vis absorbance at 252 and 280 nm and calculating the Ab concentration and DM4 concentration using binomial equations that account for the contribution of each component. The amount of unbound maytansinoid present in the final FR57scfv-huMov19-sulfo-SPDB-DM4 conjugate sample was calculated from the resulting peak areas observed in samples analyzed via HISEP column (25 cm×4.6 mm, 5 µm). The percent free maytansinoid (% FM) present in the conjugate sample was calculated using the following equation: % Free Maytansinoid=(Reverse-phase PA 252 due to DM4)/(Reverse-phase PA 252 due to DM4+Flow through PA 252 due to DM4)×100%.

Preparation of Knob-in-Hole (KIH)-FR57scfv-huMov19-Sulfo-SPDB-DM4 Conjugate

Prior to antibody conjugation, sulfo-SPDB-DM4 in-situ mixture was prepared by reacting 1.5 mM sulfo-SPDB with 1.95 mM DM4 in 30% aqueous [15 mM potassium phosphate pH 7.6) and 70% organic [(N—N-dimethylacetamide, DMA, SAFC)] at 25° C. for 90 min. During the conjugation reaction, a solution of 3.0 mg/mL of antibody was reacted with 10-fold molar excess of sulfo-SPDB-DM4 over antibody in 15 mM potassium phosphate pH 7.6 with 11% DMA (v/v), for 15-20 hours at 25° C. The reaction was purified twice into 10 mM succinate, 250 mM glycine, 0.5% sucrose, 0.01% Tween 20, pH 5.5 formulation buffer using NAP desalting columns and filtered through a syringe filter with a 0.22 µm PVDF membrane. The purified conjugate was found to have 2.9 mol DM4/mol antibody by UV-Vis, 90.6% monomer by SEC, and below 1% free drug by HPLC Hisep column analysis.

Preparation of FR57scfv-huMov19-DM21 Conjugates

The molar concentration of FR57scfv-huMov19, sulfo-GMBS, and DM21 were calculated according to Beer's law using the UV/Vis absorbance values at 280, 343, and 412 nm and extinction coefficients respectively. The linker concentration was determined by reacting the linker with 50 mM DTT in 25 mM DTT in 50 mM potassium phosphate buffer, 50 mM sodium chloride with 2 mM EDTA at pH 7.5 and measuring thiopyridine release at 343 nm. The drug concentration was determined by reacting DM21 with 10 mM DTNB [5,5-dithiobis-(2-nitrobenzoic acid)] in 50 mM potassium phosphate buffer, 50 mM sodium chloride with 2 mM EDTA at pH 7.5 and measuring absorbance at 412 nm.

Prior to conjugation, sulfo-GMBS-DM21 in-situ mixture was prepared by reacting 1.5 mM sulfo-GMBS with 1.95 mM DM21 in 60/40 (v/v) DMA and succinate buffer pH 5.0 respectively. The conjugation was carried out with 6.5 linker excess of sulfo-GMBS-DM21 over antibody at 2.5 mg/mL in 60 mM 4-(2-Hydroxyethyl)-1-piperazinepropanesulfonic acid (EPPS) pH 8.0 with 10% DMA (v/v). After a 20-22 hour incubation at 25° C., the reaction was purified into 10 mM succinate, 250 mM glycine, 0.5% sucrose, 0.01% Tween 20, pH 5.5 using NAP desalting columns and filtered through a 0.22 µm PVDF membrane filter.

The molar ratio of DM21 conjugated to antibody (DAR) and the percentage of unconjugated maytansinoid species were determined as described below. The purified conjugate was found to have 3.7 mol DM21/mol antibody by UV-Vis, 98% monomer by SEC, and below 2% free drug by HPLC Hisep column analysis.

The molar ratio of DM21 conjugated to antibody (DAR) was determined by measuring the UV/Vis absorbance at 252 and 280 nm and calculating the Ab concentration and DM21 concentration using binomial equations that account for the contribution of each component. The amount of unbound maytansinoid present in the final FR57scfv-huMov19-GMBS-DM21L conjugate sample was calculated from the resulting peak areas observed in samples analyzed via HISEP column (25 cm×4.6 mm, 5 µm). The percent free maytansinoid (% FM) present in the conjugate sample was calculated using the following equation: % Free Maytansinoid=(Reverse-phase PA 252 due to DM21)/(Reverse-phase PA 252 due to DM21+Flow through PA 252 due to DM21)×100%.

Preparation Of—Knob-in-Hole (KIH)-FR57scfv-huMov19-GMBS-DM21L Conjugates

Initial batches of KIH-FR57scfv-huMov19-GMBS-DM21L were prepared using lower concentrations of drug and linker in the in-situ mixture and lower antibody concentration during the conjugation process. Briefly, prior to conjugation, sulfo-GMBS-DM21 in-situ mixture was prepared by reacting 1.5 mM sulfo-GMBS with 1.95 mM DM21 in 60/40 (v/v) DMA and succinate buffer pH 5.0, respectively. The conjugation was carried out with 7.5 linker excess of sulfo-GMBS-DM21 over antibody at 2.5 mg/mL in 60 mM 4-(2-Hydroxyethyl)-1-piperazinepropanesulfonic acid (EPPS) pH 8.0 with 10% DMA (v/v). After a 20-22 hour incubation at 25° C., the reaction was purified twice into 10 mM succinate, 250 mM glycine, 0.5% sucrose, 0.01% Tween 20, pH 5.5 using NAP desalting columns and filtered through a 0.22 μm PVDF membrane filter. The purified conjugate was found to have 3.1 mol DM21/mol antibody by UV-Vis, 99.1% monomer by SEC, and below 2% free drug by HPLC Hisep column analysis.

Later batches of KIH-FR57scfv-huMov19-GMBS-DM21L for use in pharmacokinetic and efficacy studies were prepared using higher concentrations of drug and linker in the in-situ mixture and higher antibody concentration during the conjugation process. Briefly, prior to conjugation, sulfo-GMBS-DM21 in-situ mixture was prepared by reacting 3 mM sulfo-GMBS with 3.9 mM DM21 in 60/40 (v/v) DMA and succinate buffer pH 5.0 respectively. The conjugation was carried out with 6.5-7 linker excess of sulfo-GMBS-DM21 over antibody at 5.7-6 mg/mL in 60 mM 4-(2-Hydroxyethyl)-1-piperazinepropanesulfonic acid (EPPS) pH 8.0 with 10% DMA (v/v). After a 20-22 hour incubation at 25° C., the reaction was purified into 10 mM succinate, 250 mM glycine, 0.5% sucrose, 0.01% Tween 20, pH 5.5 using Sephadex-25 desalting columns on AKTA and filtered through a 0.22 μm PVDF membrane filter. The purified conjugate was found to have 3.1 mol DM21/mol antibody by UV-Vis, 98.7% monomer by SEC, and below 2% free drug by HPLC Hisep column analysis.

A composition comprising the KIH-FR57scfv-huMov19-GMBS-DM21L construct with a DAR of 3.5 is referred to as "IMGN151."

Example 4. Effect of Biparatopic Antibody Format on Immunoconjugate Efficacy

In Vitro Cytotoxicity of Biparatopic Immunoconjugates

The effect of the biparatopic antibody format on immunoconjugate cytotoxicity was assessed in vitro using KB, Igrov-1, and T47D cells. Sulfo-SPDB-DM4 conjugates of the parental, KIH, and Morrison's antibodies were prepared according to the methods described in Example 3. The conjugates were diluted in the appropriate culture medium and added to wells of 96-well flat-bottom plates containing $1 \times 10^3$ cells/well. The plates were incubated at 37° C., 6% $CO_2$ for 5 days. Cell viability was determined by the WST-8 assay in accordance with the manufacturer's protocol, and $IC_{50}$ were generated using a sigmoidal dose-response (variable slope) nonlinear regression curve fit (GraphPad Software Inc).

TABLE 13

| Cell Line | FRα Density (X 1000), anti-FRα conventional Ab-PE FACS | Ab-sulfo-SPDB-DM4, IC50, nM | | |
|---|---|---|---|---|
| | | Parental (M9346A) | Bivalent KIH | Tetravalent, Morrison |
| KB | ~4,000 | 0.1 | 0.09 | 0.07 |
| Igrov-1 | 500 | 2.0 | 0.2 | 0.2 |
| T47D | 100 | 20.0 | 0.2 | 1.0 |

Both of the biparatopic sulfo-SPDB-DM4 conjugates were more active than the parental antibody conjugate against two out of the three tested moderate to low FRα-expressing cell lines (Igrov-1 and T47D). The only cell line equally sensitive to the three conjugates was KB, which has very high level of target expression. The KIH conjugate demonstrated greater cytotoxic activity than the Morrison's format conjugate against the T47D cell line (i.e., cells with lowest level of target expression). However, both KIH conjugate and the Morrison's format conjugate were equally active against two other lines analyzed.

In Vivo Anti-Tumor Activity of a Tetravalent Biparatopic ADC in SCID Mice Bearing OV-90 Human Ovarian Carcinoma Xenografts The effect of the tetravalent biparatopic antibody format on immunoconjugate therapeutic efficacy was assessed in vivo using an OV-90 xenograft model. Mice were randomized into groups (n=6 per group) by tumor volume and subsequently dosed on day 7 post inoculation. The groups included a control group dosed with formulation buffer, Tetravalent-s-SPDB-DM4 at 2.5 and 5 mg/kg and M-s-SPDB-DM4 at 2.5 and 5 mg/kg. All mice were administered a single intravenous dose of the above compounds. The study was terminated on day 80 post inoculation Tumor volumes were measured two times per week in three dimensions using a caliper. The volume was expressed in mm3 using the formula Volume=½ (Length×Width×Height) (Cancer Chemother. Pharmacol. 1989 (24): 148-154. Determination of subcutaneous tumor size in athymic (nude) mice. MM Tomayko and CP Reynolds). Body weights were measured twice per week as a rough index of test agent toxicity. Activity was assessed as described in Cancer Res. 1991 September (51): 4845-4852. Experimental Antitumor Activity of Taxotere (RP 56976, NSC 628503), a Taxol Analogue. M Bissery, D Guenard, F Gueritte-Voegelein, et al.

Figure 8:
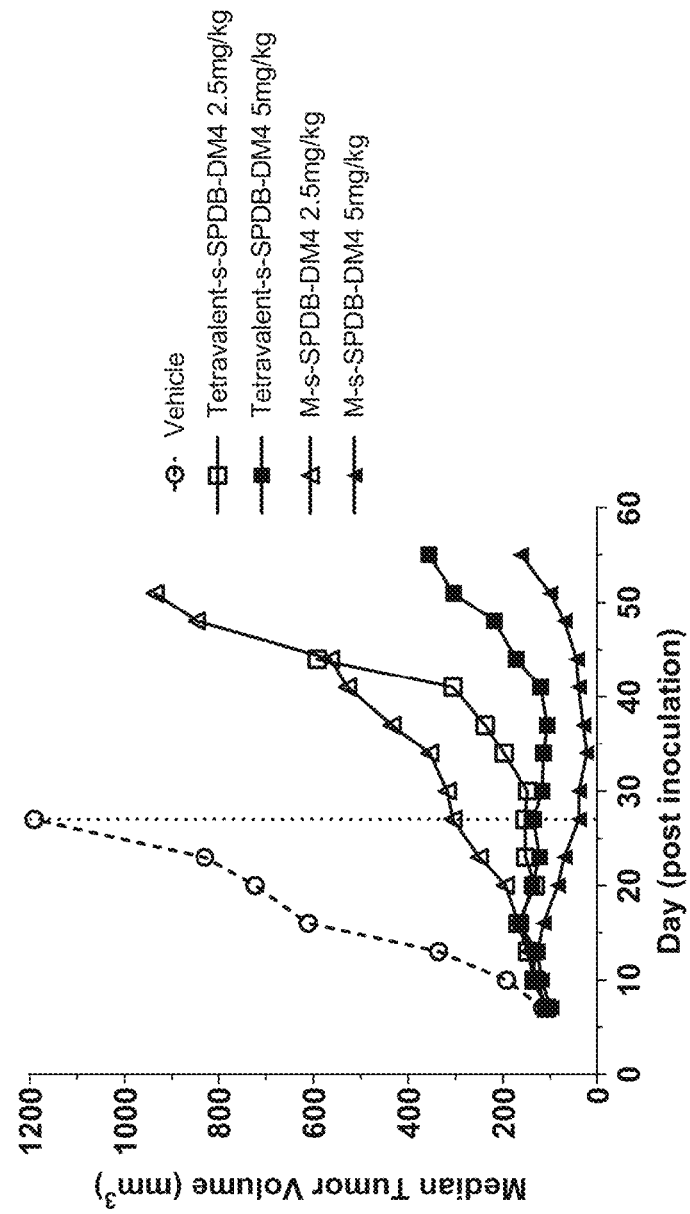
FIG. 8 shows the median tumor volume in an OV-90 xenograft model after administration of vehicle, an immunoconjugate containing a tetravalent biparatopic antibody ("Tetravalent-s-SPDB-DM4"), or an immunoconjugate containing the huMov19 antibody ("M-s-SPDB-DM4"). (See Example 4.)

The results of the study are shown in FIG. 8 and Table 14. The Tetravalent-s-SPDB-DM4 conjugate was active at both the 2.5 and 5 mg/kg doses, with T/Cs of 13% and 11%, respectively. The 2.5 mg/kg dose had a T-C of 32 days, LCK of 1.25 (active), 2/6 PRs and 0/6 CRs. The 5 mg/kg dose had a T-C of 47 days, LCK of 1.84 (active), 2/6 PRs, 2/6 CRs and 1/6 TFS. The M-s-SPDB-DM4 conjugate was active at the 2.5 mg/kg dose with a T/C of 26% and highly active at the 5 mg/kg dose with a T/C of 3%. The 2.5 mg/kg dose had a T-C of 25 days, LCK of 0.98 (inactive) and no regressions. The T-C and LCK could not be determined for the 5 mg/kg group due to necrosis at low tumor volumes. However, there were 4/6 PR, 3/6 CRs and 3/6 TFS in the group. There was minimal body weight losses of 2-5% in all groups of the study with nadir on day 13 post inoculation. Results from this study indicate that the tetravalent ADC format does not provide an improvement in activity over the parental conjugate.

TABLE 14

| Group (s-SPDB-DM4) | Ab Dose (mg/kg) | % T/C (D27) | PR | CR | Result |
|---|---|---|---|---|---|
| Tetravalent | 2.5 | 13% | 2/6 | 0/6 | Active |
| Tetravalent | 5 | 11% | 2/6 | 2/6 | Active |
| M | 2.5 | 26% | 0/6 | 0/6 | Active |
| M | 5 | 3% | 4/6 | 3/6 | Highly Active |

In Vivo Anti-Tumor Activity of a Tetravalent Biparatopic ADC in SCID Mice Bearing IGROV-1 Human Ovarian Carcinoma Xenografts The effect of the tetravalent biparatopic antibody format on immunoconjugate therapeutic efficacy was assessed in vivo using an IGROV-1 xenograft model. Mice were randomized into groups (n=8 per group) by tumor volume and subsequently dosed on day 11 post inoculation. The groups included a control group dosed with formulation buffer, Tetravalent-s-SPDB-DM4 at 100 μg/kg and M-s-SPDB-DM4 at 100 μg/kg. To account for possible under-dosing of the tetravalent conjugate due to differences in molecular weight between the tetravalent antibody and the parental antibody (i.e., a difference of 50 kDa), doses were normalized by payload in this study and all further studies. All mice were administered a single intravenous dose of the above compounds. The study was terminated on day 81 post inoculation. Tumor measurements and calculations were determined as described in the subsection above ("In vivo anti-tumor activity of a tetravalent biparatopic ADC in SCID mice bearing OV-90 human ovarian carcinoma xenografts").

Figure 9:
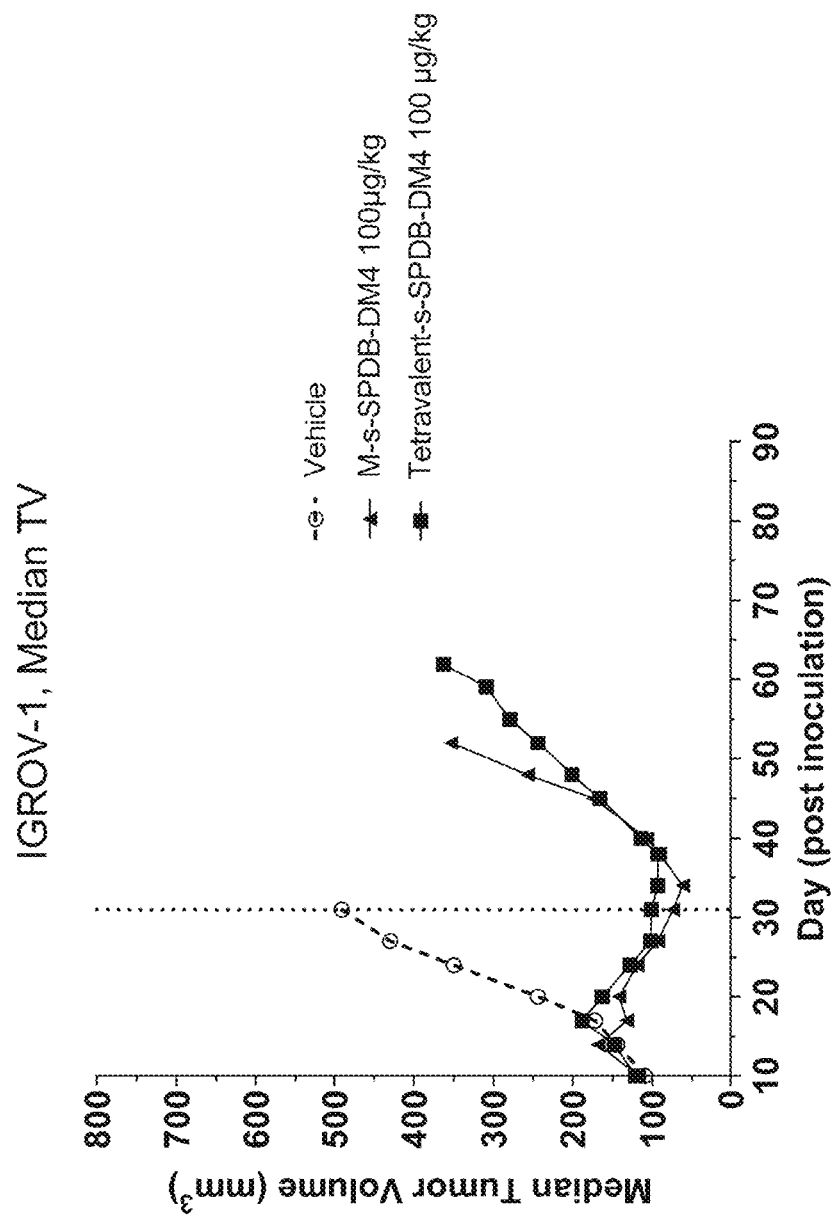
FIG. 9 shows the median tumor volume in an Igrov-1 xenograft model after administration of vehicle, Tetravalent-s-SPDB-DM4, or M-s-SPDB-DM4. (See Example 4.)

The results of the study are shown in FIG. 9 and Table 15. The Tetravalent-s-SPDB-DM4 and parental M-s-SPDB-DM4 conjugates were both active at 100 µg/kg, with T/Cs of 21% and 15%, respectively. T-C and LCK could not be determined for either group due to necrosis at low tumor volumes. The tetravalent conjugate had 2/8 PRs, 1/8 CR and 0/8 TFS, while the M-s-SPDB-DM4 had 3/8 PRs, 1/8 CR and 0/8 TFS. There was minimal weight loss for most groups in the study with the exception of the 100 µg/kg tetravalent ADC, which had 8% body weight loss at nadir on day 14 post inoculation. Again, results from this study indicate that the tetravalent ADC format does not provide an improvement in activity over the parental conjugate.

TABLE 15

| Group (s-SPDB-DM4) | DM Dose (µg/kg) | % T/C (D31) | PR | CR | Result |
|---|---|---|---|---|---|
| Tetravalent | 100 | 21% | 2/8 | 1/8 | Active |
| M | 100 | 15% | 3/8 | 1/8 | Active |

In Vivo Anti-Tumor Activity of a KIH Biparatopic ADC in SCID Mice Bearing OV-90 Human Ovarian Carcinoma Xenografts The effect of the KIH biparatopic antibody format on immunoconjugate therapeutic efficacy was assessed in vivo using an OV-90 xenograft model. Mice were randomized into groups (n=6 per group) by tumor volume and subsequently dosed on day 7 post inoculation. The groups included a control group dosed with formulation buffer, KIH-s-SPDB-DM4 at 40, 20 and 10 µg/kg and M-s-SPDB-DM4 at 20 µg/kg. All mice were administered a single intravenous dose of the above compounds. The study was terminated on day 80 post inoculation. Tumor measurements and calculations were determined as described in subsection "In vivo anti-tumor activity of a tetravalent biparatopic ADC in SCID mice bearing OV-90 human ovarian carcinoma xenografts".

Figure 10:
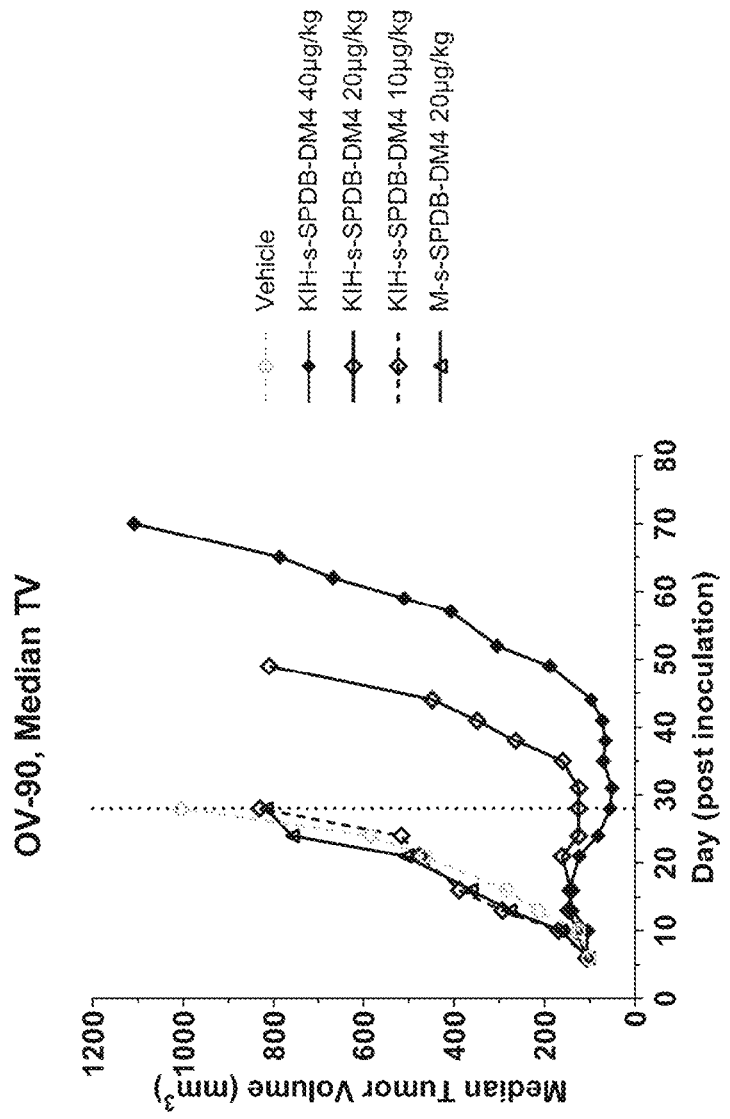
FIG. 10 shows the median tumor volume in an OV-90 xenograft model after administration of vehicle, an immunoconjugate containing a knob-in-hole biparatopic antibody ("KIH-s-SPDB-DM4"), or M-s-SPDB-DM4. (See Example 4.)

The results of the study are shown in FIG. 10 and Table 16. The KIH-s-SPDB-DM4 conjugate was highly active at 40 µg/kg, active at 20 µg/kg and inactive at 10 µg/kg, with T/Cs of 6%, 12% and 83%, respectively. The 40 µg/kg dose group had a T-C of 29 days, LCK of 1.84 (active), 3/6 PRs, 2/6 CRs and 0/6 TFS. The 20 µg/kg dose group had a T-C of 38 days, LCK of 1.32 (active) and no regressions. The 10 µg/kg group had a T-C of 2 days, LCK of 0.09 (inactive) and no regressions. The parental M-s-SPDB-DM4 conjugate was inactive at 20 µg/kg with a T/C of 81% and no regressions. T-C and LCK could not be determined for this group due to necrosis at low tumor volumes. There was no body weight loss observed in this study. In contrast to the studies performed with the tetravalent conjugate, KIH-s-SPDB-DM4 was shown to be appreciably more active than the M-s-SPDB-DM4. Based on the results of these studies, the KIH format was selected over the tetravalent format for further evaluation.

TABLE 16

| Group (s-SPDB-DM4), effector dose | % T/C | Regressions | | Results |
|---|---|---|---|---|
| | | Partial | Complete | |
| KIH 40 µg/kg | 6% | 3/6 | 2/6 | Highly Active |
| KIH 20 µg/kg | 12% | 0/6 | 0/6 | Active |
| KIH 10 µg/kg | 83% | 0/6 | 0/6 | Inactive |
| M 20 µg/kg | 81% | 0/6 | 0/6 | Inactive |

Example 5. In Vitro Activity of a Knob-in-Hole Biparatopic Antibody Conjugated to DM21

In Vitro Cytotoxicity of a Knob-in-Hole Biparatopic Antibody Conjugated to DM21

Figure 11:
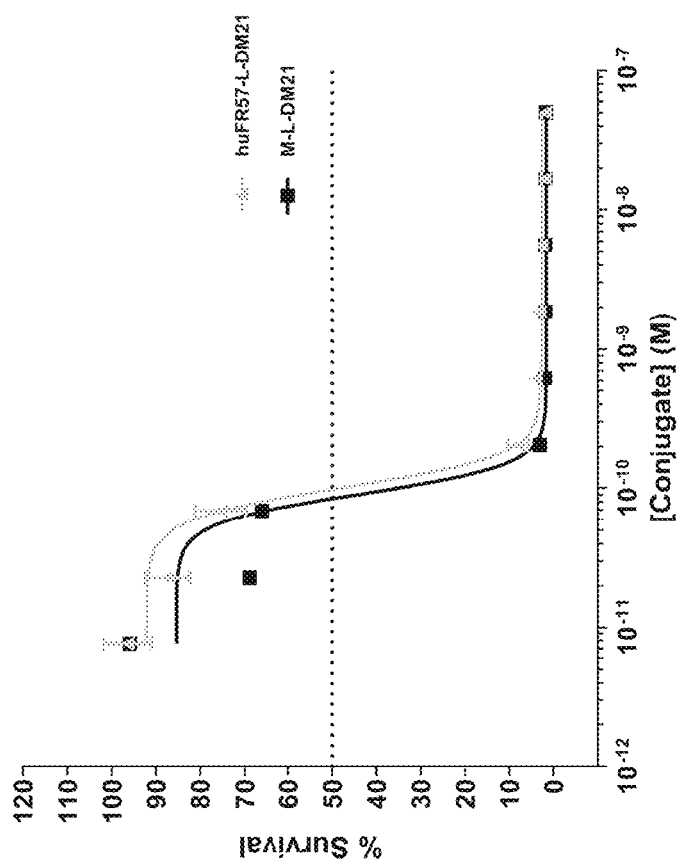
FIG. 11 shows the cytotoxic activity of immunoconjugates containing the FR57 antibody (FR57-L-DM21) or the huMov19 antibody (M-L-DM21) against KB cells. (See Example 5.)
Figures 12A, 12B, 12C, 12D, 12E:
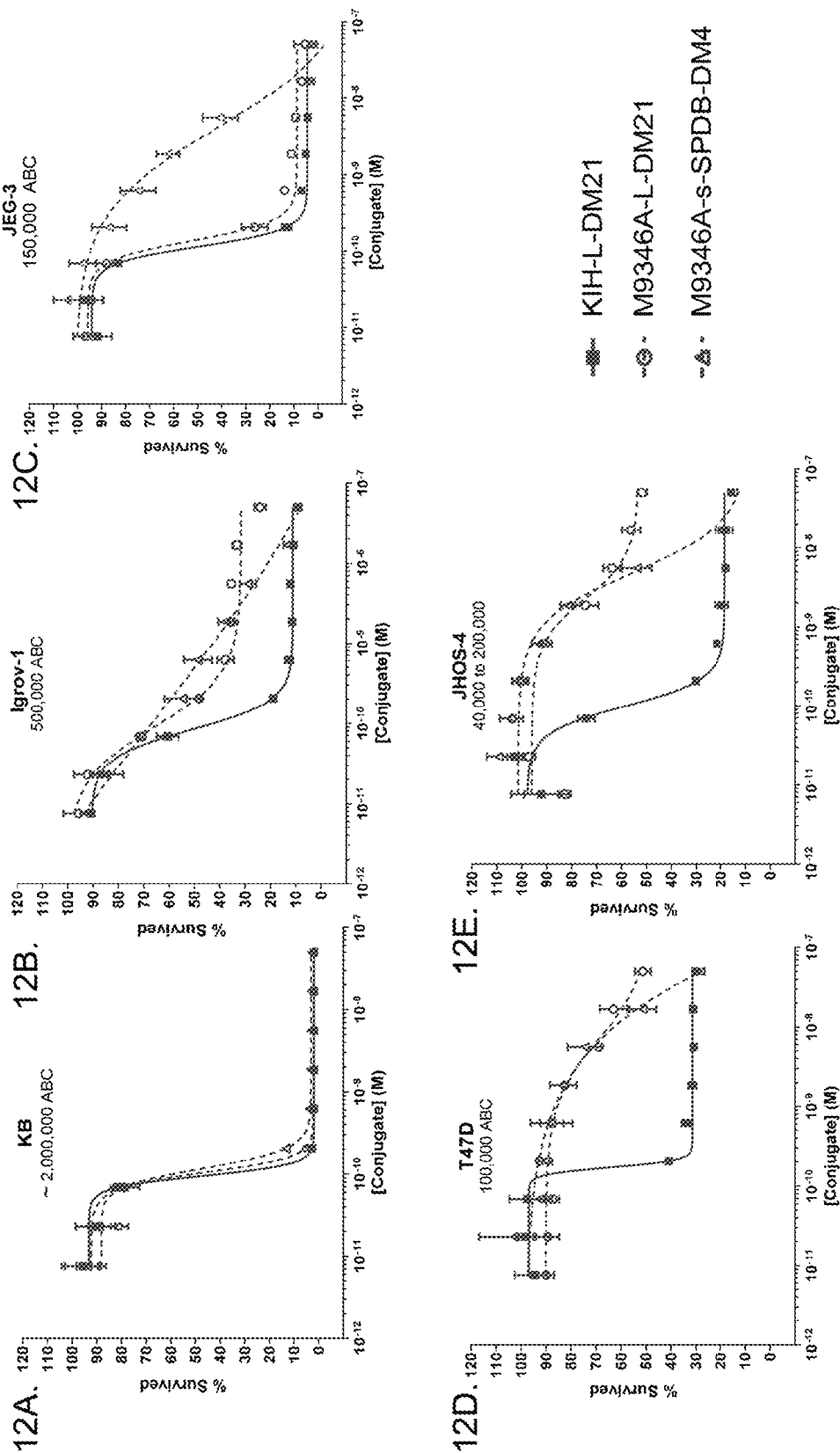
FIGS. 12A-12E show the cytotoxic activity of the biparatopic KIH-DM21 immunoconjugate, the huMov19 immunoconjugate M-DM21, and huMov19 immunoconjugate M-s-SPDB-DM4 against a panel of FRα-positive cell lines including KB cells (FIG. 12A), Igrov-1 cells (FIG. 12B), JEG-3 cells (FIG. 12C), T47D cells (FIG. 12D), and JHOS-4 cells (FIG. 12E). (See Example 5.)

The in vitro cytotoxicity of a KIH biparatopic antibody conjugated to DM21 was assessed in multiple cell lines according to the protocol described in Example 4 ("In vitro cytotoxicity of biparatopic immunoconjugates"). In an earlier study, the activity of two parental DM21 conjugates (M-DM21 and huFR57-DM21) was shown to be very similar (FIG. 11). In all further studies, the activity of KIH-DM21 was compared to conjugates of the parental M antibody (M-s-SPDB-DM4 and M-DM21) to assess the contribution of the biparatopic format and DM21 payload to overall cytotoxicity of KIH-DM21.

KIH-DM21 was appreciably more active than the two parental conjugates against three out of the five cell lines tested (Igrov-1, T47D and JHOS-4). (FIGS. 12A-12E.) Additionally, the two conjugates with the DM21 linker/payload (KIH-DM21 and M-DM21) were similarly active against Jeg-3 cells, while the M-s-SPDB-DM4 conjugate demonstrated less activity against this cell line. Only one cell line (KB), which exhibits the highest FRα level of expression, was similarly sensitive to all three conjugates. Accordingly, these results show that KIH-DM21 exhibits increased activity against most tested cell lines relative to conjugates of the parent antibody (M-s-SPDB-DM4 and M-DM21).

Additionally, the binding, internalization, and processing of KIH-DM21 and the parent monospecific antibodies were compared using $^3$H-antibodies. In tumor cells with medium (JHOS-4) and high (KB) FRα expression KIH-DM21 boosted antibody binding events and processing by 100% and 170%, respectively.

Bystander Killing Activity of a Knob-in-Hole Biparatopic Antibody Conjugated to DM21

The ability of KIH-DM21 to kill FRα-cells in a mixed cell culture was assessed in vitro using multiple cell lines. Consistent with the other in vitro cytotoxicity experiments, the parental antibody conjugates M-DM21 and M-s-SPDB-DM4 were used as controls. Mixed cultures of target-positive cells (KB, Igrov-1, Jeg-3 or T47D) and target-negative cells Namalwa/luc (i.e., Namalwa cells expressing luciferase) were exposed to 0.5 nM of the conjugates. This concentration of conjugate is not toxic to the target-negative cells when the cells are incubated alone. Various percentages of target-positive cells in the mixed cultures (from 9% to 50%) were then tested. After a 5 day exposure, the inhibition of cell proliferation of target-negative cells in the mixture was determined by One Glo (Promega) according to the manufacturer's protocol.

TABLE 17

| FRα+ cell line | FRα expression (by FACS with conventional Ab-PE) | % of FRα+ cells necessary to produce enough metabolites to kill 90% FRα+ cells | | |
|---|---|---|---|---|
| | | IMGN853 | M-DM21 | KIH-DM21 |
| KB | ~2,000,000 | 30 | 30 | Less than 10 |
| Igov-1 | 500,000 | More than 50 | 35 | 10 |
| Jeg-3 | 150,000 | More than 50 | 40 | 40 |
| T47D | 100,000 | More than 70 | More than 70 | 65 |

In all mixed cultures tested, KIH-DM21 had the highest bystander activity, followed by M-DM21. M-s-SPDB-DM4 was the least active conjugate, as shown in FIGS. 13A-13D and Table 17.

Collectively, these data indicate that the KIH biparatopic format combined with the DM21 linker/payload results in increased in vitro efficacy relative to the parental antibody conjugated to DM21 or s-SPDB-DM4.

Example 6. In Vivo Efficacy of a KIH Biparatopic Immunoconjugate

In Vivo Anti-Tumor Activity of a KIH Biparatopic ADCs in SCID Mice Bearing OV-90 Human Ovarian Carcinoma Xenografts The in vivo efficacy of KIH-DM21 was assessed and compared to KIH-s-SPDB-DM4 in an OV-90 xenograft model with low FRα expression (H-score of 30). Mice were randomized into groups (n=6 per group) by tumor volume and subsequently dosed on day 7 post inoculation. The groups included a control group dosed with formulation buffer, KIH-s-SPDB-DM4 at 40, 20 and 10 µg/kg, KIH-DM21 at 40, 20 and 10 µg/kg, M-DM21 at 20 µg/kg and M-s-SPDB-DM4 at 20 µg/kg. All mice were administered a single intravenous dose of the above compounds. The study was terminated on day 80 post inoculation. Tumor measurements and calculations were determined as described in Example 4 subsection "In vivo anti-tumor activity of a tetravalent biparatopic ADC in SCID mice bearing OV-90 human ovarian carcinoma xenografts".

Figures 14A, 14B:
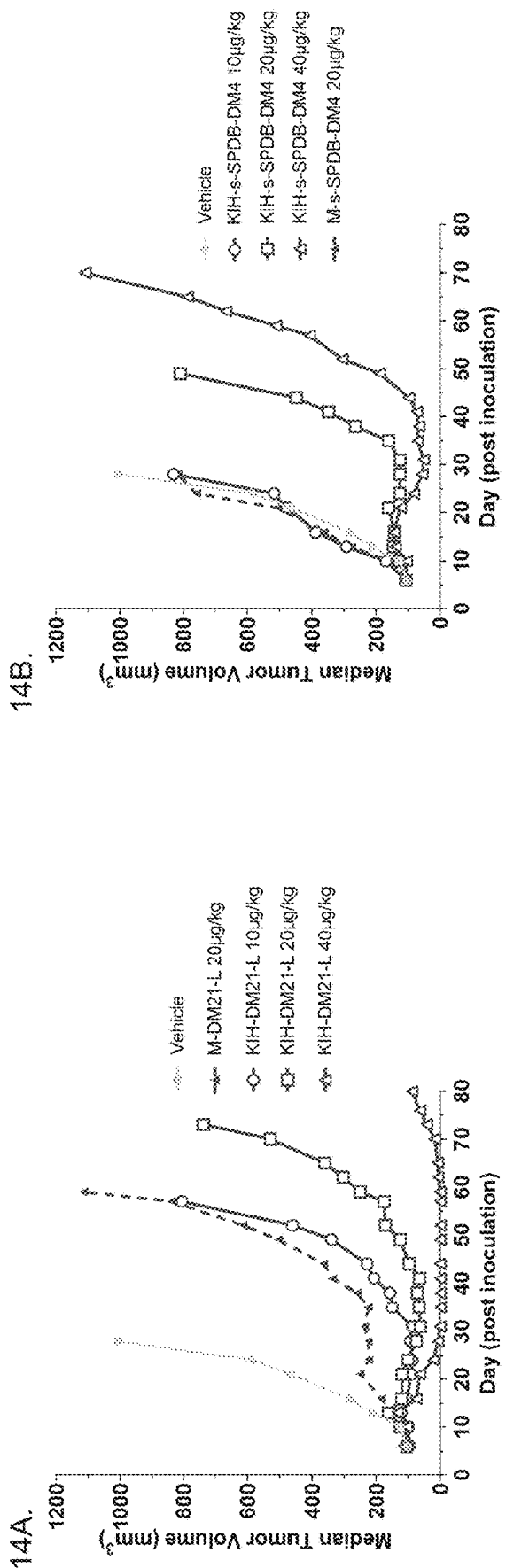
FIGS. 14A and 14B show the median tumor volumes after administration of the biparatopic immunoconjugate KIH-L-DM21 and the huMov19 immunoconjugate M-L-DM21 (FIG. 14A) or the biparatopic immunoconjugate KIH-s-SPDB-DM4 and the huMov19 immunoconjugate M-s-SPDB-DM4 (FIG. 14B) to an OV-90 xenograft model. (See Example 6.)

The results of the study are shown in FIGS. 14A-14B and Table 18. The KIH-s-SPDB-DM4 40 µg/kg dose group had a T-C of 29 days, LCK of 1.84 (active), 3/6 PRs, 2/6 CRs and 0/6 TFS. The 20 µg/kg dose group had a T-C of 38 days, LCK of 1.32 (active) and no regressions. The 10 µg/kg group had a T-C of 2 days, LCK of 0.09 (inactive) and no regressions. The parental M-s-SPDB-DM4 conjugate was inactive at 20 µg/kg with a T/C of 81% and no regressions. T-C and LCK could not be determined for this group due to necrosis at low tumor volumes. The KIH-DM21 conjugate was highly active at all doses, with a T/C of 1% for the 40 µg/kg dose, 7% for the 20 µg/kg dose and 9% for the 10 µg/kg dose. The 40 µg/kg dose had a T-C of 53 days, LCK of 2.49 (active), 5/6 PRs, 5/6 CRs and 3/6 TFS. The 20 µg/kg dose had a T-C of 42 days, LCK of 1.98 (active), 3/6 PRs, 2/6 CRs and 1/6 TFS. The 10 µg/kg dose had 2/6 PRs and 0/6 CRs. T-C and LCK could not be determined for this group due to necrosis at low tumor volumes. The M-DM21 conjugate was active at 20 µg/kg with a T/C of 22%, T-C of 30 days, LCK of 1.41 (active) and no regressions. There was no body weight loss observed in this study. In summary, DM21 conjugates were more active than s-SPDB-DM4 conjugates in both the parental and KIH biparatopic formats in this study. In addition, the biparatopic KIH conjugates were more active than their parental counterparts at matching 20 µg/kg doses within the same linker/payload format. Based on these results, KIH-DM21 was selected for evaluation in additional xenograft models.

TABLE 18

| | | Regressions | | |
|---|---|---|---|---|
| Group, effector dose | % T/C | Partial | Complete | Results |
| KIH-DM21 40 µg/kg | 1% | 5/6 | 5/6 | Highly Active |
| KIH-DM21 20 µg/kg | 7% | 3/6 | 2/6 | Highly Active |
| KIH-DM21 10 µg/kg | 9% | 2/6 | 0/6 | Highly Active |
| KIH-s-SPDB-DM4 40 µg/kg | 6% | 3/6 | 2/6 | Highly Active |
| KIH-s-SPDB-DM4 20 µg/kg | 12% | 0/6 | 0/6 | Active |
| KIH-s-SPDB-DM4 10 µg/kg | 83% | 0/6 | 0/6 | Inactive |
| M-DM21 20 µg/kg | 22% | 0/6 | 0/6 | Active |
| M-s-SPDB-DM4 20 µg/kg | 81% | 0/6 | 0/6 | Inactive |

In Vivo Anti-Tumor Activity of a KIH Biparatopic ADC in SCID Mice Bearing Ishikawa Human Endometrial Adenocarcinoma Xenografts The in vivo efficacy of a KIH biparatopic antibody conjugated to DM21 was assessed in an Ishikawa xenograft model with medium FRα expression (H-score of 100).

Mice were randomized into groups (n=6 per group) by tumor volume and subsequently dosed on day 11 post inoculation. The groups included a control group dosed with formulation buffer, KIH-DM21 at 100, 50 and 25 µg/kg, M-DM21 at 100 and 50 µg/kg and M-s-SPDB-DM4 at 100 µg/kg. All mice were administered a single intravenous dose of the above compounds. The study was terminated on day 90 post inoculation. Tumor measurements and calculations were determined as described in Example 4 subsection "In vivo anti-tumor activity of a tetravalent biparatopic ADC in SCID mice bearing OV-90 human ovarian carcinoma xenografts".

Figure 15:
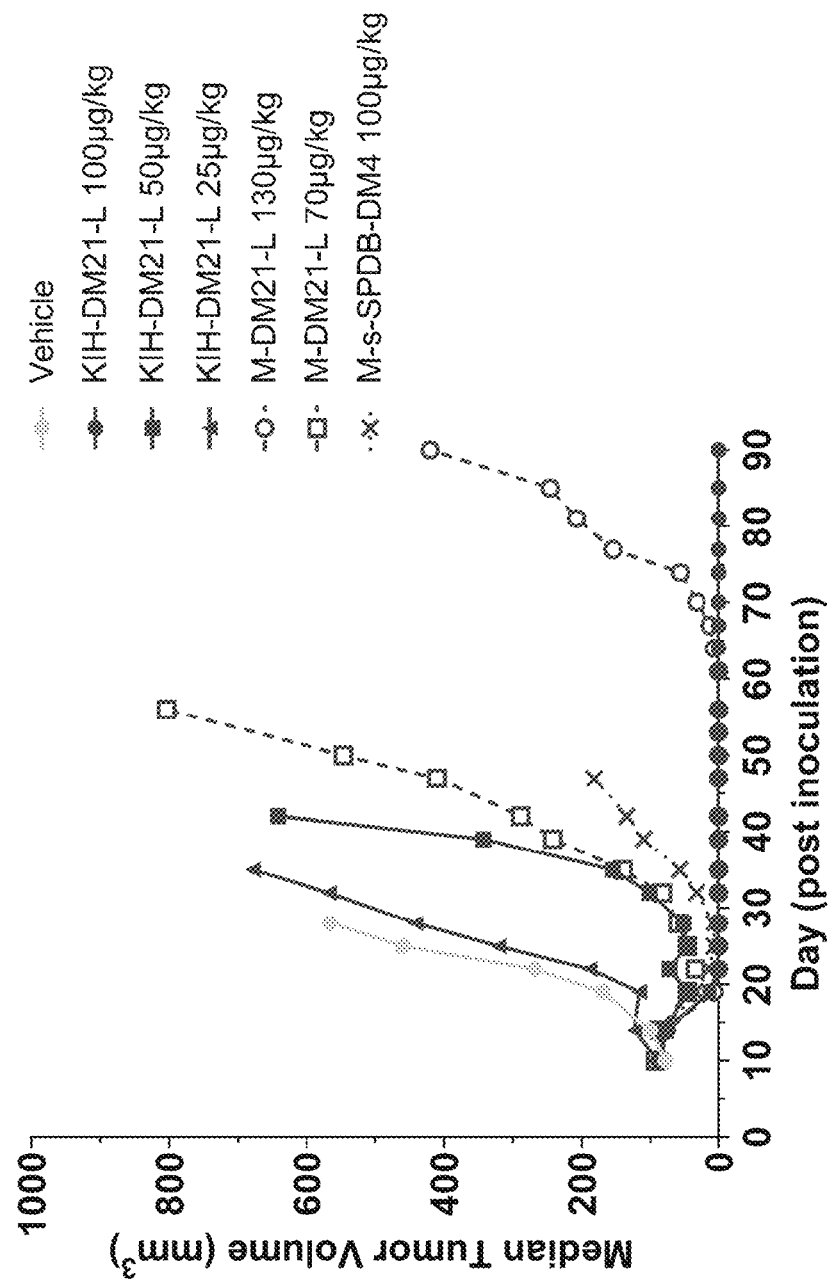
FIG. 15 shows the median tumor volume after administration of the biparatopic immunoconjugate KIH-L-DM21, immunoconjugate to an Ishikawa xenograft model compared to vehicle, the huMov19 immunoconjugate M-L-DM21, or the huMov19 immunoconjugate M-s-SPDB-DM4 ("IMGN853"). (See Example 6.)

The results of the study are shown in FIG. 15 and Table 19. The KIH-DM21 conjugate was highly active at 100 and 50 µg/kg but inactive at 25 µg/kg, with a T/Cs of 0%, 9% and 78%, respectively. The 100 µg/kg dose had a T-C of >63 days, LCK of >3.33 (highly active), 6/6 PRs, 5/6 CRs and 4/6 TFS. The 50 µg/kg dose had 3/6 PRs and 0/6 CRs. The T-C and LCK could not be determined for this group due to necrosis at low tumor volumes. The 25 µg/kg dose had a T-C of 2 days, LCK of 0.11 (inactive) and no regressions. The M-DM21 conjugate was highly active at 130 µg/kg and active at 70 µg/kg, with T/Cs of 0% and 11%, respectively. The 130 µg/kg dose had a T-C of >63 days, LCK of >3.33 (highly active), 6/6 PRs, 6/6 CRs and 0/6 TFS. The 50 µg/kg dose had a T-C of 27 days, LCK of 1.43 (active), 4/6 PRs, 2/6 CRs and 0/6 TFS. The M-s-SPDB-DM4 conjugate at 100 µg/kg dose was highly active with a T/C of 1%, 6/6 PRs and 3/6 CRs. T-C and LCK could not be determined for this group due to necrosis at low tumor volumes. There was minimal body weight losses between 1-5% in all groups in the study. In summary, KIH-DM21 was appreciably more active than the parental conjugates M-DM21 and M-s-SPDB-DM4 when dosed at 100 µg/kg. Although all three conjugates were highly active at 100 µg/kg, the duration of the response was much longer for the KIH biparatopic ADC than for the parental antibody conjugates.

TABLE 19

| Group, effector dose | % T/C | Regressions Partial | Complete | TFS | Results |
|---|---|---|---|---|---|
| KIH-DM21 100 µg/kg | 0% | 6/6 | 5/6 | 4/6 | Highly Active |
| KIH-DM21 50 µg/kg | 9% | 3/6 | 0/6 | 0/6 | Highly Active |
| KIH-DM21 25 µg/kg | 78% | 0/6 | 0/6 | 0/6 | Inactive |
| M-DM21 ~130 µg/kg | 0% | 6/6 | 6/6 | 0/6 | Highly Active |
| M-DM21 ~70 µg/kg | 11% | 4/6 | 2/6 | 0/6 | Active |
| M-s-SPDB-DM4 100 µg/kg | 1% | 6/6 | 0/6 | 0/6 | Highly Active |

In Vivo Anti-Tumor Activity of a KIH Biparatopic ADC in SCID Mice Bearing IGROV-1 Human Ovarian Carcinoma Xenografts The in vivo efficacy of a KIH biparatopic antibody conjugated to DM21 was assessed in an IGROV-1 xenograft model with medium FRα expression (H-score of 140). Mice were randomized into groups (n=8 per group) by tumor volume and subsequently dosed on day 10 post inoculation. The groups included a control group dosed with formulation buffer, KIH-DM21 at 100 and 50 µg/kg, M-DM21 at 130 and 70 µg/kg and M-s-SPDB-DM4 at 100 and 50 µg/kg. All mice were administered a single intravenous dose of the above compounds. The study was terminated on day 120 post inoculation. Tumor measurements and calculations were determined as described in Example 4 subsection "In vivo anti-tumor activity of a tetravalent biparatopic ADC in SCID mice bearing OV-90 human ovarian carcinoma xenografts"

Figure 16:
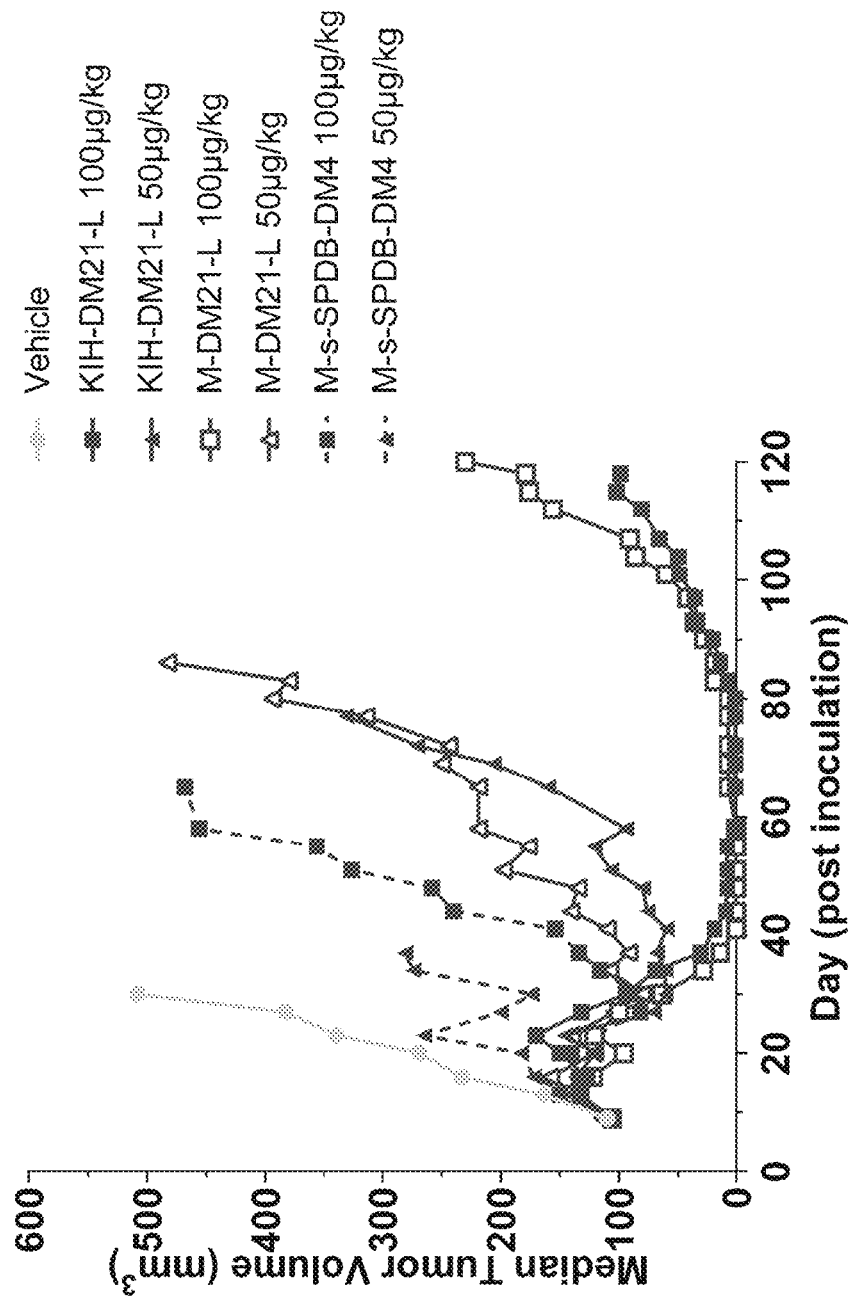
FIG. 16 shows the median tumor volume after administration of the biparatopic KIH-L-DM21 immunoconjugate to an Igrov-1 xenograft model compared to vehicle, the huMov19 immunoconjugate M-L-DM21, or the huMov19 immunoconjugate IMGN853. (See Example 6.)

The results of the study are shown in FIG. 16 and Table 20. The KIH-DM21 conjugate was active at both 100 and 50 µg/kg, with a T/Cs of 19% and 12%, respectively. The 100 µg/kg dose had a T-C of >99 days, LCK of >2.87 (highly active), 7/8 PRs, 6/8 CRs and 0/8 TFS. The 50 µg/kg dose had a T-C of 53 days, LCK of 1.53 (active), 5/8 PRs, 3/8 CRs and 0/8 TFS. The M-DM21 conjugate was active at both 130 µg/kg and 70 µg/kg, with T/Cs of 13% and 16%, respectively. The 130 µg/kg dose had a T-C of >99 days, LCK of >2.87 (highly active), 8/8 PRs, 7/8 CRs and 2/8 TFS. The 70 µg/kg dose had a T-C of 36 days, LCK of 1.04 (active), 3/8 PRs, 2/8 CRs and 0/8 TFS. The M-s-SPDB-DM4 conjugate was active at both the 100 and 50 µg/kg doses, with T/Cs of 17% and 34%, respectively. The 100 µg/kg dose had a T-C of 23 days, LCK of 0.67 (inactive), 3/8 PRs, 2/8 CRs and 0/8 TFS. The 50 µg/kg dose had a T-C of 17 days, LCK of 0.49 (inactive) and no regressions. There was minimal body weight loss of 1-5% in most groups, with the exception of the M-DM21 at 50 µg/kg (6%) and M-s-SPDB-DM4 at 50 µg/kg (7%) at nadir on day 16 post-inoculation. In summary, the parental M-s-SPDB-DM4 conjugate exhibited less in vivo efficacy than the DM21 conjugates. Additionally, KIH-DM21 and the parental M-DM21 were similarly active at the two doses tested.

TABLE 20

| Group | % T/C | Regressions Partial | Complete | Results |
|---|---|---|---|---|
| KIH-DM21 100 µg/kg | 19% | 7/8 | 6/8 | Active |
| KIH-DM21 50 µg/kg | 12% | 5/8 | 3/8 | Active |
| M-DM21 100 µg/kg | 13% | 8/8 | 7/8 | Active |
| M-DM21 50 µg/kg | 16% | 3/8 | 2/8 | Active |
| M-s-SPDB-DM4 100 µg/kg | 17% | 3/8 | 2/8 | Active |
| M-s_SPDB-DM4 50 µg/kg | 34% | 0/8 | 0/8 | Active |

In Vivo Anti-Tumor Activity of a KIH Biparatopic ADC in SCID Mice Bearing KB Human Cervical Carcinoma Xenografts The in vivo efficacy of a KIH biparatopic antibody conjugated to DM21 was assessed in a KB xenograft model with high FRα expression (H-score of 300). Mice were randomized into groups (n=6 per group) by tumor volume and subsequently dosed on day 6 post inoculation when tumors reached ~100 mm3. The groups included a control group dosed with formulation buffer, KIH-DM21 at 50 and 25 µg/kg, M-DM21 at 50 and 25 µg/kg and M-s-SPDB-DM4 at 50 and 25 µg/kg. All mice were administered a single intravenous dose of the above compounds. The study was terminated on day 120 post inoculation. Tumor measurements and calculations were determined as described in Example 4 subsection "In vivo anti-tumor activity of a tetravalent biparatopic ADC in SCID mice bearing OV-90 human ovarian carcinoma xenografts".

Figure 17:
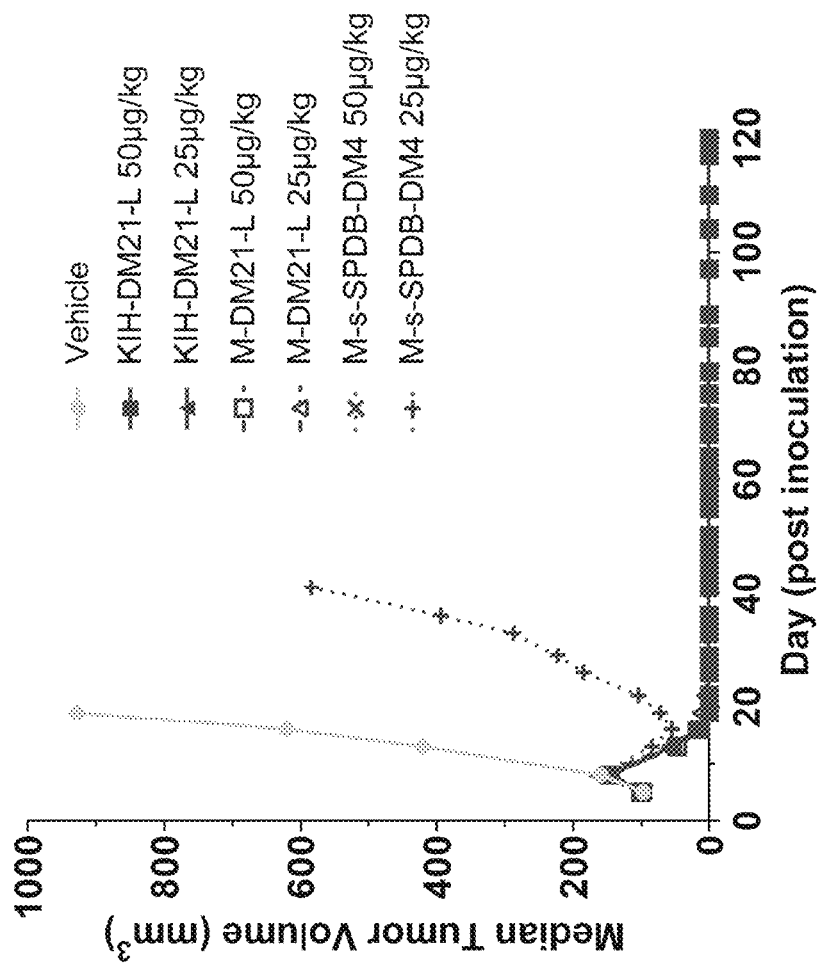
FIG. 17 shows the median tumor volume after administration of the biparatopic KIH-L-DM21 immunoconjugate to a KB xenograft model compared to vehicle, the huMov19 immunoconjugate M-L-DM21, or the huMov19 immunoconjugate M-s-SPDB-DM4. (See Example 7.)

The results of the study are shown in FIG. 17 and Table 21. The KIH-DM21 conjugate was highly active at both 50 and 25 µg/kg, with a T/Cs of 0%, T-Cs of >100 days and LCKs of >6.41 (highly active) for both doses. The 100 µg/kg dose had 6/6 PRs, 6/6 CRs and 6/6 TFS while the 25 µg/kg dose had 6/6 PRs, 5/6 CRs and 5/6 TFS. The M-DM21 conjugate was highly active at both 50 µg/kg and 25 µg/kg, with T/Cs of 0% and 2%, respectively. Both doses had T-Cs of >100 days and LCKs of >6.41 (highly active). The 50 µg/kg dose had 6/6 PRs, 6/6 CRs and 6/6 TFS while the 25 µg/kg dose had 5/6 PRs, 4/6 CRs and 4/6 TFS. The M-s-SPDB-DM4 conjugate was highly active at both 50 and 25 µg/kg, with T/Cs of 0% and 8%, respectively. The 50 µg/kg dose had a T-C of >100 days, LCK of >6.41 (highly active), 6/6 PRs, 6/6 CRs and 5/6 TFS. The 25 µg/kg dose had a T-C of 24 days, LCK of 1.54 (active), 3/6 PRs, 1/6 CRs and 1/6 TFS. There was minimal body weight loss seen in the M-DM21 and M-s-SPDB-DM4 groups of 2-4% at nadir on day 8 post inoculation. In summary, the response of M-s-SPDB-DM4 at 25 µg/kg was transient, while administration of M-s-SPDB-DM4 at 50 µg/kg resulted in long-lasting complete regression in most mice. Administration of M-DM21 and KIH-DM21 at both the 25 µg/kg and 50 µg/kg doses resulted in long-lasting complete regression in most mice.

Collectively, the in vivo efficacy studies described here indicate that KIH-DM21 was the most active conjugate in most xenograft models tested, followed by M-DM21 and M-s-SPDB-DM4.

TABLE 21

| Group | % T/C | Regressions Partial | Complete | TFS | Results |
|---|---|---|---|---|---|
| KIH-DM21 50 µg/kg | 0% | 6/6 | 6/6 | 6/6 | Highly Active |
| KIH-DM21 25 µg/kg | 0% | 6/6 | 5/6 | 5/6 | Highly Active |
| M-DM21 50 µg/kg | 0% | 6/6 | 6/6 | 6/6 | Highly Active |
| M-DM21 25 µg/kg | 2% | 5/6 | 4/6 | 4/6 | Highly Active |
| M-s-SPDB-DM4 50 µg/kg | 0% | 6/6 | 6/6 | 5/6 | Highly Active |
| M-s-SPDB-DM4 25 µg/kg | 8% | 3/6 | 1/6 | 1/6 | Highly Active |

In Vivo Anti-Tumor Activity of a KIH Biparatopic ADC in SCID Mice Bearing IMGN853-Resistant KB Human Cervical Carcinoma Xenografts The in vivo efficacy of a KIH biparatopic antibody conjugated to DM21 was assessed in an IMGN853-resistant KB xenograft model. Parental KB cells were grown in the presence of 1 nM DM1-Me. After a stably grown culture was established, cells were subcloned and clones were grown, characterized and frozen. Subclone 6A was selected for this study and mice were inoculated subcutaneously. Mice were randomized into groups (n=6 per group) by tumor volume and subsequently dosed on day 5 post inoculation when tumors reached ~100 mm³. The groups included a control group dosed with formulation buffer, KIH-L-DM21 at 40 and 20 µg/kg, M-L-DM21 at 40 and 20 µg/kg and M-s-SPDB-DM4 at 40 and 20 µg/kg. All mice were administered a single intravenous dose of the above compounds. The study was terminated on day 78 post inoculation. Tumor measurements and calculations were determined as described in the OV-90 human ovarian carcinoma xenografts experiments above.

The results of the study are shown in FIG. 19 and Table 22. The KIH-L-DM21 conjugate was highly active at both 40 and 20 µg/kg, with a T/Cs of 0%. The 40 µg/kg dose group had a T-C of >60 days, LCKs of >3.41 (highly active), 6/6 PRs, 6/6 CRs and 6/6 TFS. The 20 µg/kg dosing group had a T-C of 46 days, LCK of 2.61 (active), 6/6 PRs, 4/6 CRs and 1/6 TFS. The M-L-DM21 conjugate was highly active at both 40 µg/kg and 20 µg/kg, with T/Cs of 0% and 2%, respectively. The 40 µg/kg dose group had a T-C of >60 days, LCKs of >3.41 (highly active), 6/6 PRs, 6/6 CRs and 6/6 TFS. The 20 µg/kg dose group had a T-C of 28 days, LCK of 1.59 (active), 5/6 PRs, 2/6 CRs and 2/6 TFS. The M-s-SPDB-DM4 conjugate was highly active at 40 µg/kg but inactive at 20 µg/kg, with T/Cs of 0% and 63%, respectively. The 40 µg/kg dose had a T-C of 41 days, LCK of 2.33 (active), 6/6 PRs, 6/6 CRs and 0/6 TFS. The 20 µg/kg dose had a T-C of 6 days, LCK of 0.34 (inactive), 0/6 PRs, 0/6 CRs and 0/6 TFS. There was minimal body weight loss seen in the KIH-L-DM21 20 µg/kg group, with 3% lost at nadir on day 8 post inoculation. In summary, KIH-L-DM21 was comparably efficacious to M-L-DM21 and both KIH-L-DM21 and M-L-DM21 were more efficacious than M-s-SPDB-DM4 in this model.

TABLE 22

| Group | % T/C | Regressions Partial | Complete | TFS | Results |
|---|---|---|---|---|---|
| KIH-L-DM21 40 | 0% | 6/6 | 6/6 | 6/6 | Highly Active |
| KIH-L-DM21 20 | 0% | 6/6 | 4/6 | 1/6 | Highly Active |
| M-L-DM21 40 | 0% | 6/6 | 6/6 | 6/6 | Highly Active |
| M-L-DM21 20 | 2% | 5/6 | 2/6 | 2/6 | Highly Active |
| M-s-SPDB-DM4 40 | 0% | 6/6 | 6/6 | 0/6 | Highly Active |
| M-s-SPDB-DM4 20 | 63% | 0/6 | 0/6 | 0/6 | Inactive |

Example 7. Biparatopic Immunoconjugate Pharmacokinetics and Tolerability

The toxicity and toxicokinetic profile of a biparatopic FRα-targeting immunoconjugate was assessed in cynomolgus monkey following a single dose. Briefly, KIH-DM21 was administered as a 10 minute slow bolus infusion at dose levels of 10 or 13 mg/kg to two male monkeys/dose level. The animals were observed out to 28-days postdose to evaluate the recovery, persistence or progression of any effects. Body weights, clinical observations, and food consumption were evaluated, and blood samples were collected for clinical pathology parameters (hematology, serum chemistry, and coagulation) and toxicokinetic parameters.

All animals survived until the end of the study. There were no KIH-DM21 related effects on body weights, hematology, or serum chemistry parameters. KIH-DM21-related clinical observations noted in a single 10 Ab mg/kg group animal were reddened hind limb on Days 8 and 12, with no clinical findings noted for the remainder of the nondosing period. KIH L DM21 related higher fibrinogen values were noted on Days 4 and 8 in both dose groups. Values were similar to pretreatment values by end of the nondosing period (Day 29).

KIH-DM21 ADC shows biphasic pharmacokinetics following a single intravenous administration to monkeys. The mean terminal phase t½ of ADC was 156 hours at 10 mg/kg dose. The mean t½ for total antibody (TAb) was longer than that observed for the ADC (184 hours at 10 mg/kg dose). Comparisons of ADC and TAb concentration time profile indicated that the KIH-DM21 immunoconjugate was more stable than IMGN853 at a 10 mg/kg dose. KIH-DM21 has a longer terminal phase half-life and larger exposure metrics (AUC∞ value) than IMGN853 at 10 mg/kg dose.

TABLE 23

| PK parameters | FRα biparatopic ADC 10 mg/kg (N = 2, m) | | IMGN853 10 mg/kg (N = 10) | |
|---|---|---|---|---|
| Dose Group | ADC | Tab | ADC | TAb |
| Half-life (hr) | 156 | 184 | 98.2 | 168.9 |
| $AUC_{0-inf}$ (hr* µg/mL) | 35,400 | 42,200 | 25,583 | 30,587 |

As shown in FIGS. 18A and 18B, the FRα biparatopic immunoconjugate and IMGN853 were both well tolerated at 10 and mg/kg, and the biparatopic immunoconjugate was similarly well tolerated at 13 mg/kg. Additionally, as shown in Table 23, the FRα biparatopic immunoconjugate was more stable than IMGN853 at a 10 mg/kg dose. In particular, the biparatopic immunoconjugate exhibited a terminal half-life ~60 hours longer than IMGN853 and a total exposure ~40% higher than IMGN853.

What is claimed is:

1. An immunoconjugate represented by the following formula:

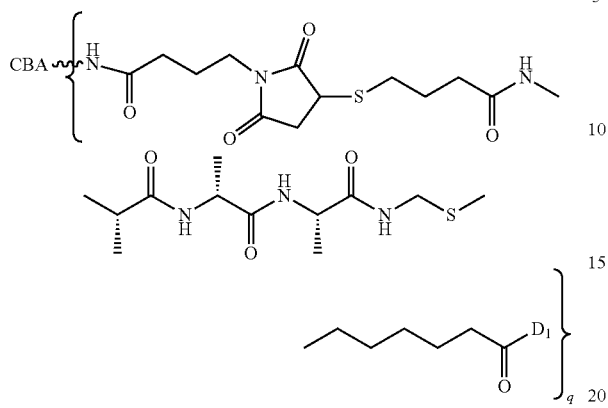

or a pharmaceutically acceptable salt thereof, wherein:
CBA is a biparatopic antibody or an antigen-binding fragment comprising the amino acid sequences of SEQ ID NOs: 41-43;
$D_1$ is represented by the following formula:

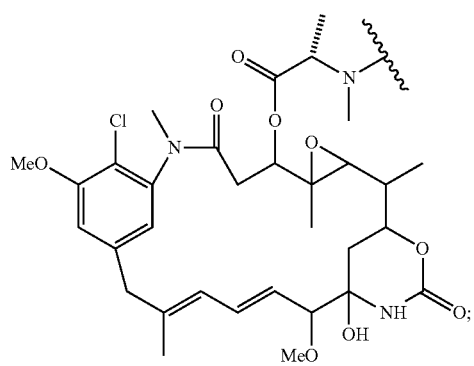

and
q is an integer from 1 to 10.

2. A composition comprising at least one immunoconjugate of claim 1, wherein the composition comprises a drug antibody ratio (DAR) of 3 to 4.

3. An immunoconjugate represented by the following formula:

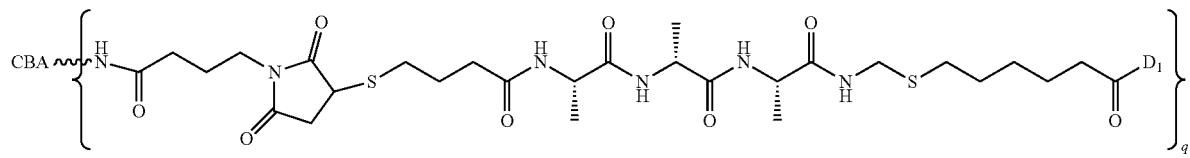

or a pharmaceutically acceptable salt thereof, wherein:
CBA is a bivalent biparatopic antibody or antigen-binding fragment thereof that specifically binds human folate receptor 1 (FRα), wherein the antibody or antigen-binding fragment comprises:

(i) a first FRα-binding domain comprising a first variable heavy chain (VH) and a first variable light chain (VL), wherein (a) the first VH comprises VH CDR1-3 comprising the amino acid sequences of SEQ ID NOs: 10-12, respectively, or SEQ ID NOs: 15, 16, and 12, respectively; and (b) the first VL comprises VL CDR1-3 comprising the amino acid sequences of SEQ ID NOs: 4-6, respectively; and (ii) a second FRα-binding domain comprising a second VH and a second VL, wherein the second VH comprises VH CDR1-3 comprising the amino acid sequences of (a) SEQ ID NOs: 7-9, respectively, or (b) SEQ ID NOs: 13, 14, and 9, respectively; and the second VL comprises VL CDR1-3 comprising the amino acid sequences of SEQ ID NOs: 1-3, respectively;

wherein the first FRα-binding domain comprises an single-chain variable fragment (scFv) and the second FRα-binding domain comprises a VH and a VL on separate polypeptides or wherein the second FRα-binding domain comprises an single-chain variable fragment (scFv) and the first FRα-binding domain comprises a VH and a VL on separate polypeptides;

wherein the bivalent biparatopic antibody or antigen-binding fragment thereof comprises an IgG heavy chain constant region and a light chain constant region; and wherein $D_1$ is represented by the following formula:

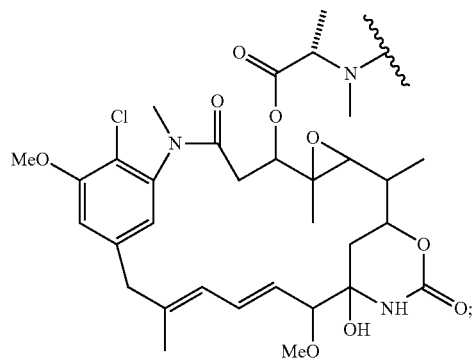

and
q is an integer from 1 to 10.

4. The immunoconjugate of claim 3, wherein the first FRα-binding domain comprises a VH and a VL on separate polypeptides and the second FRα-binding domain comprises an scFv.

5. The immunoconjugate of claim 4, wherein the scFv of the second FRα binding domain has a peptide orientation of VL-linker-VH.

6. The immunoconjugate of claim 5, wherein the linker is a glycine-serine linker.

7. The immunoconjugate of claim 3, wherein the bivalent biparatopic antibody or antigen-binding fragment thereof comprises a knob-in-hole (KIH) structure.

8. The immunoconjugate of claim 7, wherein the second FRα-binding domain is on the knob side of the KIH structure and the first FRα-binding domain is on the hole side of the KIH structure.

9. The immunoconjugate of claim 4, wherein the bivalent biparatopic antibody or antigen-binding fragment thereof comprises a knob-in-hole (KIH) structure.

10. The immunoconjugate of claim 9, wherein the second FRα-binding domain is on the knob side of the KIH structure and the first FRα-binding domain is on the hole side of the KIH structure.

11. The immunoconjugate of claim 5, wherein the bivalent biparatopic antibody or antigen-binding fragment thereof comprises a knob-in-hole (KIH) structure.

12. The immunoconjugate of claim 11, wherein the second FRα-binding domain is on the knob side of the KIH structure and the first FRα-binding domain is on the hole side of the KIH structure.

13. The immunoconjugate of claim 3, wherein the first VH of the bivalent biparatopic antibody or antigen-binding fragment comprises the amino acid sequence of SEQ ID NO:24, the first VL of the bivalent biparatopic antibody or antigen-binding fragment comprises the amino acid sequence of SEQ ID NO:19, the second VH of the bivalent biparatopic antibody or antigen-binding fragment comprises the amino acid sequence of SEQ ID NO:23, and the second VL of the bivalent biparatopic antibody or antigen-binding fragment comprises the amino acid sequence of SEQ ID NO:18.

14. The immunoconjugate of claim 13, wherein the first FRα-binding domain comprises a VH and a VL on separate polypeptides and the second FRα-binding domain comprises an scFv.

15. The immunoconjugate of claim 14, wherein the scFv of the second FRα binding domain has a peptide orientation of VL-linker-VH.

16. The immunoconjugate of claim 15, wherein the linker is a glycine-serine linker.

17. The immunoconjugate of claim 13, wherein the bivalent biparatopic antibody or antigen-binding fragment thereof comprises a knob-in-hole (KIH) structure.

18. The immunoconjugate of claim 17, wherein the second FRα-binding domain is on the knob side of the KIH structure and the first FRα-binding domain is on the hole side of the KIH structure.

19. The immunoconjugate of claim 14, wherein the bivalent biparatopic antibody or antigen-binding fragment thereof comprises a knob-in-hole (KIH) structure.

20. The immunoconjugate of claim 19, wherein the second FRα-binding domain is on the knob side of the KIH structure and the first FRα-binding domain is on the hole side of the KIH structure.

21. The immunoconjugate of claim 15, wherein the bivalent biparatopic antibody or antigen-binding fragment thereof comprises a knob-in-hole (KIH) structure.

22. The immunoconjugate of claim 21, wherein the second FRα-binding domain is on the knob side of the KIH structure and the first FRα-binding domain is on the hole side of the KIH structure.

23. The immunoconjugate of claim 16, wherein the bivalent biparatopic antibody or antigen-binding fragment thereof comprises a knob-in-hole (KIH) structure.

24. The immunoconjugate of claim 23, wherein the second FRα-binding domain is on the knob side of the KIH structure and the first FRα-binding domain is on the hole side of the KIH structure.

25. A composition comprising at least one immunoconjugate of claim 3, wherein the composition comprises a drug antibody ratio (DAR) of 3 to 4.

26. A composition comprising at least one immunoconjugate of claim 4, wherein the composition comprises a drug antibody ratio (DAR) of 3 to 4.

27. A composition comprising at least one immunoconjugate of claim 5, wherein the composition comprises a drug antibody ratio (DAR) of 3 to 4.

28. A composition comprising at least one immunoconjugate of claim 7, wherein the composition comprises a drug antibody ratio (DAR) of 3 to 4.

29. A composition comprising at least one immunoconjugate of claim 8, wherein the composition comprises a drug antibody ratio (DAR) of 3 to 4.

30. A composition comprising at least one immunoconjugate of claim 13, wherein the composition comprises a drug antibody ratio (DAR) of 3 to 4.

31. A composition comprising at least one immunoconjugate of claim 14, wherein the composition comprises a drug antibody ratio (DAR) of 3 to 4.

32. A composition comprising at least one immunoconjugate of claim 15, wherein the composition comprises a drug antibody ratio (DAR) of 3 to 4.

33. A composition comprising at least one immunoconjugate of claim 16, wherein the composition comprises a drug antibody ratio (DAR) of 3 to 4.

34. A composition comprising at least one immunoconjugate of claim 17, wherein the composition comprises a drug antibody ratio (DAR) of 3 to 4.

35. A composition comprising at least one immunoconjugate of claim 18, wherein the composition comprises a drug antibody ratio (DAR) of 3 to 4.

36. A composition comprising at least one immunoconjugate of claim 21, wherein the composition comprises a drug antibody ratio (DAR) of 3 to 4.

37. A composition comprising at least one immunoconjugate of claim 22, wherein the composition comprises a drug antibody ratio (DAR) of 3 to 4.

38. A composition comprising at least one immunoconjugate of claim 23, wherein the composition comprises a drug antibody ratio (DAR) of 3 to 4.

39. A composition comprising at least one immunoconjugate of claim 24, wherein the composition comprises a drug antibody ratio (DAR) of 3 to 4.

40. The immunoconjugate of claim 3, wherein
  (i) the VH CDR1-3 of the first FRα-binding domain comprise the amino acid sequences of SEQ ID NOs: 10-12, respectively; and
  (ii) the VH CDR1-3 of the second first FRα-binding domain comprise the amino acid sequences of SEQ ID NOs: 7-9, respectively.

41. The immunoconjugate of claim 40, wherein the first FRα-binding domain comprises a VH and a VL on separate polypeptides and the second FRα-binding domain comprises an scFv.

42. The immunoconjugate of claim 41, wherein the scFv of the second FRα binding domain has a peptide orientation of VL-linker-VH.

43. A composition comprising at least one immunoconjugate of claim 40, wherein the composition comprises a drug antibody ratio (DAR) of 3 to 4.

44. The immunoconjugate of claim 3, wherein
  (i) the VH CDR1-3 of the first FRα-binding domain comprise the amino acid sequences of SEQ ID NOs: 15, 16, and 12, respectively; and (ii) the VH CDR1-3 of the second first FRα-binding domain comprise the amino acid sequences of SEQ ID NOs: 13, 14, and 9, respectively.

45. The immunoconjugate of claim 44, wherein the first FRα-binding domain comprises a VH and a VL on separate polypeptides and the second FRα-binding domain comprises an scFv.

46. The immunoconjugate of claim 45, wherein the scFv of the second FRα binding domain has a peptide orientation of VL-linker-VH.

47. A composition comprising at least one immunoconjugate of claim 44, wherein the composition comprises a drug antibody ratio (DAR) of 3 to 4.

* * * * *

UNITED STATES PATENT AND TRADEMARK OFFICE
CERTIFICATE OF CORRECTION

PATENT NO. : 11,396,543 B2  
APPLICATION NO. : 16/860822  
DATED : July 26, 2022  
INVENTOR(S) : Ab et al.

Page 1 of 3

It is certified that error appears in the above-identified patent and that said Letters Patent is hereby corrected as shown below:

In the Drawings

On sheet 4 of 22, delete "FIG." and insert -- FIGS. --, therefor.

On sheet 5 of 22, delete "FIG." and insert -- FIGS. --, therefor.

On sheet 6 of 22, delete "FIG." and insert -- FIGS. --, therefor.

In the Specification

In Column 2, Line 52, delete "second." and insert -- second --, therefor.

In Column 3, Line 35, delete "add" and insert -- acid --, therefor.

In Column 3, Line 38, after "SEQ" insert -- ID --.

In Column 3, Lines 50-51, delete "and body" and insert -- antibody --, therefor.

In Column 6, Lines 3-8, delete " 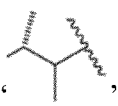 " and insert -- 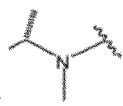 --, therefor.

In Column 6, Lines 55-59, delete " 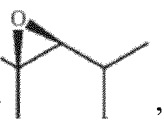 " and insert -- 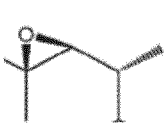 --, therefor.

In Column 22, Line 20, delete "(NETS-" and insert -- (NHS --, therefor.

In Column 25, Line 15, delete "6)" and insert -- 6.) --, therefor.

Signed and Sealed this  
Eighteenth Day of April, 2023

Katherine Kelly Vidal  
*Director of the United States Patent and Trademark Office*

CERTIFICATE OF CORRECTION (continued)
U.S. Pat. No. 11,396,543 B2

In Column 25, Line 63, delete "(MA)" and insert -- (RIA) --, therefor.

In Column 27, Line 8, delete "(e.g.," and insert -- e.g., --, therefor.

In Column 28, Line 65, delete "toxicity" and insert -- toxicity. --, therefor.

In Column 32, Line 59, delete "and)(BLAST" and insert -- and XBLAST --, therefor.

In Column 33, Line 10, delete "Blossum" and insert -- Blosum --, therefor.

In Column 36, Line 58, delete "body)" and insert -- body --, therefor.

In Column 38, Line 55, delete "embodiments" and insert -- embodiments. --, therefor.

In Column 45, Line 57, delete "biaparatopic" and insert -- biparatopic --, therefor.

In Column 47, Line 26, delete "biaparatopic" and insert -- biparatopic --, therefor.

In Column 47, Line 36, delete "Alternatively" and insert -- Alternatively, --, therefor.

In Column 49, Line 28, delete "respectively)" and insert -- respectively --, therefor.

In Column 49, Line 40, delete "respectively)" and insert -- respectively --, therefor.

In Column 49, Line 48, delete "NO:17" and insert -- NO:17. --, therefor.

In Column 64, Line 60, delete "FcγRIM" and insert -- FcγRIIB --, therefor.

In Column 66, Line 63, delete "(relative" and insert -- relative --, therefor.

In Column 68, Line 33, delete "I332E;" and insert -- I332E; --, therefor.

In Column 68, Line 36, delete "index" and insert -- index. --, therefor.

In Column 75, Line 53, delete "(e.g.," and insert -- e.g., --, therefor.

In Column 75, Line 54, delete "(e.g.," and insert -- e.g., --, therefor.

In Column 77, Line 12, delete "CRL7O3O" and insert -- CRL7030 --, therefor.

In Column 78, Lines 14-18, delete " 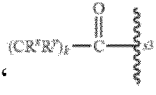 " and insert -- 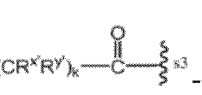 --, therefor.

In Column 78, Lines 21-25, delete " 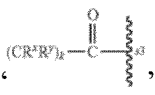 " and insert -- 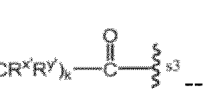 --, therefor.

CERTIFICATE OF CORRECTION (continued)
U.S. Pat. No. 11,396,543 B2

In Column 79, Line 30, delete "$B^{y'}$" and insert -- $R^{y'}$ --, therefor.

In Column 102, Line 15, delete "2.1" and insert -- 2.1. --, therefor.

In Column 102, Line 26, delete "Isalm" and insert -- Aslam --, therefor.

In Column 102, Line 46, delete "amidocaproate" and insert -- aminocaproate --, therefor.

In Column 102, Line 62, delete "(sulfo-MB S)" and insert -- (sulfo-MBS) --, therefor.

In Column 103, Line 59, delete "analogs" and insert -- analogs. --, therefor.

In Column 104, Lines 34-40, delete " " and insert --  --, therefor.

In Column 107, Line 50, after "-deacetyl" insert -- -$N$-$^{2'}$ --.

In Column 107, Line 51, delete "-$N^T$-" and insert -- $N^{2'}$ --, therefor.

In Column 115, Line 54, delete "Alternatively" and insert -- Alternatively, --, therefor.

In Column 123, TABLE 11, Line 24, delete "Mov19scFy1*" and insert -- Mov19scFv1* --, therefor.

In Column 124, Line 51, delete "CO2" and insert -- $CO_2$ --, therefor.

In Column 126, Line 20, delete "412 nm" and insert -- 412 nm. --, therefor.

In Column 127, TABLE 13, Line 7, delete "-4,000" and insert -- ~4,000 --, therefor.

In Column 128, Line 15, delete "inoculation" and insert -- inoculation. --, therefor.

In Column 133, Line 32, delete "xenografts" and insert -- xenografts. --, therefor.

SEQUENCE LISTING

<160> NUMBER OF SEQ ID NOS: 64

<210> SEQ ID NO 1
<211> LENGTH: 11
<212> TYPE: PRT
<213> ORGANISM: Artificial Sequence
<220> FEATURE:
<223> OTHER INFORMATION: FR57 VL-CDR1

<400> SEQUENCE: 1

Arg Ala Ser Gln Asn Ile Asn Asn Asn Leu His
1               5                   10

<210> SEQ ID NO 2
<211> LENGTH: 7
<212> TYPE: PRT
<213> ORGANISM: Artificial Sequence
<220> FEATURE:
<223> OTHER INFORMATION: FR57 VL-CDR2

<400> SEQUENCE: 2

Tyr Val Ser Gln Ser Val Ser
1               5

<210> SEQ ID NO 3
<211> LENGTH: 10
<212> TYPE: PRT
<213> ORGANISM: Artificial Sequence
<220> FEATURE:
<223> OTHER INFORMATION: FR57 VL-CDR3

<400> SEQUENCE: 3

Gln Gln Ser Asn Ser Trp Pro His Tyr Thr
1               5                   10

<210> SEQ ID NO 4
<211> LENGTH: 15
<212> TYPE: PRT
<213> ORGANISM: Artificial Sequence
<220> FEATURE:
<223> OTHER INFORMATION: huMov19 VL-CDR1

<400> SEQUENCE: 4

Lys Ala Ser Gln Ser Val Ser Phe Ala Gly Thr Ser Leu Met His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: huMov19 VL-CDR2

<400> SEQUENCE: 5

Arg Ala Ser Asn Leu Glu Ala
1               5

<210> SEQ ID NO 6
<211> LENGTH: 9
<212> TYPE: PRT
<213> ORGANISM: Artificial Sequence
<220> FEATURE:
<223> OTHER INFORMATION: huMov19 VL-CDR3

<400> SEQUENCE: 6

Gln Gln Ser Arg Glu Tyr Pro Tyr Thr
1               5

<210> SEQ ID NO 7
<211> LENGTH: 5
<212> TYPE: PRT
<213> ORGANISM: Artificial Sequence
<220> FEATURE:
<223> OTHER INFORMATION: FR57 VH-CDR1

<400> SEQUENCE: 7

Ser Phe Gly Met His
1               5

<210> SEQ ID NO 8
<211> LENGTH: 17
<212> TYPE: PRT
<213> ORGANISM: Artificial Sequence
<220> FEATURE:
<223> OTHER INFORMATION: FR57 VH-CDR2

<400> SEQUENCE: 8

Tyr Ile Ser Ser Gly Ser Ser Thr Ile Ser Tyr Ala Asp Ser Val Lys
1               5                   10                  15

Gly

<210> SEQ ID NO 9
<211> LENGTH: 9
<212> TYPE: PRT
<213> ORGANISM: Artificial Sequence
<220> FEATURE:
<223> OTHER INFORMATION: FR57 VH-CDR3

<400> SEQUENCE: 9

Glu Ala Tyr Gly Ser Ser Met Glu Tyr
1               5

<210> SEQ ID NO 10
<211> LENGTH: 5
<212> TYPE: PRT
<213> ORGANISM: Artificial Sequence
<220> FEATURE:
<223> OTHER INFORMATION: huMov19 VH-CDR1

<400> SEQUENCE: 10

Gly Tyr Phe Met Asn
1               5

<210> SEQ ID NO 11
<211> LENGTH: 17
<212> TYPE: PRT
<213> ORGANISM: Artificial Sequence
<220> FEATURE:
<223> OTHER INFORMATION: huMov19 VH-CDR2

<400> SEQUENCE: 11

Arg Ile His Pro Tyr Asp Gly Asp Thr Phe Tyr Asn Gln Lys Phe Gln
1               5                   10                  15

Gly

<210> SEQ ID NO 12
<211> LENGTH: 9
<212> TYPE: PRT
<213> ORGANISM: Artificial Sequence
<220> FEATURE:
<223> OTHER INFORMATION: huMov19 VH-CDR3

<400> SEQUENCE: 12

Tyr Asp Gly Ser Arg Ala Met Asp Tyr
1               5

<210> SEQ ID NO 13
<211> LENGTH: 10
<212> TYPE: PRT
<213> ORGANISM: Artificial Sequence
<220> FEATURE:
<223> OTHER INFORMATION: FR57 VH-CDR1

<400> SEQUENCE: 13

Gly Phe Thr Phe Ser Ser Phe Gly Met His
1               5                   10

<210> SEQ ID NO 14
<211> LENGTH: 10
<212> TYPE: PRT
<213> ORGANISM: Artificial Sequence
<220> FEATURE:
<223> OTHER INFORMATION: FR57 VH-CDR2

<400> SEQUENCE: 14

Tyr Ile Ser Ser Gly Ser Ser Thr Ile Ser
1               5                   10

<210> SEQ ID NO 15
<211> LENGTH: 10
<212> TYPE: PRT
<213> ORGANISM: Artificial Sequence
<220> FEATURE:
<223> OTHER INFORMATION: huMov19 VH-CDR1

<400> SEQUENCE: 15

Gly Tyr Thr Phe Thr Gly Tyr Phe Met Asn
1               5                   10

<210> SEQ ID NO 16
<211> LENGTH: 10
<212> TYPE: PRT
<213> ORGANISM: Artificial Sequence
<220> FEATURE:
<223> OTHER INFORMATION: huMov19 VH-CDR2

<400> SEQUENCE: 16

Arg Ile His Pro Tyr Asp Gly Asp Thr Phe
1               5                   10

<210> SEQ ID NO 17
<211> LENGTH: 108
<212> TYPE: PRT
<213> ORGANISM: Artificial Sequence
<220> FEATURE:
<223> OTHER INFORMATION: FR57 Light Chain Variable Sequence

<400> SEQUENCE: 17

Glu Ile Val Leu Thr Gln Ser Pro Ala Thr Leu Ser Val Thr Pro Gly
1               5                   10                  15

Asp Arg Val Ser Leu Ser Cys Arg Ala Ser Gln Asn Ile Asn Asn Asn
            20                  25                  30

Leu His Trp Tyr Gln Gln Lys Pro Gly Gln Ser Pro Arg Leu Leu Ile
        35                  40                  45

Lys Tyr Val Ser Gln Ser Val Ser Gly Ile Pro Asp Arg Phe Ser Gly
    50                  55                  60

Ser Gly Ser Gly Thr Asp Phe Thr Leu Ser Ile Ser Ser Val Glu Pro 65                  70                  75                  80

Glu Asp Phe Gly Met Tyr Phe Cys Gln Gln Ser Asn Ser Trp Pro His
                    85                  90                  95

Tyr Thr Phe Gly Gln Gly Thr Lys Leu Glu Ile Lys
                100                 105

<210> SEQ ID NO 18
<211> LENGTH: 108
<212> TYPE: PRT
<213> ORGANISM: Artificial Sequence
<220> FEATURE:
<223> OTHER INFORMATION: FR57, F83E, Q101C Light Chain Variable Sequence

<400> SEQUENCE: 18

Glu Ile Val Leu Thr Gln Ser Pro Ala Thr Leu Ser Val Thr Pro Gly
1               5                   10                  15

Asp Arg Val Ser Leu Ser Cys Arg Ala Ser Gln Asn Ile Asn Asn Asn
                20                  25                  30

Leu His Trp Tyr Gln Gln Lys Pro Gly Gln Ser Pro Arg Leu Leu Ile
            35                  40                  45

Lys Tyr Val Ser Gln Ser Val Ser Gly Ile Pro Asp Arg Phe Ser Gly
    50                  55                  60

Ser Gly Ser Gly Thr Asp Phe Thr Leu Ser Ile Ser Ser Val Glu Pro
65                  70                  75                  80

Glu Asp Glu Gly Met Tyr Phe Cys Gln Gln Ser Asn Ser Trp Pro His
                85                  90                  95

Tyr Thr Phe Gly Cys Gly Thr Lys Leu Glu Ile Lys
                100                 105

<210> SEQ ID NO 19
<211> LENGTH: 111
<212> TYPE: PRT
<213> ORGANISM: Artificial Sequence
<220> FEATURE:
<223> OTHER INFORMATION: huMov19 Light Chain Variable Sequence

<400> SEQUENCE: 19

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
                20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
                100                 105                 110

<210> SEQ ID NO 20
<211> LENGTH: 111
<212> TYPE: PRT
<213> ORGANISM: Artificial Sequence
<220> FEATURE:
<223> OTHER INFORMATION: huMov19G104C Light Chain Variable Sequence

<400> SEQUENCE: 20

```
Asp Ile Val Leu Thr Gln Ser Pro Leu Ser Leu Ala Val Ser Leu Gly
 1               5                  10                  15

Gln Pro Ala Ile Ile Ser Cys Lys Ala Ser Gln Ser Val Ser Phe Ala
             20                  25                  30

Gly Thr Ser Leu Met His Trp Tyr His Gln Lys Pro Gly Gln Gln Pro
             35                  40                  45

Arg Leu Leu Ile Tyr Arg Ala Ser Asn Leu Glu Ala Gly Val Pro Asp
 50                  55                  60

Arg Phe Ser Gly Ser Gly Ser Lys Thr Asp Phe Thr Leu Thr Ile Ser
 65                  70                  75                  80

Pro Val Glu Ala Glu Asp Ala Ala Thr Tyr Tyr Cys Gln Gln Ser Arg
                 85                  90                  95

Glu Tyr Pro Tyr Thr Phe Gly Cys Gly Thr Lys Leu Glu Ile Lys
            100                 105                 110
```

<210> SEQ ID NO 21
<211> LENGTH: 111
<212> TYPE: PRT
<213> ORGANISM: Artificial Sequence
<220> FEATURE:
<223> OTHER INFORMATION: huMov19A87E; G104C Light Chain Variable
      Sequence

<400> SEQUENCE: 21

```
Asp Ile Val Leu Thr Gln Ser Pro Leu Ser Leu Ala Val Ser Leu Gly
 1               5                  10                  15

Gln Pro Ala Ile Ile Ser Cys Lys Ala Ser Gln Ser Val Ser Phe Ala
             20                  25                  30

Gly Thr Ser Leu Met His Trp Tyr His Gln Lys Pro Gly Gln Gln Pro
             35                  40                  45

Arg Leu Leu Ile Tyr Arg Ala Ser Asn Leu Glu Ala Gly Val Pro Asp
 50                  55                  60

Arg Phe Ser Gly Ser Gly Ser Lys Thr Asp Phe Thr Leu Thr Ile Ser
 65                  70                  75                  80

Pro Val Glu Ala Glu Asp Glu Ala Thr Tyr Tyr Cys Gln Gln Ser Arg
                 85                  90                  95

Glu Tyr Pro Tyr Thr Phe Gly Cys Gly Thr Lys Leu Glu Ile Lys
            100                 105                 110
```

<210> SEQ ID NO 22
<211> LENGTH: 118
<212> TYPE: PRT
<213> ORGANISM: Artificial Sequence
<220> FEATURE:
<223> OTHER INFORMATION: FR57 Heavy  Chain Variable Sequence

<400> SEQUENCE: 22

```
Glu Val Gln Leu Val Glu Ser Gly Gly Gly Leu Val Gln Pro Gly Gly
 1               5                  10                  15

Ser Arg Arg Leu Ser Cys Ala Ala Ser Gly Phe Thr Phe Ser Ser Phe
             20                  25                  30

Gly Met His Trp Val Arg Gln Ala Pro Gly Lys Gly Leu Glu Trp Val
             35                  40                  45

Ala Tyr Ile Ser Ser Gly Ser Ser Thr Ile Tyr Ala Asp Ser Val
 50                  55                  60

Lys Gly Arg Phe Thr Ile Ser Arg Asp Asn Ser Lys Lys Thr Leu Leu
 65                  70                  75                  80
```

```
Leu Gln Met Thr Ser Leu Arg Ala Glu Asp Thr Ala Met Tyr Tyr Cys
                85                  90                  95

Ala Arg Glu Ala Tyr Gly Ser Ser Met Glu Tyr Trp Gly Gln Gly Thr
            100                 105                 110

Leu Val Thr Val Ser Ser
        115

<210> SEQ ID NO 23
<211> LENGTH: 118
<212> TYPE: PRT
<213> ORGANISM: Artificial Sequence
<220> FEATURE:
<223> OTHER INFORMATION: FR57 E6Q; G44C Heavy  Chain Variable Sequence

<400> SEQUENCE: 23

Glu Val Gln Leu Val Gln Ser Gly Gly Gly Leu Val Gln Pro Gly Gly
1               5                   10                  15

Ser Arg Arg Leu Ser Cys Ala Ala Ser Gly Phe Thr Phe Ser Ser Phe
            20                  25                  30

Gly Met His Trp Val Arg Gln Ala Pro Gly Lys Cys Leu Glu Trp Val
        35                  40                  45

Ala Tyr Ile Ser Ser Gly Ser Thr Ile Ser Tyr Ala Asp Ser Val
50                  55                  60

Lys Gly Arg Phe Thr Ile Ser Arg Asp Asn Ser Lys Lys Thr Leu Leu
65                  70                  75                  80

Leu Gln Met Thr Ser Leu Arg Ala Glu Asp Thr Ala Met Tyr Tyr Cys
                85                  90                  95

Ala Arg Glu Ala Tyr Gly Ser Ser Met Glu Tyr Trp Gly Gln Gly Thr
            100                 105                 110

Leu Val Thr Val Ser Ser
        115

<210> SEQ ID NO 24
<211> LENGTH: 118
<212> TYPE: PRT
<213> ORGANISM: Artificial Sequence
<220> FEATURE:
<223> OTHER INFORMATION: huMov19 Heavy  Chain Variable Sequence

<400> SEQUENCE: 24

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 25
```

```
<211> LENGTH: 107
<212> TYPE: PRT
<213> ORGANISM: Artificial Sequence
<220> FEATURE:
<223> OTHER INFORMATION: huMov19 S44C Heavy  Chain Variable Sequence

<400> SEQUENCE: 25

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Cys Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr
            100                 105

<210> SEQ ID NO 26
<211> LENGTH: 118
<212> TYPE: PRT
<213> ORGANISM: Artificial Sequence
<220> FEATURE:
<223> OTHER INFORMATION: huMov19 A16E; S44C Heavy  Chain Variable
      Sequence

<400> SEQUENCE: 26

Gln Val Gln Leu Val Gln Ser Gly Ala Glu Val Val Lys Pro Gly Glu
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Cys Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 27
<211> LENGTH: 246
<212> TYPE: PRT
<213> ORGANISM: Artificial Sequence
<220> FEATURE:
<223> OTHER INFORMATION: FR57scFv1

<400> SEQUENCE: 27

Glu Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser Ser Phe
            20                  25                  30
```

-continued

Gly Met His Trp Val Arg Gln Ala Pro Gly Lys Gly Leu Glu Trp Val
             35                  40                  45

Ala Tyr Ile Ser Ser Gly Ser Ser Thr Ile Ser Tyr Ala Asp Ser Val
     50                  55                  60

Lys Gly Arg Phe Thr Ile Ser Arg Asp Asn Ser Lys Lys Thr Leu Leu
 65                  70                  75                  80

Leu Gln Met Thr Ser Leu Arg Ala Glu Asp Thr Ala Met Tyr Tyr Cys
                 85                  90                  95

Ala Arg Glu Ala Tyr Gly Ser Ser Met Glu Tyr Trp Gly Gln Gly Thr
             100                 105                 110

Leu Val Thr Val Ser Ser Gly Gly Gly Ser Gly Gly Gly Ser
         115                 120                 125

Gly Gly Gly Gly Ser Gly Gly Gly Ser Glu Ile Val Leu Thr Gln
     130                 135                 140

Ser Pro Ala Thr Leu Ser Val Thr Pro Gly Asp Arg Val Ser Leu Ser
145                 150                 155                 160

Cys Arg Ala Ser Gln Asn Ile Asn Asn Asn Leu His Trp Tyr Gln Gln
                 165                 170                 175

Lys Pro Gly Gln Ser Pro Arg Leu Leu Ile Lys Tyr Val Ser Gln Ser
             180                 185                 190

Val Ser Gly Ile Pro Asp Arg Phe Ser Gly Ser Gly Ser Gly Thr Asp
         195                 200                 205

Phe Thr Leu Ser Ile Ser Ser Val Glu Pro Glu Asp Phe Gly Met Tyr
     210                 215                 220

Phe Cys Gln Gln Ser Asn Ser Trp Pro His Tyr Thr Phe Gly Gln Gly
225                 230                 235                 240

Thr Lys Leu Glu Ile Lys
                 245

<210> SEQ ID NO 28
<211> LENGTH: 246
<212> TYPE: PRT
<213> ORGANISM: Artificial Sequence
<220> FEATURE:
<223> OTHER INFORMATION: FR57scFv2

<400> SEQUENCE: 28

Glu Ile Val Leu Thr Gln Ser Pro Ala Thr Leu Ser Val Thr Pro Gly
 1               5                  10                  15

Asp Arg Val Ser Leu Ser Cys Arg Ala Ser Gln Asn Ile Asn Asn Asn
             20                  25                  30

Leu His Trp Tyr Gln Gln Lys Pro Gly Gln Ser Pro Arg Leu Leu Ile
         35                  40                  45

Lys Tyr Val Ser Gln Ser Val Ser Gly Ile Pro Asp Arg Phe Ser Gly
     50                  55                  60

Ser Gly Ser Gly Thr Asp Phe Thr Leu Ser Ile Ser Ser Val Glu Pro
 65                  70                  75                  80

Glu Asp Glu Gly Met Tyr Phe Cys Gln Gln Ser Asn Ser Trp Pro His
                 85                  90                  95

Tyr Thr Phe Gly Cys Gly Thr Lys Leu Glu Ile Lys Gly Gly Gly Gly
             100                 105                 110

Ser Gly Gly Gly Gly Ser Gly Gly Gly Gly Ser Gly Gly Gly Gly Ser
         115                 120                 125

Glu Val Gln Leu Val Gln Ser Gly Gly Gly Leu Val Gln Pro Gly Gly
     130                 135                 140

Ser Arg Arg Leu Ser Cys Ala Ala Ser Gly Phe Thr Phe Ser Ser Phe
145                 150                 155                 160

Gly Met His Trp Val Arg Gln Ala Pro Gly Lys Cys Leu Glu Trp Val
                165                 170                 175

Ala Tyr Ile Ser Ser Gly Ser Ser Thr Ile Ser Tyr Ala Asp Ser Val
            180                 185                 190

Lys Gly Arg Phe Thr Ile Ser Arg Asp Asn Ser Lys Lys Thr Leu Leu
        195                 200                 205

Leu Gln Met Thr Ser Leu Arg Ala Glu Asp Thr Ala Met Tyr Tyr Cys
    210                 215                 220

Ala Arg Glu Ala Tyr Gly Ser Ser Met Glu Tyr Trp Gly Gln Gly Thr
225                 230                 235                 240

Leu Val Thr Val Ser Ser
                245

<210> SEQ ID NO 29
<211> LENGTH: 246
<212> TYPE: PRT
<213> ORGANISM: Artificial Sequence
<220> FEATURE:
<223> OTHER INFORMATION: FR57scFv3wt

<400> SEQUENCE: 29

Glu Ile Val Leu Thr Gln Ser Pro Ala Thr Leu Ser Val Thr Pro Gly
1               5                   10                  15

Asp Arg Val Ser Leu Ser Cys Arg Ala Ser Gln Asn Ile Asn Asn Asn
            20                  25                  30

Leu His Trp Tyr Gln Gln Lys Pro Gly Gln Ser Pro Arg Leu Leu Ile
        35                  40                  45

Lys Tyr Val Ser Gln Ser Val Ser Gly Ile Pro Asp Arg Phe Ser Gly
    50                  55                  60

Ser Gly Ser Gly Thr Asp Phe Thr Leu Ser Ile Ser Ser Val Glu Pro
65                  70                  75                  80

Glu Asp Phe Gly Met Tyr Phe Cys Gln Gln Ser Asn Ser Trp Pro His
                85                  90                  95

Tyr Thr Phe Gly Gln Gly Thr Lys Leu Glu Ile Lys Gly Gly Gly Gly
            100                 105                 110

Ser Gly Gly Gly Gly Ser Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Arg Arg Leu Ser Cys Ala Ala Ser Gly Phe Thr Phe Ser Ser Phe
145                 150                 155                 160

Gly Met His Trp Val Arg Gln Ala Pro Gly Lys Gly Leu Glu Trp Val
                165                 170                 175

Ala Tyr Ile Ser Ser Gly Ser Ser Thr Ile Ser Tyr Ala Asp Ser Val
            180                 185                 190

Lys Gly Arg Phe Thr Ile Ser Arg Asp Asn Ser Lys Lys Thr Leu Leu
        195                 200                 205

Leu Gln Met Thr Ser Leu Arg Ala Glu Asp Thr Ala Met Tyr Tyr Cys
    210                 215                 220

Ala Arg Glu Ala Tyr Gly Ser Ser Met Glu Tyr Trp Gly Gln Gly Thr
225                 230                 235                 240

Leu Val Thr Val Ser Ser
                245

<210> SEQ ID NO 30
<211> LENGTH: 249
<212> TYPE: PRT
<213> ORGANISM: Artificial Sequence
<220> FEATURE:
<223> OTHER INFORMATION: Mov19scFv1

<400> SEQUENCE: 30

```
Gln Val Gln Leu Val Gln Ser Gly Ala Glu Val Val Lys Pro Gly Ala
1               5                   10                  15
Ser Val Lys Ile Ser Cys Lys Ala Ser Gly Tyr Thr Phe Thr Gly Tyr
            20                  25                  30
Phe Met Asn Trp Val Lys Gln Ser Pro Gly Gln Ser Leu Glu Trp Ile
        35                  40                  45
Gly Arg Ile His Pro Tyr Asp Gly Asp Thr Phe Tyr Asn Gln Lys Phe
    50                  55                  60
Gln Gly Lys Ala Thr Leu Thr Val Asp Lys Ser Ser Asn Thr Ala His
65                  70                  75                  80
Met Glu Leu Leu Ser Leu Thr Ser Glu Asp Phe Ala Val Tyr Tyr Cys
                85                  90                  95
Thr Arg Tyr Asp Gly Ser Arg Ala Met Asp Tyr Trp Gly Gln Gly Thr
            100                 105                 110
Thr Val Thr Val Ser Ser Gly Gly Gly Ser Gly Gly Gly Gly Ser
        115                 120                 125
Gly Gly Gly Gly Ser Gly Gly Gly Ser Asp Ile Val Leu Thr Gln
    130                 135                 140
Ser Pro Leu Ser Leu Ala Val Ser Leu Gly Gln Pro Ala Ile Ile Ser
145                 150                 155                 160
Cys Lys Ala Ser Gln Ser Val Ser Phe Ala Gly Thr Ser Leu Met His
                165                 170                 175
Trp Tyr His Gln Lys Pro Gly Gln Gln Pro Arg Leu Leu Ile Tyr Arg
            180                 185                 190
Ala Ser Asn Leu Glu Ala Gly Val Pro Asp Arg Phe Ser Gly Ser Gly
        195                 200                 205
Ser Lys Thr Asp Phe Thr Leu Thr Ile Ser Pro Val Glu Ala Glu Asp
    210                 215                 220
Ala Ala Thr Tyr Tyr Cys Gln Gln Ser Arg Glu Tyr Pro Tyr Thr Phe
225                 230                 235                 240
Gly Gly Gly Thr Lys Leu Glu Ile Lys
                245
```

<210> SEQ ID NO 31
<211> LENGTH: 249
<212> TYPE: PRT
<213> ORGANISM: Artificial Sequence
<220> FEATURE:
<223> OTHER INFORMATION: Mov19scFv2

<400> SEQUENCE: 31

```
Asp Ile Val Leu Thr Gln Ser Pro Leu Ser Leu Ala Val Ser Leu Gly
1               5                   10                  15
Gln Pro Ala Ile Ile Ser Cys Lys Ala Ser Gln Ser Val Ser Phe Ala
            20                  25                  30
Gly Thr Ser Leu Met His Trp Tyr His Gln Lys Pro Gly Gln Gln Pro
        35                  40                  45
Arg Leu Leu Ile Tyr Arg Ala Ser Asn Leu Glu Ala Gly Val Pro Asp
```

```
                50                  55                  60
Arg Phe Ser Gly Ser Gly Ser Lys Thr Asp Phe Thr Leu Thr Ile Ser
 65                  70                  75                  80

Pro Val Glu Ala Glu Asp Ala Ala Thr Tyr Tyr Cys Gln Gln Ser Arg
                 85                  90                  95

Glu Tyr Pro Tyr Thr Phe Gly Cys Gly Thr Lys Leu Glu Ile Lys Gly
            100                 105                 110

Gly Gly Gly Ser Gly Gly Gly Gly Ser Gly Gly Gly Gly Ser Gly Gly
            115                 120                 125

Gly Gly Ser Gln Val Gln Leu Val Gln Ser Gly Ala Glu Val Val Lys
        130                 135                 140

Pro Gly Ala Ser Val Lys Ile Ser Cys Lys Ala Ser Gly Tyr Thr Phe
145                 150                 155                 160

Thr Gly Tyr Phe Met Asn Trp Val Lys Gln Ser Pro Gly Gln Cys Leu
                165                 170                 175

Glu Trp Ile Gly Arg Ile His Pro Tyr Asp Gly Asp Thr Phe Tyr Asn
            180                 185                 190

Gln Lys Phe Gln Gly Lys Ala Thr Leu Thr Val Asp Lys Ser Ser Asn
        195                 200                 205

Thr Ala His Met Glu Leu Leu Ser Leu Thr Ser Glu Asp Phe Ala Val
    210                 215                 220

Tyr Tyr Cys Thr Arg Tyr Asp Gly Ser Arg Ala Met Asp Tyr Trp Gly
225                 230                 235                 240

Gln Gly Thr Thr Val Thr Val Ser Ser
                245
```

<210> SEQ ID NO 32
<211> LENGTH: 249
<212> TYPE: PRT
<213> ORGANISM: Artificial Sequence
<220> FEATURE:
<223> OTHER INFORMATION: Mov19scFv3

<400> SEQUENCE: 32

```
Asp Ile Val Leu Thr Gln Ser Pro Leu Ser Leu Ala Val Ser Leu Gly
 1               5                  10                  15

Gln Pro Ala Ile Ile Ser Cys Lys Ala Ser Gln Ser Val Ser Phe Ala
                 20                  25                  30

Gly Thr Ser Leu Met His Trp Tyr His Gln Lys Pro Gly Gln Gln Pro
             35                  40                  45

Arg Leu Leu Ile Tyr Arg Ala Ser Asn Leu Glu Ala Gly Val Pro Asp
         50                  55                  60

Arg Phe Ser Gly Ser Gly Ser Lys Thr Asp Phe Thr Leu Thr Ile Ser
 65                  70                  75                  80

Pro Val Glu Ala Glu Asp Ala Ala Thr Tyr Tyr Cys Gln Gln Ser Arg
                 85                  90                  95

Glu Tyr Pro Tyr Thr Phe Gly Cys Gly Thr Lys Leu Glu Ile Lys Gly
            100                 105                 110

Gly Gly Gly Ser Gly Gly Gly Gly Ser Gly Gly Gly Gly Ser Gly Gly
            115                 120                 125

Gly Gly Ser Gln Val Gln Leu Val Gln Ser Gly Ala Glu Val Val Lys
        130                 135                 140

Pro Gly Glu Ser Val Lys Ile Ser Cys Lys Ala Ser Gly Tyr Thr Phe
145                 150                 155                 160

Thr Gly Tyr Phe Met Asn Trp Val Lys Gln Ser Pro Gly Gln Cys Leu
```

```
                        165                 170                 175
Glu Trp Ile Gly Arg Ile His Pro Tyr Asp Gly Asp Thr Phe Tyr Asn
                180                 185                 190

Gln Lys Phe Gln Gly Lys Ala Thr Leu Thr Val Asp Lys Ser Ser Asn
            195                 200                 205

Thr Ala His Met Glu Leu Leu Ser Leu Thr Ser Glu Asp Phe Ala Val
        210                 215                 220

Tyr Tyr Cys Thr Arg Tyr Asp Gly Ser Arg Ala Met Asp Tyr Trp Gly
225                 230                 235                 240

Gln Gly Thr Thr Val Thr Val Ser Ser
                245

<210> SEQ ID NO 33
<211> LENGTH: 711
<212> TYPE: PRT
<213> ORGANISM: Artificial Sequence
<220> FEATURE:
<223> OTHER INFORMATION: mov19-IgG1-FR57scFv-HC

<400> SEQUENCE: 33

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
```

```
            275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
            355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Ser
            435                 440                 445
Gly Gly Gly Gly Ser Gly Gly Gly Ser Gly Gly Gly Gly Ser Glu
    450                 455                 460
Val Gln Leu Val Glu Ser Gly Gly Leu Val Gln Pro Gly Gly Ser
465                 470                 475                 480
Arg Arg Leu Ser Cys Ala Ala Ser Gly Phe Thr Phe Ser Ser Phe Gly
                485                 490                 495
Met His Trp Val Arg Gln Ala Pro Gly Lys Gly Leu Glu Trp Val Ala
            500                 505                 510
Tyr Ile Ser Ser Gly Ser Ser Thr Ile Ser Tyr Ala Asp Ser Val Lys
            515                 520                 525
Gly Arg Phe Thr Ile Ser Arg Asp Asn Ser Lys Lys Thr Leu Leu Leu
    530                 535                 540
Gln Met Thr Ser Leu Arg Ala Glu Asp Thr Ala Met Tyr Tyr Cys Ala
545                 550                 555                 560
Arg Glu Ala Tyr Gly Ser Ser Met Glu Tyr Trp Gly Gln Gly Thr Leu
                565                 570                 575
Val Thr Val Ser Ser Gly Gly Gly Gly Ser Gly Gly Gly Gly Ser Gly
                580                 585                 590
Gly Gly Gly Ser Gly Gly Gly Gly Ser Glu Ile Val Leu Thr Gln Ser
            595                 600                 605
Pro Ala Thr Leu Ser Val Thr Pro Gly Asp Arg Val Ser Leu Ser Cys
            610                 615                 620
Arg Ala Ser Gln Asn Ile Asn Asn Asn Leu His Trp Tyr Gln Gln Lys
625                 630                 635                 640
Pro Gly Gln Ser Pro Arg Leu Leu Ile Lys Tyr Val Ser Gln Ser Val
                645                 650                 655
Ser Gly Ile Pro Asp Arg Phe Ser Gly Ser Gly Ser Gly Thr Asp Phe
                660                 665                 670
Thr Leu Ser Ile Ser Ser Val Glu Pro Glu Asp Phe Gly Met Tyr Phe
            675                 680                 685
Cys Gln Gln Ser Asn Ser Trp Pro His Tyr Thr Phe Gly Gln Gly Thr
            690                 695                 700
```

-continued

Lys Leu Glu Ile Lys Arg Thr
705             710

<210> SEQ ID NO 34
<211> LENGTH: 218
<212> TYPE: PRT
<213> ORGANISM: Artificial Sequence
<220> FEATURE:
<223> OTHER INFORMATION: huMov19LC

<400> SEQUENCE: 34

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 35
<211> LENGTH: 714
<212> TYPE: PRT
<213> ORGANISM: Artificial Sequence
<220> FEATURE:
<223> OTHER INFORMATION: FR57-IgG1-mov19scFv1-HC

<400> SEQUENCE: 35

Glu Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Ser Thr Ile Ser Tyr Ala Asp Ser Val
    50                  55                  60

Lys Gly Arg Phe Thr Ile Ser Arg Asp Asn Ser Lys Lys Thr Leu Leu

```
                65                  70                  75                  80
Leu Gln Met Thr Ser Leu Arg Ala Glu Asp Thr Ala Met Tyr Tyr Cys
                    85                  90                  95
Ala Arg Glu Ala Tyr Gly Ser Ser Met Glu Tyr Trp Gly Gln Gly Thr
                100                 105                 110
Leu Val Thr Val Ser Ser Ala Ser Thr Lys Gly Pro Ser Val Phe Pro
                115                 120                 125
Leu Ala Pro Ser Ser Lys Ser Thr Ser Gly Gly Thr Ala Ala Leu Gly
                130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Lys Val Glu Pro Lys Ser Cys Asp Lys Thr
                210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Asn Ser Thr Tyr Arg Val Val
                290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Ser
                435                 440                 445
Gly Gly Gly Gly Ser Gly Gly Gly Ser Gly Gly Gly Gly Ser Gln
                450                 455                 460
Val Gln Leu Val Gln Ser Gly Ala Glu Val Val Lys Pro Gly Ala Ser
465                 470                 475                 480
Val Lys Ile Ser Cys Lys Ala Ser Gly Tyr Thr Phe Thr Gly Tyr Phe
                485                 490                 495
```

Met Asn Trp Val Lys Gln Ser Pro Gly Gln Ser Leu Glu Trp Ile Gly
            500                 505                 510

Arg Ile His Pro Tyr Asp Gly Asp Thr Phe Tyr Asn Gln Lys Phe Gln
        515                 520                 525

Gly Lys Ala Thr Leu Thr Val Asp Lys Ser Ser Asn Thr Ala His Met
530                 535                 540

Glu Leu Leu Ser Leu Thr Ser Glu Asp Phe Ala Val Tyr Tyr Cys Thr
545                 550                 555                 560

Arg Tyr Asp Gly Ser Arg Ala Met Asp Tyr Trp Gly Gln Gly Thr Thr
                565                 570                 575

Val Thr Val Ser Ser Gly Gly Gly Gly Ser Gly Gly Gly Gly Ser Gly
            580                 585                 590

Gly Gly Ser Gly Gly Gly Gly Ser Asp Ile Val Leu Thr Gln Ser
        595                 600                 605

Pro Leu Ser Leu Ala Val Ser Leu Gly Gln Pro Ala Ile Ile Ser Cys
    610                 615                 620

Lys Ala Ser Gln Ser Val Ser Phe Ala Gly Thr Ser Leu Met His Trp
625                 630                 635                 640

Tyr His Gln Lys Pro Gly Gln Gln Pro Arg Leu Leu Ile Tyr Arg Ala
                645                 650                 655

Ser Asn Leu Glu Ala Gly Val Pro Asp Arg Phe Ser Gly Ser Gly Ser
            660                 665                 670

Lys Thr Asp Phe Thr Leu Thr Ile Ser Pro Val Glu Ala Glu Asp Ala
        675                 680                 685

Ala Thr Tyr Tyr Cys Gln Gln Ser Arg Glu Tyr Pro Tyr Thr Phe Gly
    690                 695                 700

Gly Gly Thr Lys Leu Glu Ile Lys Arg Thr
705                 710

<210> SEQ ID NO 36
<211> LENGTH: 215
<212> TYPE: PRT
<213> ORGANISM: Artificial Sequence
<220> FEATURE:
<223> OTHER INFORMATION: FR57LC

<400> SEQUENCE: 36

Glu Ile Val Leu Thr Gln Ser Pro Ala Thr Leu Ser Val Thr Pro Gly
1               5                   10                  15

Asp Arg Val Ser Leu Ser Cys Arg Ala Ser Gln Asn Ile Asn Asn Asn
            20                  25                  30

Leu His Trp Tyr Gln Gln Lys Pro Gly Gln Ser Pro Arg Leu Leu Ile
        35                  40                  45

Lys Tyr Val Ser Gln Ser Val Ser Gly Ile Pro Asp Arg Phe Ser Gly
    50                  55                  60

Ser Gly Ser Gly Thr Asp Phe Thr Leu Ser Ile Ser Ser Val Glu Pro
65                  70                  75                  80

Glu Asp Phe Gly Met Tyr Phe Cys Gln Gln Ser Asn Ser Trp Pro His
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 37
<211> LENGTH: 708
<212> TYPE: PRT
<213> ORGANISM: Artificial Sequence
<220> FEATURE:
<223> OTHER INFORMATION: FR57scFv2-mov19-IgG1-HC

<400> SEQUENCE: 37

Glu Ile Val Leu Thr Gln Ser Pro Ala Thr Leu Ser Val Thr Pro Gly
1               5                   10                  15

Asp Arg Val Ser Leu Ser Cys Arg Ala Ser Gln Asn Ile Asn Asn Asn
                20                  25                  30

Leu His Trp Tyr Gln Gln Lys Pro Gly Gln Ser Pro Arg Leu Leu Ile
            35                  40                  45

Lys Tyr Val Ser Gln Ser Val Ser Gly Ile Pro Asp Arg Phe Ser Gly
        50                  55                  60

Ser Gly Ser Gly Thr Asp Phe Thr Leu Ser Ile Ser Ser Val Glu Pro
65                  70                  75                  80

Glu Asp Glu Gly Met Tyr Phe Cys Gln Gln Ser Asn Ser Trp Pro His
                85                  90                  95

Tyr Thr Phe Gly Cys Gly Thr Lys Leu Glu Ile Lys Gly Gly Gly Gly
            100                 105                 110

Ser Gly Gly Gly Gly Ser Gly Gly Gly Ser Gly Gly Gly Gly Ser
        115                 120                 125

Glu Val Gln Leu Val Gln Ser Gly Gly Gly Leu Val Gln Pro Gly Gly
    130                 135                 140

Ser Arg Arg Leu Ser Cys Ala Ala Ser Gly Phe Thr Phe Ser Ser Phe
145                 150                 155                 160

Gly Met His Trp Val Arg Gln Ala Pro Gly Lys Cys Leu Glu Trp Val
                165                 170                 175

Ala Tyr Ile Ser Ser Gly Ser Ser Thr Ile Ser Tyr Ala Asp Ser Val
            180                 185                 190

Lys Gly Arg Phe Thr Ile Ser Arg Asp Asn Ser Lys Lys Thr Leu Leu
        195                 200                 205

Leu Gln Met Thr Ser Leu Arg Ala Glu Asp Thr Ala Met Tyr Tyr Cys
    210                 215                 220

Ala Arg Glu Ala Tyr Gly Ser Ser Met Glu Tyr Trp Gly Gln Gly Thr
225                 230                 235                 240

Leu Val Thr Val Ser Ser Gly Gly Gly Ser Gly Gly Gly Gly Ser
                245                 250                 255

Gly Gly Gly Gly Ser Gln Val Gln Leu Val Gln Ser Gly Ala Glu Val
            260                 265                 270

Val Lys Pro Gly Ala Ser Val Lys Ile Ser Cys Lys Ala Ser Gly Tyr
        275                 280                 285
```

```
Thr Phe Thr Gly Tyr Phe Met Asn Trp Val Lys Gln Ser Pro Gly Gln
    290                 295                 300

Ser Leu Glu Trp Ile Gly Arg Ile His Pro Tyr Asp Gly Asp Thr Phe
305                 310                 315                 320

Tyr Asn Gln Lys Phe Gln Gly Lys Ala Thr Leu Thr Val Asp Lys Ser
                325                 330                 335

Ser Asn Thr Ala His Met Glu Leu Leu Ser Leu Thr Ser Glu Asp Phe
            340                 345                 350

Ala Val Tyr Tyr Cys Thr Arg Tyr Asp Gly Ser Arg Ala Met Asp Tyr
        355                 360                 365

Trp Gly Gln Gly Thr Thr Val Thr Val Ser Ser Ala Ser Thr Lys Gly
    370                 375                 380

Pro Ser Val Phe Pro Leu Ala Pro Ser Ser Lys Ser Thr Ser Gly Gly
385                 390                 395                 400

Thr Ala Ala Leu Gly Cys Leu Val Lys Asp Tyr Phe Pro Glu Pro Val
                405                 410                 415

Thr Val Ser Trp Asn Ser Gly Ala Leu Thr Ser Gly Val His Thr Phe
            420                 425                 430

Pro Ala Val Leu Gln Ser Ser Gly Leu Tyr Ser Leu Ser Ser Val Val
        435                 440                 445

Thr Val Pro Ser Ser Ser Leu Gly Thr Gln Thr Tyr Ile Cys Asn Val
    450                 455                 460

Asn His Lys Pro Ser Asn Thr Lys Val Asp Lys Lys Val Glu Pro Lys
465                 470                 475                 480

Ser Cys Asp Lys Thr His Thr Cys Pro Pro Cys Pro Ala Pro Glu Leu
                485                 490                 495

Leu Gly Gly Pro Ser Val Phe Leu Phe Pro Pro Lys Pro Lys Asp Thr
            500                 505                 510

Leu Met Ile Ser Arg Thr Pro Glu Val Thr Cys Val Val Val Asp Val
        515                 520                 525

Ser His Glu Asp Pro Glu Val Lys Phe Asn Trp Tyr Val Asp Gly Val
    530                 535                 540

Glu Val His Asn Ala Lys Thr Lys Pro Arg Glu Glu Gln Tyr Asn Ser
545                 550                 555                 560

Thr Tyr Arg Val Val Ser Val Leu Thr Val Leu His Gln Asp Trp Leu
                565                 570                 575

Asn Gly Lys Glu Tyr Lys Cys Lys Val Ser Asn Lys Ala Leu Pro Ala
            580                 585                 590

Pro Ile Glu Lys Thr Ile Ser Lys Ala Lys Gly Gln Pro Arg Glu Pro
        595                 600                 605

Gln Val Tyr Thr Leu Pro Pro Ser Arg Asp Glu Leu Thr Lys Asn Gln
    610                 615                 620

Val Ser Leu Thr Cys Leu Val Lys Gly Phe Tyr Pro Ser Asp Ile Ala
625                 630                 635                 640

Val Glu Trp Glu Ser Asn Gly Gln Pro Glu Asn Asn Tyr Lys Thr Thr
                645                 650                 655

Pro Pro Val Leu Asp Ser Asp Gly Ser Phe Phe Leu Tyr Ser Lys Leu
            660                 665                 670

Thr Val Asp Lys Ser Arg Trp Gln Gln Gly Asn Val Phe Ser Cys Ser
        675                 680                 685

Val Met His Glu Ala Leu His Asn His Tyr Thr Gln Lys Ser Leu Ser
    690                 695                 700
```

Leu Ser Pro Gly
705

<210> SEQ ID NO 38
<211> LENGTH: 218
<212> TYPE: PRT
<213> ORGANISM: Artificial Sequence
<220> FEATURE:
<223> OTHER INFORMATION: huMov19LCv1-6

<400> SEQUENCE: 38

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 39
<211> LENGTH: 708
<212> TYPE: PRT
<213> ORGANISM: Artificial Sequence
<220> FEATURE:
<223> OTHER INFORMATION: FR57scFv3wt-mov19-IgG1-HC

<400> SEQUENCE: 39

Glu Ile Val Leu Thr Gln Ser Pro Ala Thr Leu Ser Val Thr Pro Gly
1               5                   10                  15

Asp Arg Val Ser Leu Ser Cys Arg Ala Ser Gln Asn Ile Asn Asn Asn
            20                  25                  30

Leu His Trp Tyr Gln Gln Lys Pro Gly Gln Ser Pro Arg Leu Leu Ile
        35                  40                  45

Lys Tyr Val Ser Gln Ser Val Ser Gly Ile Pro Asp Arg Phe Ser Gly
    50                  55                  60

Ser Gly Ser Gly Thr Asp Phe Thr Leu Ser Ile Ser Ser Val Glu Pro
65                  70                  75                  80

-continued

Glu Asp Phe Gly Met Tyr Phe Cys Gln Gln Ser Asn Ser Trp Pro His
                85                  90                  95

Tyr Thr Phe Gly Gln Gly Thr Lys Leu Glu Ile Lys Gly Gly Gly Gly
                100                 105                 110

Ser Gly Gly Gly Gly Ser Gly Gly Gly Ser Gly Gly Gly Gly Ser
            115                 120                 125

Glu Val Gln Leu Val Glu Ser Gly Gly Gly Leu Val Gln Pro Gly Gly
        130                 135                 140

Ser Arg Arg Leu Ser Cys Ala Ala Ser Gly Phe Thr Phe Ser Ser Phe
145                 150                 155                 160

Gly Met His Trp Val Arg Gln Ala Pro Gly Lys Gly Leu Glu Trp Val
                165                 170                 175

Ala Tyr Ile Ser Ser Gly Ser Ser Thr Ile Ser Tyr Ala Asp Ser Val
                180                 185                 190

Lys Gly Arg Phe Thr Ile Ser Arg Asp Asn Ser Lys Lys Thr Leu Leu
                195                 200                 205

Leu Gln Met Thr Ser Leu Arg Ala Glu Asp Thr Ala Met Tyr Tyr Cys
        210                 215                 220

Ala Arg Glu Ala Tyr Gly Ser Ser Met Glu Tyr Trp Gly Gln Gly Thr
225                 230                 235                 240

Leu Val Thr Val Ser Ser Gly Gly Gly Ser Gly Gly Gly Gly Ser
                245                 250                 255

Gly Gly Gly Gly Ser Gln Val Gln Leu Val Gln Ser Gly Ala Glu Val
            260                 265                 270

Val Lys Pro Gly Ala Ser Val Lys Ile Ser Cys Lys Ala Ser Gly Tyr
        275                 280                 285

Thr Phe Thr Gly Tyr Phe Met Asn Trp Val Lys Gln Ser Pro Gly Gln
        290                 295                 300

Ser Leu Glu Trp Ile Gly Arg Ile His Pro Tyr Asp Gly Asp Thr Phe
305                 310                 315                 320

Tyr Asn Gln Lys Phe Gln Gly Lys Ala Thr Leu Thr Val Asp Lys Ser
                325                 330                 335

Ser Asn Thr Ala His Met Glu Leu Leu Ser Leu Thr Ser Glu Asp Phe
            340                 345                 350

Ala Val Tyr Tyr Cys Thr Arg Tyr Asp Gly Ser Arg Ala Met Asp Tyr
        355                 360                 365

Trp Gly Gln Gly Thr Thr Val Thr Val Ser Ser Ala Ser Thr Lys Gly
370                 375                 380

Pro Ser Val Phe Pro Leu Ala Pro Ser Ser Lys Ser Thr Ser Gly Gly
385                 390                 395                 400

Thr Ala Ala Leu Gly Cys Leu Val Lys Asp Tyr Phe Pro Glu Pro Val
                405                 410                 415

Thr Val Ser Trp Asn Ser Gly Ala Leu Thr Ser Gly Val His Thr Phe
                420                 425                 430

Pro Ala Val Leu Gln Ser Ser Gly Leu Tyr Ser Leu Ser Ser Val Val
        435                 440                 445

Thr Val Pro Ser Ser Ser Leu Gly Thr Gln Thr Tyr Ile Cys Asn Val
        450                 455                 460

Asn His Lys Pro Ser Asn Thr Lys Val Asp Lys Lys Val Glu Pro Lys
465                 470                 475                 480

Ser Cys Asp Lys Thr His Thr Cys Pro Pro Cys Pro Ala Pro Glu Leu
                485                 490                 495

Leu Gly Gly Pro Ser Val Phe Leu Phe Pro Pro Lys Pro Lys Asp Thr
                500                 505                 510

Leu Met Ile Ser Arg Thr Pro Glu Val Thr Cys Val Val Val Asp Val
        515                 520                 525

Ser His Glu Asp Pro Glu Val Lys Phe Asn Trp Tyr Val Asp Gly Val
530                 535                 540

Glu Val His Asn Ala Lys Thr Lys Pro Arg Glu Glu Gln Tyr Asn Ser
545                 550                 555                 560

Thr Tyr Arg Val Val Ser Val Leu Thr Val Leu His Gln Asp Trp Leu
                565                 570                 575

Asn Gly Lys Glu Tyr Lys Cys Lys Val Ser Asn Lys Ala Leu Pro Ala
            580                 585                 590

Pro Ile Glu Lys Thr Ile Ser Lys Ala Lys Gly Gln Pro Arg Glu Pro
        595                 600                 605

Gln Val Tyr Thr Leu Pro Pro Ser Arg Asp Glu Leu Thr Lys Asn Gln
    610                 615                 620

Val Ser Leu Thr Cys Leu Val Lys Gly Phe Tyr Pro Ser Asp Ile Ala
625                 630                 635                 640

Val Glu Trp Glu Ser Asn Gly Gln Pro Glu Asn Asn Tyr Lys Thr Thr
                645                 650                 655

Pro Pro Val Leu Asp Ser Asp Gly Ser Phe Phe Leu Tyr Ser Lys Leu
            660                 665                 670

Thr Val Asp Lys Ser Arg Trp Gln Gln Gly Asn Val Phe Ser Cys Ser
        675                 680                 685

Val Met His Glu Ala Leu His Asn His Tyr Thr Gln Lys Ser Leu Ser
    690                 695                 700

Leu Ser Pro Gly
705

<210> SEQ ID NO 40
<211> LENGTH: 218
<212> TYPE: PRT
<213> ORGANISM: Artificial Sequence
<220> FEATURE:
<223> OTHER INFORMATION: huMov19LCv1-6

<400> SEQUENCE: 40

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 41
<211> LENGTH: 479
<212> TYPE: PRT
<213> ORGANISM: Artificial Sequence
<220> FEATURE:
<223> OTHER INFORMATION: FR57scFv2-Fc-knob (C220S, T366W)

<400> SEQUENCE: 41

```
Glu Ile Val Leu Thr Gln Ser Pro Ala Thr Leu Ser Val Thr Pro Gly
1               5                   10                  15

Asp Arg Val Ser Leu Ser Cys Arg Ala Ser Gln Asn Ile Asn Asn Asn
            20                  25                  30

Leu His Trp Tyr Gln Gln Lys Pro Gly Gln Ser Pro Arg Leu Leu Ile
        35                  40                  45

Lys Tyr Val Ser Gln Ser Val Ser Gly Ile Pro Asp Arg Phe Ser Gly
    50                  55                  60

Ser Gly Ser Gly Thr Asp Phe Thr Leu Ser Ile Ser Ser Val Glu Pro
65                  70                  75                  80

Glu Asp Glu Gly Met Tyr Phe Cys Gln Gln Ser Asn Ser Trp Pro His
                85                  90                  95

Tyr Thr Phe Gly Cys Gly Thr Lys Leu Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Gln Ser Gly Gly Gly Leu Val Gln Pro Gly Gly
    130                 135                 140

Ser Arg Arg Leu Ser Cys Ala Ala Ser Gly Phe Thr Phe Ser Ser Phe
145                 150                 155                 160

Gly Met His Trp Val Arg Gln Ala Pro Gly Lys Cys Leu Glu Trp Val
                165                 170                 175

Ala Tyr Ile Ser Ser Gly Ser Ser Thr Ile Ser Tyr Ala Asp Ser Val
            180                 185                 190

Lys Gly Arg Phe Thr Ile Ser Arg Asp Asn Ser Lys Lys Thr Leu Leu
        195                 200                 205

Leu Gln Met Thr Ser Leu Arg Ala Glu Asp Thr Ala Met Tyr Tyr Cys
    210                 215                 220

Ala Arg Glu Ala Tyr Gly Ser Ser Met Glu Tyr Trp Gly Gln Gly Thr
225                 230                 235                 240

Leu Val Thr Val Ser Ser Gly Ser Glu Pro Lys Ser Ser Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285
```

```
Thr Pro Glu Val Thr Cys Val Val Asp Val Ser His Glu Asp Pro
    290                 295                 300
Glu Val Lys Phe Asn Trp Tyr Val Asp Gly Val Glu Val His Asn Ala
305                 310                 315                 320
Lys Thr Lys Pro Arg Glu Glu Gln Tyr Asn Ser Thr Tyr Arg Val Val
                325                 330                 335
Ser Val Leu Thr Val Leu His Gln Asp Trp Leu Asn Gly Lys Glu Tyr
            340                 345                 350
Lys Cys Lys Val Ser Asn Lys Ala Leu Pro Ala Pro Ile Glu Lys Thr
        355                 360                 365
Ile Ser Lys Ala Lys Gly Gln Pro Arg Glu Pro Gln Val Tyr Thr Leu
370                 375                 380
Pro Pro Ser Arg Glu Glu Met Thr Lys Asn Gln Val Ser Leu Trp Cys
385                 390                 395                 400
Leu Val Lys Gly Phe Tyr Pro Ser Asp Ile Ala Val Glu Trp Glu Ser
                405                 410                 415
Asn Gly Gln Pro Glu Asn Asn Tyr Lys Thr Thr Pro Pro Val Leu Asp
            420                 425                 430
Ser Asp Gly Ser Phe Phe Leu Tyr Ser Lys Leu Thr Val Asp Lys Ser
        435                 440                 445
Arg Trp Gln Gln Gly Asn Val Phe Ser Cys Ser Val Met His Glu Ala
    450                 455                 460
Leu His Asn His Tyr Thr Gln Lys Ser Leu Ser Leu Ser Pro Gly
465                 470                 475
```

<210> SEQ ID NO 42
<211> LENGTH: 447
<212> TYPE: PRT
<213> ORGANISM: Artificial Sequence
<220> FEATURE:
<223> OTHER INFORMATION: Mov19-Fc-hole (T366S, L368A, Y407V)

<400> SEQUENCE: 42

```
Gln Val Gln Leu Val Gln Ser Gly Ala Glu Val Val Lys Pro Gly Ala
1               5                   10                  15
Ser Val Lys Ile Ser Cys Lys Ala Ser Gly Tyr Thr Phe Thr Gly Tyr
            20                  25                  30
Phe Met Asn Trp Val Lys Gln Ser Pro Gly Gln Ser Leu Glu Trp Ile
        35                  40                  45
Gly Arg Ile His Pro Tyr Asp Gly Asp Thr Phe Tyr Asn Gln Lys Phe
    50                  55                  60
Gln Gly Lys Ala Thr Leu Thr Val Asp Lys Ser Ser Asn Thr Ala His
65                  70                  75                  80
Met Glu Leu Leu Ser Leu Thr Ser Glu Asp Phe Ala Val Tyr Tyr Cys
                85                  90                  95
Thr Arg Tyr Asp Gly Ser Arg Ala Met Asp Tyr Trp Gly Gln Gly Thr
            100                 105                 110
Thr Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
```

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200             205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 43
<211> LENGTH: 218
<212> TYPE: PRT
<213> ORGANISM: Artificial Sequence
<220> FEATURE:
<223> OTHER INFORMATION: Mov19-LC

<400> SEQUENCE: 43

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

-continued

```
Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 44
<211> LENGTH: 479
<212> TYPE: PRT
<213> ORGANISM: Artificial Sequence
<220> FEATURE:
<223> OTHER INFORMATION: FR57scFv3wt-Fc-knob (C220S, T366W)

<400> SEQUENCE: 44

```
Glu Ile Val Leu Thr Gln Ser Pro Ala Thr Leu Ser Val Thr Pro Gly
1               5                   10                  15

Asp Arg Val Ser Leu Ser Cys Arg Ala Ser Gln Asn Ile Asn Asn Asn
            20                  25                  30

Leu His Trp Tyr Gln Gln Lys Pro Gly Gln Ser Pro Arg Leu Leu Ile
        35                  40                  45

Lys Tyr Val Ser Gln Ser Val Ser Gly Ile Pro Asp Arg Phe Ser Gly
    50                  55                  60

Ser Gly Ser Gly Thr Asp Phe Thr Leu Ser Ile Ser Ser Val Glu Pro
65                  70                  75                  80

Glu Asp Phe Gly Met Tyr Phe Cys Gln Gln Ser Asn Ser Trp Pro His
                85                  90                  95

Tyr Thr Phe Gly Gln Gly Thr Lys Leu Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Arg Arg Leu Ser Cys Ala Ala Ser Gly Phe Thr Phe Ser Ser Phe
145                 150                 155                 160

Gly Met His Trp Val Arg Gln Ala Pro Gly Lys Gly Leu Glu Trp Val
                165                 170                 175

Ala Tyr Ile Ser Ser Gly Ser Ser Thr Ile Ser Tyr Ala Asp Ser Val
            180                 185                 190

Lys Gly Arg Phe Thr Ile Ser Arg Asp Asn Ser Lys Lys Thr Leu Leu
        195                 200                 205

Leu Gln Met Thr Ser Leu Arg Ala Glu Asp Thr Ala Met Tyr Tyr Cys
    210                 215                 220

Ala Arg Glu Ala Tyr Gly Ser Ser Met Glu Tyr Trp Gly Gln Gly Thr
225                 230                 235                 240
```

-continued

```
Leu Val Thr Val Ser Ser Gly Ser Glu Pro Lys Ser Ser Asp Lys Thr
                245                 250                 255
His Thr Cys Pro Pro Cys Pro Ala Pro Glu Leu Leu Gly Gly Pro Ser
            260                 265                 270
Val Phe Leu Phe Pro Pro Lys Pro Lys Asp Thr Leu Met Ile Ser Arg
        275                 280                 285
Thr Pro Glu Val Thr Cys Val Val Val Asp Val Ser His Glu Asp Pro
    290                 295                 300
Glu Val Lys Phe Asn Trp Tyr Val Asp Gly Val Glu Val His Asn Ala
305                 310                 315                 320
Lys Thr Lys Pro Arg Glu Glu Gln Tyr Asn Ser Thr Tyr Arg Val Val
                325                 330                 335
Ser Val Leu Thr Val Leu His Gln Asp Trp Leu Asn Gly Lys Glu Tyr
            340                 345                 350
Lys Cys Lys Val Ser Asn Lys Ala Leu Pro Ala Pro Ile Glu Lys Thr
        355                 360                 365
Ile Ser Lys Ala Lys Gly Gln Pro Arg Glu Pro Gln Val Tyr Thr Leu
    370                 375                 380
Pro Pro Ser Arg Glu Glu Met Thr Lys Asn Gln Val Ser Leu Trp Cys
385                 390                 395                 400
Leu Val Lys Gly Phe Tyr Pro Ser Asp Ile Ala Val Glu Trp Glu Ser
                405                 410                 415
Asn Gly Gln Pro Glu Asn Asn Tyr Lys Thr Thr Pro Pro Val Leu Asp
            420                 425                 430
Ser Asp Gly Ser Phe Phe Leu Tyr Ser Lys Leu Thr Val Asp Lys Ser
        435                 440                 445
Arg Trp Gln Gln Gly Asn Val Phe Ser Cys Ser Val Met His Glu Ala
    450                 455                 460
Leu His Asn His Tyr Thr Gln Lys Ser Leu Ser Leu Ser Pro Gly
465                 470                 475

<210> SEQ ID NO 45
<211> LENGTH: 447
<212> TYPE: PRT
<213> ORGANISM: Artificial Sequence
<220> FEATURE:
<223> OTHER INFORMATION: Mov19-Fc-hole (T366S, L368A, Y407V)

<400> SEQUENCE: 45

Gln Val Gln Leu Val Gln Ser Gly Ala Glu Val Val Lys Pro Gly Ala
1               5                   10                  15
Ser Val Lys Ile Ser Cys Lys Ala Ser Gly Tyr Thr Phe Thr Gly Tyr
            20                  25                  30
Phe Met Asn Trp Val Lys Gln Ser Pro Gly Gln Ser Leu Glu Trp Ile
        35                  40                  45
Gly Arg Ile His Pro Tyr Asp Gly Asp Thr Phe Tyr Asn Gln Lys Phe
    50                  55                  60
Gln Gly Lys Ala Thr Leu Thr Val Asp Lys Ser Ser Asn Thr Ala His
65                  70                  75                  80
Met Glu Leu Leu Ser Leu Thr Ser Glu Asp Phe Ala Val Tyr Tyr Cys
                85                  90                  95
Thr Arg Tyr Asp Gly Ser Arg Ala Met Asp Tyr Trp Gly Gln Gly Thr
            100                 105                 110
Thr Val Thr Val Ser Ser Ala Ser Thr Lys Gly Pro Ser Val Phe Pro
        115                 120                 125
```

Leu Ala Pro Ser Ser Lys Ser Thr Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 46
<211> LENGTH: 218
<212> TYPE: PRT
<213> ORGANISM: Artificial Sequence
<220> FEATURE:
<223> OTHER INFORMATION: Mov19-LC

<400> SEQUENCE: 46

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
 50                  55                  60

Arg Phe Ser Gly Ser Gly Ser Lys Thr Asp Phe Thr Leu Thr Ile Ser
 65                  70                  75                  80

Pro Val Glu Ala Glu Asp Ala Ala Thr Tyr Tyr Cys Gln Gln Ser Arg
                 85                  90                  95

Glu Tyr Pro Tyr Thr Phe Gly Gly Thr Lys Leu Glu Ile Lys Arg
             100                 105                 110

Thr Val Ala Ala Pro Ser Val Phe Ile Phe Pro Pro Ser Asp Glu Gln
             115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215

<210> SEQ ID NO 47
<211> LENGTH: 447
<212> TYPE: PRT
<213> ORGANISM: Artificial Sequence
<220> FEATURE:
<223> OTHER INFORMATION: huMov19 full length heavy chain

<400> SEQUENCE: 47

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
 50                 55                  60

Gln Gly Lys Ala Thr Leu Thr Val Asp Lys Ser Ser Asn Thr Ala His
 65                 70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
            435                 440                 445

<210> SEQ ID NO 48
<211> LENGTH: 218
<212> TYPE: PRT
<213> ORGANISM: Artificial Sequence
<220> FEATURE:
<223> OTHER INFORMATION: huMov19 full length light chain

<400> SEQUENCE: 48

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

-continued

```
Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 49
<211> LENGTH: 4
<212> TYPE: PRT
<213> ORGANISM: Artificial Sequence
<220> FEATURE:
<223> OTHER INFORMATION: glycine/serine linker

<400> SEQUENCE: 49

Gly Gly Gly Ser
1

<210> SEQ ID NO 50
<211> LENGTH: 5
<212> TYPE: PRT
<213> ORGANISM: Artificial Sequence
<220> FEATURE:
<223> OTHER INFORMATION: glycine/serine linker

<400> SEQUENCE: 50

Gly Gly Gly Gly Ser
1               5

<210> SEQ ID NO 51
<211> LENGTH: 15
<212> TYPE: PRT
<213> ORGANISM: Artificial Sequence
<220> FEATURE:
<223> OTHER INFORMATION: glycine/serine linker

<400> SEQUENCE: 51

Gly Gly Gly Gly Ser Gly Gly Gly Gly Ser Gly Gly Gly Gly Ser
1               5                   10                  15

<210> SEQ ID NO 52
<211> LENGTH: 20
<212> TYPE: PRT
<213> ORGANISM: Artificial Sequence
<220> FEATURE:
<223> OTHER INFORMATION: glycine/serine linker

<400> SEQUENCE: 52

Gly Gly Gly Gly Ser Gly Gly Gly Gly Ser Gly Gly Gly Gly Ser Gly
1               5                   10                  15

Gly Gly Gly Ser
            20

<210> SEQ ID NO 53
<211> LENGTH: 257
```

```
<212> TYPE: PRT
<213> ORGANISM: Homo sapiens

<400> SEQUENCE: 53

Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
                20                  25                  30

Leu Leu Asn Val Cys Met Asn Ala Lys His His Lys Glu Lys Pro Gly
            35                  40                  45

Pro Glu Asp Lys Leu His Glu Gln Cys Arg Pro Trp Arg Lys Asn Ala
        50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
        130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
                180                 185                 190

Trp Thr His Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
        210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 54
<211> LENGTH: 4
<212> TYPE: PRT
<213> ORGANISM: Artificial Sequence
<220> FEATURE:
<223> OTHER INFORMATION: peptide

<400> SEQUENCE: 54

Ala Leu Ala Leu
1

<210> SEQ ID NO 55
<211> LENGTH: 4
<212> TYPE: PRT
<213> ORGANISM: Artificial Sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: Beta-Ala
```

<400> SEQUENCE: 55

Ala Leu Ala Leu
1

<210> SEQ ID NO 56
<211> LENGTH: 4
<212> TYPE: PRT
<213> ORGANISM: Artificial Sequence
<220> FEATURE:
<223> OTHER INFORMATION: peptide

<400> SEQUENCE: 56

Gly Phe Leu Gly
1

<210> SEQ ID NO 57
<211> LENGTH: 118
<212> TYPE: PRT
<213> ORGANISM: Artificial Sequence
<220> FEATURE:
<223> OTHER INFORMATION: huMov19 S44C Heavy Chain Variable Sequence

<400> SEQUENCE: 57

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Cys Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 58

<400> SEQUENCE: 58

000

<210> SEQ ID NO 59
<211> LENGTH: 216
<212> TYPE: PRT
<213> ORGANISM: Artificial Sequence
<220> FEATURE:
<223> OTHER INFORMATION: wild-type IgG Fc Region

<400> SEQUENCE: 59

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
210                 215

<210> SEQ ID NO 60
<211> LENGTH: 215
<212> TYPE: PRT
<213> ORGANISM: Artificial Sequence
<220> FEATURE:
<223> OTHER INFORMATION: IgG2 Fc region

<400> SEQUENCE: 60

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
 50                  55                  60

Phe Asn Ser Thr Phe Arg Val Val Ser Val Leu Thr Val Val His Gln
 65                  70                  75                  80

Asp Trp Leu Asn Gly Lys Glu Tyr Lys Cys Lys Val Ser Asn Lys Gly
                 85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
130                 135                 140

Asp Ile Ala Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

```
Ser Cys Ser Val Met His Glu Ala Leu His Asn His Tyr Thr Gln Lys
        195                 200                 205

Ser Leu Ser Leu Ser Pro Gly
        210                 215

<210> SEQ ID NO 61
<211> LENGTH: 216
<212> TYPE: PRT
<213> ORGANISM: Artificial Sequence
<220> FEATURE:
<223> OTHER INFORMATION: IgG4 Fc region

<400> SEQUENCE: 61

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly
    210                 215

<210> SEQ ID NO 62
<211> LENGTH: 216
<212> TYPE: PRT
<213> ORGANISM: Artificial Sequence
<220> FEATURE:
<223> OTHER INFORMATION: IgG1 CH2 and CH3 (L234A/L235A)

<400> SEQUENCE: 62

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60
```

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 63
<211> LENGTH: 216
<212> TYPE: PRT
<213> ORGANISM: Artificial Sequence
<220> FEATURE:
<223> OTHER INFORMATION: IgG1 CH2 and CH3 (N297A)

<400> SEQUENCE: 63

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Ala Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

```
Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 64
<211> LENGTH: 216
<212> TYPE: PRT
<213> ORGANISM: Artificial Sequence
<220> FEATURE:
<223> OTHER INFORMATION: IgG1 CH2 and CH3 (N297Q)

<400> SEQUENCE: 64

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Gln Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```